(12) United States Patent
Bothe et al.

(10) Patent No.: US 10,435,396 B2
(45) Date of Patent: Oct. 8, 2019

(54) 2-SUBSTITUTED INDAZOLES, METHODS FOR PRODUCING SAME, PHARMACEUTICAL PREPARATIONS THAT CONTAIN SAME, AND USE OF SAME TO PRODUCE DRUGS

(71) Applicant: Bayer Pharma Aktiengesellschaft, Berlin (DE)

(72) Inventors: Ulrich Bothe, Berlin (DE); Holger Siebeneicher, Berlin (DE); Nicole Schmidt, Wuppertal (DE); Judith Günther, Berlin (DE); Holger Steuber, Berlin (DE); Ulf Bömer, Glienicke (DE); Martin Lange, Berlin (DE); Reinhard Nubbemeyer, Berlin (DE); Nicholas Charles Ray, Harlow (GB); Pascal Savy, Harlow (GB)

(73) Assignee: Bayer Pharma Aktiegesellschaft, Berlin (DE)

( * ) Notice: Subject to any disclaimer, the term of this patent is extended or adjusted under 35 U.S.C. 154(b) by 0 days.

(21) Appl. No.: 16/081,209

(22) PCT Filed: Feb. 28, 2017

(86) PCT No.: PCT/EP2017/054577
§ 371 (c)(1),
(2) Date: Aug. 30, 2018

(87) PCT Pub. No.: WO2017/148902
PCT Pub. Date: Sep. 8, 2017

(65) Prior Publication Data
US 2019/0071432 A1   Mar. 7, 2019

(30) Foreign Application Priority Data

Mar. 3, 2016  (EP) .................................... 16158542

(51) Int. Cl.
| | | |
|---|---|---|
| *C07D 405/14* | (2006.01) | |
| *C07D 409/14* | (2006.01) | |
| *C07D 401/14* | (2006.01) | |
| *C07D 413/14* | (2006.01) | |
| *C07D 417/14* | (2006.01) | |
| *C07D 487/08* | (2006.01) | |
| *A61P 19/02* | (2006.01) | |
| *A61P 25/04* | (2006.01) | |
| *A61P 29/00* | (2006.01) | |
| *A61P 35/00* | (2006.01) | |

(52) U.S. Cl.
CPC ......... *C07D 405/14* (2013.01); *C07D 401/14* (2013.01); *C07D 409/14* (2013.01); *C07D 413/14* (2013.01); *C07D 417/14* (2013.01); *C07D 487/08* (2013.01); *A61P 19/02* (2018.01); *A61P 25/04* (2018.01); *A61P 29/00* (2018.01); *A61P 35/00* (2018.01)

(58) Field of Classification Search
None
See application file for complete search history.

(56) References Cited

U.S. PATENT DOCUMENTS

| | | |
|---|---|---|
| 8,293,923 B2 | 10/2012 | Guckian et al. |
| 9,951,086 B2 | 4/2018 | Bothe et al. |
| 2002/0156081 A1 | 10/2002 | Hirst et al. |
| 2007/0185058 A1 | 8/2007 | Conte |
| 2010/0094000 A1 | 4/2010 | Fukumoto et al. |
| 2013/0274241 A1 | 10/2013 | Jorand-Lebrun et al. |
| 2015/0133422 A1 | 5/2015 | Crosignani et al. |
| 2016/0311833 A1 | 10/2016 | Bothe |
| 2017/0349570 A1 | 12/2017 | Bothe |
| 2018/0201609 A1* | 7/2018 | Gummadi ............ C07D 487/04 |
| 2018/0289685 A1 | 10/2018 | Bothe |
| 2019/0106407 A1 | 4/2019 | Thaler |
| 2019/0112270 A1 | 4/2019 | Thaler |

(Continued)

FOREIGN PATENT DOCUMENTS

| | | |
|---|---|---|
| WO | WO2004113281 A1 | 12/2004 |
| WO | WO2005082866 A2 | 9/2005 |

(Continued)

OTHER PUBLICATIONS

Abbate, A. et al. (2010). "Interleukin-1 Blockade With Anakinra to Prevent Adverse Cardiac Remodeling After Acute Myocardial Infarction (Virginia Commonwealth University Anakinra Remodeling Trial [VCU-ART] Pilot Study," The American Journal of Cardiology 105: 1371-1377.

Abbate, A. et al. (2013). "Effects of Interleukin-1 Blockade With Anakinra on Adverse Cardiac Remodeling and Heart Failure After Acute Myocardial Infarction [from the Virginia Commonwealth University-Anakinra Remodeling Trial (2) (VCU-ART2) Pilot Study]," 111: 1394-1400.

(Continued)

*Primary Examiner* — Kamal A Saeed
(74) *Attorney, Agent, or Firm* — Morrison & Foerster LLP

(57) ABSTRACT

The present application relates to novel substituted indazoles, to processes for preparation thereof, to the use thereof alone or in combinations for treatment and/or prophylaxis of diseases, and to the use thereof for production of medicaments for treatment and/or prophylaxis of diseases, especially for treatment and/or prophylaxis of endometriosis and endometriosis-associated pain and other endometriosis-associated symptoms such as dysmenorrhoea, dyspareunia, dysuria and dyschezia, of lymphoma, rheumatoid arthritis, spondyloarthritis (especially psoriatic spondyloarthritis and Bekhterev's disease), lupus erythematosus, multiple sclerosis, macular degeneration, COPD, gout, fatty liver disorders, insulin resistance, neoplastic disorders and psoriasis.

8 Claims, No Drawings

(56) References Cited

U.S. PATENT DOCUMENTS

| | | | |
|---|---|---|---|
| 2019/0125736 A1 | 5/2019 | Rausch | |
| 2019/0144420 A1 | 5/2019 | Thaler | |

FOREIGN PATENT DOCUMENTS

| | | | |
|---|---|---|---|
| WO | WO2005082866 A3 | 4/2006 | |
| WO | WO2006061715 A2 | 6/2006 | |
| WO | WO2006061715 A3 | 11/2006 | |
| WO | WO2007091107 A1 | 8/2007 | |
| WO | WO2007142584 A1 | 12/2007 | |
| WO | WO2009117421 A2 | 9/2009 | |
| WO | WO2009117421 A3 | 1/2010 | |
| WO | WO2009024341 A8 | 4/2010 | |
| WO | WO2011153588 A1 | 12/2011 | |
| WO | WO2012061926 A1 | 5/2012 | |
| WO | WO2012107475 A1 | 8/2012 | |
| WO | WO2012112743 A1 | 8/2012 | |
| WO | WO2013042137 A1 | 3/2013 | |
| WO | WO2013106254 A1 | 7/2013 | |
| WO | WO2013174744 A1 | 11/2013 | |
| WO | WO2014008992 A1 | 1/2014 | |
| WO | WO2015091426 A1 | 6/2015 | |
| WO | WO2015104662 A1 | 7/2015 | |
| WO | WO2015104688 A1 | 7/2015 | |
| WO | WO2015193846 A1 | 12/2015 | |
| WO | WO2016083433 A1 | 6/2016 | |
| WO | WO2016174183 A1 | 11/2016 | |
| WO | WO2017009798 A1 | 1/2017 | |
| WO | WO2017186689 A1 | 11/2017 | |
| WO | WO2017186693 A1 | 11/2017 | |
| WO | WO2017186700 A1 | 11/2017 | |
| WO | WO2017186703 A1 | 11/2017 | |
| WO | WO2017207386 A1 | 12/2017 | |
| WO | WO2017207481 A1 | 12/2017 | |

OTHER PUBLICATIONS

Ahmad, R. et al. (2015). "Increased expression of the interleukin-1 receptor-associated kinase (IRAK)-1 is associated with adipose tissue inflammatory state in obesity," Diabetology & Metabolic Syndrome 7(71): 1-16.

Akash, M.S.H. et al. (2012). "Interleukin-1 Receptor Antagonist: A New Therapy for Type 2 Diabetes Mellitus," Journal of Pharmaceutical Sciences 101(5): 1647-1658.

Akcay, A. et al. (2011). "IL-33 Exacerbates Acute Kidney Injury," J Am Soc Nephrol 22: 2057-2067.

Akoum, A. et al. (2007). "Imbalance in the expression of the activating type I and the inhibitory type II interleukin 1 receptors in endometriosis," Human Reproduction 22(5): 1464-1473.

Allhorn, S. et al. (2008). "TLR3 and TLR4 expression in healthy and diseased human endometrium," Reproductive Biology and Endocrinology 6:40.

Ashimori, A. et al. (1990). "Novel 1,4-Dihydropyridine Calcium Antagonists. I. Synthesis and Hypotensive Activity of 4-(Substituted Pyridyl)-1,4-dihydropyridine Derivatives," Chem. Pharm. Bull. 38(9): 2446-2458.

Ballak, D.B. et al. (2015). "IL-1 family members in the pathogenesis and treatment of metabolic disease: Focus on adipose tissue inflammation and insulin resistance," Cytokine 75: 280-290.

Bauer, E M. et al. (2012). "High Mobility Group Box 1 Contributes to the Pathogenesis of Experimental Pulmonary Hypertension via Activation of Toll-like Receptor 4," Molecular Medicine 18: 1509-1518.

Benias, P.C. et al. (2012). "Hepatic expression of toll-like receptors 3, 4, and 9 in primary biliary cirrhosis and chronic hepatitis C," Clinics and Research in Hepatology and Gastroenterology 36: 448-454.

Bijani, F.M. et al. (2012). "Toll-like Receptor Signaling Pathways in Cardiovascular Diseases: Challenges and Opportunities," International Review of Immunology 31(5): 379-395.

Bomfim, G.F. et al. (Feb. 1, 2015). "Toll-like receptor 4 inhibition reduces vascular inflammation in spontaneously hypertensive rats," Life Sci. 122: 1-7.

Bomfim, G.F. et al. (Jun. 2012). "Toll like receptor 4 contributes to blood pressure regulation and vascular contraction in spontaneously hypertensive rat," Clin Sci (Lond) 122(11): 535-543.

Brenner, M. et al. (2009). "Targeted treatment of pyoderma gangrenosum in PAPA (pyogenic arthritis, pyoderma gangrenosum and acne) syndrome with the recombinant human interleukin-1 receptor antagonist anakinra," British Journal of Dermatology 161: 1199-1201.

Brough, D. et al. (Oct. 2011). "Regulation of interleukin-1 in acute brain injury," Trends in Pharmacological Sciences 32(10): 617-622.

Brovko, D.A. et al. (2001). "Regioselective Synthesis of 2-N-Substituted 6-Nitro-and 4,6,-Dinitroindazoles," Chemistry of Heterocyclic Compounds 37(4): 504-505.

Bunting, M.M. et al. (2013). "Interleukin-33 Drives Activation of Alveolar Macrophages and Airway Inflammation in a Mouse Model of Acute Exacerbation of Chronic Asthma," BioMed Research International 10 pages.

Byers, D.E. et al. (2013). "Long-term IL-33-producing epithelial progenitor cells in chronic obstructive lung disease," The Journal of Clinical Investigation 123(9): 3967-3982.

Béraud, D. et al. (2012). "Misfolded α-synuclein and toll-like receptors: therapeutic targets for Parkinson's disease," 18S1: S17-S20.

Cameron, B. et al. (Oct. 24, 2012). "Loss of Interleukin Receptor-Associated Kinase 4 Signaling Suppresses Amyloid Pathology and Alters Microglial Phenotype in a Mouse Model of Alzheimer's Disease," The Journal of Neuroscience 32(43): 15112-15123.

Candia, L. et al. (2007). "Toll-like receptor-2 expression is upregulated in antigen-presenting cells from patients with psoriatic arthritis: a pathogenic role for innate immunity," J. Rheumatol 34: 374-379.

Cario, E. (2010). "Toll-like Receptors in Inflammatory Bowel Diseases: A Decade Later," Inflamm Bowel Dis 16(9): 1583-1597.

Carrasco, S. et al. (2011). "Toll-like reception (TLR) 2 is upregulated on peripheral blook monocytes of patients with psoriatic arthritis: a role for a gram-positive inflammatory trigger," Clinical and Experimental Rheumatology 29: 958-962.

Carty, M. et al. (2011). "Evaluating the role of Toll-like receptors in diseases of the central nervous system," Biochemical Pharmacology 81: 825-837.

Caso, F. et al. (2014). "Biological Treatments in Behçet's Disease: Beyond Anti-TNF Therapy," Mediators of Inflammation Article ID 107421, 14 pages.

Ceccarelli, S. et al. (Nov. 28, 2014). "Toll-like receptor-mediated signaling cascade as a regulator of the inflammation network during alcoholic liver disease," World J Gastroenterol 20(44): 16443-16451.

Cevikbas, F. et al. (2012). "IL-33: A Novel Danger Signal System in Atopic Dermatitis," Journal of Investigative Dermatology 132: 1326-1329.

Chang, J.H. et al. (2012). "Recent advances in Toll-like receptors and anterior uveitis," Clinical and Experimental Ophthalmology 40: 821-828.

Chen, D-Y. et al. (2013). "Involvement of TLR7 MyD88-dependent signaling pathway in the pathogenesis of adult-onset Still's disease," Arthritis Research & Therapy 15: 1-12.

Chen, X. (2015). "Significance of TLR4/MyD88 expression in breast cancer," Int J Clin Exp Pathol 8(6): 7034-7039.

Chiang, E.Y. et al. (2011). "Immune Complex-Mediated Cell Activation from Systemic Lupus Erythematosus and Rhematoid Arthritis Patients Elaborate Different Requirement for IRAK1/4 Kinase Activity across Human Cell Types," J Immunol 186: 1279-1288.

Choi, J-W. et al. (2013). "MYD88 expression and L265P mutation in diffuse large B-cell lymphoma," Human Pathology 44: 1375-1381.

Chopra, P. et al. (2013). "Treatment of Complex Regional Pain Syndrome (CRPS) Using Low Dose Naltrexone (LDN)," J Neuroimmune Pharmacol 8: 470-476.

Christensen, S.R. et al. (2006). "Toll-like Receptor 7 and TLR9 Dictate Autoantibody Specificity and Have Opposing Inflammatory and Regulatory Roles in a Murine Model of Lupus," Immunity 25: 417-428.

(56) References Cited

OTHER PUBLICATIONS

Christia, P. et al. (Sep. 2013). "Targeting inflammatory pathways in myocardial infarction," Eur J Clin Invest 43(9): 986-995.
Ciccia, F. et al. (2015). "Difference in the expression of IL-9 and IL-17 correlates with different histological pattern of vascular wall injury in gian cell arteritis," Rheumatology 54: 1596-1604.
Cordiglieri, C. et al. (2014). "Innate immunity in myasthenia gravis thymus: Pathogenic effects of Toll-like receptor 4 signaling on autoimmunity," Journal of Autoimmunity 52: 74-89.
Cottet, F. et al. (2002). "Trifluoromethyl-Substituted Pyridines Through Displacement of Iodine by in situ Generated (Trifluoromethyle)copper," Eur. J. Org. Chem. 2: 327-330.
Cottet, F. et al. (2003). "Recommendable Routes to Trifluoromethyl-Substituted Pyridine- and Quinolinecarboxylic Acids," Eur. J. Org. Chem. 8: 1559-1568.
Cottet, F. et al. (2004). "Logistic flexibility in the preparation of isomeric halopyridinecarboxylic acids," Tetrahedron 60: 11869-11874.
Cottet, F. et al. (2004). "Futher Metalations and Funcionalizations of Chloro-, Bromo- and Iodo(trifluoromethyl) pyridines," Synthesis 10: 1619-1624.
Couillin, I. et al. (2009). "IL-1R1/MyD88 Signaling in Critical for Elastase-Induced Lung Inflammation and Emphysema," J Immunol 183: 8195-8202.
Csak, T. et al. (Jan. 13, 2011). "Deficiency in myeloid differentiation factor-2 and toll-like receptor 4 expression attenuates nonalcoholic steatohepatitis and fibrosis in mice," Am J Physiol Gastrointest Liver Physiol 300: G433-G411.
D'Elia, E. et al. (2015). "Successful treatmeant of subacute constrictive pericarditis with interleukin-1β receptor antagonist (anakinra)," Rheumatol, 294-295.
Dasu, M.R. et al. (2012). "Toll-like receptors and diabetes: a therapeutic perspective," Clinical Science 122: 203-214.
Datta, S. et al. (2004). "Toll IL-1 Receptors Differ in Their Ability to Promote the Stabilization of Adenosine and Uridine-Rich Elements Containing mRNA," J Immunol 173: 2755-2761.
David, B.T. et al. (2013). "A toll-like receptor 9 antagonist reduces pain hypersensitivity and the inflammatory response in spinal cord injury," Neurobiology of Disease 54: 194-205.
Davidson, D.J. et al. (2006). "IRAK-4 Mutation (Q293X): Rapid Detection and Characterization of Defective Post-Transcriptional TLR/IL-1R Responses in Human Myeloid and Non-Myeloid Cells," J. Immunol 177: 8202-8211.
De Koning, H.D. (2014). "Schnitzler's syndrome: lessons from 281 cases," Clinical and Translational Allergy 4(41): 1-15.
Del Rey, A. et al. (2012). "Chronic neuropathic pain-like behavior and brain-borne IL-1β," Ann. N.Y. Acad. Sci. 1262: 101-107.
Denes, A. et al. (2013). "Central and haematopoietic interleukin-1 both contribute to ischaemic brain injury in mice," Disease Models & Mechanisms 6: 1043-1048.
Deng, J. et al. (Feb. 27, 2009). "TLR4 and TLR5 induce distinct types of vasculitis," Circ Res. 104(4): 488-495.
Devaraj, S. et al. (Aug. 31, 2011). "Knockout of Toll-like Receptor-2 attenuates both the Pro-Inflammatory State of Diabetes and Incipient Diabetic Nephropathy," Arterioscler Thromb Vasc Biol. 31(8): 1796-1804.
Dinarello, C.A. (2009). "Immunological and Inflammatory Functions of the Interleukin-1 Family," Annu. Rev. Immunol. 27:519-550.
Dinarello, C.A. (2011). "A clinical perspective of IL-1β as the gatekeeper of inflammation," Eur. J. Immunol. 41: 1203-1217.
Dispenza, M.C. et al. (2012). "Systemic isotretinoin therapy normalizes exaggerated TLF-2-mediated innate immune responses in acne patients," J. Invest Dermatol. 132(9): 2198-2205.
Dubaniewicz, A. (2013). "Microbial and human heat shock proteins as 'danger signals' in sarcoidosis," Human Immunology 74; 1550-1558.

El-Faham, A. et al. (2011). , "Peptide-Coupling Reagents" Chapter 12 in Amino Acids, Peptides and Proteins in Organic Chemistry, vol. 3—Building Blocks, Catalysis and Coupling Chemistry, Hughes, A.B. ed., Wiley, pp. 407-444.
Fang, Y. et al. (2011). "Toll-like receptor and its roles in myocardial ischemic/reperfusion injury," Med Sci Monit 17(4): RA100-109.
Falck-Hansen, M. et al. (2013). "Toll-Like Receptors in Atherosclerosis," Int. J. Mol. Sci. 14: 14008-14023.
Flannery, S. et al. (2010). "The interleukin-1 receptor-associated kinases: Critical regulators of innate immune signalling," Biochemical Pharmacology 80:1981-1991.
Foster, A.M. et al. (2014). "IL-36 promotes myeloid cell infiltration, activation and inflammatory activity in skin," J Immunol. 192(12): 6053-6061.
Frangogiannis, N.G. (May 2015). "Inflammation in cardiac injury, repair and regeneration," Curr Opin Cardiol 30(3): 240-245.
Freeman, C.M. et al. (2013). "Lung CD8+ T cells in COPD have increased expression of bacterial TLRs," Respiratory Research 14: 13.
Fresno, M. et al. (2011). "Toll-like receptors, inflammation, metabolism and obesity," Archives of Physiology and Biochemistry 117(3): 151-164.
Gadakh, A.V. et al. (2012). "Heteroaryl Hydroxycarbonylation: An efficient, robust, practically scalable approach using formyl acetate as the co source," Synthetic Communications 42: 658-666.
Gambuzza, M. et al. (2011). "Targeting Toll-like receptors: Emerging therapeutics from multiple sclerosis management," Journal of Neuroimmunology 239: 1-12.
Gerdes, H. et al. (1980). "3-Oxatricyclo[5.3.1.01,4]undec4-en, ein stark gespannter Vierring-Enolether," Chem. Ber. 113: 1907-1920. English Translation of Abstract only.
Gilliet, M. et al. (2004). "Psoriasis Triggered by Toll-like Receptor 7 Agonist Imiquimod in the Presence of Dermal Plasmacytoid Dendritic Cell Precursors," Arch Dermatol 140: 1490-1495.
Goh, F.G. et al. (2012). "Intrinsic danger: activation of Toll-like receptors in rheumatoid arthritis," Rheumatology 51: 7-23.
Gresnigt, M.S. et al. (2013). "Biology of IL-36 cytokines and their role in disease," Seminars in Immunology 25: 458-465.
Guerrero, A.T.G. et al. (2012). "Toll-like receptor 2/MyD88 signaling mediates zymosan-induced joint hypernociception in mice: Participation of TNF-α, IL-1β and CXCL1/KC," European Journal of Pharmacology 674: 51-57.
Guo, H. et al. (2012). "Toll-like receptor 2 siRNA suppresses corneal inflammation and attenuates Aspergillus fumigatus keratitis in rats," Immunology and Cell Biology 90: 352-357.
Gül, A. et al. (2012). "Interleukin-1β-regulating antibody XOMA 052 (gevokizumab) in the treatment of acute exacerbations of resistant uveitis of Behçet's disease: an open-label pilot study," Ann Rheum Dis 71:563-566.
Haenuki, Y. et al. (2012). "A critical role of IL-33 in experimental allergic rhinitis," J Allergy Clin Immunol 130(1): 184-194.
Han, P. et al. (2013). "Interleukin-33 Mediates Formalin-Induced inflammatory pain in mice," Neuroscience 241: 59-66.
Han, Y. et al. (2013). "Associations of pri-miR-34b/c and pre-miR-196a2 Polymorphisms and Their Multiplicative Interactions with Hepatitis B Virus Mutations with Hepatocellular Carcinoma Risk," PLOS One 8(3): e58564.
Hao, L-Y. et al. (2013). "Inflammasomes in inflammatory bowel disease pathogenesis," Current Opinion 29(4): 363-369.
Heimesaat, M.M. et al. (2007). "Shift Towards Pro-inflammatory Intestinal Bacteria Aggravates Acute Murine Colitis via Toll-like Receptors 2 and 4," PLoS ONE 7: 1-7.
Heimesaat, M.M. et al. (2010). "MyD88/TLR9 mediated immunopathology and gut microbiota dynamics in a novel murine model of intestinal graft-versus-host disease," Gut 59: 1079-1087.
Henderson, C. et al. (2010). "Monogenic IL-1 Mediated Autoinflammatory and Immunodeficiency Syndromes: Finding the Right Balance in Response to Danger Signals," Clin Immunol. 135(2): 210-222.
Hernanz, R. et al. (2015). "Toll-like receptor 4 contributes to vascular remodeling and endothelial dysfunction in angiotensin II-induced hypertension," British Journal of Pharmacology 172: 3159-3176.

(56) References Cited

OTHER PUBLICATIONS

Hilberath, J.N. et al. (Aug. 2017). "Resolution of Toll-like receptor 4-mediated acute lung injury is linked to eicosanoids and suppressor of cytokine signaling 3," The FASEB Journal 25(6): 1827-1835.
Hoffmann, R. (Dec. 1999). "The Potential Role of Cytokines and T Cells in Alopecia Areata," Journal of Investigative Dermatology Symposium Proceedings 4(3): 235-238.
Holle, J.U. et al. (2013). "Toll-like receptor TLR2 and TLR9 ligation triggers neutrophil activation in granulomatosis with polyangiitis," Rheumatology 52: 1183-1189.
Holtmann, H. et al. (2001). "The MAPK Kinase Kinase TAK1 Plays a Central Role in Coupling the Interleukin-1 Receptor to Both Transcriptional and RNA-targeted Mechanisms of Gene Regulation," The Journal of Biological Chemistry 276(5): 3508-3516.
Hu, J. et al. (2011). "A general and efficient approach to 2H-indazoles and 1H-pyrazoles through copper-catalyzed intramaolecular N—N bond formation under mild conditions," CHem. Commun. 47: 10133-10135.
Hynes, J. et al. (2014). "Advances in the Discovery of Small-Molecule IRAK4 Inhibitors," Annual Reports in Medicinal Chemistry 49: 117-133.
Imaoka, H. et al. (2008). "Interleukin-18 production and pulmonary function in COPD," Eur Respir J. 31: 287-297.
Jain, S. et al. (2015). "Effectiveness and Safety of Anakinra for Management of Refractory Pericarditis," The American Journal of Cardiology 116: 1277-1279.
Janeway, C.A. et al. (2002). "Innate Immune Recognition," Annu. Rev. Immunol. 20:197-216.
Jeyaseelan, S. et al. (Mar. 2005). "Distinct Roles of Pattern Recognition Receptors CD14 and Toll-Like Receptor 4 in Acute Lung Injury," Infection and Immunity 73(3): 1754-1763.
Jialal, I. et al. (2014). "Global toll-like receptor 4 knockout results in decreased renal inflammation, fibrosis and podocytophathy," Journal of Diabetes and Its Complications 28: 755-761.
Kaarniranta, K. et al. (2009). "Age-related macular degeneration: activation of innate immunity system via pattern recognition receptors," J Mol Med 87: 117-123.
Kamari, Y. et al. (Nov. 2011). Lack of Interleukin-1α or Interleukin-1β Inhibits Transformation of Steatosis to Steatohepatitis Liver Fibrosis in Hypercholesteroleic Mice, J Hepatol 55(5): 1086-1094.
Kang, M-J. et al. (2007). "IL-18 is Inducted and IL-18 Receptor a Plays a Critical Role in the Pathogenesis of Cigarette Smoke-Induced Pulmonary Emphysema and Inflammation," J Immunol 178: 1948-1959.
Kaplan, M. et al. (2014). "Effectiveness of interleukin-1 receptor antagonist (Anakinra) on cerulean-induced experimental acute pancreatitis in rats," Scandinavian Journal of Gastroenterology 49: 1124-1130.
Kawayama, T. et al. (2012). "Interleukin-18 in Pulmonary Inflammatory Diseases," Journal of Interferon & Cytokine Research 32(10): 443-451.
Kezic, J. et al. (2011). "Endotoxin-induced uveitis is primarily dependent on radiation-resistant cells and on MyD88 but not TRIF," Journal of Leukocyte Biology 90(2): 305-311.
Kfoury, A. et al. (2013). "MyD88 in DNA Repair and Cancer Cell Resistance to Genotoxic Drugs," J Natl Cancer Inst 105: 937-946.
Khan, K.N. et al. (Aug. 2013). "Toll-like receptor system and endometriosis," J. Obstet. Gynaecol. Res., 39(8): 1281-1292.
Kim , T.W. et al. (Jan. 2011). "The Critical Role of IL-1 Receptor-Associated Kinase 4-Mediated NF-kB Activation in Modified Low-Density Lipoprotein-Induced Inflammatory Gene Expression and Atherosclerosis," J Immunol 186: 2871-2880.
Kim, D. et al. (2009). "Toll-Like Receptors in Peripheral Nerve Injury and Neuropathic Pain," Current Topics in Microbiology and Immunology 336: 169-186.
Kim, G-T et al. (2010). "Expression of TLR2, TLR4, and TLR9 in dermatomyositis and polymyositis," Clin Rheumatol 29: 273-279.
Kim, K.H. et al. (2012). "Expression and significance of the TLR4/MyD88 signaling pathway in ovarian epithelial cancers," World Journal of Surgical Oncology 10: 193.
Kim, T.W. et al. (2007). "A critical role for IRAK4 kinase activity in Toll-like receptor-mediated innate immunity," JEM 204(5):1025-1036.
Kitazawa, M. et al. (Nov. 2011). "Blocking IL-1 Signaling Rescues Cognition, Attenuates Tau Pathology, and Restores Neuronal β-Catenin Pathway Function in an Alzheimer's Disease Model," J Immunol 187: 6539-6549.
Kobori, A. et al. (2010). "Interleukin-33 expression is specifically enhanced in inflamed mucosa of ulcerative colitis," J. Gastroenterol 45: 999-1007.
Kollewe, C. et al. (2004). "Sequential Autophosphorylation Steps in the Interleukin-1 Receptor-associated Kinase-1 Regulate its Availability as an Adapter in Interleukin-1 Signaling," The Journal of Biological Chemistry 279(7): 5227-5236.
Kovach, M.A. et al. (2011). "Toll like receptors in diseases of lung," International Immunopharmacology 11: 1399-1406.
Kreisel, D. et al. (2013). "Innate immunity and organ transplantation: focus on lung transplantation," Transpl Int. 26(1): 2-10.
Ku, C. et al. (2007). "Selective predisposition to bacterial infections in IRAK-4-deficient children: IRAK-4-dependent TLRs are otherwise redundant in protective immunity," JEM 204(10):2407-2422.
Kumar, M.R. et al. (2011). "Consecutive Condensation, C—N and N—N Bond Formations: A Copper-Catalyzed One-Pot Three-Component Synthesis of 2H-indazole," Organic Letters 13(13): 3542-3545.
Kusakabe, K. et al. (2013). "Indazole-Based Potent and Cell-Active Mps1 Kinase Inhibitors: Rational Design from Pan-Kinase Inhibitor Anthrapyrazolone (SP600125)," J. Med. Chem 56: 4343-4356.
Kwok, Y.H. et al. (2012). "Increased Responsiveness of Peripheral Blood Mononuclear Cells to In Vitro TLF 2, 4 and 7 Ligand Stimulationin Chronic Pain Patients," PLOS One 7(8): 1-8.
Lawson, C. et al. (2008). "Abnormal interleukin 1 receptor types I and II gene expression in eutopic and ectopic endometrial tissues of women with endometriosis," Journal of Reproductive Immunology 77: 75-84.
Lee et al. (2015). "Absence of toll-like receptor 4 (TLR4) extends survival in the hSOD1 G93A mouse model of amyotrophic lateral sclerosis," Journal of Neuroinflammation 12: 90.
Lee, H.S. et al. (2012). "Expression of Toll-like receptor 4 Contributes to Corneal Inflammation in Experimental Dry Eye Disease," Invest Ophthalmol Vis Sci. 53(9): 5632-5640.
Leventhal, J.S. et al. (2012). "Toll-like receptors in transplantation: sensing and reacting to injury," Kidney International 81: 826-832.
Li, D. et al. (2014). "IL-33 promotes ST2-dependent lung fibrosis by the induction of alternatively activated macrophages and innate lymphoid cells in mice," J. Allergy Clin Immunol 134(6): 1422-1432.e11.
Li, J. et al. (2013). "Toll-like receptors as therapeutic targets for autoimmune connective tissue diseases," Pharmacology & Therapeutics 138: 441-451.
Li, X. (2015). "Protective effect of neutralizing anti-IL-18α monoclonal antibody on a mouse model of acute graft-versus-host disease," Oncology Reports 34: 2031-2039.
Liang, B. et al. (2013). "Myeloid Differentiation Factor 88 Promotes Growth and Metastasis of Human Hepatocellular Carcinoma," Clin Cancer Res 19(11): 2905-2916.
Lim, J-E et al. (Sep. 2011). "MyD88 Deficiency Ameliorates β-Amyloidosis in an Animal Model of Alzheimer's Disease," The American Journal of Pathology 179(3): 1095-1103.
Liu, T. et al. (2013). "New insights into the mechanisms of itch: are pain and itch controlled by distinct mechanisms?" Pflugers Arch. 465(12): 1-24.
Liu, X-J et al. (2014). "Nociceptive neurons regulate innate and adaptive immunity and neuropathic pain through MyD88 adapter," Cell Research 24: 1374-1377.
Liu, Y. et al. (2015). "Toll-like receptor 5 deficiency attenuates interstitial cardiac fibrosis and dysfunction induced by pressure overload by inhibiting inflammation and the endothelial-mesenchymal transition," Biochimical et Biophsica Acta1852: 2456-2466.
Liu-Bryan, R. et al. (2005). "Innate Immunity Conferred by Toll-like Receptors 2 and 4 and Myeloid Differentiation Factor 88

(56) References Cited

OTHER PUBLICATIONS

Expression is Pivotal to Monosodium Urate Monohydrate Crystal-Induced Inflammation," Arthritis & Rheumatism 52(9): 2936-2946.
Lloyd, C.M. et al. (2010). "IL-33 family members and asthma—bridging innate and adaptive immune responses," Curr Opin Immunol 22(6): 800-806.
Lucking, U. (2013). "Sulfoximines: A Neglected Opportunity in Medicinal Chemistry," Medicinal Chemistry 125: 9570-9580.
Lugrin, J. et al. (2015). "Cutting Edge: IL-1α is a Crucial Danger Signal Triggering Acute Myocardial Inflammation during Myocardial Infarction," The Journal of Immunology 194: 499-503.
Maekawa, Y. et al. (2009). "Survival and Cardiac Remodeling After Myocardial Infarction are Critically Dependent on the Host Innate Immune Interleukin-1 Receptor-Associated Kinase-4 Signaling," Circulation 120: 1401-1414.
Malkov, A.V. et al. (2003). "A long-range chiral relay via tertiary amide group in asymmetric catalysis: new amino acid-derived N,P-ligands for copper-catalyzed conjugate addition," Chem Commun, 1948-1949.
Margaritopoulos, G.A. et al. (2010). "Investigation of Toll-like receptors in the pathogenesis of fibrotic and granulomatous disorders: a bronchoalveolar lavage study," Fibrogenesis & Tissue Repair 3: 20.
Martínez-González, I. et al. (2013). "Human Mesenchymal Stem Cells Overexpressing the IL-33 Antagonist Soluble IL-1 Receptor-Like-1 Attenuate Endotoxin-Induced Acute Lung Injury," Am J Respir Cell Mol Biol 49(4): 552-562.
McGettrick, A.F. et al. (2007). "Toll-like receptors: key activators of leucocytes and regulator of haematopoiesis," British Journal of Haematology 139: 185-193.
Miller, L.S. (2008). "Toll-like receptors in skin," Adv Dermatol. 24: 71-87.
Min, W. et al. (2015). "Baicalin Protects Keratinocytes from Toll-like Receptor-4 Mediated DNA Damage and Inflammation Following Ultraviolet Irradiation," Photochemistry and Photobiology, 91: 1435-1443.
Minkis, K. et al. (2012). "Interleukin 1 Receptor Antagonist Deficiency Presenting as Infantile Pustulosis Mimicking Infantile Pustular Psoriasis," Arch Dermatol. 148(6): 747-752.
Miura, K. et al. (2010). "Toll-Like Receptor 9 Promotes Steatohepatitis by induction of Interleukin-1β in Mice," Gastroenterology 139: 323-334.
Miura, K. et al. (Jun. 21, 2014). "Role of gut microbiota and Toll-like receptors in nonalcoholic fatty liver disease," World J Gastroenterology 20(23): 7381-7391.
Monclus, M. et al. (1995). "Asymmetric synthesis of fluorinated L-tyrosine and meta-L-tyrosines," Journal of Fluorine Chemistry 70: 39-43.
Morytko, M. et al. (2008). "Synthesis and in vitro activity of N1-cyano-4-(2-phenylacetyl)-N-o-tolylpiperzaine-1-carboximidamide P2X7 antagonists," Bioorganic & Medicinal Chemistry Letters 18: 2093-2096.
Motshwene, P.G. et al. (2009). "An Oligomeric Signaling Platform Formed by the Toll-like Receptor Signal Transducers MyD88 and IRAK-4," The Journal of Biological Chemistry 284(37):25404-25411.
Márquez, A. et al. (2014). "Influence of the IL17A locus in giant cell arteritis susceptibility," Ann Rheum Dis 73: 1742-1745.
Nadigel, J. et al. (2011). "Cigarette smoke increases TLR4 and TLR9 expression and induces cytokine production from CD8+ T cells in chronic obstructive pulmonary disease," Respiratory Research 12: 149.
Nakanishi, W. et al. (2013). "IL-33, but Not IL-25, Is Crucial for the Development of House Dust Mite Antigen-Induced Allergic Rhinitis," PLoS ONE 8(10): 1-8.
Narayanan, S. et al. (2008). "Interleukin-1 Receptor-1-deficient Mice Show Attenuated Production of Ocular Surface Inflammatory Cytokines in Experimental Dry Eye," Cornea 27(7): 811-817.
Ngo, V.N. et al. (Feb. 3, 2011). "Oncogenically active MYD88 mutations in human lymphoma," Nature 470: 115-119.

Nickerson, K.M. et al. (2010). "TLR9 Regulates TLR7- and MyD88-Dependent Autoantibody Production and Disease in a Murine Model of Lupus," J Immunol 184: 1840-1848.
Nicotra, L. et al. (2012). "Toll-Like Receptors in Chronic Pain," Exp Neurol. 234(2): 316-329.
Niebuhr, M. et al. (2008). "Dysregulation of toll-like receptor-2 (TLR-2)-induced effects in monocytes from patients with atopic dermatitis: impact of the TLR-2 R753Q polymorphism," Allergy 63: 728-734.
Noelker, C. et al. (2013). "Toll like receptor 4 mediates cell death in a mouse MPTP model of Parkinson disease," Scientific Reports 3: 1393.
Nordström, D. et al. (2012). "Beneficial Effect of Interleukin 1 Inhibition with Anakinra in Adult-onset Still's Disease. An Open, Randomized, Multicenter Study," The Journal of Rheumatology 39(10): 2008-2011.
Nozaki, Y. et al. (2004). "Polymorphisms of Interleukin-1β and β3-Adrenergic Receptor in Japanese Patients With Nonalcoholic Steatohepatitis," Alcohol Clin Exp Res. 28(8): 106S-110S.
O'Hara, F. et al. (2013). "Radical-Based Regioselective C—H Functionalization of Electron-Deficient Heteroarenes: Scope, Tunability, and Predicatbility," J Am Chem Soc. 135(32): 12122-12134.
Ochi, A. et al. (2012). "MyD88 inhibition amplifies dendritic cell capacity to promote pancreatic carcinogenesis via Th2 cells," J. Exp. Med. 209(9): 1671-1687.
Okiyama, N. et al. (Nov. 2012). "T Lymphocytes and Muscle Condition Act Like Seeds and Soil in a Murine Polymyositis Model," Arthritis & Rheumatism 64(11): 3741-3749.
Ouziel, R. et al. (Jun. 2012). "The ST2 Pathway is Involved in Acute Pancreatitis," The American Journal of Pathology 180(6): 2330-2339.
Oyama, J. et al. (2004). "Reduced Myocardial Ischemia-Reperfusion Injury in Toll-Like Receptor 4-Deficient Mice," Circulation 109: 784-789.
Park, H.J. et al. (Jan. 2014). "Toll-like receptor signaling regulates cisplatin-induced mechanical allodynia in mice," Cancer Chemother Pharmacol. 73(1): 25-34.
Pauwels, N.S. et al. (2011). "Role of IL-1α and the Nlrp3/caspase-1/IL-1β axis in cigarette smoke-induced pulmonary inflammation and COPD," European Respiratory Journal 38(5): 1019-1028.
Pettersson, T. et al. (2012). "Setting up TRAPS," Annals of Medicine 44: 109-118.
Piggott, D.A. et al. (Feb. 2005). "MyD88-dependent induction of allergic Th2 responses to intranasal antigen," The Journal of Clinical Investigation 115(2): 459-467.
Price, E.W. et al. (2014). "Modular syntheses of H4octapa and H2dedpa, and yttrium coordination chemistry relevant to 86Y/90Y radiopharmaceuticlas," Dalton Transactions 43: 7176-7190.
Puente, X.S. et al. (Jul. 7, 2011). "Whole-genome sequencing identifies recurrent mutations in chronic lymphocytic leukaemia," Nature 475: 101.
Qi, Y. et al. (2014). "Retinal Ischemia/Reperfusion Injury is Mediated by Toll-like Receptor 4 Activation of NLRP3 Inflammasomes," Invest Ophthalmol Vis Sci 55:5466-5475.
Qiu, C. et al. (2013). "Anti-interleukin-33 inhibits cigarette smoke-induced lung inflammation in mice," Immunology 138: 76-82.
Rakoff-Nahoum, S. et al. (2006). "Role of Toll-like Receptors in Spontaneous Commensal-Dependent Colitis," Immunity 25: 319-329.
Ramirez Cruz, N.E et al. (2004). "Toll-like receptors: dysregulation in vivo in patients with acute respiratory distress syndrome," Revista Alergia Mexico 51(6): 210-217.
Ramirez, S.R. et al. (2012). "Toll-like Receptors and Diabetes Complications: Recent Advances," Current Diabetes Reviews 8: 480-488.
Redfern, R. L. et al. (2010). "Toll-like receptors in ocular surface disease," Experimental Eye Research 90: 679-687.
Rekhter, M. et al. (2008). "Genetic ablation of IRAK4 kinase activity inhibits vascular lesion formation," Biochemical and Biophysical Research Communications 367: 642-648.
Roger, T. et al. (Feb. 17, 2009). "Protection from lethal Gram-negative bacterial sepsis by targeting Toll-like receptor 4," PNAS 106(7): 2348-2352.

(56) References Cited

OTHER PUBLICATIONS

Roh, Y-S. et al. (2013). "Toll-like Receptors in Alcoholic Liver Disease, Non-Alcoholic Steatohepatitis and Carcinogenesis," J Gastroenterol Hepatol. 28(01): 38-42.
Ruperto, N. et al. (2012). "Two Randomized Trials of Canakinumab in Systemic Juvenile Idiopathic Arthritis," The New England Journal of Medicine 367(25): 2396-2406.
Ryu, H.C. et al. (2014). "2-Alkyl/alkeyl substituted pyridine C-region analogues of 2-(3-fluoro-4-methylsulfonylaminophenyl)propanamides as highly potent TRPV1 antagonists," Bioorganic & Medicinal Chemistry Letters 24: 4039-4043.
Saluja, R. et al. (2015). "The role of the IL-33/IL-1RL1 axis in mast cell and basophil activation in allergic disorders," Molecular Immunology 63: 80-85.
Santulli, P. et al. (2013). Profibrotic interleukin-33 is correlated with uterine leiomyoma tumour burden, Human Reproduction 28(8): 2126-2133.
Scanzello, C.R. et al. (2008). "Innate immune system activation in osteoarthritis: is osteoarthritis a chronic wound?" Current Opinion in Rheumatology 20: 565-572.
Schmidt, E. et al. (1996). "Detection of IL-1α, IL-1β and IL-1 receptor antagonist in blister fluid of bullous pemphigoid," Journal of Dermatological Science 11: 142-147.
Schmidt, M. et al. (Sep. 2010). "Crucial role for human Toll-like receptor 4 in the development of contact allergy to nickel," Nature Immunology 11(9): 814-820.
Schrepf, A. et al. (Oct. 2015). "Toll-like Receptor 4 and Comorbid Pain in Interstitial Cystitis/Bladder Pain Syndrome: A Multidisciplinary Approach to the Study of Chronic Pelvic Pain Research Network Study," Brain Behav Immun. 49: 66-74.
Sedimbi, S.K. et al. (2013). "IL-18 in inflammatory and autoimmune disease," Cell. Mol. Life Sci. 70: 4795-4802.
Seki, H. et al. (2010). "effect of Toll-like receptor 4 inhibitor on LPS-induced lung injury," Inflamm. Res. 59: 837-845.
Selway, J.L. et al. (2013). "Toll-like receptor 2 activation and comedogenesis: implications for the pathogenesis of acne," BMC Dermatology 13(10): 1-7.
Seneviratne, A.N. et al. (2012). "Toll-like receptors and macrophage activation in atherosclerosis," Clinica Chimica Acta 413: 3-14.
Shi, Y. et al. (2010). "Monosodium urate crystals in inflammation and immunity," Immunological Reviews 233: 203-217.
Shimizu, M. et al. (2006). "Synthesis and biological activities of new 1α,25-dihydroxy-19-norvitamin D3 analogs with modifications in both the A-ring and the side chain," Bioorganic & Medicinal Chemistry 14: 4277-4294.
Sikora, J. et al. (2012). "Imbalance in Cytokines from interleukin-1 Family—Role in Pathogenesis of Endometriosis," 68: 138-145.
Srivastava, R. et al. (2012). "Augmentation of Therapeutic Responses in Melanoma by Inhibition of IRAK-1,-4," Cancer Research 72(23): 6209-621.
Staschke, K.A. et al. (2009). "IRAK4 kinase Activity is Required for Th17 Differentiation and Th17-mediated Disease," J Immunol 183(1): 568-577.
Stojsavljevic, S. et al. (Dec. 28, 2014). "Adipokines and proinflammatory cytokines, the key mediators in the pathogenesis of nonalcoholic fatty liver disease," World Journal of Gastroenterology 20(48): 18070-18091.
Stokes, J.A. (2013). "Toll-like receptor signaling adapter proteins govern spread of neuropathic pain and recovery following nerve injury in male mice," Journal of Neuroinflammation 10(148): 1-14.
Sun, M. et al. (2014). "The Role of Interleukin-1 Receptor-Associated Kinases in Vogt-Koyanagi-Herada Disease," PLOS ONE 9(4): 1-8.
Sun, Y. et al. (2009). "Inhibition of Corneal Inflammation by the TLR4 Antagonist Eritoran Tetrasodium (E5564)," Invest Ophthalmol Vis Sci. 50(3): 1247-1254.
Suzuki, N. et al. (2002). "Severe impairment of interleukin-1 and Toll-like receptor signaling in mice lacking IRAK-4," Nature 416: 750-754.

Swamy, K.C.K. et al (2009). "Mitsunobu and Related Reactions: Advances and Applications," Chem. Rev. 109: 2551-2651.
Szczepanski, M.J. et al. (Apr. 1, 2009). "Triggering of Toll-like Receptor 4 Expressed on Human head and Neck Squamous Cell Carcinoma Promotes Tumor Development and Protects the Tumor from immune Attack," Cancer Res 69(7): 3105-3113.
Takami, A. et al. (2004). "Design and synthesis of Rho kinase inhibitors (I)," Bioorganic & Medicinal Chemistry 12: 2115-2137.
Talabot-Ayer, D. et al. (2014). "Immune-mediated experimental arthritis in IL-33 deficient mice," Cytokine 69: 68-74.
Terhorst, D. et al. (2010). "The Role of Toll-Like Receptors in Host Defenses and Their Relevance to Dermatologic Disease," Am J. Clin Dermatol 11(1): 1-10.
Thompson, J. A. et al. (2013). "Potential role of Toll-like receptors in programming of vascular dysfunction," Clinical Science 125: 19-25.
Tietze, L.F. et al. (2009). :Synthesis of Novel Structurally Simplified Estrogen Analogues with Electron-Donating Groups in Ring A, Synthesis 12: 2040-2060.
Timmers, L. et al. (2008). "Toll-Like Receptor 4 Mediates Maladaptive Left Ventricular Remodeling and Impairs Cardiac Function After Myocardial Infraction," Circ Res. 102: 257-264.
Timper, K. et al. (2015). "Safety, pharmacokinetics, and preliminary efficacy of a specific anti-IL-1alpha therapeutic antibody (MABp1) in patients with type 2 diabetes mellitus," Journal of Diabetes and Its Complications 29: 955-960.
Treon, S.P. et al. (Aug. 30, 2012). "MYD88 L265P Somatic Mutation in Walderntröm's Macroglobulinemia," The New England Journal of Medicine 367(9): 826-833.
Tsuchiya, H.M. et al. (1955). "Factors Affecting Molecular Weight of Enzymatically Synthesized Dextran," J Chem Soc 77: 2412-2319.
U.S. Appl. No. 16/097,506, filed Oct. 29, 2018, for Thaler et al.
U.S. Appl. No. 16/306,235, filing date unknown, inventor not yet available.
U.S. Appl. No. 16/377,025, filed Apr. 5, 2019, for Bothe et al.
Valaperti, A. et al. (2013). "Innate Immune Interleukin-1 Receptor-Associated Kinase 4 Exacerbates Viral Myocarditis by Reducing CCR5+CD11b+Monocyte Migration and Impairing Interferon Production," Circulation 128: 1542-1554.
Valeur, E. et al. (2009). "Amide bond formation: beyond the myth of coupling reagents," Chem. Soc. Rev. 38: 606-631.
Van Der Watt, J.J. et al. (2014). "Plasma cytokine profiles in HIV-1 infected patients developing neuropathic symptoms shortly after commencing antiretroviral therapy: a case-control study," BMC Infectious Diseases 14: 71.
Vennegaard, M.T. et al. (2014). "Epicutaneous exposure to nickel induces nickel allergy in mice via a MyD88-dependent and interleukin-1-dependent pathway," Contact Dermatitis 71: 224-232.
Vidyacharan, S. et al. (2014). "A facile synthesis of 2H-indazoles under neat conditions and further transformation into aza-γ-carboline alkaloid analogues in a tandem one-pot fashion," RSC Adv. 4: 34232-34236.
Viguier, M. et al. (2010). "Successful Treatment of Generalized Pustular Psoriasis With the Interleukin-1-Receptor Antagonist Anakinra: Lack of Correlation with IL1RN Mutations," Annals of Internal Medicine 153: 66-67.
Vijmasi, T. et al. (2013). "Topical administration of interleukin-1 receptor antagonist as a therapy for aqueous-deficient dry eye in autoimmune disease," Molecular Vision 19: 1957-1965.
Volin, M.V. et al. (2011). "Interleukin-18: A Mediator of Inflammation and Angiogenesis in Rheumatoid Arthritis," Journal of Interferon & Cytokine Research 31(10): 745-781.
Wallace, D.J. et al. (2011). "Development of a Fit-for-Purpose Large-Scale Synthesis of an Oral PARP Inhibitor," Org. Process Res. Dev.15: 831-840.
Walsh, D. et al. (2013). "Pattern recognition receptors-Molecular orchestrators of inflammation in inflammatory bowel disease," Cytokine & Growth Factor Reviews 24: 91-104.
Wan, Y.Y. et al. (2006). "The kinase TAK1 integrates antigen and cytokine receptor signaling for T cell development, survival and function," Nature Immunology 7(8): 851-858.

(56) References Cited

OTHER PUBLICATIONS

Wang, C. et al. (2001). "TAK1 is a ubiquitin-dependent kinase of MMK and IKK," Nature 412: 346-351.

Wang, E. et al. (2010). "High expression of Toll-like receptor 4/myeloid differentiation factor 88 signals correlates with poor prognosis in colorectal cancer," British Journal of Cancer 102: 908-915.

Wang, L. et al. (2015). "Picroside II protects rat kidney against ischemia/reperfusion-induced oxidative stress and Inflammation by the TLR4/NF-κB pathway," Experimental and Therapeutic Medicine 9: 1253-1258.

Wang, Y-C. et al. (2013). "Toll-like Receptor 4 Antagonist Attenuates Intracerebral Hemorrhage-Induced Brain Injury," Stroke 44: 2545-2552.

Wolf, G. et al. (2008). "Interleukin-1 signaling in required for induction and maintenance of postoperative incisional pain: Genetic and pharmacological studies in mice," Brain, Behavior, and Immunity 22: 1072-1077.

Wollina, U. et al. (2013). "Acne inversa (Hidradenitis suppurativa): A review with a focus on pathogenesis and treatment," Indian Dermatology Online Journal 4(1): 1-11.

Won, K.A. et al. (Mar. 2014). "The Glial-Neuronal GRK2 Pathway Participates in the Development of Trigeminal Neuropathic Pain in Rats," The Journal of Pain 15(3): 250-261.

Wong, L. et al. (2015). "Experimental Autoimmune Prostatitis Induces Microglial Activation in the Spinal Cord," The Prostate 75: 50-59.

Xiang, M. et al. (2010). "Association of Toll-Like Receptor Signaling and Reactive Oxygen Species: A Potential Therapeutic Target for Posttrauma Acute Lung Injury," Mediators of Inflammation 2010: 916425.

Xiang, W. et al. (2015). "Role of Toll-like receptor/MYD88 signaling in neurodegenerative diseases," Rev. Neurosci. 26(4): 407-414.

Yamada, A. et al. (2017). "Targeting IL-1 in Sjögren's syndrome," Expert Opin. Ther. Targets 17(4): 393-401.

Yang, H. et al. (2005). "IL-1 Receptor Antagonist-Mediated Therapeutic Effect in Murine Myasthenia Gravis is Associated with Suppressed Serum Proinflammatory Cytokines, C3, and Anti-Acetylcholine Receptor IgG1," The Journal of Immunology 175: 2018-2025.

Yang, L. et al. (May 2012). "Toll-like receptors in liver fibrosis: cellular crosstalk and mechanisms," Frontiers in Physiology 3(138): 1-18.

Yap, D. Y. H. et al. (2013). "The role of cytokines in the pathogenesis on systemic lupus erythematosus—from bench to bedside," Nephrology 18: 243-255.

Ye, D. et al. (2012). "Toll-like receptor-4 mediates obesity-induced non-alcoholic steatohepatitis through activation of X-box binding protein-1 in mice," Gut 61: 1058-1067.

Yin, H. et al.(2012). "Adenovirus-mediated delivery of soluble ST2 attenuates ovalbumin-induced allergic asthma in mice," Clinical & Experimental Immunology 170: 1-9.

Zambrano-Zaragoza, J.F. et al. (2014). "Th17 Cells in Autoimmune and Infectious Diseases," International Journal of Inflammation 1-12.

Zhang, Y-B. et al. (2009). "Increased expression of Toll-like receptors 4 and 9 in human lung cancer," Mol Biol Rep 36: 1475-1481.

Zhao, J. et al. (2011). "Altered biliary epithelial cell and monocyte responses to lipopolysaccharide as a TLR ligand in patients with primary biliary cirrhosis," Scandinavian Journal of Gastroenterology 46: 485-494.

Zhao, J. et al. (2013). "Spinal Interleukin-33 and its receptor ST2 contribute to bone cancer-induced pain in mice," Neuroscience 253: 172-182.

Zhao, S. et al. (Jul. 2014). "Toll-like receptors and prostate cancer," Frontiers in Immunology 5(352): 1-6.

Zhu, F-G. et al. (2013). "A novel antagonist of Toll-like receptors 7, 8 and 9 suppresses lupus disease-associated parameters in NZBW/F1 mice," Autoimmunity 46(7): 419-428.

Zong, M. (2014). "Anakinra treatment in patients with refractory inflammatory myopathies and possible predictive response biomarkers: a mechanistic study with 12 months follow-up," Ann Rheum Dis 73: 913-920.

\* cited by examiner

2-SUBSTITUTED INDAZOLES, METHODS FOR PRODUCING SAME, PHARMACEUTICAL PREPARATIONS THAT CONTAIN SAME, AND USE OF SAME TO PRODUCE DRUGS

CROSS REFERENCE TO RELATED APPLICATIONS

This application is a national stage application under 35 U.S.C. § 371 of International Application No. PCT/EP2017/054577, filed internationally on Feb. 28, 2017, which claims the benefit of European Application No. 16158542.7, filed Mar. 3, 2016.

The present application relates to novel 2-substituted indazoles, to processes for preparation thereof, to the use of the novel substituted indazoles for treatment and/or prophylaxis of diseases and to the use thereof for production of medicaments for treatment and/or prophylaxis of diseases, especially of proliferative disorders such as autoimmune disorders, of metabolic and inflammatory disorders, for example rheumatoid arthritis, spondyloarthritis (especially psoriatic spondyloarthritis and Bekhterev's disease), chronic obstructive pulmonary disease (abbreviation: COPD), multiple sclerosis, systemic lupus erythematosus, gout, metabolic syndrome, fatty liver hepatitis, insulin resistance, endometriosis and inflammation-induced or chronic pain, and of lymphoma.

The present invention relates to novel 2-substituted indazoles of the general formula (I) which inhibit interleukin-1 receptor-associated kinase 4 (IRAK4).

Human IRAK4 (interleukin-1 receptor-associated kinase 4) plays a key role in the activation of the immune system. Therefore, this kinase is an important therapeutic target molecule for the development of inflammation-inhibiting substances. IRAK4 is expressed by a multitude of cells and mediates the signal transduction of Toll-like receptors (TLR), except for TLR3, and receptors of the interleukin (IL)-1β family consisting of the IL-1R (receptor), IL-18R, IL-33R and IL-36R (Janeway and Medzhitov, Annu. Rev. Immunol., 2002; Dinarello, Annu. Rev. Immunol., 2009; Flannery and Bowie, Biochemical Pharmacology, 2010).

Neither IRAK4 knockout mice nor human cells from patients lacking IRAK4 react to stimulation by TLRs (except for TLR3) and the IL-1β family (Suzuki, Suzuki, et al., Nature, 2002; Davidson, Currie, et al., The Journal of Immunology, 2006; Ku, von Bernuth, et al., JEM, 2007; Kim, Staschke, et al., JEM, 2007).

The binding of the TLR ligands or the ligands of the IL-1β family to the respective receptor leads to recruitment and binding of MyD88 [Myeloid differentiation primary response gene (88)] to the receptor. As a result, MyD88 interacts with IRAK4, resulting in the formation of an active complex which interacts with and activates the kinases IRAK1 or IRAK2 (Kollewe, Mackensen, et al., Journal of Biological Chemistry, 2004; Precious et al., J. Biol. Chem., 2009). As a result of this, the NF (nuclear factor)-κB signalling pathway and the MAPK (mitogen-activated protein kinase) signal pathway is activated (Wang, Deng, et al., Nature, 2001). The activation both of the NF-κB signal pathway and of the MAPK signal pathway leads to processes associated with different immune processes. For example, there is increased expression of various inflammatory signal molecules and enzymes such as cytokines, chemokines and COX-2 (cyclooxygenase-2), for example, and increased mRNA stability of inflammation-associated genes, for example COX-2, IL-6 (interleukin-6), IL-8 (Holtmann, Enninga, et al., Journal of Biological Chemistry, 2001; Datta, Novotny, et al., The Journal of Immunology, 2004). Furthermore, these processes may be associated with the proliferation and differentiation of particular cell types, for example monocytes, macrophages, dendritic cells, T cells and B cells (Wan, Chi, et al., Nat Immunol, 2006; McGettrick and J. O'Neill, British Journal of Haematology, 2007).

The central role of IRAK4 in the pathology of various inflammatory disorders had already been shown by direct comparison of wild-type (WT) mice with genetically modified animals having a kinase-inactivated form of IRAK4 (IRAK4 KDKI). IRAK4 KDKI animals have an improved clinical picture in the animal model of multiple sclerosis, atherosclerosis, myocardial infarction and Alzheimer's disease (Rekhter, Staschke, et al., Biochemical and Biophysical Research Communication, 2008; Maekawa, Mizue, et al., Circulation, 2009; Staschke, Dong, et al., The Journal of Immunology, 2009; Kim, Febbraio, et al., The Journal of Immunology, 2011; Cameron, Tse, et al., The Journal of Neuroscience, 2012). Furthermore, it was found that deletion of IRAK4 in the animal model protects against virus-induced myocarditis by virtue of an improved anti-viral reaction with simultaneously reduced systemic inflammation (Valaperti, Nishii, et al., Circulation, 2013). It has also been shown that the expression of IRAK4 correlates with the degree of Vogt-Koyanagi-Harada syndrome (Sun, Yang, et al., PLoS ONE, 2014). In addition, the high relevance of IRAK4 for immune complex-mediated IFNα (interferon-alpha) production by plasmacytoid dendritic cells, a key process in the pathogenesis of systemic lupus erythematosus (SLE), has been shown (Chiang et al., The Journal of Immunology, 2010). Furthermore, the signalling pathway is associated with obesity (Ahmad, R., P. Shihab, et al., Diabetology & Metabolic Syndrome, 2015).

As well as the essential role of IRAK4 in congenital immunity, there are also hints that IRAK4 influences the differentiation of what are called the Th17 T cells, components of adaptive immunity. In the absence of IRAK4 kinase activity, fewer IL-17-producing T cells (Th17 T cells) are generated compared to WT mice. The inhibition of IRAK4 enables the prophylaxis and/or treatment of atherosclerosis, type 1 diabetes mellitus, rheumatoid arthritis, spondyloarthritis (especially psoriatic spondyloarthritis and Bekhterev's disease), lupus erythematosus, psoriasis, vitiligo, giant cell arteritis, chronic inflammatory bowel disorder and viral disorders, for example HIV (human immunodeficiency virus), hepatitis virus (Staschke, et al., The Journal of Immunology, 2009; Marquez, et al., Ann Rheum Dis, 2014; Zambrano-Zaragoza, et al., International Journal of Inflammation, 2014; Wang, et al., Experimental and Therapeutic Medicine, 2015; Ciccia, et al., Rheumatology, 2015).

Owing to the central role of IRAK4 in the MyD88-mediated signal cascade of TLRs (except for TLR3) and the IL-1 receptor family, the inhibition of IRAK4 can be utilized for the prophylaxis and/or treatment of disorders mediated by the receptors mentioned. TLRs as well as components of the IL-1 receptor family are involved in the pathogenesis of rheumatic arthritis, psoriatic arthritis, myasthenia gravis, vasculitis, for example Behçet's disease, granulomatosis with polyangiitis and giant cell arteritis, pancreatitis, systemic lupus erythematosus, dermamyositis and polymyositis, metabolic syndrome including, for example, insulin resistance, hypertension, dyslipoproteinemia and adiposi-tase, diabetes mellitus (type 1 and type 2), diabetic nephropathy, osteoarthritis, Sjögren syndrome and sepsis (Yang, Tuzun, et al., J Immunol, 2005; Candia, Marquez et al., The Journal of Rheumatology, 2007; Scanzello, Plaas, et al. Curr Opin Rheumatol, 2008; Deng, Ma-Krupa, et al., Circ Res, 2009; Roger, Froidevaux, et al, PNAS, 2009; Devaraj, Tobias, et al., Arterioscler Thromb Vasc Biol, 2011; Kim, Cho, et al., Clin Rheumatol, 2010; Carrasco et al., Clinical and Experimental Rheumatology, 2011; Gambuzza, Licata, et al., Journal of Neuroimmunology, 2011; Fresno, Archives Of Physiology And Biochemistry, 2011; Volin and Koch, J Interferon Cytokine Res, 2011; Akash, Shen, et al., Journal of Pharmaceutical Sciences, 2012; Goh and Midwood, Rheumatology, 2012; Dasu, Ramirez, et al., Clinical Science, 2012; Ouziel, Gustot, et al., Am J Patho, 2012; Ramirez and Dasu, Curr Diabetes Rev, 2012, Okiyama et al., Arthritis Rheum, 2012; Chen et al., Arthritis Research & Therapy, 2013; Holle, Windmoller, et al., Rheumatology (Oxford), 2013; Li, Wang, et al., Pharmacology & Therapeutics, 2013; Sedimbi, Hagglof, et al., Cell Mol Life Sci, 2013; Caso, Costa, et al., Mediators of Inflammation, 2014; Cordiglieri, Marolda, et al., J Autoimmun, 2014; Jialal, Major, et al., J Diabetes Complications, 2014; Kaplan, Yazgan, et al., Scand J Gastroenterol, 2014; Talabot-Aye, et al., Cytokine, 2014; Zong, Dorph, et al., Ann Rheum Di, 2014; Ballak, Stienstra, et al., Cytokine, 2015; Timper, Seelig, et al., J Diabetes Complications, 2015). Skin diseases such as psoriasis, atopic dermatitis, Kindler's syndrome, bullous pemphigoid, allergic contact dermatitis, alopecia areata, acne inversa and acne vulgaris are associated with the IRAK4-mediated TLR signalling pathway or the IL-1R family (Schmidt, Mittnacht, et al., J Dermatol Sci, 1996; Hoffmann, J Investig Dermatol Symp Proc, 1999; Gilliet, Conrad, et al., Archives of Dermatology, 2004; Niebuhr, Langnickel, et al., Allergy, 2008; Miller, Adv Dermatol, 2008; Terhorst, Kalali, et al., Am J Clin Dermatol, 2010; Viguier, Guigue, et al., Annals of Internal Medicine, 2010; Cevikbas, Steinhoff, J Invest Dermatol, 2012; Minkis, Aksentijevich, et al., Archives of Dermatology, 2012; Dispenza, Wolpert, et al., J Invest Dermatol, 2012; Minkis, Aksentijevich, et al., Archives of Dermatology, 2012; Gresnigt and van de Veerdonk, Seminars in Immunology, 2013; Selway, Kurczab, et al., BMC Dermatology, 2013; Sedimbi, Hagglof, et al., Cell Mol Life Sci, 2013; Wollina, Koch, et al. Indian Dermatol Online, 2013; Foster, Baliwag, et al., The Journal of Immunology, 2014). Pulmonary disorders such as pulmonary fibrosis, obstructive pulmonary disease (COPD), acute respiratory distress syndrome (ARDS), acute lung injury (ALI), interstitial lung disease (ILD), sarcoidosis and pulmonary hypertension also show an association with various TLR-mediated signal pathways. The pathogenesis of the pulmonary disorders may be either infectiously mediated or non-infectiously mediated processes (Ramirez Cruz, Maldonado Bernal, et al., Rev Alerg Mex, 2004; Jeyaseelan, Chu, et al., Infection and Immunity, 2005; Seki, Tasaka, et al., Inflammation Research, 2010; Xiang, Fan, et al., Mediators of Inflammation, 2010; Margaritopoulos, Antoniou, et al., Fibrogenesis & Tissue Repair, 2010; Hilberath, Carlo, et al., The FASEB Journal, 2011; Nadigel, Prefontaine, et al., Respiratory Research, 2011; Kovach and Standiford, International Immunopharmacology, 2011; Bauer, Shapiro, et al., Mol Med, 2012; Deng, Yang, et al., PLoS One, 2013; Freeman, Martinez, et al., Respiratory Research, 2013; Dubaniewicz, A., Human Immunology, 2013). TLRs and also IL-1R family members are also involved in the pathogenesis of other inflammatory disorders such as allergy, Behçet's disease, gout, lupus erythematosus, adult-onset Still's disease, pericarditis and chronic inflammatory bowel disorders such as ulcerative colitis and Crohn's disease, transplant rejection and graft-versus-host reaction, and so inhibition of IRAK4 here is a suitable prophylactic and/or therapeutic approach (Liu-Bryan, Scott, et al., Arthritis & Rheumatism, 2005; Piggott, Eisenbarth, et al., J Clin Inves, 2005; Christensen, Shupe, et al., Immunity, 2006; Cario, Inflammatory Bowel Diseases, 2010; Nickerson, Christensen, et al., The Journal of Immunology, 2010; Rakoff-Nahoum, Hao, et al., Immunity, 2006; Heimesaat, Fischer, et al., PLoS ONE, 2007; Heimesaat, Nogai, et al., Gut, 2010; Kobori, Yagi, et al., J Gastroenterol, 2010; Schmidt, Raghavan, et al., Nat Immunol, 2010; Shi, Mucsi, et al., Immunological Reviews, 2010; Leventhal and Schroppel, Kidney Int, 2012; Chen, Lin, et al., Arthritis Res Ther, 2013; Hao, Liu, et al., Curr Opin Gastroenterol, 2013; Kreisel and Goldstein, Transplant International, 2013; Li, Wang, et al., Pharmacology & Therapeutics, 2013; Walsh, Carthy, et al., Cytokine & Growth Factor Reviews, 2013; Zhu, Jiang, et al., Autoimmunity, 2013; Yap and Lai, Nephrology, 2013; Vennegaard, Dyring-Andersen, et al., Contact Dermatitis, 2014; D'Elia, Brucato, et al., Clin Exp Rheumatol, 2015; Jain, Thongprayoon, et al., Am J Cardiol., 2015; Li, Zhang, et al., Oncol Rep., 2015).

Gynaecological disorders mediated by TLR and the IL-1R family, such as adenomyosis, dysmenorrhoea, dyspareunia and endometriosis, especially endometriosis-associated pain and other endometriosis-associated symptoms such as dysmenorrhoea, dyspareunia, dysuria and dyschezia, can be positively influenced by the prophylactic and/or therapeutic use of IRAK4 inhibitors (Akoum, Lawson, et al., Human Reproduction, 2007; Allhom, Boing, et al., Reproductive Biology and Endocrinology, 2008; Lawson, Bourcier, et al., Journal of Reproductive Immunology, 2008; Sikora, Mielczarek-Palacz, et al., American Journal of Reproductive Immunology, 2012; Khan, Kitajima, et al., Journal of Obstetrics and Gynaecology Research, 2013; Santulli, Borghese, et al., Human Reproduction, 2013). The prophylactic and/or therapeutic use of IRAK4 inhibitors can also have a positive influence on atherosclerosis (Seneviratne, Sivagurunathan, et al., Clinica Chimica Acta, 2012; Falck-Hansen, Kassiteridi, et al., International Journal of Molecular Sciences, 2013; Sedimbi, Hagglof, et al., Cell Mol Life Sci, 2013).

In addition to the disorders already mentioned, IRAK4-mediated TLR processes have been described in the pathogenesis of eye disorders such as retinal ischaemia, keratitis, allergic conjunctivitis, keratoconjunctivitis sicca, macular degeneration and uveitis (Kaarniranta and Salminen, J Mol Med (Berl), 2009; Sun and Pearlman, Investigative Ophthalmology & Visual Science, 2009; Redfern and McDermott, Experimental Eye Research, 2010; Kezic, Taylor, et al., J Leukoc Biol, 2011; Chang, McCluskey, et al., Clinical & Experimental Ophthalmology, 2012; Guo, Gao, et al., Immunol Cell Biol, 2012; Lee, Hattori, et al., Investigative Ophthalmology & Visual Science, 2012; Qi, Zhao, et al., Investigative Ophthalmology & Visual Science, 2014).

The inhibition of IRAK4 is also a suitable therapeutic approach for fibrotic disorders, for example hepatic fibrosis, myocarditis, primary biliary cirrhosis, cystic fibrosis (Zhao, Zhao, et al., Scand J Gastroenterol, 2011; Benias, Gopal, et al., Clin Res Hepatol Gastroenterol, 2012; Yang, L. and E. Seki, Front Physiol, 2012; Liu, Hu, et al., Biochim Biophys Acta., 2015).

By virtue of the key position that IRAK4 has in disorders mediated by TLR- and the IL-1R family, it is possible to treat chronic liver disorders, for example fatty liver hepatitis and especially non-alcoholic fatty liver disease (NAFLD) and/or non-alcoholic steatohepatitis (NASH), alcoholic steatohepatitis (ASH) in a preventative and/or therapeutic manner with IRAK4 inhibitors (Nozaki, Saibara, et al., Alcohol Clin Exp Res, 2004; Csak, T., A. Velayudham, et al., Am J Physiol Gastrointest Liver Physiol, 2011; Miura, Kodama, et al., Gastroenterology, 2010; Kamari, Shaish, et al., J Hepatol, 2011; Ye, Li, et al., Gut, 2012; Roh, Seki, J Gastroenterol Hepatol, 2013; Ceccarelli, S., V. Nobili, et al., World J Gastroenterol, 2014; Miura, Ohnishi, World J Gastroenterol, 2014; Stojsavljevic, Palcic, et al., World J Gastroenterol, 2014).

Because of the central role of IRAK4 in TLR-mediated processes, the inhibition of IRAK4 also enables the treatment and/or prevention of cardiovascular and neurological disorders, for example myocardial reperfusion damage, myocardial infarction, hypertension (Oyama, Blais, et al., Circulation, 2004; Timmers, Sluijter, et al., Circulation Research, 2008; Fang and Hu, Med Sci Monit, 2011; Bijani, International Reviews of Immunology, 2012; Bomfim, Dos Santos, et al., Clin Sci (Lond), 2012; Christia and Frangogiannis, European Journal of Clinical Investigation, 2013; Thompson and Webb, Clin Sci (Lond), 2013; Hernanz, Martinez-Revelles, et al., British Journal of Pharmacology, 2015; Frangogiannis, Curr Opin Cardiol, 2015; Bomfim, Echem, et al., Life Sciences, 2015), and also Alzheimer's disease, stroke, craniocerebral trauma, amyotrophic lateral sclerosis (ALS) and Parkinson's (Brough, Tyrrell, et al., Trends in Pharmacological Sciences, 2011; Carty and Bowie, Biochemical Pharmacology, 2011; Denes, Kitazawa, Cheng, et al., The Journal of Immunology, 2011; Lim, Kou, et al., The American Journal of Pathology, 2011; Béraud and Maguire-Zeiss, Parkinsonism & Related Disorders, 2012; Denes, Wilkinson, et al., Disease Models & Mechanisms, 2013; Noelker, Morel, et al., Sci. Rep., 2013; Wang, Wang, et al., Stroke, 2013; Xiang, Chao, et al., Rev Neurosci, 2015; Lee, Lee, et al., J Neuroinflammation, 2015).

Because of the involvement of TLR-mediated signals and IL-1 receptor family-mediated signals via IRAK4 in the case of pruritus and pain, including acute, chronic, inflammatory and neuropathic pain, there may be assumed to be a therapeutic effect in the indications mentioned through the inhibition of IRAK4. Examples of pain include hyperalgesia, allodynia, premenstrual pain, endometriosis-associated pain, post-operative pain, interstitial cystitis, CRPS (complex regional pain syndrome), trigeminal neuralgia, prostatitis, pain caused by spinal cord injury, inflammation-induced pain, lower back pain, cancer pain, chemotherapy-associated pain, HIV treatment-induced neuropathy, burn-induced pain and chronic pain (Wolf, Livshits, et al., Brain, Behavior, and Immunity, 2008; Kim, Lee, et al., Toll-like Receptors: Roles in Infection and Neuropathology, 2009; del Rey, Apkarian, et al., Annals of the New York Academy of Sciences, 2012; Guerrero, Cunha, et al., European Journal of Pharmacology, 2012; Kwok, Hutchinson, et al., PLoS ONE, 2012; Nicotra, Loram, et al., Experimental Neurology, 2012; Chopra and Cooper, J Neuroimmune Pharmacol, 2013; David, Ratnayake, et al., Neurobiology of Disease, 2013; Han, Zhao, et al., Neuroscience, 2013; Liu and Ji, Pflugers Arch., 2013; Stokes, Cheung, et al., Journal of Neuroinflammation, 2013; Zhao, Zhang, et al., Neuroscience, 2013; Liu, Zhang, et al., Cell Research, 2014; Park, Stokes, et al., Cancer Chemother Pharmacol, 2014; Van der Watt, Wilkinson, et al., BMC Infect Dis, 2014; Won, K. A., M. J. Kim, et al., J Pain, 2014; Min, Ahmad, et al., Photochem Photobiol., 2015; Schrepf, Bradley, et al., Brain Behav Immun, 2015; Wong, L., J. D. Done, et al., Prostate, 2015).

This also applies to some oncological disorders. Particular lymphomas, for example ABC-DLBCL (activated B-cell diffuse large-cell B-cell lymphoma), mantle cell lymphoma and Waldenström's disease, and also chronic lymphatic leukaemia, melanoma, pancreatic tumour and liver cell carcinoma, are characterized by mutations in MyD88 or changes in MyD88 activity which can be treated by an IRAK4 inhibitor (Ngo, Young, et al., Nature, 2011; Puente, Pinyol, et al., Nature, 2011; Ochi, Nguyen, et al., J Exp Med, 2012; Srivastava, Geng, et al., Cancer Research, 2012; Treon, Xu, et al., New England Journal of Medicine, 2012; Choi, Kim, et al., Human Pathology, 2013; (Liang, Chen, et al., Clinical Cancer Research, 2013). In addition, MyD88 plays an important role in ras-dependent tumours, and so IRAK4 inhibitors are also suitable for treatment thereof (Kfoury, A., K. L. Corf, et al., Journal of the National Cancer Institute, 2013). There can also be assumed to be a therapeutic effect in breast cancer, ovarian carcinoma, colorectal carcinoma, head and neck carcinoma, lung cancer, prostate cancer through the inhibition of IRAK4, since the indications mentioned are associated with the signalling pathway (Szczepanski, Czystowska, et al., Cancer Res, 2009; Zhang, He, et al., Mol Biol Rep, 2009; Wang, Qian, et al., Br J Cancer Kim, 2010; Jo, et al., World J Surg Oncol, 2012; Zhao, Zhang, et al.; Front Immunol, 2014; Chen, Zhao, et al., Int J Clin Exp Pathol, 2015).

Inflammatory disorders such as CAPS (cryopyrin-associated periodic syndromes) including FCAS (familial cold autoinflammatory syndrome), MWS (Muckle-Wells syndrome), NOMID (neonatal-onset multisystem inflammatory disease) and CONCA (chronic infantile, neurological, cutaneous, and articular) syndrome; FMF (familial mediterranean fever), HIDS (hyper-IgD syndrome), TRAPS (tumour necrosis factor receptor 1-associated periodic syndrome), juvenile idiopathic arthritis, adult-onset Still's disease, Adamantiades-Behçet's disease, rheumatoid arthritis, osteoarthritis, keratoconjunctivitis sicca, PAPA syndrome (pyogenic arthritis, Pyoderma gangraenosum and acne), Schnitzler's syndrome and Sjögren syndrome are treated by blocking the IL-1 signal pathway; therefore here, too, an IRAK4 inhibitor is suitable for treatment of the diseases mentioned (Narayanan, Corrales, et al., Cornea, 2008; Brenner, Ruzicka, et al., British Journal of Dermatology, 2009; Henderson and Goldbach-Mansky, Clinical Immunology, 2010; Dinarello, European Journal of Immunology, 2011; Gul, Tugal-Tutkun, et al., Ann Rheum Dis, 2012; Pettersson, Annals of MedicinePetterson, 2012; Ruperto, Brunner, et al., New England Journal of Medicine, 2012; Nordstrom, Knight, et al., The Journal of Rheumatology, 2012; Vijmasi, Chen, et al., Mol Vis, 2013; Yamada, Arakaki, et al., Opinion on Therapeutic Targets, 2013; de Koning, Clin Transl Allergy, 2014). The ligand of IL-33R, IL-33, is involved particularly in the pathogenesis of acute kidney failure, and so the inhibition of IRAK4 for prophylaxis and/or treatment is a suitable therapeutic approach (Akcay, Nguyen, et al., Journal of the American Society of Nephrology, 2011). Components of the IL-1 receptor family are associated with myocardial infarction, different pulmonary disorders such as asthma, COPD, idiopathic interstitial pneumonia, allergic rhinitis, pulmonary fibrosis and acute respiratory distress syndrome (ARDS), and so prophylactic and/or therapeutic action is to be expected in the indications mentioned through the inhibition of IRAK4 (Kang, Homer, et al., The Journal of Immunology, 2007; Imaoka, Hoshino, et al., European Respiratory Journal, 2008; Couillin, Vasseur, et al., The Journal of Immunology, 2009; Abbate, Kontos, et al., The American Journal of Cardiology, 2010; Lloyd, Current Opinion in Immunology, 2010; Pauwels, Bracke, et al., European Respiratory Journal, 2011; Haenuki, Matsushita, et al., Journal of Allergy and Clinical Immunology, 2012; Yin, Li, et al., Clinical & Experimental Immunology, 2012; Abbate, Van Tassell, et al., The American Journal of Cardiology, 2013; Alexander-Brett, et al., The Journal of Clinical Investigation, 2013; Bunting, Shadie, et al., BioMed Research International, 2013; Byers, Alexander-Brett, et al., The Journal of Clinical Investigation, 2013; Kawayama, Okamoto, et al., J Interferon Cytokine Res, 2013; Martinez-González, Roca, et al., American Journal of Respiratory Cell and Molecular Biology, 2013; Nakanishi, Yamaguchi, et al., PLoS ONE, 2013; Qiu, Li, et al., Immunology, 2013; Li, Guabiraba, et al., Journal of Allergy and Clinical Immunology, 2014; Saluja, Ketelaar, et al., Molecular Immunology, 2014; Lugrin, Parapanov, et al., The Journal of Immunology, 2015).

The prior art discloses a multitude of IRAK4 inhibitors (see, for example, Annual Reports in Medicinal Chemistry (2014), 49, 117-133).

U.S. Pat. No. 8,293,923 and US20130274241 disclose IRAK4 inhibitors having a 3-substituted indazole structure. There is no description of 2-substituted indazoles.

WO2013106254 and WO2011153588 disclose 2,3-disubstituted indazole derivatives. WO2007091107 describes 2-substituted indazole derivatives for the treatment of Duchenne muscular dystrophy. 5,6-Disubstituted indazole derivatives are not disclosed in WO2007091107.

WO2009024341 describes indazoles as insecticides, these having an additional substituent at the 7 position.

WO2013042137 describes benzothiazoles, benzoxazoles and benzimidazoles as IRAK4 inhibitors, each of these having a morpholine radical at the 2 position, but none having a cyclic substituent joined to the 2 position via a carbon. WO2013042137 does not describe indazoles.

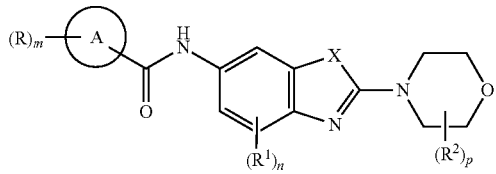

WO2015104688 reports further bicyclic IRAK4 inhibitors with a fused 6-membered and 5-membered bicyclic heteroaromatic ring system. These inhibitors are substituted on the 5-membered heteroaromatic ring by a saturated nitrogen-containing heterocyclyl ring bonded to the bicyclic system via the nitrogen atom. There is no description of indazoles as the bicyclic system.

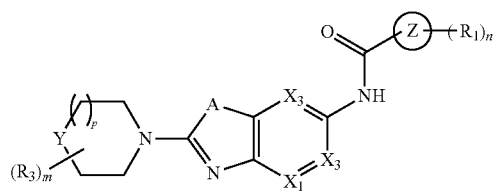

WO2015091426 describes indazoles substituted at the 2 position by a carboxamide side chain.

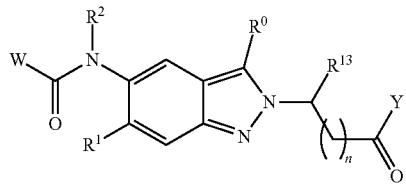

There is no disclosure of compounds having cyclic substituents bonded directly to the 2 position of the indazole.

WO2015104662 discloses 2-substituted indazoles of the following general formula:

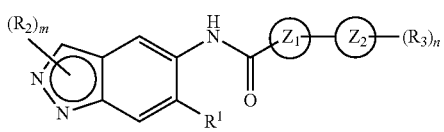

in which $R^2$ is an alkyl or cycloalkyl group. There are explicit descriptions of indazoles having a methyl, 2-methoxyethyl and cyclopentyl group at the 2 position (Examples 1, 4, 7 and 76). There is no description of 2-substituted indazoles having a heterocyclic saturated ring bonded via a carbon atom in the 2 position of the indazole in WO2015104662.

WO2015193846 discloses 2-substituted indazoles of the following general formula:

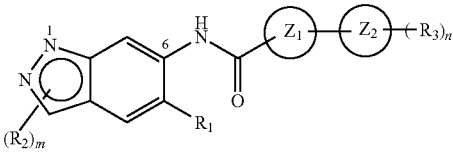

in which $Z^1$ and $Z^2$ are each an optionally substituted cycloalkyl, aryl or heteroaryl group. $R^2$ may be a hydrogen, halogen, an amino group, or an in each case optionally substituted alkyl, cycloalkyl, aryl, heterocyclo, arylalkyl or heterocycloalkyl group. There are explicit descriptions of indazole derivatives in which $R^2$ is a methyl radical and $Z^1$ and/or $Z^2$ are hetaryl groups, where the —NH(C═O)$Z^1$—$Z^2$—($R^3$)$_n$ substituent is bonded at the 6 position of the indazole skeleton. There is no description of indazole derivatives having an —NH(C═O)$Z^1$—$Z^2$—($R^3$)$_n$ substituent bonded to the 5 position. There is no description of indazole derivatives having a saturated heterocycle bonded via a carbon atom in the 2 position in WO2015193846. The problem addressed by the present invention is that of providing novel compounds that act as inhibitors of interleukin-1 receptor associated kinase-4 (IRAK4).

The present invention provides compounds of the general formula (I)

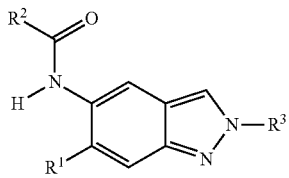

(I)

in which

R[1] is halogen, cyano, C(=O)OH, C(=O)OR$^a$, C(=O)NH$_2$, C(=O)N(H)R$^a$, C(=O)N(R$^a$)R$^b$, C(=O)R$^d$, hydroxyl or C$_1$-C$_6$-alkyl, where the C$_1$-C$_6$-alkyl radical may optionally be mono- or polysubstituted identically or differently by hydroxyl, halogen, cyano, C(=O)OH, C(=O)OR$^a$, S(=O)$_2$—C$_1$-C$_6$-alkyl, NH$_2$, NHR$^a$, N(R$^a$)R$^b$, an optionally mono- to hexa-fluorine-substituted C$_1$-C$_6$-alkoxy or C$_3$-C$_7$-cycloalkoxy, a 4- to 7-membered heterocycloalkyl optionally mono- to trisubstituted identically or differently by R$^c$, or is C$_1$-C$_6$-alkoxy, where the C$_1$-C$_6$-alkoxy radical may optionally be mono- or polysubstituted identically or differently by hydroxyl, halogen, cyano, C(=O)OH, C(=O)OR$^a$, S(=O)$_2$—C$_1$-C$_6$-alkyl, NH$_2$, NHR$^a$, N(R$^a$)R$^b$, an optionally mono- to tetra-fluorine-substituted C$_3$-C$_7$-cycloalkyl, an optionally mono- to penta-fluorine-substituted C$_1$-C$_6$-alkoxy, an optionally mono- to tetra-fluorine-substituted C$_3$-C$_7$-cycloalkoxy, a 4- to 7-membered heterocycloalkyl optionally mono- or polysubstituted identically or differently by R$^c$, or is C$_3$-C$_7$-cycloalkyloxy or 4- to 7-membered heterocycloalkyloxy in which C$_3$-C$_7$-cycloalkyloxy and 4- to 7-membered heterocycloalkyloxy may optionally be mono- or polysubstituted identically or differently by hydroxyl, fluorine, cyano, C$_1$-C$_6$-alkyl or C$_1$-C$_6$-alkoxy;

R$^a$ is C$_1$-C$_6$-alkyl, C$_3$-C$_7$-cycloalkyl, 4- to 7-membered heterocycloalkyl, in which C$_1$-C$_6$-alkyl, C$_3$-C$_7$-cycloalkyl and 4- to 7-membered heterocycloalkyl may optionally be mono- or polysubstituted identically or differently by fluorine, hydroxyl, cyano, C$_1$-C$_4$-alkyl, C$_1$-C$_4$-alkoxy or C$_3$-C$_7$-cycloalkyl;

R$^b$ is C$_1$-C$_6$-alkyl or C$_3$-C$_7$-cycloalkyl;

or R$^a$ and R$^b$ together with the nitrogen atom form a 5- or 6-membered heterocycle which may optionally be mono- or disubstituted identically or differently by hydroxyl, halogen, cyano, or C$_1$-C$_6$-alkyl;

R$^c$ is hydroxyl, fluorine, chlorine, cyano, C$_1$-C$_4$-alkyl or C$_1$-C$_4$-alkoxy;

R$^d$ is hydrogen, C$_3$-C$_7$-cycloalkyl, or C$_1$-C$_6$-alkyl which may optionally be substituted by a hydroxyl group;

R[2] is 5-membered heteroaryl which is monosubstituted by R[4] and monosubstituted by R[5] or R[2] is 6-membered heteroaryl which is monosubstituted by R[4] and mono- or disubstituted identically or differently by R[5];

R[3] is a group selected from:

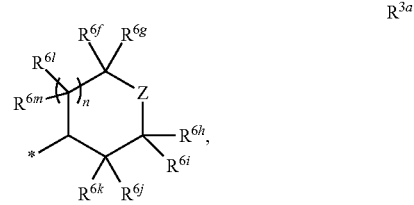

R$^{3a}$

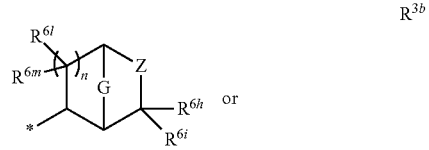

R$^{3b}$ or

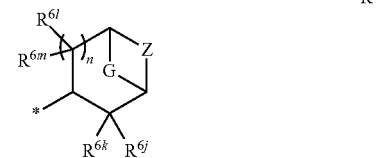

R$^{3c}$ where * represents the bonding site of the group to the rest of the molecule;

R[4] is hydrogen, halogen, hydroxyl, C(=O)OH, cyano, NH$_2$, NHR$^a$, N(R$^a$)R$^b$, C(=O)R$^a$, N(H)C(=O)R$^a$, C(=O)NH$_2$, C(=O)N(H)R$^a$, C(=O)N(R$^a$)R$^b$, S(=O)R$^a$, S(=O)$_2$R$^a$, S(=O)$_2$NH$_2$, S(=O)$_2$NHR$^a$ or S(=O)$_2$N(R$^a$)R$^b$, or is C$_1$-C$_6$-alkyl where C$_1$-C$_6$-alkyl may optionally be substituted by one to five fluorine atoms and may optionally be mono- or disubstituted identically or differently by hydroxyl, bromine, chlorine, cyano, C(=O)OH, S(=O)$_2$—C$_1$-C$_6$-alkyl, NH$_2$, NHR$^a$, N(R$^a$)R$^b$, C$_3$-C$_7$-cycloalkyl, C$_1$-C$_4$-alkoxy, C$_3$-C$_7$-cycloalkoxy, trifluoromethoxy, or is C$_1$-C$_6$-alkoxy where C$_1$-C$_6$-alkoxy may optionally be substituted by one to five fluorine atoms and may optionally be mono- or disubstituted identically or differently by hydroxyl, chlorine, bromine, cyano, C(=O)OH, S(=O)$_2$—C$_1$-C$_6$-alkyl, NH$_2$, NHR$^a$, N(R$^a$)R$^b$, C$_3$-C$_7$-cycloalkyl, C$_1$-C$_4$-alkoxy, C$_3$-C$_7$-cycloalkoxy, trifluoromethoxy, or is C$_3$-C$_7$-cycloalkyl or is C$_3$-C$_7$-cycloalkyloxy where C$_3$-C$_7$-cycloalkyl and C$_3$-C$_7$-cycloalkyloxy may optionally be substituted by one to four fluorine atoms and may optionally be mono- or disubstituted identically or differently by hydroxyl, chlorine, bromine, cyano, C(=O)R$^d$, C(=O)OH, C$_1$-C$_6$-alkyl or C$_1$-C$_4$-alkoxy, or is 4-7-membered heterocycloalkyl which may optionally be substituted by one to four fluorine atoms and may optionally be mono- or disubstituted identically or differently by hydroxyl, chlorine, bromine, cyano, NH$_2$, NHR$^a$, N(R$^a$)R$^b$, C(=O)R$^d$, C(=O)OH, C$_1$-C$_6$-alkyl, trifluoromethyl, 2,2,2-trifluoroethyl, cyclopropyl, cyclopropylmethyl or C$_1$-C$_4$-alkoxy, or is phenyl or 5- or 6-membered heteroaryl in which phenyl and 5- or 6-membered heteroaryl may optionally be mono- to disubstituted identically or differently by fluorine, chlorine, bromine, hydroxyl, cyano, C(=O)OH, S(=O)$_2$—C$_1$-C$_4$-alkyl, NH$_2$, NHR$^a$, N(R$^a$)R$^b$, N(H)C(=O)R$^a$, C$_1$-C$_4$-alkoxy, trifluoromethoxy or C$_1$-C$_4$-alkyl, where C$_1$-C$_4$-alkyl may optionally be mono- to trisubstituted by fluorine;

$R^5$ is hydrogen, halogen, hydroxyl, cyano, $C_1$-$C_4$-alkoxy, trifluoromethoxy or $C_1$-$C_6$-alkyl, in which $C_1$-$C_6$-alkyl may optionally be substituted by one to five fluorine atoms, $R^{6f}$ is hydrogen, fluorine, C(=O)OH, C(=O)NH$_2$, trifluoromethyl, hydroxymethyl, methoxymethyl, cyano or $C_1$-$C_6$-alkyl;

$R^{6g}$ is hydrogen, fluorine or $C_1$-$C_6$-alkyl, or $R^{6f}$ and $R^{6g}$ together with the carbon atom to which they are bonded form a $C_3$-$C_7$-cycloalkyl, or $R^{6f}$ and $R^{6g}$ together are an oxo group;

$R^{6h}$ is hydrogen, trifluoromethyl or $C_1$-$C_6$-alkyl;

$R^{6i}$ is hydrogen or $C_1$-$C_6$-alkyl, or $R^{6h}$ and $R^{6i}$ together are an oxo group;

$R^{6j}$ is hydrogen, fluorine, NH$_2$, N(H)R$^a$, N(R$^a$)R$^b$, $C_1$-$C_6$-alkyl, hydroxyl, cyano, $C_1$-$C_4$-alkoxy, C(=O)OH, C(=O)NH$_2$, C(=O)N(H)R$^a$, C(=O)N(R$^a$)R$^b$, hydroxymethyl, dimethylaminomethyl, trifluoromethyl;

$R^{6k}$ is hydrogen, fluorine or $C_1$-$C_6$-alkyl, or $R^{6j}$ and $R^{6k}$ together with the carbon atom form a $C_3$-$C_7$-cycloalkyl;

$R^{6l}$ is hydrogen or methyl;

$R^{6m}$ is hydrogen or methyl;

G is —CH$_2$— or —CH$_2$CH$_2$—;

n in the formula $R^{3a}$ is 0, 1 or 2, n in the formula $R^{3b}$ is 1 or 2, n in the formula $R^{3c}$ is 0 or 1, z is a group selected from NR$^7$, O, S, S(=O), S(=O)$_2$, S(=O)(=NH);

$R^7$ is hydrogen, C(=O)R$^e$, C(=O)OR$^a$, C(=O)NH$_2$, C(=O)N(H)R$^a$, C(=O)N(R$^a$)R$^b$, S(=O)$_2$R$^a$, S(=O)$_2$NH$_2$, S(=O)$_2$N(R$^a$)H, S(=O)$_2$N(R$^a$)R$^b$, S(=O)$_2$NHC(=O)CH$_3$, S(=O)$_2$NHC(=O)CH$_2$CH$_3$ or $C_1$-$C_6$-alkyl, where $C_1$-$C_6$-alkyl may optionally be mono- to pentasubstituted by fluorine atoms and mono- to disubstituted identically or differently by hydroxyl, chlorine, bromine, cyano, C(=O)R$^a$, C(=O)OH, C(=O)NH$_2$, C(=O)N(H)R$^a$, C(=O)N(R$^a$)R$^b$, S(=O)$_2$—$C_1$-$C_6$-alkyl, NH$_2$, NHR$^a$, N(R$^a$)R$^b$, morpholin-4-yl, 4-methylpiperazin-1-yl, $C_3$-$C_7$-cycloalkyl, $C_1$-$C_4$-alkoxy or $C_3$-$C_7$-cycloalkoxy;

or is $C_3$-$C_7$-cycloalkyl which may optionally be mono- to tetrasubstituted by fluorine atoms and may optionally be mono- to disubstituted identically or differently by hydroxyl, methyl, ethyl, trifluoromethyl or cyano;

or is a 4-7-membered heterocycloalkyl bonded to the rest of the molecule by a carbon atom or is 4-7-membered heterocycloalkyl-$C_1$-$C_4$-alkyl which may optionally be mono- to hexasubstituted by fluorine atoms and mono- to trisubstituted identically or differently by hydroxyl, chlorine, bromine, cyano, $C_1$-$C_6$-alkyl, $C_1$-$C_6$-alkoxy, trifluoromethyl, 2,2,2-trifluoroethyl, trifluoromethoxy, cyclopropyl, cyclopropylmethyl;

$R^e$ is $C_1$-$C_6$-alkyl, where $C_1$-$C_6$-alkyl may optionally be mono- to trisubstituted identically or differently by hydroxyl, fluorine, chlorine, cyano, C(=O)R$^a$, C(=O)OH, NH$_2$, NHR$^a$, N(R$^a$)R$^b$, $C_3$-$C_7$-cycloalkyl, $C_1$-$C_4$-alkoxy, trifluoromethoxy or $C_3$-$C_7$-cycloalkoxy or $R^e$ is $C_3$-$C_7$-cycloalkyl, where $C_3$-$C_7$-cycloalkyl may optionally be mono- to tetrasubstituted by fluorine and may optionally be monosubstituted by hydroxyl, and the diastereomers, enantiomers, metabolites, salts, solvates thereof or solvates of the salts thereof.

One embodiment of the invention encompasses compounds of the general formula (I)

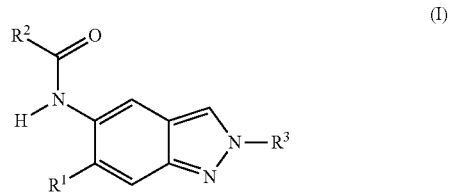

(I)

in which $R^1$ is halogen, cyano, C(=O)OH, C(=O)OR$^a$, C(=O)NH$_2$, C(=O)N(H)R$^a$, C(=O)N(R$^a$)R$^b$, C(=O)R$^d$, hydroxyl or $C_1$-$C_6$-alkyl, where the $C_1$-$C_6$-alkyl radical may optionally be mono- or polysubstituted identically or differently by hydroxyl, halogen, cyano, C(=O)OH, C(=O)OR$^a$, S(=O)$_2$—$C_1$-$C_6$-alkyl, NH$_2$, NHR$^a$, N(R$^a$)R$^b$, an optionally mono- to hexa-fluorine-substituted $C_1$-$C_6$-alkoxy or $C_3$-$C_7$-cycloalkoxy, a 4- to 7-membered heterocycloalkyl optionally mono- to trisubstituted identically or differently by R$^c$, or is $C_1$-$C_6$-alkoxy, where the $C_1$-$C_6$-alkoxy radical may optionally be mono- or polysubstituted identically or differently by hydroxyl, halogen, cyano, C(=O)OH, C(=O)OR$^a$, S(=O)$_2$—$C_1$-$C_6$-alkyl, NH$_2$, NHR$^a$, N(R$^a$)R$^b$, an optionally mono- to tetra-fluorine-substituted $C_3$-$C_7$-cycloalkyl, an optionally mono- to penta-fluorine-substituted $C_1$-$C_6$-alkoxy, an optionally mono- to tetra-fluorine-substituted $C_3$-$C_7$-cycloalkoxy, a 4- to 7-membered heterocycloalkyl optionally mono- or polysubstituted identically or differently by R$^c$, or is $C_3$-$C_7$-cycloalkyloxy or 4- to 7-membered heterocycloalkyloxy in which $C_3$-$C_7$-cycloalkyloxy and 4- to 7-membered heterocycloalkyloxy may optionally be mono- or polysubstituted identically or differently by hydroxyl, fluorine, cyano, $C_1$-$C_6$-alkyl or $C_1$-$C_6$-alkoxy;

$R^a$ is $C_1$-$C_6$-alkyl, $C_3$-$C_7$-cycloalkyl, 4- to 7-membered heterocycloalkyl, in which $C_1$-$C_6$-alkyl, $C_3$-$C_7$-cycloalkyl and 4- to 7-membered heterocycloalkyl may optionally be mono- or polysubstituted identically or differently by fluorine, hydroxyl, cyano, $C_1$-$C_4$-alkyl, $C_1$-$C_4$-alkoxy or $C_3$-$C_7$-cycloalkyl;

$R^b$ is $C_1$-$C_6$-alkyl or $C_3$-$C_7$-cycloalkyl;

or $R^a$ and $R^b$ together with the nitrogen atom form a 5- or 6-membered heterocycle which may optionally be mono- or disubstituted identically or differently by hydroxyl, halogen, cyano, or $C_1$-$C_6$-alkyl;

$R^c$ is hydroxyl, fluorine, chlorine, cyano, $C_1$-$C_4$-alkyl or $C_1$-$C_4$-alkoxy;

$R^d$ is hydrogen, $C_3$-$C_7$-cycloalkyl, or $C_1$-$C_6$-alkyl which may optionally be substituted by a hydroxyl group;

$R^2$ is 5-membered heteroaryl which is monosubstituted by $R^4$ and monosubstituted by $R^5$ or $R^2$ is 6-membered heteroaryl which is monosubstituted by $R^4$ and mono- or disubstituted identically or differently by $R^5$;

$R^3$ is a group selected from:

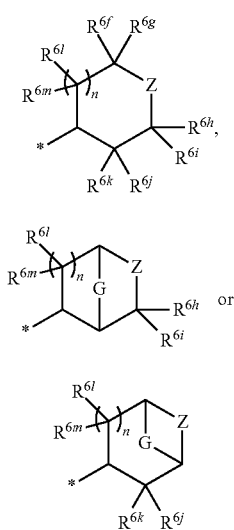

where * represents the bonding site of the group to the rest of the molecule;

$R^4$ is hydrogen, halogen, hydroxyl, C(=O)OH, cyano, $NH_2$, $NHR^a$, $N(R^a)R^b$, $C(=O)R^a$, $N(H)C(=O)R^a$, $C(=O)NH_2$, $C(=O)N(H)R^a$, $C(=O)N(R^a)R^b$, $S(=O)R^a$, $S(=O)_2R^a$, $S(=O)_2NH_2$, $S(=O)_2NHR^a$ or $S(=O)_2N(R^a)R^b$, or is $C_1$-$C_6$-alkyl where
  $C_1$-$C_6$-alkyl may optionally be substituted by one to five fluorine atoms and may optionally be mono- or disubstituted identically or differently by hydroxyl, bromine, chlorine, cyano, C(=O)OH, $S(=O)_2$—$C_1$-$C_6$-alkyl, $NH_2$, $NHR^a$, $N(R^a)R^b$, $C_3$-$C_7$-cycloalkyl, $C_1$-$C_4$-alkoxy, $C_3$-$C_7$-cycloalkoxy, trifluoromethoxy, or is $C_1$-$C_6$-alkoxy where
  $C_1$-$C_6$-alkoxy may optionally be substituted by one to five fluorine atoms and may optionally be mono- or disubstituted identically or differently by hydroxyl, chlorine, bromine, cyano, C(=O)OH, $S(=O)_2$—$C_1$-$C_6$-alkyl, $NH_2$, $NHR^a$, $N(R^a)R^b$, $C_3$-$C_7$-cycloalkyl, $C_1$-$C_4$-alkoxy, $C_3$-$C_7$-cycloalkoxy, trifluoromethoxy, or is $C_3$-$C_7$-cycloalkyl or is $C_3$-$C_7$-cycloalkyloxy where
  $C_3$-$C_7$-cycloalkyl and $C_3$-$C_7$-cycloalkyloxy may optionally be substituted by one to four fluorine atoms and may optionally be mono- or disubstituted identically or differently by hydroxyl, chlorine, bromine, cyano, $C(=O)R^d$, C(=O)OH, $C_1$-$C_6$-alkyl or $C_1$-$C_4$-alkoxy, or is 4-7-membered heterocycloalkyl which may optionally be substituted by one to four fluorine atoms and may optionally be mono- or disubstituted identically or differently by hydroxyl, chlorine, bromine, cyano, $NH_2$, $NHR^a$, $N(R^a)R^b$, $C(=O)R^d$, C(=O)OH, $C_1$-$C_6$-alkyl, trifluoromethyl, 2,2,2-trifluoroethyl, cyclopropyl, cyclopropylmethyl or $C_1$-$C_4$-alkoxy, or is phenyl or 5- or 6-membered heteroaryl in which
phenyl and 5- or 6-membered heteroaryl may optionally be mono- to disubstituted identically or differently by fluorine, chlorine, bromine, hydroxyl, cyano, C(=O)OH, $S(=O)_2$—$C_1$-$C_4$-alkyl, $NH_2$, $NHR^a$, $N(R^a)R^b$, $N(H)C(=O)R^a$, $C_1$-$C_4$-alkoxy, trifluoromethoxy or $C_1$-$C_4$-alkyl, where $C_1$-$C_4$-alkyl may optionally be mono- to trisubstituted by fluorine;

$R^5$ is hydrogen, halogen, hydroxyl, cyano, $C_1$-$C_4$-alkoxy, trifluoromethoxy or $C_1$-$C_6$-alkyl, in which $C_1$-$C_6$-alkyl may optionally be substituted by one to five fluorine atoms, $R^{6f}$ is hydrogen, fluorine, C(=O)OH, $C(=O)NH_2$, trifluoromethyl, hydroxymethyl, methoxymethyl, cyano or $C_1$-$C_6$-alkyl;

$R^{6g}$ is hydrogen, fluorine or $C_1$-$C_6$-alkyl, or $R^{6f}$ and $R^{6g}$ together with the carbon atom to which they are bonded form a $C_3$-$C_7$-cycloalkyl, or $R^{6f}$ and $R^{6g}$ together are an oxo group;

$R^{6h}$ is hydrogen, trifluoromethyl or $C_1$-$C_6$-alkyl;

$R^{6i}$ is hydrogen or $C_1$-$C_6$-alkyl, or $R^{6h}$ and $R^{6i}$ together are an oxo group;

$R^{6j}$ is hydrogen, fluorine, $NH_2$, $N(H)R^a$, $N(R^a)R^b$, $C_1$-$C_6$-alkyl, hydroxyl, cyano, $C_1$-$C_4$-alkoxy, C(=O)OH, $C(=O)NH_2$, $C(=O)N(H)R^a$, $C(=O)N(R^a)R^b$, hydroxymethyl, dimethylaminomethyl, trifluoromethyl;

$R^{6k}$ is hydrogen, fluorine or $C_1$-$C_6$-alkyl, or $R^{6j}$ and $R^{6k}$ together with the carbon atom form a $C_3$-$C_7$-cycloalkyl;

$R^{6l}$ is hydrogen or methyl;

$R^{6m}$ is hydrogen or methyl;

G is —$CH_2$— or —$CH_2CH_2$—;

n in the formula $R^{3a}$ is 0, 1 or 2, n in the formula $R^{3b}$ is 1 or 2, n in the formula $R^{3c}$ is 0 or 1, z is a group selected from $NR^7$, O, S, S(=O), $S(=O)_2$, S(=O)(=NH);

$R^7$ is hydrogen, $C(=O)R^e$, $C(=O)OR^a$, $C(=O)NH_2$, $C(=O)N(H)R^a$, $C(=O)N(R^a)R^b$, $S(=O)_2R^a$, $S(=O)_2NH_2$, $S(=O)_2N(R^a)H$, $S(=O)_2N(R^a)R^b$, $S(=O)_2NHC(=O)CH_3$, $S(=O)_2NHC(=O)CH_2CH_3$ or $C_1$-$C_6$-alkyl, where $C_1$-$C_6$-alkyl may optionally be mono- to pentasubstituted by fluorine atoms or $C_1$-$C_6$-alkyl may optionally be mono- to disubstituted identically or differently by hydroxyl, chlorine, bromine, cyano, $C(=O)R^a$, C(=O)OH, $C(=O)NH_2$, $C(=O)N(H)R^a$, $C(=O)N(R^a)R^b$, $S(=O)_2$—$C_1$-$C_6$-alkyl, $NH_2$, $NHR^a$, $N(R^a)R^b$, morpholin-4-yl, 4-methylpiperazin-1-yl, $C_3$-$C_7$-cycloalkyl, $C_1$-$C_4$-alkoxy or $C_3$-$C_7$-cycloalkoxy or $C_1$-$C_6$-alkyl may optionally be mono- to pentasubstituted by fluorine atoms and mono- to disubstituted identically or differently by hydroxyl, chlorine, bromine, cyano, $C(=O)R^a$, C(=O)OH, $C(=O)NH_2$, $C(=O)N(H)R^a$, $C(=O)N(R^a)R^b$, $S(=O)_2$—$C_1$-$C_6$-alkyl, $NH_2$, $NHR^a$, $N(R^a)R^b$, morpholin-4-yl, 4-methylpiperazin-1-yl, $C_3$-$C_7$-cycloalkyl, $C_1$-$C_4$-alkoxy or $C_3$-$C_7$-cycloalkoxy;

or is $C_3$-$C_7$-cycloalkyl which may optionally be mono- to tetrasubstituted by fluorine atoms and may optionally be mono- to disubstituted identically or differently by hydroxyl, methyl, ethyl, trifluoromethyl or cyano;

or is a 4-7-membered heterocycloalkyl bonded to the rest of the molecule by a carbon atom or is 4-7-membered heterocycloalkyl-$C_1$-$C_4$-alkyl which may optionally be mono- to hexasubstituted by fluorine atoms and mono- to trisubstituted identically or differently by hydroxyl, chlorine, bromine, cyano, $C_1$-$C_6$-alkyl, $C_1$-$C_6$-alkoxy, trifluoromethyl, 2,2,2-trifluoroethyl, trifluoromethoxy, cyclopropyl, cyclopropylmethyl;

$R^e$ is $C_1$-$C_6$-alkyl, where $C_1$-$C_6$-alkyl may optionally be mono- to trisubstituted identically or differently by hydroxyl, fluorine, chlorine, cyano, $C(=O)R^a$, C(=O)OH, $NH_2$, $NHR^a$, $N(R^a)R^b$, $C_3$-$C_7$-cycloalkyl, $C_1$-$C_4$-alkoxy, trifluoromethoxy or $C_3$-$C_7$-cycloalkoxy or $R^e$ is $C_3$-$C_7$-cycloalkyl, where $C_3$-$C_7$-cycloalkyl may optionally be mono- to tetrasubstituted by fluorine and may optionally be monosubstituted by hydroxyl, and the diastereomers, enantiomers, metabolites, salts, solvates thereof or solvates of the salts thereof.

The novel IRAK4 inhibitors are especially suitable for treatment and for prevention of proliferative, metabolic and inflammatory disorders characterized by an overreacting immune system. Particular mention should be made here of inflammatory skin disorders, cardiovascular disorders, lung disorders, eye disorders, neurological disorders, pain disorders and cancer.

In addition, the novel IRAK4 inhibitors are suitable for treatment and prevention of autoimmune and inflammatory disorders, especially rheumatoid arthritis, multiple sclerosis, systemic lupus erythematosus, spondyloarthritis and gout, of metabolic disorders, especially hepatic disorders such as fatty liver, and of gynaecological disorders, especially of endometriosis and of endometriosis-associated pain and other endometriosis-associated symptoms such as dysmenorrhoea, dyspareunia, dysuria and dyschezia.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "x HCl", "x CF$_3$COOH", "x Na$^+$" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition by the preparation and/or purification processes described.

Compounds of the invention are the compounds of the formula (I) and the salts, solvates and solvates of the salts thereof, the compounds that are encompassed by formula (I) and are of the formulae mentioned below and the salts, solvates and solvates of the salts thereof and the compounds that are encompassed by formula (I) and are cited below as working examples and the salts, solvates and solvates of the salts thereof if the compounds that are encompassed by formula (I) and are mentioned below are not already salts, solvates and solvates of the salts.

Preferred salts in the context of the present invention are physiologically acceptable salts of the compounds according to the invention. However, the invention also encompasses salts which themselves are unsuitable for pharmaceutical applications but which can be used, for example, for the isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates in the context of the invention are described as those forms of the compounds according to the invention which form a complex in the solid or liquid state by coordination with solvent molecules. Hydrates are a specific form of the solvates in which the coordination is with water.

The compounds according to the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatographic processes are preferably used for this purpose, especially HPLC chromatography on an achiral or chiral phase.

If the compounds according to the invention can occur in tautomeric forms, the present invention encompasses all the tautomeric forms.

The present invention also encompasses all suitable isotopic variants of the compounds according to the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as 2H (deuterium), 3H (tritium), 13C, 14C, 15N, 17O, 18O, 32P, 33P, 33S, 34S, 35S, 36S, 18F, 36Cl, 82Br, 123I, 124I, 129I and 131I. Particular isotopic variants of a compound according to the invention, such as, in particular, those in which one or more radioactive isotopes have been incorporated, may be beneficial, for example, for the examination of the mechanism of action or of the active ingredient distribution in the body; because of the comparative ease of preparability and detectability, particularly compounds labelled with 3H or 14C isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by the processes known to those skilled in the art, for example by the methods described further below and the procedures described in the working examples, by using corresponding isotopic modifications of the respective reagents and/or starting compounds.

The present invention further provides all the possible crystalline and polymorphous forms of the compounds according to the invention, where the polymorphs may be present either as single polymorphs or as a mixture of a plurality of polymorphs in all concentration ranges.

The present invention additionally also encompasses prodrugs of the compounds according to the invention. The term "prodrugs" in this context refers to compounds which may themselves be biologically active or inactive but are reacted (for example metabolically or hydrolytically) to give compounds according to the invention during their residence time in the body.

In the context of the present invention, unless specified otherwise, the substituents have the following meanings:

Alkyl in the context of the invention is a straight-chain or branched alkyl radical having the particular number of carbon atoms specified. Examples include methyl, ethyl, n-propyl, isopropyl, n-butyl, isobutyl, 1-methylpropyl, 2-methylpropyl, tert-butyl, n-pentyl, 1-ethylpropyl, 1-methylbutyl, 2-methylbutyl, 3-methylbutyl, 2,2-dimethylpropyl, n-hexyl, 1-methylpentyl, 2-methylpentyl, 3-methylpentyl, 4-methylpentyl, 1-ethylbutyl and 2-ethylbutyl. Preference is given to methyl, ethyl, n-propyl, isopropyl, n-butyl, tert-butyl, 2-methylbutyl, 3-methylbutyl and 2,2-dimethylpropyl. Particular preference is given to methyl, ethyl and isopropyl.

Cycloalkyl in the context of the invention is a monocyclic saturated alkyl radical having the number of carbon atoms specified in each case. Examples include cyclopropyl, cyclobutyl, cyclopentyl, cyclohexyl and cycloheptyl. Preference is given to cyclopropyl, cyclobutyl, cyclopentyl and cyclohexyl. Particular preference is given to cyclopropyl.

Alkoxy in the context of the invention is a straight-chain or branched alkoxy radical having the particular number of carbon atoms specified. 1 to 6 carbon atoms are preferred. Examples include methoxy, ethoxy, n-propoxy, isopropoxy, 1-methylpropoxy, n-butoxy, isobutoxy, tert-butoxy, n-pentoxy, isopentoxy, 1-ethylpropoxy, 1-methylbutoxy, 2-methylbutoxy, 3-methylbutoxy and n-hexoxy. Particular preference is given to a linear or branched alkoxy radical having 1 to 4 carbon atoms. Examples which may be mentioned as being preferred are methoxy, ethoxy, n-propoxy, 1-methylpropoxy, n-butoxy and isobutoxy. Very particular preference is given to methoxy and ethoxy.

Halogen in the context of the invention is fluorine, chlorine, bromine and iodine. Preference is given to fluorine and chlorine. Particular preference is given to fluorine.

Hydroxyl in the context of the invention is OH.

Heterocycloalkyl

The term "4- to 7-membered heterocycloalkyl" refers to a monocyclic saturated heterocycle having a total of 4 to 7 ring atoms, in which one or two ring carbon atoms are replaced by identical or different heteroatoms from the group of N, O and S; the heterocycloalkyl group may be bonded to the rest of the molecule via any one of the carbon atoms or, if present, a nitrogen atom.

The heterocycloalkyl group may, although this is not intended to constitute a restriction, for example, be a 4-membered ring such as azetidinyl, oxetanyl or thietanyl; or a 5-membered ring such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl; or a 6-membered ring such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, or a 7-membered ring such as azepanyl, 1,4-diazepanyl or 1,4-oxazepanyl.

Preference is given to 4- to 6-membered heterocycloalkyl.

Particular preference is given to oxetanyl, azetidinyl, pyrrolidinyl, morpholinyl, piperazinyl and piperidinyl.

Heterocycloalkyloxy

The term "4- to 7-membered heterocycloalkyloxy group" refers to a monocyclic saturated heterocycloalkyloxy group having a total of 4 to 7 ring atoms, in which one or two ring carbon atoms are replaced by identical or different heteroatoms from the group of N, O and S. The heterocycloalkyloxy group may be bonded via any carbon atom to the oxygen atom which joins the heterocycloalkyloxy group to the rest of the molecule. A preferred heteroatom in the ring is a nitrogen atom or an oxygen atom.

Preference is given to 4- to 6-membered heterocycloalkyloxy groups. Examples include oxetan-3-yloxy, azetidin-3-yloxy, tetrahydrofuran-3-yloxy, tetrahydro-2H-pyran-4-yloxy and piperidin-4-yloxy.

Preference is given to oxetan-3-yloxy and tetrahydrofuran-3-yloxy.

Heteroaryl

The term "heteroaryl" is understood to mean a monovalent monocyclic aromatic ring system which has 5 or 6 ring atoms and contains at least one ring heteroatom and optionally one, two or three further ring heteroatoms from the group of N, O and S, and which is bonded to the rest of the molecule via a ring carbon atom or optionally (if the valency allows it) via a ring nitrogen atom.

Examples of 5-membered heteroaryl groups ("5-membered heteroaryl") include thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl. Examples of 6-membered heteroaryl groups ("6-membered heteroaryl") include pyridinyl, pyridazinyl, pyrimidinyl, pyrazinyl or triazinyl.

In general, and unless stated otherwise, the heteroaryl radicals include all possible isomeric forms, for example tautomers and positional isomers in relation to the attachment point to the rest of the molecule. For example, the term "pyridinyl" includes pyridin-2-yl, pyridin-3-yl and pyridin-4-yl. A further illustrative example is the term "thiazolyl", which includes 1,3-thiazol-4-yl, 1,3-thiazol-5-yl and 1,3-thiazol-2-yl. Said examples are cited for illustration of the definition and are in no way to be understood as a limitation to the terms mentioned.

Preferred 5-membered heteroaryl are oxazolyl, thiazolyl and pyrazolyl. Particular preference is given to pyrazol-3-yl, 1,3-thiazol-4-yl and 1,3-thiazol-2-yl. Very particular preference is given to pyrazol-3-yl and 1,3-thiazol-4-yl.

Preferred 6-membered heteroaryl is pyridinyl. Particular preference is given to pyridin-2-yl and pyridin-4-yl. Very particular preference is given to pyridin-2-yl.

A symbol * at a bond denotes the bonding site in the molecule.

When radicals in the compounds according to the invention are substituted, the radicals may be mono- or polysubstituted, unless specified otherwise. In the context of the present invention, all radicals which occur more than once are defined independently of one another. Substitution by one, two or three identical or different substituents is preferred.

When $R^7$ is $C_1$-$C_6$-alkyl which may optionally be mono- to pentasubstituted by fluorine atoms and mono- to disubstituted identically or differently by hydroxyl, chlorine, bromine, cyano, $C(=O)R^a$, $C(=O)OH$, $C(=O)NH_2$, $C(=O)N(H)R^a$, $C(=O)N(R^a)R^b$, $S(=O)_2$—$C_1$-$C_6$-alkyl, $NH_2$, $NHR^a$, $N(R^a)R^b$, morpholin-4-yl, 4-methylpiperazin- 1-yl, $C_3$-$C_7$-cycloalkyl, $C_1$-$C_4$-alkoxy or $C_3$-$C_7$-cycloalkoxy, the substitution of the $C_1$-$C_6$-alkyl should be understood as follows:

When $R^7$ is $C_1$-$C_6$-alkyl, $C_1$-$C_6$-alkyl may either be unsubstituted or mono- to pentasubstituted by fluorine atoms, or $C_1$-$C_6$-alkyl may be unsubstituted or mono- to disubstituted identically or differently by hydroxyl, chlorine, bromine, cyano, C(=O)$R^a$, C(=O)OH, C(=O)NH$_2$, C(=O)N(H)$R^a$, C(=O)N($R^a$)$R^b$, S(=O)$_2$—$C_1$-$C_6$-alkyl, NH$_2$, NHR$^a$, N($R^a$)$R^b$, morpholin-4-yl, 4-methylpiperazin-1-yl, $C_3$-$C_7$-cycloalkyl, $C_1$-$C_4$-alkoxy or $C_3$-$C_7$-cycloalkoxy or $C_1$-$C_6$-alkyl may be unsubstituted or mono- to pentasubstituted by fluorine atoms and mono- to disubstituted identically or differently by hydroxyl, chlorine, bromine, cyano, C(=O)$R^a$, C(=O)OH, C(=O)NH$_2$, C(=O)N(H)$R^a$, C(=O)N($R^a$)$R^b$, S(=O)$_2$—$C_1$-$C_6$-alkyl, NH$_2$, NHR$^a$, N($R^a$)$R^b$, morpholin-4-yl, 4-methylpiperazin-1-yl, $C_3$-$C_7$-cycloalkyl, $C_1$-$C_4$-alkoxy or $C_3$-$C_7$-cycloalkoxy.

Preferred embodiments of the present invention are compounds of the formula (I) in which $R^1$ is a $C_1$-$C_3$-alkyl radical substituted by a hydroxyl group. Particular preference is given to hydroxymethyl, 1-hydroxyethyl and 2-hydroxypropan-2-yl. Very particular preference is given to 2-hydroxypropan-2-yl.

Further preferred embodiments of the present invention are compounds in which $R^1$ is a $C_1$-$C_6$-alkoxy radical which may optionally be substituted by $C_3$-$C_7$-cycloalkyl. Preference is given here to a $C_1$-$C_4$-alkoxy radical or a cyclopropylmethoxy radical. Particular preference is given to cyclopropylmethoxy, ethoxy and methoxy. Very particular preference is given to cyclopropylmethoxy and methoxy.

In further preferred embodiments of the present invention, $R^1$ is a 2,2,2-trifluoroethoxy radical or 2,2-difluoroethoxy radical.

In further preferred embodiments of the present invention, $R^1$ is C(=O)NH$_2$.

In further preferred embodiments of the present invention, $R^1$ is C(=O)OH.

In further preferred embodiments of the present invention, $R^1$ is a C(=O)($C_1$-$C_4$-alkyl)-group. Particular preference is given to C(=O)CH$_3$.

Preferred embodiments of the present invention are compounds in which $R^2$ is a pyridin-2-yl radical substituted at the 6 position by $C_1$-$C_6$-alkyl, where $C_1$-$C_6$-alkyl may optionally be substituted by up to 5 fluorine atoms. Alternatively, $R^2$ is a pyridin-2-yl radical substituted at the 6 position by cyano, chlorine, cyclopropyl, cyclopropylmethyl, NH$_2$, NH($C_1$-$C_4$-alkyl), N($C_1$-$C_4$-alkyl)$_2$, $C_1$-$C_4$-alkoxy, 2,2,2-trifluoroethoxy, 2-hydroxypropan-2-yl, morpholin-4-yl, 4-methylpiperazin-1-yl or piperazin-1-yl.

For $R^2$, particular preference is given to a pyridin-2-yl radical substituted at the 6 position by trifluoromethyl, difluoromethyl, methyl, 2,2,2-trifluoroethyl, 1,1-difluoroethyl, ethyl, isopropyl, tert-butyl, cyano, chlorine, cyclopropyl, cyclopropylmethyl, NH$_2$, NH($C_1$-$C_4$-alkyl), N($C_1$-$C_4$-alkyl)$_2$, $C_1$-$C_4$-alkoxy, 2,2,2-trifluoroethoxy, 2-hydroxypropan-2-yl, morpholin-4-yl, 4-methylpiperazin-1-yl or piperazin-1-yl. Most preferably, $R^2$ is 6-(trifluoromethyl)pyridin-2-yl, 6-(difluoromethyl)pyridin-2-yl, 6-(1,1-difluoroethyl)pyridin-2-yl, 6-aminopyridin-2-yl and 6-(2-hydroxypropan-2-yl)pyridin-2-yl. Among these, preference is given to 6-(trifluoromethyl)pyridin-2-yl.

In addition, for $R^2$, preference is given to an optionally substituted 1,3-thiazole radical, especially an optionally substituted 1,3-thiazol-2-yl or 1,3-thiazol-4-yl. Particular preference is given to 4-cyclopropyl-1,3-thiazol-2-yl and 1,3-thiazol-2-yl, where the 1,3-thiazol-2-yl radical is substituted at the 4 position by $C_1$-$C_6$-alkyl and the $C_1$-$C_6$-alkyl radical may optionally be substituted by 1 to 5 fluorine atoms. Particular preference is additionally given to 2-cyclopropyl-1,3-thiazol-4-yl and 1,3-thiazol-4-yl, where the 1,3-thiazol-4-yl radical is substituted at the 2 position by $C_1$-$C_6$-alkyl and the $C_1$-$C_6$-alkyl radical may optionally be substituted by 1 to 5 fluorine atoms.

Especially preferred for $R^2$ are 4-methyl-1,3-thiazol-2-yl, 2-methyl-1,3-thiazol-4-yl, 4-(trifluoromethyl)-1,3-thiazol-2-yl or 2-(trifluoromethyl)-1,3-thiazol-4-yl. Very particular preference is given to 4-(trifluoromethyl)-1,3-thiazol-2-yl.

A further preferred embodiment for $R^2$ is a pyrazole radical, especially pyrazol-3-yl. Particular preference is given to 1-($C_1$-$C_6$-alkyl)-1H-pyrazol-3-yl, where the $C_1$-$C_6$-alkyl substituent may contain 1 to 5 fluorine atoms. Particular preference is also given to 1-cyclopropyl-1H-pyrazol-3-yl and 1-cyclopropylmethyl-1H-pyrazol-3-yl. Very particular preference is given to 1-methyl-1H-pyrazol-3-yl, 1-ethyl-1H-pyrazol-3-yl, 1-(2,2,2-trifluoroethyl)-1H-pyrazol-3-yl and 1-(difluoromethyl)-1H-pyrazol-3-yl. Among these, particular preference is given to 1-(difluoromethyl)-1H-pyrazol-3-yl.

Preferred embodiments for $R^3$ are tetrahydro-2H-pyran-4-yl, 2,6-dimethyltetrahydro-2H-pyran-4-yl, tetrahydrofuran-3-yl, (3S)-tetrahydrofuran-3-yl, (3R)-tetrahydrofuran-3-yl and 5,5-dimethyltetrahydrofuran-3-yl. Particular preference is given to tetrahydro-2H-pyran-4-yl, tetrahydrofuran-3-yl, (3S)-tetrahydrofuran-3-yl and (3R)-tetrahydrofuran-3-yl.

Further preferred embodiments of $R^3$ are 1-oxidotetrahydro-2H-thiopyran-4-yl, 1,1-dioxidotetrahydro-2H-thiopyran-4-yl, 1-oxidotetrahydrothiophen-3-yl, 1,1-dioxidotetrahydrothiophen-3-yl, (3S)-1,1-dioxidotetrahydrothiophen-3-yl and (3R)-1,1-dioxidotetrahydrothiophen-3-yl. Particular preference is given to 1,1-dioxidotetrahydro-2H-thiopyran-4-yl, 1,1-dioxidotetrahydrothiophen-3-yl, (3S)-1,1-dioxidotetrahydrothiophen-3-yl and (3R)-1,1-dioxidotetrahydrothiophen-3-yl.

Further preferred embodiments of $R^3$ are tetrahydro-2H-thiopyran-4-yl and tetrahydrothiophen-3-yl.

In the context of a further preferred embodiment, $R^3$ is a group

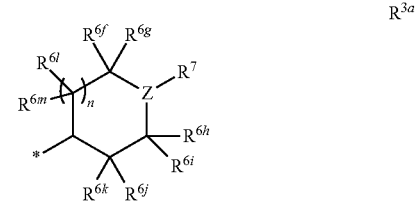

$R^{3a}$ where z is nitrogen;
$R^{6f}$ is hydrogen or methyl, preferably hydrogen;
$R^{6g}$ is hydrogen or methyl, preferably hydrogen;
$R^{6h}$ is hydrogen or methyl, preferably hydrogen;
$R^{6i}$ is hydrogen or methyl, preferably hydrogen;
$R^{6j}$ is hydrogen or methyl, preferably hydrogen;
$R^{6k}$ is hydrogen or methyl, preferably hydrogen;
$R^{6l}$ is hydrogen or methyl, preferably hydrogen;
$R^{6m}$ is hydrogen or methyl, preferably hydrogen;

$R^7$ is hydrogen, $C(=O)CH_2OH$, $C(=O)C(CH_3)_2OH$, $S(=O)_2NH_2$, $S(=O)_2NHC(=O)CH_3$, $C_1$-$C_4$-alkyl, 2,2,2-trifluoroethyl, cyclopropyl, cyclopropylmethyl, 2-(dimethylamino)ethyl, 2-aminoethyl, 2-(diethylamino)ethyl, 2-(methylamino)ethyl, 3-(dimethylamino)propyl, 2-hydroxyethyl, 3-hydroxypropyl, 2-hydroxypropyl, 3-hydroxy-3-methylbutyl, 2-methoxyethyl, oxetan-3-yl, oxetan-3-ylmethyl, tetrahydrofuran-3-yl, 1-methylpiperidin-4-yl, 1-ethylpiperidin-4-yl, pyrrolidin-3-yl, 1-methylpyrrolidin-3-yl, azetidin-3-yl, 1-methylazetidin-3-yl, azetidin-3-yl, azetidin-3-ylmethyl, 1-methylazetidin-3-ylmethyl;

$R^7$ is preferably hydrogen, $C(=O)CH_2OH$, $S(=O)_2NH_2$, $S(=O)_2NHC(=O)CH_3$, methyl, ethyl, 2,2,2-trifluoroethyl, 2-(dimethylamino)ethyl, 2-hydroxyethyl, 3-hydroxy-3-methylbutyl, oxetan-3-yl, 1-methylpiperidin-4-yl;

$R^7$ is most preferably hydrogen, methyl, 2,2,2-trifluoroethyl, 2-(dimethylamino)ethyl, 2-hydroxyethyl, 3-hydroxy-3-methylbutyl, oxetan-3-yl or 1-methylpiperidin-4-yl;

n has the definition n=0, 1, and preferably n=1.

In the context of a further embodiment, $R^3$ is a group

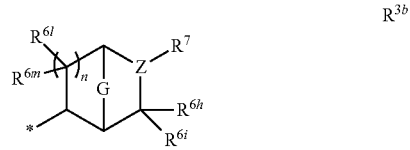

$R^{3b}$ in which
z is nitrogen;
$R^{6h}$, $R^{6i}$, $R^{6l}$ $R^{6m}$ are hydrogen;
G has the definition —$CH_2CH_2$— or —$CH_2$— and is preferably —$CH_2$—;
n has the definition n=1, 2, and preferably n=1;
$R^7$ is hydrogen, $C(=O)CH_2OH$, $S(=O)_2NH_2$, $S(=O)_2NHC(=O)CH_3$, methyl, ethyl, 2,2,2-trifluoroethyl, 2-(dimethylamino)ethyl, 2-hydroxyethyl, 3-hydroxy-3-methylbutyl, oxetan-3-yl, 1-methylpiperidin-4-yl, and is preferably hydrogen or methyl.

In the context of a further embodiment, $R^3$ is a group

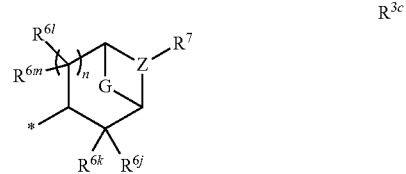

$R^{3c}$ in which
z is nitrogen;
$R^{6j}$, $R^{6k}$, $R^{6l}$ $R^{6m}$ are hydrogen;
G has the definition —$CH_2CH_2$—;
n has the definition n=1;
$R^7$ is hydrogen, $C(=O)CH_2OH$, $S(=O)_2NH_2$, $S(=O)_2NHC(=O)CH_3$, methyl, ethyl, 2,2,2-trifluoroethyl, 2-(dimethylamino)ethyl, 2-hydroxyethyl, 3-hydroxy-3-methylbutyl, oxetan-3-yl, 1-methylpiperidin-4-yl, and is preferably hydrogen or methyl.

Preferred embodiments for $R^4$ are cyclopropyl, $C_1$-$C_6$-alkyl, and $C_1$-$C_6$-alkyl substituted by one to five fluorine atoms. Particular preference is given to methyl, ethyl, 2,2,2-trifluoroethyl, 1,1-difluoroethyl, difluoromethyl and trifluoromethyl. Very particular preference is given to trifluoromethyl.

Preferred embodiments for $R^5$ are hydrogen, fluorine, chlorine, cyano, methoxy, $C_1$-$C_6$-alkyl, and $C_1$-$C_6$-alkyl substituted by one to five fluorine atoms. Particular preference is given to hydrogen, fluorine, chlorine, cyano, methyl, ethyl and trifluoromethyl. Very particular preference is given to hydrogen, fluorine and methyl. Hydrogen is especially preferred.

Preferred embodiments for $R^a$ are $C_1$-$C_6$-alkyl, cyclopropyl, cyclopropylmethyl, oxetan-3-yl, azetidin-3-yl, 1-methylazetidin-3-yl, tetrahydrofuran-3-yl, pyrrolidin-3-yl, 1-methylpyrrolidin-3-yl, piperidin-4-yl, 1-methylpiperidin-4-yl, 2,2,2-trifluoroethyl, 2-hydroxyethyl. Particular preference is given to $C_1$-$C_4$-alkyl. Very particular preference is given to methyl.

Preferred embodiments for $R^b$ are $C_1$-$C_4$-alkyl and cyclopropyl. Particular preference is given to methyl and ethyl.

Preferred embodiments for $R^c$ are hydroxyl, fluorine, methyl, ethyl, methoxy and ethoxy. Particular preference is given to fluorine and methyl.

Preferred embodiments for $R^d$ are cyclopropyl and $C_1$-$C_6$-alkyl which may optionally be mono- or disubstituted by hydroxyl. Particular preference is given to $C_1$-$C_4$-alkyl which may optionally be monosubstituted by hydroxyl. Most preferably, $R^d$ is methyl or hydroxymethyl.

A preferred embodiment for $R^e$ is $C_1$-$C_6$-alkyl which may optionally be mono- or disubstituted by hydroxyl. Particular preference is given to $C_1$-$C_4$-alkyl monosubstituted by hydroxyl. Most preferably, $R^e$ is hydroxymethyl.

Preference is additionally given to compounds of the formula (I) in which $R^1$ is fluorine, chlorine, cyano, $C(=O)OH$, $C(=O)OR^a$, $C(=O)NH_2$, $C(=O)N(H)R^a$, $C(=O)N(R^a)R^b$, hydroxyl or $C_1$-$C_6$-alkyl, where the $C_1$-$C_6$-alkyl radical may optionally be substituted by hydroxyl, or is $C_1$-$C_6$-alkoxy, where the $C_1$-$C_6$-alkoxy radical may optionally be mono- to trisubstituted by fluorine and optionally substituted by hydroxyl, by an optionally mono- to di-fluorine-substituted $C_3$-$C_6$-cycloalkyl, or by an optionally mono- to di-fluorine-substituted oxetane or tetrahydrofuran, or is $C_3$-$C_6$-cycloalkyloxy, oxetan-3-yloxy or tetrahydrofuran-3-yloxy;

$R^a$ is $C_1$-$C_6$-alkyl;

$R^b$ is $C_1$-$C_6$-alkyl;

$R^2$ is a group selected from the following general formulae II to VII, IX and X, in which $R^2$ is optionally monosubstituted by $R^5$ and

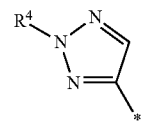

II

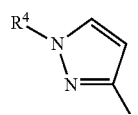

III

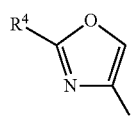

IV

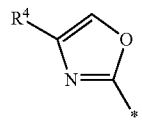

V

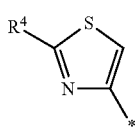

VI

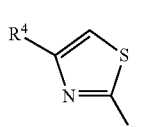

VII

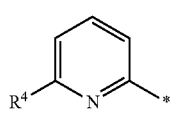

IX

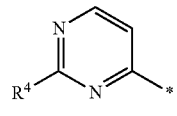

X

* represents the bonding site of the group to the rest of the molecule and $R^4$ in the formulae II and III is hydrogen, $C(=O)R^a$ or $C_1$-$C_6$-alkyl, where $C_1$-$C_6$-alkyl may optionally be mono- to trisubstituted by fluorine and monosubstituted by hydroxyl or monosubstituted by cyclopropyl, or is $C_3$-$C_6$-cycloalkyl, or is pyridinyl optionally mono- or disubstituted identically or differently by fluorine, chlorine or $C_1$-$C_4$-alkyl and $R^4$ in the formulae IV to VII is hydrogen, fluorine, chlorine, hydroxyl, cyano, $C(=O)R^a$, $NH_2$, $NHR^a$, $N(R^a)R^b$, or $C_1$-$C_6$-alkyl, where $C_1$-$C_6$-alkyl may optionally be mono- to trisubstituted by fluorine and optionally monosubstituted by hydroxyl or cyclopropyl, or is $C_1$-$C_6$-alkoxy which may optionally be mono- to tetrasubstituted by fluorine, or is $C_3$-$C_6$-cycloalkyl, $C_3$-$C_6$-cycloalkyloxy or pyridinyl, where the pyridinyl radical may optionally be mono- or disubstituted identically or differently by fluorine, chlorine or $C_1$-$C_4$-alkyl and $R^4$ in the formulae IX and X is hydrogen, cyano, $NH_2$, $NHC_1$-$C_4$-alkyl, $N(C_1$-$C_4$-alkyl)($C_1$-$C_4$-alkyl), cyclopropyl or $C_1$-$C_6$-alkyl, where $C_1$-$C_6$-alkyl may optionally be mono- or trisubstituted by fluorine and may optionally be monosubstituted by hydroxyl or cyclopropyl, or is pyridinyl optionally mono- or disubstituted identically or differently by fluorine, chlorine or $C_1$-$C_4$-alkyl or is morpholin-1-yl, 4-methylpiperazin-1-yl, piperazin-1-yl, piperidin-1-yl, pyrrolidin-1-yl;

$R^5$ is hydrogen, fluorine, chlorine, cyano, $C_1$-$C_4$-alkyl;

$R^3$ is an $R^{3a}$ group

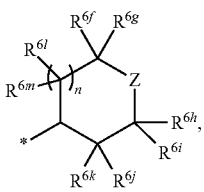

where * represents the bonding site of the group to the rest of the molecule;
$R^{6f}$ is hydrogen or $C_1$-$C_4$-alkyl;
$R^{6g}$ is hydrogen or $C_1$-$C_4$-alkyl;
$R^{6h}$ is hydrogen or $C_1$-$C_4$-alkyl;
$R^{6i}$ is hydrogen or $C_1$-$C_4$-alkyl;
or $R^{6h}$ and $R^{6i}$ together are an oxo group;
$R^{6j}$ is hydrogen or methyl;
$R^{6k}$ is hydrogen or methyl;
$R^{6l}$ is hydrogen;
$R^{6m}$ is hydrogen;
n is 0 or 1;
z is a group selected from $NR^7$, O, S, $S(=O)$, $S(=O)_2$, $S(=O)(=NH)$;
$R^7$ is hydrogen, $C(=O)R^e$, $S(=O)_2R^a$, $S(=O)_2NH_2$, $S(=O)_2N(R^a)H$, $S(=O)_2N(R^a)R^b$, $S(=O)_2NHC(=O)CH_3$, $S(=O)_2NHC(=O)CH_2CH_3$ or $C_1$-$C_6$-alkyl, where $C_1$-$C_6$-alkyl may optionally be mono- to trisubstituted by fluorine and may optionally be mono- to disubstituted by hydroxyl and may optionally be substituted by $N(R^a)R^b$, cyclopropyl, methoxy or ethoxy,
or is $C_3$-$C_6$-cycloalkyl or oxetan-3-yl, tetrahydrofuran-3-yl, tetrahydro-2H-pyran-4-yl, 1-methylazetidin-3-yl, 1-methylpyrrolidin-3-yl, 1-methylpiperidin-4-yl;
$R^e$ is $C_1$-$C_3$-alkyl, where $C_1$-$C_3$-alkyl may optionally be substituted by hydroxyl;
or $R^3$ is an $R^{3b}$ group

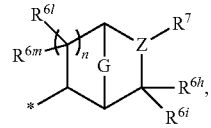

in which G is $-CH_2-$;
n is 1;
$R^{6h}$, $R^{6i}$, $R^{6m}$, $R^{6l}$ are hydrogen;
$R^7$ is hydrogen, $C(=O)CH_2OH$, $S(=O)_2NH_2$, $S(=O)_2NHC(=O)CH_3$, methyl, ethyl, 2,2,2-trifluoroethyl, 2-(dimethylamino)ethyl, 2-hydroxyethyl, 3-hydroxy-3-methylbutyl, oxetan-3-yl, 1-methylpiperidin-4-yl.

Particular preference is given to compounds of the formula (I) in which
$R^1$ is chlorine, $C(=O)OH$, $C(=O)OMe$, $C(=O)NH_2$, hydroxyl, $C_1$-$C_3$-alkyl substituted by a hydroxyl group, unsubstituted $C_1$-$C_3$-alkoxy or cyclopropylmethoxy,
$R^2$ is a group selected from the following general formulae III, VI, VII, VIII, IX or X

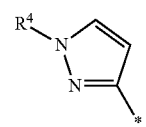

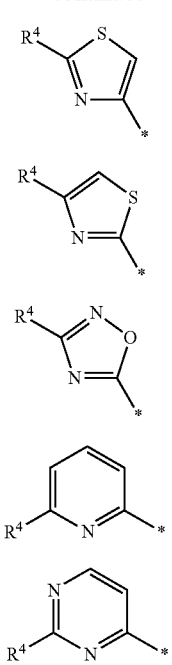

and
* represents the bonding site of the group to the rest of the molecule and

R⁴ in the formula III
is hydrogen or $C_1$-$C_4$-alkyl, where $C_1$-$C_4$-alkyl may optionally be substituted by up to three fluorine atoms or monosubstituted by hydroxyl, or is pyridin-4-yl, and R⁴ in the formulae VI, VII and VIII
is hydrogen, cyano, $C_3$-$C_6$-cycloalkyl or $C_3$-$C_6$-alkyl, where $C_1$-$C_4$-alkyl may optionally be substituted by up to three fluorine atoms or monosubstituted by hydroxyl, or is pyridin-4-yl, and R⁴ in the formulae IX and X
is hydrogen, cyano, $NH_2$, $NHC_1$-$C_4$-alkyl, $N(C_1$-$C_4$-alkyl)($C_1$-$C_4$-alkyl), cyclopropyl or $C_1$-$C_4$-alkyl, where $C_1$-$C_4$-alkyl may optionally be substituted by up to 3 fluorine atoms or monosubstituted by hydroxyl,
or is pyridinyl, morpholin-1-yl, 4-methylpiperazin-1-yl or piperazin-1-yl;

R³ is tetrahydro-2H-pyran-4-yl, 1,1-dioxidotetrahydro-2H-thiopyran-4-yl, 1-imino-1-oxidohexahydro-1λ⁴-thiopyran-4-yl, 5-oxopyrrolidin-3-yl, tetrahydrofuran-3-yl, (3S)-tetrahydrofuran-3-yl, (3R)-tetrahydrofuran-3-yl, (3S)-tetrahydrothiophen-3-yl, 1,1-dioxidotetrahydrothiophen-3-yl, (3S)-1,1-dioxidotetrahydrothiophen-3-yl, (3R)-1,1-dioxidotetrahydrothiophen-3-yl or tetrahydro-2H-thiopyran-4-yl, or R³ is an $R^{3d}$ group

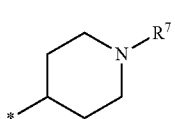

where * represents the bonding site of the group to the rest of the molecule;

R⁷ is hydrogen, C(=O)CH₂OH, S(=O)₂NH₂, S(=O)₂NHC(=O)CH₃, methyl, ethyl, 2,2,2-trifluoroethyl, 2-(dimethylamino)ethyl, 2-hydroxyethyl, 3-hydroxy-3-methylbutyl or oxetan-3-yl, 1-methylpiperidin-4-yl.

Further preferred are compounds of the formula (I) in which

R¹ is chlorine, C(=O)NH₂, 2-hydroxypropan-2-yl, methoxy, cyclopropylmethoxy,

R² is 6-(trifluoromethyl)pyridin-2-yl, 6-(difluoromethyl)pyridin-2-yl, 6-(1,1-difluoroethyl)pyridin-2-yl, 6-(morpholin-4-yl)pyridin-2-yl, 2-methyl-1,3-thiazol-4-yl, 6-aminopyridin-2-yl, 2-isopropylpyrimidin-4-yl, 6-(2-hydroxypropan-2-yl)-pyridin-2-yl, 4-(trifluoromethyl)-1,3-thiazol-2-yl, 3-(pyridin-4-yl)-1,2,4-oxadiazol-5-yl, 3-methyl-1,2,4-oxadiazol-5-yl or 1-(difluoromethyl)-1H-pyrazol-3-yl, R³ is tetrahydro-2H-pyran-4-yl, 1,1-dioxidotetrahydro-2H-thiopyran-4-yl, 1-imino-1-oxidohexahydro-1λ⁴-thiopyran-4-yl, 5-oxopyrrolidin-3-yl, tetrahydrofuran-3-yl, (3S)-tetrahydrofuran-3-yl, (3R)-tetrahydrofuran-3-yl, 1,1-dioxidotetrahydrothiophen-3-yl, (3S)-1,1-dioxidotetrahydrothiophen-3-yl or (3R)-1,1-dioxidotetrahydrothiophen-3-yl,
or R³ is piperidin-4-yl, 1-(2,2,2-trifluoroethyl)piperidin-4-yl, 1-methylpiperidin-4-yl, 1-glycoloylpiperidin-4-yl, 1'-methyl-1,4'-bipiperidin-4-yl, 1-(acetylsulphamoyl)piperidin-4-yl, [2-(dimethylamino)ethyl]piperidin-4-yl, 1-(oxetan-3-yl)piperidin-4-yl, 1-(2-hydroxyethyl)piperidin-4-yl, 1-(3-hydroxy-3-methylbutyl)piperidin-4-yl.

Very particular preference is likewise given to compounds of the formula (I) in which R¹ is C(=O)NH₂, 2-hydroxypropan-2-yl or methoxy, R² is 6-(trifluoromethyl)pyridin-2-yl, 6-(difluoromethyl)pyridin-2-yl, 6-aminopyridin-2-yl, 4-(trifluoromethyl)-1,3-thiazol-2-yl, 1-(difluoromethyl)-1H-pyrazol-3-yl, R³ is tetrahydro-2H-pyran-4-yl, 1,1-dioxidotetrahydro-2H-thiopyran-4-yl, tetrahydrofuran-3-yl, (3S)-tetrahydrofuran-3-yl, (3R)-tetrahydrofuran-3-yl or (3S)-1,1-dioxidotetrahydrothiophen-3-yl
or R³ is piperidin-4-yl, 1-(2,2,2-trifluoroethyl)piperidin-4-yl, 1-methylpiperidin-4-yl, 1-glycoloylpiperidin-4-yl, 1'-methyl-1,4'-bipiperidin-4-yl, 1-(acetylsulphamoyl)piperidin-4-yl, [2-(dimethylamino)ethyl]piperidin-4-yl, 1-(oxetan-3-yl)piperidin-4-yl, 1-(2-hydroxyethyl)piperidin-4-yl or 1-(3-hydroxy-3-methylbutyl)piperidin-4-yl.

Very particular preference is given to the following compounds according to the invention:

(1) N-[6-methoxy-2-(tetrahydro-2H-pyran-4-yl)-2H-indazol-5-yl]-6-(trifluoromethyl)pyridine-2-carboxamide (2) N-[6-methoxy-2-(piperidin-4-yl)-2H-indazol-5-yl]-6-(trifluoromethyl)pyridine-2-carboxamide (3) N-{6-methoxy-2-[1-(2,2,2-trifluoroethyl)piperidin-4-yl]-2H-indazol-5-yl}-6-(trifluoromethyl)pyridine-2-carboxamide (4) N-[6-methoxy-2-(1-methylpiperidin-4-yl)-2H-indazol-5-yl]-6-(trifluoromethyl)pyridine-2-carboxamide (5) N-[2-(1-glycoloylpiperidin-4-yl)-6-methoxy-2H-indazol-5-yl]-6-(trifluoromethyl)pyridine-2-carboxamide (6) N-[6-methoxy-2-(1'-methyl-1,4'-bipiperidin-4-yl)-2H-indazol-5-yl]-6-(trifluoromethyl)pyridine-2-carboxamide (7) N-[6-methoxy-2-(1-sulphamoylpiperidin-4-yl)-2H-indazol-5-yl]-6-(trifluoromethyl)pyridine-2-carboxamide (8) N-{2-[1-(acetylsulphamoyl)piperidin-4-yl]-6-methoxy-2H-indazol-5-yl}-6-(trifluoromethyl)pyridine-2-carboxamide (9) N-(2-{1-[2-(dimethylamino)ethyl]piperidin-4-yl}-6-methoxy-2H-indazol-5-yl)-6-(trifluoromethyl)pyridine-2-carboxamide

(10) N-{6-methoxy-2-[1-(oxetan-3-yl)piperidin-4-yl]-2H-indazol-5-yl}-6-(trifluoromethyl)pyridine-2-carboxamide

(11) N-[2-(1,1-dioxidotetrahydro-2H-thiopyran-4-yl)-6-methoxy-2H-indazol-5-yl]-6-(trifluoromethyl)pyridine-2-carboxamide

(12) N-[6-methoxy-2-(1-oxidotetrahydro-2H-thiopyran-4-yl)-2H-indazol-5-yl]-6-(trifluoromethyl)pyridine-2-carboxamide

(13) N-{2-[1-(2-hydroxyethyl)piperidin-4-yl]-6-methoxy-2H-indazol-5-yl}-6-(trifluoromethyl)pyridine-2-carboxamide

(14) rel-N-{2-[(1R,4R,5S)-2-azabicyclo[2.2.1]hept-5-yl]-6-methoxy-2H-indazol-5-yl}-6-(trifluoromethyl)pyridine-2-carboxamide

(15) rel-N-{2-[(1R,4R,5R)-2-azabicyclo[2.2.1]hept-5-yl]-6-methoxy-2H-indazol-5-yl}-6-(trifluoromethyl)pyridine-2-carboxamide

(16) N-[2-(1,1-dioxidotetrahydro-2H-thiopyran-4-yl)-6-hydroxy-2H-indazol-5-yl]-6-(trifluoromethyl)pyridine-2-carboxamide

(17) N-[6-(cyclopropylmethoxy)-2-(1,1-dioxidotetrahydro-2H-thiopyran-4-yl)-2H-indazol-5-yl]-6-(trifluoromethyl)pyridine-2-carboxamide

(18) rel-N-{6-methoxy-2-[(1R,4R,5S)-2-methyl-2-azabicyclo[2.2.1]hept-5-yl]-2H-indazol-5-yl}-6-(trifluoromethyl)pyridine-2-carboxamide

(19) rel-N-{6-methoxy-2-[(1R,4R,5R)-2-methyl-2-azabicyclo[2.2.1]hept-5-yl]-2H-indazol-5-yl}-6-(trifluoromethyl)pyridine-2-carboxamide

(20) N-[2-(1-imino-1-oxidohexahydro-1$\lambda^4$-thiopyran-4-yl)-6-methoxy-2H-indazol-5-yl]-6-(trifluoromethyl)pyridine-2-carboxamide (isomer 1)

(21) N-[2-(1-imino-1-oxidohexahydro-1$\lambda^4$-thiopyran-4-yl)-6-methoxy-2H-indazol-5-yl]-6-(trifluoromethyl)pyridine-2-carboxamide (isomer 2)

(22) N-[6-methoxy-2-(5-oxopyrrolidin-3-yl)-2H-indazol-5-yl]-6-(trifluoromethyl)pyridine-2-carboxamide

(23) 6-(difluoromethyl)-N-[6-methoxy-2-(tetrahydro-2H-pyran-4-yl)-2H-indazol-5-yl]pyridine-2-carboxamide

(24) N-[6-methoxy-2-(tetrahydro-2H-pyran-4-yl)-2H-indazol-5-yl]-6-(morpholin-4-yl)pyridine-2-carboxamide

(25) N-[6-methoxy-2-(tetrahydro-2H-pyran-4-yl)-2H-indazol-5-yl]-2-methyl-1,3-thiazole-4-carboxamide

(26) 6-amino-N-[6-methoxy-2-(tetrahydro-2H-pyran-4-yl)-2H-indazol-5-yl]pyridine-2-carboxamide

(27) 2-isopropyl-N-[6-methoxy-2-(tetrahydro-2H-pyran-4-yl)-2H-indazol-5-yl]pyrimidine-4-carboxamide

(28) 6-(2-hydroxypropan-2-yl)-N-[6-methoxy-2-(tetrahydro-2H-pyran-4-yl)-2H-indazol-5-yl]pyridine-2-carboxamide

(29) N-[6-methoxy-2-(tetrahydrofuran-3-yl)-2H-indazol-5-yl]-6-(trifluoromethyl)pyridine-2-carboxamide

(30) N-[6-chloro-2-(tetrahydro-2H-pyran-4-yl)-2H-indazol-5-yl]-6-(trifluoromethyl)pyridine-2-carboxamide

(31) N-[6-chloro-2-(tetrahydro-2H-pyran-4-yl)-2H-indazol-5-yl]-6-(difluoromethyl)pyridine-2-carboxamide

(32) N-[6-chloro-2-(1,1-dioxidotetrahydro-2H-thiopyran-4-yl)-2H-indazol-5-yl]-6-(2-hydroxypropan-2-yl)pyridine-2-carboxamide

(33) methyl 2-(tetrahydro-2H-pyran-4-yl)-5-({[6-(trifluoromethyl)pyridin-2-yl]carbonyl}amino)-2H-indazole-6-carboxylate

(34) N-[6-(2-hydroxypropan-2-yl)-2-(tetrahydro-2H-pyran-4-yl)-2H-indazol-5-yl]-6-(trifluoromethyl)pyridine-2-carboxamide

(35) methyl 2-[(3S)-tetrahydrofuran-3-yl]-5-({[6-(trifluoromethyl)pyridin-2-yl]carbonyl}amino)-2H-indazole-6-carboxylate

(36) N-{6-(2-hydroxypropan-2-yl)-2-[(3S)-tetrahydrofuran-3-yl]-2H-indazol-5-yl}-6-(trifluoromethyl)pyridine-2-carboxamide

(37) methyl 2-[(3R)-tetrahydrofuran-3-yl]-5-({[6-(trifluoromethyl)pyridin-2-yl]carbonyl}amino)-2H-indazole-6-carboxylate

(38) N-{6-(2-hydroxypropan-2-yl)-2-[(3R)-tetrahydrofuran-3-yl]-2H-indazol-5-yl}-6-(trifluoromethyl)pyridine-2-carboxamide

(39) methyl 2-[(3S)-tetrahydrothiophen-3-yl]-5-({[6-(trifluoromethyl)pyridin-2-yl]carbonyl}amino)-2H-indazole-6-carboxylate

(40) N-{6-(2-hydroxypropan-2-yl)-2-[(3S)-tetrahydrothiophen-3-yl]-2H-indazol-5-yl}-6-(trifluoromethyl)pyridine-2-carboxamide

(41) N-{2-[(3S)-1,1-dioxidotetrahydrothiophen-3-yl]-6-(2-hydroxypropan-2-yl)-2H-indazol-5-yl}-6-(trifluoromethyl)pyridine-2-carboxamide

(42) methyl 2-(tetrahydro-2H-thiopyran-4-yl)-5-({[6-(trifluoromethyl)pyridin-2-yl]carbonyl}amino)-2H-indazole-6-carboxylate

(43) N-[6-(2-hydroxypropan-2-yl)-2-(tetrahydro-2H-thiopyran-4-yl)-2H-indazol-5-yl]-6-(trifluoromethyl)pyridine-2-carboxamide

(44) N-[2-(1,1-dioxidotetrahydro-2H-thiopyran-4-yl)-6-(2-hydroxypropan-2-yl)-2H-indazol-5-yl]-6-(trifluoromethyl)pyridine-2-carboxamide

(45) methyl 2-(piperidin-4-yl)-5-({[6-(trifluoromethyl)pyridin-2-yl]carbonyl}amino)-2H-indazole-6-carboxylate

(46) N-[6-(2-hydroxypropan-2-yl)-2-(piperidin-4-yl)-2H-indazol-5-yl]-6-(trifluoromethyl)pyridine-2-carboxamide

(47) N-[6-methoxy-2-(tetrahydro-2H-pyran-4-yl)-2H-indazol-5-yl]-4-(trifluoromethyl)-1,3-thiazole-2-carboxamide

(48) N-[6-methoxy-2-(tetrahydro-2H-pyran-4-yl)-2H-indazol-5-yl]-3-(pyridin-4-yl)-1,2,4-oxadiazole-5-carboxamide

(49) N-[6-methoxy-2-(tetrahydro-2H-pyran-4-yl)-2H-indazol-5-yl]-3-methyl-1,2,4-oxadiazole-5-carboxamide

(50) N-[6-chloro-2-(tetrahydro-2H-pyran-4-yl)-2H-indazol-5-yl]-4-(trifluoromethyl)-1,3-thiazole-2-carboxamide

(51) 1-(difluoromethyl)-N-[6-methoxy-2-(tetrahydro-2H-pyran-4-yl)-2H-indazol-5-yl]-1H-pyrazole-3-carboxamide

(52) N-{2-[1-(3-hydroxy-3-methylbutyl)piperidin-4-yl]-6-methoxy-2H-indazol-5-yl}-6-(trifluoromethyl)pyridine-2-carboxamide

(53) 2-(piperidin-4-yl)-5-({[6-(trifluoromethyl)pyridin-2-yl]carbonyl}amino)-2H-indazole-6-carboxamide

(54) 2-(piperidin-4-yl)-5-({[6-(trifluoromethyl)pyridin-2-yl]carbonyl}amino)-2H-indazole-6-carboxylic acid

(55) methyl 2-(1-methylpiperidin-4-yl)-5-({[6-(trifluoromethyl)pyridin-2-yl]carbonyl}amino)-2H-indazole-6-carboxylate

(56) 2-[1-(3-hydroxy-3-methylbutyl)piperidin-4-yl]-5-({[6-(trifluoromethyl)pyridin-2-yl]carbonyl}amino)-2H-indazole-6-carboxamide

(57) 2-(1-methylpiperidin-4-yl)-5-({[6-(trifluoromethyl)pyridin-2-yl]carbonyl}amino)-2H-indazole-6-carboxamide

(58) N-{6-methoxy-2-[1-(2-methoxyethyl)piperidin-4-yl]-2H-indazol-5-yl}-6-(trifluoromethyl)pyridine-2-carboxamide.

The following compounds are especially preferred:
(34) N-[6-(2-hydroxypropan-2-yl)-2-(tetrahydro-2H-pyran-4-yl)-2H-indazol-5-yl]-6-(trifluoromethyl)pyridine-2-carboxamide
(44) N-[2-(1,1-dioxidotetrahydro-2H-thiopyran-4-yl)-6-(2-hydroxypropan-2-yl)-2H-indazol-5-yl]-6-(trifluoromethyl)pyridine-2-carboxamide
(46) N-[6-(2-hydroxypropan-2-yl)-2-(piperidin-4-yl)-2H-indazol-5-yl]-6-(trifluoromethyl)pyridine-2-carboxamide The compounds according to the invention act as inhibitors of IRAK4 kinase and have an unforeseeable useful pharmacological activity spectrum.

Thus, in addition to the subject matter mentioned above, the present invention also provides the use of the compounds according to the invention for treatment and/or prophylaxis of diseases in man and animals.

Treatment and/or prophylaxis of gynaecological disorders, inflammatory skin disorders, cardiovascular disorders, pulmonary disorders, eye disorders, autoimmune disorders, pain disorders, metabolic disorders, gout, hepatic disorders, metabolic syndrome, insulin resistance and cancers with the IRAK4 inhibitors according to the invention is particularly preferred.

The compounds according to the invention are suitable for prophylaxis and/or treatment of various disorders and disease-related states, especially disorders mediated by TLR (except for TLR3) and/or the IL-1 receptor family and/or disorders whose pathology is mediated directly by IRAK4. IRAK4-associated disorders include multiple sclerosis, atherosclerosis, myocardial infarction, Alzheimer's disease, virus-induced myocarditis, gout, Vogt-Koyanagi-Harada syndrome, lupus erythematosus, psoriasis, spondyloarthritis and arthritis.

The compounds according to the invention can also be used for prophylaxis and/or treatment of disorders mediated by MyD88 and TLR (except for TLR3). This includes multiple sclerosis, rheumatoid arthritis, spondyloarthritis (especially psoriatic spondyloarthritis and Bekhterev's disease), metabolic syndrome including insulin resistance, diabetes mellitus, osteoarthritis, Sjögren syndrome, giant cell arteritis, sepsis, poly- and dermatomyositis, skin disorders such as psoriasis, atopic dermatitis, alopecia areata, acne inversa and acne vulgaris, pulmonary disorders such as pulmonary fibrosis, chronic obstructive pulmonary disease (COPD), acute respiratory distress syndrome (ARDS), acute lung injury (ALI), interstitial lung disease (ILD), sarcoidosis and pulmonary hypertension.

Because of the mechanism of action of the compounds according to the invention, they are suitable for prophylaxis and/or treatment of the TLR-mediated disorders Behçet's disease, gout, endometriosis and endometriosis-associated pain and other endometriosis-associated symptoms such as dysmenorrhoea, dyspareunia, dysuria and dyschezia. In addition, the compounds according to the invention are suitable for prophylaxis and/or treatment in the case of transplant rejection, lupus erythematosus, adult-onset Still's disease and chronic inflammatory bowel disorders such as ulcerative colitis and Crohn's disease.

In addition to the disorders already listed, the use of the compounds according to the invention is also suitable for treatment and/or prevention of the following disorders: eye disorders such as keratitis, allergic conjunctivitis, keratoconjunctivitis sicca, macular degeneration and uveitis; cardiovascular disorders such as atherosclerosis, myocardial reperfusion damage, myocardial infarction, hypertension and neurological disorders such as Alzheimer's disease, stroke and Parkinson's.

The mechanism of action of the compounds according to the invention also enables the prophylaxis and/or treatment of hepatic disorders mediated by TLR and the IL-1 receptor family, especially NAFLD, NASH, ASH, liver fibrosis and liver cirrhosis.

The prophylaxis and/or treatment of pruritus and pain, especially of acute, chronic, inflammatory and neuropathic pain, is also provided by the compounds according to the invention.

Because of the mechanism of action of the compounds according to the invention, they are suitable for prophylaxis and/or treatment of oncological disorders such as lymphoma, chronic lymphatic leukaemia, melanoma and liver cell carcinoma, breast cancer, and Ras-dependent tumours.

Moreover, the compounds according to the invention are suitable for the treatment and/or prevention of disorders mediated via the IL-1 receptor family. These disorders include CAPS (cryopyrin-associated periodic syndromes) including FCAS (familial cold autoinflammatory syndrome), MWS (Muckle-Wells syndrome), NOMID (neonatal-onset multisystem inflammatory disease) and CONCA (chronic infantile, neurological, cutaneous, and articular) syndrome, FMF (familial mediterranean fever), HIDS (hyper-IgD syndrome), TRAPS (tumour necrosis factor receptor 1-associated periodic syndrome), juvenile idiopathic arthritis, adult-onset Still's disease, Adamantiades-Behçet's disease, rheumatoid arthritis, psoriasis, arthritis, Bekhterev's disease, osteoarthritis, keratoconjunctivitis sicca und Sjögren syndrome, multiple sclerosis, lupus erythematosus, alopecia areata, type 1 diabetes mellitus, type 2 diabetes mellitus and the sequelae of myocardial infarction. Pulmonary disorders such as asthma, COPD, idiopathic interstitial pneumonia and ARDS, gynaecological disorders such as endometriosis and endometriosis-associated pain and other endometriosis-associated symptoms such as dysmenorrhoea, dyspareunia, dysuria and dyschezia, chronic-inflammatory bowel disorders such as Crohn's disease and ulcerative colitis are associated with dysregulation of the IL-1 receptor family and are suitable for therapeutic and/or prophylactic use of the compounds according to the invention.

The compounds according to the invention can also be used for treatment and/or prevention of IL1 receptor family-mediated neurological disorders such as stroke, Alzheimer's, craniocerebral trauma, and dermatological disorders such as psoriasis, atopic dermatitis, acne inversa, alopecia areata and allergic contact dermatitis.

In addition, the compounds according to the invention are suitable for the treatment and/or prophylaxis of pain disorders, especially of acute, chronic, inflammatory and neuropathic pain. This preferably includes hyperalgesia, allodynia, pain from arthritis (such as osteoarthritis, rheumatoid arthritis and spondyloarthritis), premenstrual pain, endometriosis-associated pain, post-operative pain, pain from interstitial cystitis, CRPS (complex regional pain syndrome), trigeminal neuralgia, pain from prostatitis, pain caused by spinal cord injuries, inflammation-induced pain, lower back pain, cancer pain, chemotherapy-associated pain, HIV treatment-induced neuropathy, burn-induced pain and chronic pain.

The present invention further also provides a method for treatment and/or prevention of disorders, especially the disorders mentioned above, using an effective amount of at least one of the compounds according to the invention.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The compounds according to the invention can be used alone or, if required, in combination with other active ingredients. The present invention further provides medicaments comprising at least one of the compounds according to the invention and one or more further active ingredients, in particular for the treatment and/or prevention of the disorders mentioned above. Preferred examples of suitable combination active ingredients include:

In general terms, these include active ingredients such as antibacterial (e.g. penicillins, vancomycin, ciprofloxacin), antiviral (e.g. aciclovir, oseltamivir) and antimycotic (e.g. naftifin, nystatin) substances and gamma globulins, immunomodulatory and immunosuppressive compounds such as cyclosporin, Methotrexat®, TNF antagonists (e.g. Humira®, etanercept, infliximab), IL-1 inhibitors (e.g. anakinra, canakinumab, rilonacept), phosphodiesterase inhibitors (e.g. apremilast), Jak/STAT inhibitors (e.g. tofacitinib, baricitinib, GLPG0634), leflunomid, cyclophosphamide, rituximab, belimumab, tacrolimus, rapamycin, mycophenolate mofetil, interferons, corticosteroids (e.g. prednisone, prednisolone, methylprednisolone, hydrocortisone, betamethasone), cyclophosphamide, azathioprine and sulfasalazine; paracetamol, non-steroidal anti-inflammatory substances (NSAIDS) (aspirin, ibuprofen, naproxen, etodolac, celecoxib, colchicine). The following should be mentioned for tumour therapy: immunotherapy (e.g. aldesleukin, alemtuzumab, basiliximab, catumaxomab, celmoleukin, denileukin-diftitox, eculizumab, edrecolomab, gemtuzumab, ibritumomab-tiuxetan, imiquimod, interferon-alpha, interferon-beta, interferon-gamma, ipilimumab, lenalidomid, lenograstim, mifamurtid, ofatumumab, oprelvekin, picibanil, plerixafor, polysaccharide-K, sargramostim, sipuleucel-T, tasonermin, teceleukin, tocilizumab), antiproliferative substances such as, for example but not exclusively, amsacrine, arglabin, arsenic trioxide, asparaginase, bleomycin, busulfan, dactinomycin, docetaxel, epirubicin, peplomycin, trastuzumab, rituximab, obinutuzumab, ofatumumab, tositumomab, aromatase inhibitors (e.g. exemestane, fadrozole, formestane, letrozole, anastrozole, vorozole), antiestrogens (e.g. chlormadinone, fulvestrant, mepitiostane, tamoxifen, toremifen), estrogens (e.g. estradiol, polyestradiol phosphate, raloxifen), gestagens (e.g. medroxyprogesteron, megestrol), topoisomerase I inhibitors (e.g. irinotecan, topotecan), topoisomerase II inhibitors (e.g. amrubicin, daunorubicin, elliptinium acetate, etoposide, idarubicin, mitoxantrone, teniposide), microtubuli-active substances (e.g. cabazitaxel, eribulin, paclitaxel, vinblastine, vincristine, vindesine, vinorelbine), telomerase inhibitors (e.g. imetelstat), alkylating substances and histone deacetylase inhibitors (e.g. bendamustine, carmustine, chlormethine, dacarbazine, estramustine, ifosfamid, lomustine, mitobronitol, mitolactol, nimustine, prednimustine, procarbazine, ranimustine, streptozotocine, temozolomide, thiotepa, treosulfan, trofosfamid, vorinostat, romidepsin, panobinostat); substances which influence cell differentiation processes such as abarelix, aminoglutethimide, bexarotene, MMP inhibitors (peptide mimetics, non-peptide mimetics and tetracyclines, for example marimastat, BAY 12-9566, BMS-275291, clodronate, prinomastat, doxycycline), mTOR inhibitors (e.g. sirolimus, everolimus, temsirolimus, zotarolimus), antimetabolites (e.g. clofarabine, doxifluridine, methotrexate, 5-fluorouracil, cladribine, cytarabine, fludarabine, mercaptopurine, pemetrexed, raltitrexed, tegafur, tioguanine), platinum compounds (e.g. carboplatin, cisplatin, cisplatinum, eptaplatin, lobaplatin, miriplatin, nedaplatin, oxaliplatin); antiangiogenic compounds (e.g. bevacizumab), antiandrogenic compounds (e.g. bevacizumab, enzalutamide, flutamide, nilutamide, bicalutamide, cyproterone, cyproterone acetate), proteasome inhibitors (e.g. bortezomib, carfilzomib, oprozomib, ONYX0914), gonadoliberin agonists and antagonists (e.g. abarelix, buserelin, deslorelin, ganirelix, goserelin, histrelin, triptorelin, degarelix, leuprorelin), methionine aminopeptidase inhibitors (e.g. bengamide derivatives, TNP-470, PPI-2458), heparanase inhibitors (e.g. SST0001, PI-88); inhibitors of genetically modified Ras protein (e.g. farnesyl transferase inhibitors such as lonafarnib, tipifarnib), HSP90 inhibitors (e.g. geldamycin derivatives such as 17-allylaminogeldanamycin, 17-demethoxygeldanamycin (17AAG), 17-DMAG, retaspimycin hydrochloride, IPI-493, AUY922, BIIB028, STA-9090, KW-2478), kinesin spindle protein inhibitors (e.g. SB715992, SB743921, pentamidine/chlorpromazine), MEK (mitogen-activated protein kinase) inhibitors (e.g. trametinib, BAY 86-9766 (refametinib), AZD6244), kinase inhibitors (e.g.: sorafenib, regorafenib, lapatinib, sutent, dasatinib, cetuximab, BMS-908662, GSK2118436, AMG 706, erlotinib, gefitinib, imatinib, nilotinib, pazopanib, roniciclib, sunitinib, vandetanib, vemurafenib), hedgehog signal inhibitors (e.g. cyclopamine, vismodegib), BTK (Bruton's tyrosine kinase) inhibitors (e.g. ibrutinib), JAK/pan-JAK (Janus kinase) inhibitors (e.g. SB-1578, baricitinib, tofacitinib, pacritinib, momelotinib, ruxolitinib, VX-509, AZD-1480, TG-101348), PI3K inhibitors (e.g. BAY 1082439, BAY 80-6946 (copanlisib), ATU-027, SF-1126, DS-7423, GSK-2126458, buparlisib, PF-4691502, BYL-719, XL-147, XL-765, idelalisib), SYK (spleen tyrosine kinase) inhibitors (e.g. fostamatinib, Excellair, PRT-062607), p53 gene therapy, bisphosphonates (e.g. etridonate, clodronate, tiludronate, pamidronate, alendronic acid, ibandronate, risedronate, zoledronate). Examples of active ingredients for combination include the following: rituximab, cyclophosphamide, doxorubicin, doxorubicin in combination with oestrone, vincristine, chlorambucil, fludarabin, dexamethasone, cladribin, prednisone, 131I-chTNT, abirateron, aclarubicin, alitretinoin, bisantren, calcium folinate, calcium levofolinate, capecitabin, carmofur, clodronic acid, romiplostim, crisantaspase, darbepoetin alfa, decitabin, denosumab, dibrospidium chloride, eltrombopag, endostatin, epitiostanol, epoetin alfa, filgrastim, fotemustin, gallium nitrate, gemcitabin, glutoxim, histamine dihydrochloride, hydroxycarbamide, improsulfan, ixabepilon, lanreotid, lentinan, levamisol, lisurid, lonidamin, masoprocol, methyltestosterone, methoxsalen, methyl aminolevulinate, miltefosin, mitoguazon, mitomycin, mitotan, nelarabin, nimotuzumab, nitracrin, omeprazol, palifermin, panitumumab, pegaspargase, PEG epoetin beta (methoxy-PEG epoetin beta), peg-filgrastim, peg interferon alfa-2b, pentazocin, pentostatin, perfosfamid, pirarubicin, plicamycin, poliglusam, porfimer-sodium, pralatrexate, quinagolid, razoxan, sizofiran, sobuzoxan, sodium glycididazole, tamibaroten, the combination of tegafur and gimeracil and oteracil, testosterone, tetrofosmin, thalidomide, thymalfasin, trabectedin, tretinoin, trilostan, tryptophan, ubenimex, vapreotid, yttrium-90 glass microbeads, zinostatin, zinostatin stimalamer.

Also suitable for tumour therapy is a combination of a non-drug therapy such as chemotherapy (e.g. azacitidine, belotecan, enocitabine, melphalan, valrubicin, vinflunin, zorubicin), radiotherapy (e.g. I-125 seeds, palladium-103 seed, radium-223 chloride) or phototherapy (e.g. temoporfin, talaporfin) which is accompanied by a drug treatment with the IRAK4 inhibitors according to the invention or which, after the non-drug tumour therapy such as chemotherapy, radiotherapy or phototherapy has ended, are supplemented by a drug treatment with the IRAK4 inhibitors according to the invention.

In addition to those mentioned above, the IRAK4 inhibitors according to the invention can also be combined with the following active ingredients:

active ingredients for Alzheimer's therapy, for example acetylcholinesterase inhibitors (e.g. donepezil, rivastigmine, galantamin, tacrine), NMDA (N-methyl-D-aspartate) receptor antagonists (e.g. memantine); L-DOPA/carbidopa (L-3, 4-dihydroxyphenylalanine), COMT (catechol-O-methyltransferase) inhibitors (e.g. entacapon), dopamine agonists (e.g. ropinrol, pramipexol, bromocriptin), MAO-B (monoaminooxidase-B) inhibitors (e.g. selegilin), anticholinergics (e.g. trihexyphenidyl) and NMDA antagonists (e.g. amantadin) for treatment of Parkinson's; beta-interferon (IFN-beta) (e.g. IFN beta-1b, IFN beta-1a Avonex® and Betaferon®), glatiramer acetate, immunoglobulins, natalizumab, fingolimod and immunosuppressants such as mitoxantrone, azathioprine and cyclophosphamide for treatment of multiple sclerosis; substances for treatment of pulmonary disorders, for example beta-2-sympathomimetics (e.g. salbutamol), anticholinergics (e.g. glycopyrronium), methylxanthines (e.g. theophylline), leukotriene receptor antagonists (e.g. montelukast), PDE-4 (phosphodiesterase type 4) inhibitors (e.g. roflumilast), methotrexate, IgE antibodies, azathioprine and cyclophosphamide, cortisol-containing preparations; substances for treatment of osteoarthritis such as non-steroidal anti-inflammatory substances (NSAIDs). In addition to the two therapies mentioned, methotrexate and biologics for B-cell and T-cell therapy (e.g. rituximab, abatacept) should be mentioned for rheumatoid disorders, for example rheumatoid arthritis, spondyloarthritis and juvenile idiopathic arthritis. Neurotrophic substances such as acetylcholinesterase inhibitors (e.g. donepezil), MAO (monoaminooxidase) inhibitors (e.g. selegiline), interferons and anticonvulsives (e.g. gabapentin); active ingredients for treatment of cardiovascular disorders such as beta-blockers (e.g. metoprolol), ACE inhibitors (e.g. benazepril), angiotensin receptor blockers (e.g. losartan, valsartan), diuretics (e.g. hydrochlorothiazide), calcium channel blockers (e.g. nifedipine), statins (e.g. simvastatin, fluvastatin); anti-diabetic drugs, for example metformin, glinides (e.g. nateglinide), DPP-4 (dipeptidyl peptidase-4) inhibitors (e.g. linagliptin, saxagliptin, sitagliptin, vildagliptin), SGLT2 (sodium/glucose cotransporter 2) inhibitors/gliflozin (e.g. dapagliflozin, empagliflozin), incretin mimetics (hormone glucose-dependent insulinotropic peptide (GIP) and glucagon-like peptid 1 (GLP-1) analogues/agonists) (e.g. exenatide, liraglutide, lixisenatide), α-glucosidase inhibitors (e.g. acarbose, miglitol, voglibiose) and sulphonylureas (e.g. glibenclamide, tolbutamide), insulin sensitizers (e.g. pioglitazone) and insulin therapy (e.g. NPH insulin, insulin lispro), substances for treatment of hypoglycaemia for treatment of diabetes and metabolic syndrome. Lipid-lowering drugs, for example fibrates (e.g. bezafibrate, etofibrate, fenofibrate, gemfibrozil), nicotinic acid derivatives (e.g. nicotinic acid/laropiprant), ezetimib, statins (e.g. simvastatin, fluvastatin), anion exchangers (e.g. cholestyramine, colestipol, colesevelam). Active ingredients such as mesalazine, sulfasalazine, azathioprine, 6-mercaptopurine or methotrexate, probiotic bacteria (Mutaflor, VSL#3®, *Lactobacillus* GG, *Lactobacillus plantarum, L. acidophilus, L. casei, Bifidobacterium infantis* 35624, *Enterococcus fecium* SF68, *Bifidobacterium longum, Escherichia coli* Nissle 1917), antibiotics, for example ciprofloxacin and metronidazole, anti-diarrhoea drugs, for example loperamide, or laxatives (bisacodyl) for treatment of chronic-inflammatory bowel disorders. Immunosuppressants such as glucocorticoids and non-steroidale anti-inflammatory substances (NSAIDs), cortisone, chloroquin, cyclosporine, azathioprine, belimumab, rituximab, cyclophosphamide for treatment of lupus erythematosus. By way of example but not exclusively, calcineurin inhibitors (e.g. tacrolimus and ciclosporin), cell division inhibitors (e.g. azathioprine, mycophenolate mofetil, mycophenolic acid, everolimus or sirolimus), rapamycin, basiliximab, daclizumab, anti-CD3 antibodies, anti-T-lymphocyte globulin/anti-lymphocyte globulin for organ transplants. Vitamin D3 analogues, for example calcipotriol, tacalcitol or calcitriol, salicylic acid, urea, ciclosporine, methotrexate, efalizumab for dermatological disorders.

Mention should also be made of medicaments comprising at least one of the compounds according to the invention and one or more further active ingredients, in particular EP4 inhibitors (prostaglandin E2 receptor 4 inhibitors), P2X3 inhibitors (P2X purinoceptor 3), PTGES inhibitors (prostaglandin E synthase inhibitors) or AKR1C3 inhibitors (aldoketo reductase family 1 member C3 inhibitors), for treatment and/or prevention of the aforementioned disorders.

The compounds according to the invention can act systemically and/or locally. For this purpose, they can be administered in a suitable manner, for example by the oral, parenteral, pulmonal, nasal, sublingual, lingual, buccal, rectal, dermal, transdermal or conjunctival route, via the ear or as an implant or stent.

The compounds according to the invention can be administered in administration forms suitable for these administration routes.

Suitable administration forms for oral administration are those which work according to the prior art and release the compounds according to the invention rapidly and/or in a modified manner and which contain the compounds according to the invention in crystalline and/or amorphous and/or dissolved form, for example tablets (uncoated or coated tablets, for example with gastric juice-resistant or retarded-dissolution or insoluble coatings which control the release of the inventive compound), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

For the other administration routes, suitable examples are inhalation medicaments (including powder inhalers, nebulizers), nasal drops, solutions or sprays; tablets for lingual, sublingual or buccal administration, films/oblates or capsules, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Preference is given to oral or parenteral administration, especially oral administration.

The compounds according to the invention can be converted to the administration forms mentioned. This can be accomplished in a manner known per se by mixing with inert, non-toxic, pharmaceutically suitable auxiliaries. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colourants (e.g. inorganic pigments, for example iron oxides) and flavour and/or odour correctors.

The present invention further provides medicaments which comprise at least one compound according to the invention, typically together with one or more inert, non-toxic, pharmaceutically suitable excipients, and the use thereof for the aforementioned purposes.

In general, it has been found to be advantageous in the case of parenteral administration to administer amounts of about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight.

It may nevertheless be necessary in some cases to deviate from the stated amounts, specifically as a function of body weight, route of administration, individual response to the active ingredient, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for liquid/liquid solutions are based in each case on volume.

Preparation of the Compounds According to the Invention

The preparation of the compounds according to the invention is illustrated by the synthesis schemes which follow.

Starting materials used for synthesis of some of the compounds according to the invention are carboxylic acids $R^2$—$CO_2H$ in which $R^2$ is as defined in the formula (I), which are commercially available or can be prepared by routes known from the literature or analogously to routes known from the literature (see, for example, European Journal of Organic Chemistry 2003, 8, 1559-1568, Chemical and Pharmaceutical Bulletin, 1990, 38, 9, 2446-2458, Synthetic Communications 2012, 42, 658-666, Tetrahedron, 2004, 60, 51, 11869-11874). Some carboxylic acids $R^2$—$CO_2H$ in which $R^2$ is as defined in the formula (I) can be prepared proceeding from carboxylic esters by hydrolysis (cf., for example, the reaction of ethyl 6-(hydroxymethyl) pyridine-2-carboxylate with aqueous sodium hydroxide solution in methanol, WO2004113281) or—in the case of a tert-butyl ester—by reaction with an acid, for example hydrogen chloride or trifluoroacetic acid (cf, for example, Dalton Transactions, 2014, 43, 19, 7176-7190). The carboxylic acids $R^2$—$CO_2H$ can also be used in reactions in the form of their alkali metal salts. Carboxylic esters as starting materials for the preparation of the carboxylic acids $R^2$—$CO_2H$ can optionally be prepared from halogenated units $R^2$—I, $R^2$—Br or $R^2$—Cl with $R^2$ as defined in formula (I), by reaction in a carbon monoxide atmosphere, optionally under elevated pressure, in the presence of a phosphine ligand, for example 1,3-bis(diphenylphosphino)propane, a palladium compound, for example palladium(II) acetate, and a base, for example triethylamine, with addition of ethanol or methanol in a solvent, for example dimethyl sulphoxide (for preparation methods see, for example, WO2012112743, WO 2005082866, Chemical Communications (Cambridge, England), 2003, 15, 1948-1949, WO200661715). The starting materials $R^2$—I, $R^2$—Br or $R^2$—Cl are either commercially available or can be prepared by routes known from the literature. Illustrative preparation methods are detailed in WO2012061926, European Journal of Organic Chemistry, 2002, 2, 327-330, Synthesis, 2004, 10, 1619-1624, Journal of the American Chemical Society, 2013, 135, 32, 12122-12134, Bioorganic and Medicinal Chemistry Letters, 2014, 24, 16, 4039-4043, US2007185058, WO2009117421.

Some of the azide compounds (Intermediates 2) required for synthesis of the compounds according to the invention can be prepared according to Synthesis Scheme 1. Proceeding from suitable aldehydes that are known from the literature (illustrative synthesis methods: Synthesis, 2009, 12, 2040-2060; Journal of Fluorine Chemistry, 1995, 70, 39-44) or commercially available, it is possible to prepare Intermediates 1 by nitration. It is possible here to make use of nitration methods known to those skilled in the art (illustrative synthesis methods: WO2013174744, Journal of Medicinal Chemistry, 2013, 56, 4343-4356). Preference is given to the use of nitrate acid or potassium nitrate in concentrated sulphuric acid. The Intermediates 1 can then be converted to the Intermediates 2 with azides, for example sodium azide, in a solvent, for example dimethyl sulphoxide.

Synthesis Scheme 1

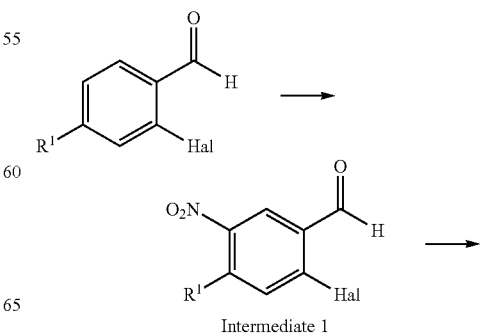

Intermediate 1

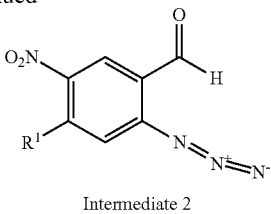

Intermediate 2

Hal is fluorine or chlorine, preferably fluorine.

The substituent $R^1$ has the definition given in the general formula (I).

Proceeding from suitable azide compounds (Intermediates 2), it is possible by reaction with primary amines to prepare indazoles (Intermediates 3) (Synthesis Scheme 2). For this purpose, useful methods, for example, include those from Chemical Communications 2011, 47, 10133-10135 and RSC Adv., 2014, 4, 34232-34236. Alternatively, however, it is also possible to use related methods as described, for example, in Organic Process Research and Development, 2011, 15, 4, 831-840, Chemistry of Heterocyclic Compounds, 2001, 37, 504-505 and Organic Letters, 2011, 13, 3542-3545. Preference is given to the reaction of Intermediate 2 with an amine $R^3$—$NH_2$ with $R^3$ as defined for formula (I) in a solvent, for example dichloromethane, in the presence of activated molecular sieve. Alternatively, it is also possible to use trimethoxymethane (CAS 149-73-5), and toluene as solvent.

If necessary, the amines $R^3$—$NH_2$ used may have functional groups which may have been protected beforehand with a protecting group. This protecting group can be detached after the reaction or else in a later step of the synthesis of the compounds according to the invention (for the introduction and detachment of suitable protecting groups, see also P. G. M. Wuts, T. W. Greene, *Greene's Protective Groups in Organic Synthesis*, Fourth Edition, ISBN: 9780471697541).

Synthesis Scheme 2

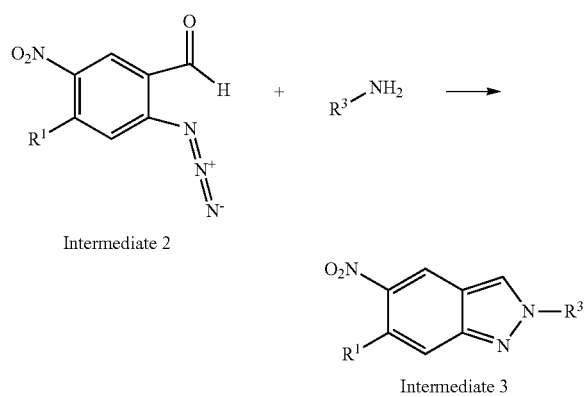

Intermediate 2

Intermediate 3

The substituents $R^1$ and $R^3$ have the definitions given in the general formula (I).

Alternatively, Intermediates 3 can also be prepared proceeding from the Intermediates 7 (see Synthesis Scheme 3). For this purpose, useful reactions are those with chlorine compounds ($R^3$—Cl), bromide compounds ($R^3$—Br), iodine compounds ($R^3$—I), methanesulphonates ($R^3$—OMs) or 4-methylbenzenesulphonates ($R^3$—OTs). The halide compounds or 4-methylbenzenesulphonates used are commercially available or can be prepared analogously to routes known from literature (for the preparation of 4-methylbenzenesulphonates, one example is the reaction of an appropriate alcohol with 4-methylbenzenesulphonyl chloride in the presence of triethylamine or pyridine; see, for example, Bioorganic and Medicinal Chemistry, 2006, 14, 12, 4277-4294). Optionally, in the case of use of chlorine compounds or bromine compounds, it is also possible to add an alkali metal iodide such as potassium iodide or sodium iodide. Bases used may, for example, be potassium carbonate, caesium carbonate or sodium hydride. Useful solvents include, for example, 1-methylpyrrolidin-2-one, DMF, DMSO or THF. If necessary, the halogen compounds or 4-methylbenzenesulphonates used may have functional groups which may have been protected with a protecting group beforehand (see also P. G. M. Wuts, T. W. Greene, *Greene's Protective Groups in Organic Synthesis*, Fourth Edition, ISBN: 9780471697541). If, for example, halogen compounds or alkyl 4-methylbenzenesulphonates having one or more hydroxyl groups are used, these hydroxyl groups may optionally be protected by a tert-butyl(dimethyl)silyl group or a similar silicon-containing protecting group familiar to those skilled in the art. Alternatively, the hydroxyl groups may also be protected by the tetrahydro-2H-pyran (THP) group or by the acetyl or benzoyl group. The protecting groups used can then be detached subsequently to the synthesis of Intermediate 3, or else as the last stage for release of the compounds according to the invention. If, for example, a tert-butyl(dimethylsilyl) group is used as protecting group, it can be detached using tetrabutylammonium fluoride in a solvent such as THF, for example. A THP protecting group can be detached, for example, using 4-methylbenzenesulphonic acid (optionally in monohydrate form). Acetyl groups or benzoyl groups can be detached by treatment with aqueous sodium hydroxide solution.

Alternatively, Intermediate 3 can be prepared via Mitsunobu reaction (see, for example, K. C. K. Swamy et. al. Chem. Rev. 2009, 109, 2551-2651) of Intermediate 7 with alcohol compounds ($R^3$—OH). It is possible to utilize various phosphines such as triphenylphosphine, tributylphosphine or 1,2-diphenylphosphinoethane in combination with diisopropyl azodicarboxylate (CAS 2446-83-5) or further diazene derivatives mentioned in the literature (K. C. K. Swamy et. al., Chem. Rev. 2009, 109, 2551-2651). Preference is given to the use of triphenylphosphine and diisopropyl azodicarboxylate. If the alcohol compound ($R^3$—OH) bears a functional group, it is possible—as in the abovementioned reactions with halogen compounds—to use known protecting group strategies (further pointers can be found in P. G. M. Wuts, T. W. Greene, Greene's Protective Groups in Organic Synthesis, Fourth Edition, ISBN: 9780471697541).

Synthesis Scheme 3

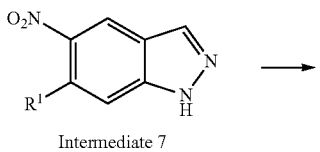

Intermediate 7

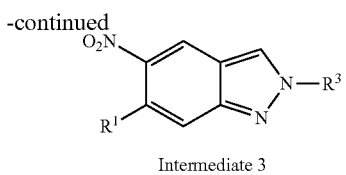

Intermediate 3

The substituents R[1] and R[3] have the definitions given in the general formula (I).

Selected Intermediates 7 can be obtained by nitration of suitable 6-substituted indazoles (see Synthesis Scheme 4). Useful methods for this purpose are nitration methods known to those skilled in the art, for example the use of nitric acid in combination with concentrated sulphuric acid. Some Intermediates 7 are known from the literature or commercially available or can be synthesized analogously to routes known from the literature (cf., for example, *Bioorganic and Medicinal Chemistry*, 2004, 12, 2115-2137).

Synthesis Scheme 4

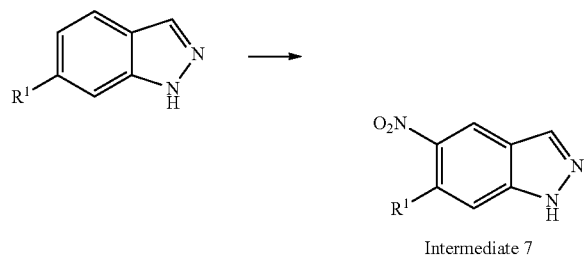

Intermediate 7

The substituent R[1] has the definitions given in the general formula (I).

Proceeding from the Intermediates 3, it is possible to prepare Intermediates 4 by reduction of the nitro group (see Synthesis Scheme 5). For example, the nitro group can be reduced with palladium on carbon under a hydrogen atmosphere (cf., for example, WO2013174744 for the reduction of 6-isopropoxy-5-nitro-1H-indazole to 6-isopropoxy-1H-indazol-5-amine) or by the use of iron and ammonium chloride in water and ethanol (see, for example, also Journal of the Chemical Society, 1955, 2412-2419), or by the use of tin(II) chloride (CAS 7772-99-8) (cf., for example, *Bioorganic and Medicinal Chemistry*, 2004, 12, 2115-2137). The use of iron and ammonium chloride in water and ethanol and the use of palladium on carbon under a hydrogen atmosphere are preferred.

Synthesis Scheme 5

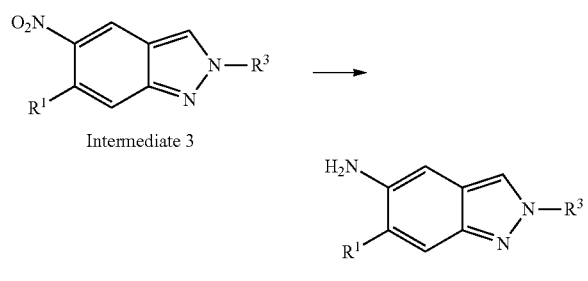

Intermediate 3

Intermediate 4

The substituents R[1] and R[3] have the definitions given in the general formula (I).

Proceeding from the Intermediates 4, it is possible to prepare inventive compounds of the general formula (I) (see Synthesis Scheme 6). For this purpose, it is possible to use various coupling reagents known from the literature (Amino Acids, Peptides and Proteins in Organic Chemistry, Vol. 3—Building Blocks, Catalysis and Coupling Chemistry, Andrew B. Hughes, Wiley, Chapter 12-Peptide-Coupling Reagents, 407-442; Chem. Soc. Rev., 2009, 38, 606). For example, it is possible to use 1-(3-dimethylaminopropyl)-3-ethylcarbodiimide hydrochloride in combination with 1-hydroxy-1H-benzotriazole hydrate (HOBt, WO2012107475; Bioorg. Med. Chem. Lett., 2008, 18, 2093), (1H-benzotriazol-1-yloxy)(dimethylamino)-N,N-dimethylmethaniminium tetrafluoroborate (TBTU, CAS 125700-67-6), (dimethylamino)-N,N-dimethyl(3H-[1,2,3]triazolo[4,5-b]pyridin-3-yloxy)methaniminium hexafluorophosphate (HATU, CAS 148893-10-1), propanephosphonic anhydride (as solution in ethyl acetate or DMF, CAS68957-94-8) or di-1H-imidazol-1-ylmethanone (CDI) as coupling reagents, with addition of a base such as triethylamine or N-ethyl-N-isopropylpropan-2-amine in each case to the reaction mixture. The coupling reagents are preferably HATU, N-[3-(dimethylamino)propyl]-N'-ethylcarbodiimide (EDC, CAS 1892-57-5) in combination with 1H-benzotriazol-1-ole hydrate (1:1) (HOBt, CAS123333-53-9) and TBTU. A base used with preference is N-ethyl-N-isopropylpropan-2-amine. Preferred solvents are THF or DMF.

Synthesis Scheme 6

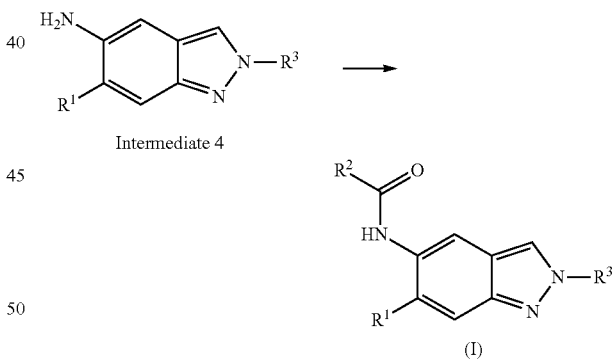

Preparation of compounds of the general formula (I) from Intermediate 4. The substituents R[1], R[2] and R[3] have the definitions given in the general formula (I).

Proceeding from 6-substituted indazoles that are known from the literature or commercially available, it is possible to prepare selected Intermediates 6 by Mitsunobu reaction with alcohols (R[3]—OH) or by alkylation with the appropriate halide reagents R[3]—Cl, R[3]—Br, R[3]—I or methanesulphonates (R[3]—OMs) or 4-methylbenzenesulphonates (R[3]—OTs) (cf. Synthesis Scheme 7). Useful methods for the Mitsunobu reaction and the alkylation are as described in Synthesis Scheme 3. For synthesis of Intermediate 3 proceeding from Intermediate 6, it is possible to employ nitration methods as described in Synthesis Scheme 4.

Synthesis Scheme 7

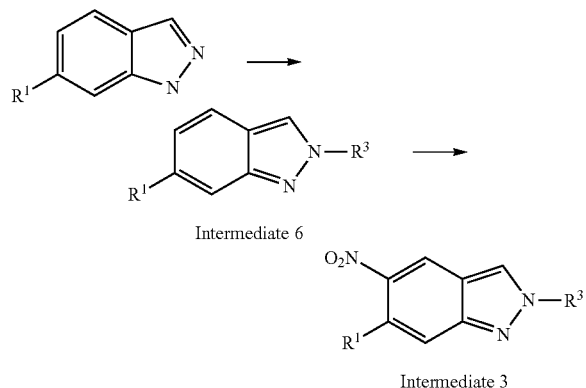

Intermediate 6

Intermediate 3

Alternative preparation of Intermediate 3: The substituents $R^1$ and $R^3$ have the definitions given in the general formula (I).

Alternatively, it is possible to obtain the compounds of the general formula (I) proceeding from Intermediate 5. For this purpose, Intermediate 5 can be reacted with halogen compounds $R^3$—I, $R^3$—Br, $R^3$—Cl, methanesulphonates ($R^3$—OMs) or 4-methylbenzenesulphonates ($R^3$—OTs) as described in Synthesis Scheme 3. Intermediate 5 can be prepared from the corresponding 5-aminoindazole by an amide synthesis with a carboxylic acid $R^2$—$CO_2H$ in the presence of a coupling reagent as described in Synthesis Scheme 6. Suitable 5-aminoindazoles are commercially available or can be prepared by routes known from the literature.

Synthesis Scheme 8

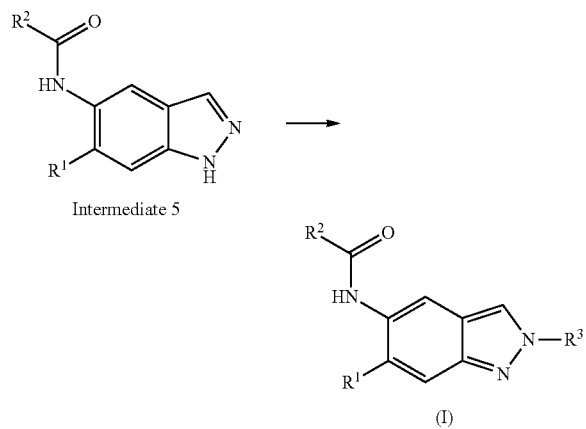

Intermediate 5

(I)

Preparation of compounds of the general formula (I) from Intermediate 5. The substituents $R^1$, $R^2$ and $R^3$ have the definitions given in the general formula (I).

If $R^1$ in the general formula (I) is defined as —$CO_2Me$ (see formula (I)-a), this —$CO_2Me$ group can be converted to alternative functional groups as known to those skilled in the art. More particularly, by reaction with methylmagnesium bromide, it is possible to obtain compounds of the general formula (I) with the definition $R^1$=—$C(OH)(CH_3)_2$. In addition, by reaction with ammonia, it is possible to prepare compounds of the general formula (I) in which $R^1$=—$CO_2NH_2$.

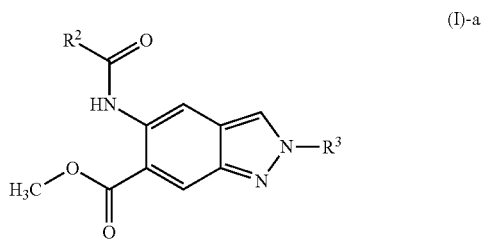

(I)-a

The substituents $R^2$ and $R^3$ have the definitions given in the general formula (I).

If $R^3$ has suitable functional groups, these can be derivatized by methods known to those skilled in the art (cf., for example, *Science of Synthesis*, Georg Thieme Verlag). For example, secondary amines can be converted to tertiary amino groups in the manner of an alkylation (cf., for example, the alkylation of 1-(piperidin-4-yl)-1H-indazole with 1-bromo-2-(2-methoxyethoxy)ethane in WO2007142584 or the alkylation of a pyrazole-piperidine derivative with 2-bromoethanol in US2015133422) or in the manner of a reductive amination (cf., for example, WO20148992 for a reductive amination with oxetan-3-one or US2002156081 for the reductive amination of a piperidine derivative with acetaldehyde). For the reductive amination, preference is given to the use of sodium triacetoxyborohydride in the presence of acetic acid. For the alkylation, preference is given to the use of potassium carbonate as base. Furthermore, secondary amines can be reacted with carboxylic acids in the manner of an amide coupling (for example by use of conditions as in Synthesis Scheme 6).

If, for example, the functional group is a sulphide group, this can be oxidized by methods known in the literature to a sulphoxide or sulphone group. If the group is a sulphoxide group, this can likewise be oxidized to a sulphone group or sulphoximine group (cf. *Angewandte Chemie*, 2013, 125, 9570). For the oxidation steps, it is possible to use, for example, 3-chloroperbenzoic acid (CAS 937-14-4) (in this regard, see also, for example, US201094000 for the oxidation of a 2-(methylsulphanyl)ethyl-1H-pyrazole derivative to a 2-(methylsulphinyl)ethyl-1H-pyrazole derivative and the oxidation of a further 2-(methylsulphanyl)ethyl-1H-pyrazole derivative to a 2-(methylsulphonyl)ethyl-1H-pyrazole derivative). If the functional group is a keto group, this can be reduced by reduction methods known to those skilled in the art to an alcohol group (see, for example, *Chemische Berichte*, 1980, 113, 1907-1920 for the use of sodium borohydride).

Synthesis of the Example Compounds

| Abbreviations and elucidations | |
|---|---|
| DMF | N,N-dimethylformamide |
| DMSO | dimethyl sulphoxide |
| THF | tetrahydrofuran |
| RT | room temperature |
| d. Th. | of theory |
| HPLC | high-performance liquid chromatography |
| h | hour(s) |
| min | minute(s) |
| UPLC | ultrahigh-performance liquid chromatography |
| DAD | diode array detector |
| ELSD | evaporating light scattering detector |
| ESI | electrospray ionization |

| Abbreviations and elucidations | |
|---|---|
| SQD | single quadrupole detector |
| CPG | core pulled precision glass |

The term sodium chloride solution always means a saturated aqueous sodium chloride solution.

The chemical names of the intermediates and examples were generated using the ACD/LABS (Batch Version 12.01.) software.

Methods

In some cases, the compounds according to the invention and precursors and/or intermediates thereof were analysed by LC-MS.

LC-MS Methods (Analytical):

Method A:

MS instrument: Waters ZMD mass spectrometer; HPLC instrument: Agilent 1100; column: Phenomenex Luna C18 (2) 3.0 micron 30 mm×4.6 mm; mobile phase A: water 0.1% formic acid, mobile phase B: acetonitrile 0.1% formic acid; gradient: 0.0 min 95% A→0.5 min 95% A→4.5 min 5% A→5.5 min 5% A; flow rate: 2.0 ml/min; UV detection: 190-450 nM.

Method B:

MS instrument: Waters Micromass ZQ2000; HPLC instrument: Waters Acquity UPLC system; column: Acquity UPLC BEH C18 1.7 micron 100 mm×2.1 mm; mobile phase A: water 0.1% formic acid, mobile phase B: acetonitrile 0.1% formic acid; gradient: 0.0 min 95% A→0.4 min 95% A→6.0 min 5% A→6.8 min 5% A; flow rate: 0.4 ml/min; UV detection: PDA.

Method C: UPLC (MeCN—HCOOH):

Instrument: Waters Acquity UPLC-MS SQD 3001; column: Acquity UPLC BEH C18 1.7 50×2.1 mm; eluent A: water+0.1% by vol. of formic acid (99%), eluent B: acetonitrile; gradient: 0-1.6 min 1-99% B, 1.6-2.0 min 99% B; flow 0.8 ml/min; temperature: 60° C.; injection: 2 µl; DAD scan: 210-400 nm; MS ESI+, ESI−, scan range 160-1000 m/z; ELSD.

Method D: UPLC (MeCN—NH$_3$):

Instrument: Waters Acquity UPLC-MS SQD 3001; column: Acquity UPLC BEH C18 1.7 50×2.1 mm; eluent A: water+0.2% by vol. of ammonia (32%), eluent B: acetonitrile; gradient: 0-1.6 min 1-99% B, 1.6-2.0 min 99% B; flow 0.8 ml/min; temperature: 60° C.; injection: 2 µl; DAD scan: 210-400 nm; MS ESI+, ESI−, scan range 160-1000 m/z; ELSD.

In some cases, the compounds according to the invention and the precursors and/or intermediates thereof were purified by the following illustrative preparative HPLC methods:

LC-MS Methods (Preparative):

Method E:

MS instrument: Agilent 1260 Infinity purification system. Agilent 6100 series single quadrupole LC/MS; column: XSEELECT CSH Prep C18 5 µm OBD, 30×150 mm; mobile phase A: 0.1% aqueous formic acid, mobile phase B: 0.1% formic acid in acetonitrile; gradient: 10%-95%, 22 min, centred around a specifically focussed gradient; flow rate: 60 ml/min. Sample: injection of 20-60 mg/ml solution in DMSO (+optionally formic acid and water)

Method F:

MS instrument: Agilent 1260 Infinity purification system. Agilent 6100 series single quadrupole LC/MS; column: XBridge Prep C18 5 µm OBD, 30×150 mm; mobile phase A: 0.1% aqueous ammonia, mobile phase B: 0.1% ammonia in acetonitrile; gradient: 10%-95%, 22 min, centred around a specifically focussed gradient; flow rate: 60 ml/min. Sample: injection of a 20-60 mg/ml solution in DMSO (+optionally formic acid and water)

Method G:

System: Waters Autopurification system: Pump 2545, Sample Manager 2767, CFO, DAD 2996, ELSD 2424, SQD; column: XBridge C18 5 µm 100×30 mm; eluent A: water+0.1% by vol. of formic acid, eluent B: acetonitrile; gradient: 0-8 min 10-100% B, 8-10 min 100% B; flow: 50 ml/min; temperature: room temperature; solution: max. 250 mg/max. 2.5 ml DMSO or DMF; injection: 1×2.5 ml; detection: DAD scan range 210-400 nm; MS ESI+, ESI−, scan range 160-1000 m/z.

Method H:

Waters Autopurification system: Pump 254, Sample Manager 2767, CFO, DAD 2996, ELSD 2424, SQD 3100; column: XBridge C18 5 µm 10×30 mm; eluent A: water+0.2% by vol. of ammonia (32%), eluent B: methanol; gradient: 0-8 min 30-70% B; flow: 50 ml/min; temperature: room temperature; detection: DAD scan range 210-400 nm; MS ESI+, ESI−, scan range 160-1000 m/z; ELSD.

In some cases, substance mixtures were purified by column chromatography on silica gel.

For preparation of some of the compounds according to the invention and the precursors and/or intermediates thereof, a column chromatography purification ("flash chromatography") was conducted on silica gel using Isolera® devices from Biotage. This was done using cartridges from Biotage, for example the "SNAP Cartridge, KP_SIL" cartridge of different size and "Interchim Puriflash Silica HP 15 UM flash column" cartridges from Interchim of different size.

Starting Compounds

Intermediate V2-1

Methyl 6-(2-hydroxypropan-2-yl)pyridine-2-carboxylate

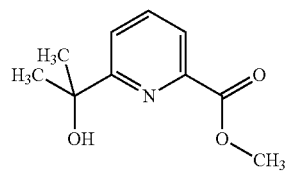

2.00 g (9.26 mmol) of 2-(6-bromopyridin-2-yl)propan-2-ol (CAS 638218-78-7) were dissolved in 20 ml of methanol and 20 ml of DMSO. Subsequently, 250 mg of 1,3-bis (diphenylphosphino)propane, 130 mg of palladium(II) acetate and 3 ml of triethylamine were added. The reaction mixture was purged three times with carbon monoxide at room temperature and stirred under a 13 bar carbon monoxide atmosphere for 30 min. The carbon monoxide atmosphere was removed by applying a vacuum and the mixture was stirred under a 14 bar carbon monoxide atmosphere at 100° C. for 24 h. The autoclave was decompressed, water was added to the reaction mixture, and the reaction mixture was extracted three times with ethyl acetate, washed with saturated aqueous sodium hydrogencarbonate solution and sodium chloride solution, filtered through a hydrophobic filter and concentrated. This gave 1.60 g of a crude product.

UPLC-MS (Method C): $R_t$=0.76 min (UV detector: TIC), mass found 195.00.

Intermediate V3-1

Potassium 6-(2-hydroxypropan-2-yl)pyridine-2-carboxylate

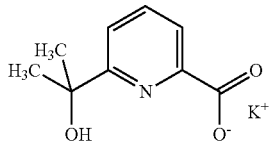

1.60 g of the crude product of Intermediate 0-1 were initially charged in 15 ml of methanol, 0.74 g of potassium hydroxide was added and the mixture was stirred at 50° C. for 16.5 h. After concentration, this gave 2.1 g of a residue which was used without further purification.

UPLC-MS (Method C): $R_t$=0.47 min (UV detector: TIC), mass found 181.00.

Intermediate 1A

2-Fluoro-4-methoxy-5-nitrobenzaldehyde

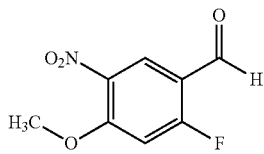

To 21 ml of cooled sulphuric acid were added 3 g (19.5 mmol) of 2-fluoro-4-methoxybenzaldehyde [CAS: 331-64-6], and the solution was kept cooled within a temperature range between −25° C. and −15° C. 1.83 g of 70% nitrating acid were added dropwise and the mixture was stirred between −25° C. and −15° C. for 45 minutes. The mixture was added to ice-water (100 ml) and left to stand for 30 minutes, and the solids were filtered off and washed with water. The solids were dissolved in dichloromethane, and the solution was washed with sodium hydrogencarbonate solution and concentrated. After purification by flash chromatography (Biotage Isolera, 100 g silica gel column, cyclohexane/ethyl acetate gradient), 2.73 g (13.7 mmol) of the title compound were obtained.

LC-MS (Method A): Rt=3.19 min; m/z=200 (M+H)+
$^1$H-NMR (300 MHz, CDCl$_3$): δ=4.06 (s, 3H), 6.87 (d, 1H), 8.45 (d, 1H), 10.22 (s, 1H)

Intermediate 1B

4-Chloro-2-fluoro-5-nitrobenzaldehyde

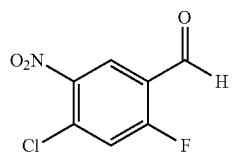 [SMILES: O=Cc1cc([N+](=O)[O-])c(Cl)cc1F]

To a solution, cooled to 0° C., of 2.81 g of potassium nitrate in 21 ml of sulphuric acid were added 4.0 g of 4-chloro-2-fluorobenzaldehyde, and the mixture was stirred at 0° C. for 0.5 h and at room temperature for 1 h. The mixture was added to ice-water and extracted twice with dichloromethane. The combined organic phases were washed with saturated sodium hydrogencarbonate solution, and the organic phase was removed and concentrated. This gave 5.1 g of the title compound.

$^1$H-NMR (300 MHz, CDCl3): δ=7.47 (d, 1H), 8.46 (d, 1H), 10.31 (s, 1H)

Intermediate 2A

2-Azido-4-methoxy-5-nitrobenzaldehyde

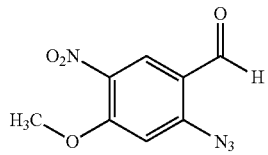 [SMILES: COc1cc(N=[N+]=[N-])c(C=O)cc1[N+](=O)[O-]]

To a solution of 2.73 g (13.7 mmol) of 2-fluoro-4-methoxy-5-nitrobenzaldehyde (Intermediate 1A) in 50 ml of dimethyl sulphoxide were added 1.78 g (27 mmol) of sodium azide, and the mixture was stirred at room temperature for 0.5 h. The mixture was diluted with 500 ml of ethyl acetate, washed three times with water and sodium chloride solution, dried over sodium sulphate, filtered and concentrated. This gave 2.91 g (13.1 mmol) of the title compound.

LC-MS (Method A): Rt=3.41 min; no ionization (M+H)+
$^1$H-NMR (300 MHz, CDCl$_3$): δ=4.09 (s, 3H), 6.80 (s, 1H), 8.46 (s, 1H), 10.20 (s, 1H)

Intermediate 2B

2-Azido-4-chloro-5-nitrobenzaldehyde

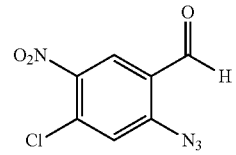 [SMILES: [N-]=[N+]=Nc1cc(Cl)c([N+](=O)[O-])cc1C=O]

5.1 g of 4-chloro-2-fluoro-5-nitrobenzaldehyde (Intermediate 1B) were reacted analogously to the preparation of Intermediate 1B with 1.63 g of sodium azide in 80 ml of DMSO within 1 h. This gave 5.35 g of the title compound.

$^1$H-NMR (300 MHz, CDCl3): δ=7.43 (s, 1H), 8.46 (s, 1H), 10.28 (s, 1H)

Intermediate 3A

6-Methoxy-5-nitro-2-(tetrahydro-2H-pyran-4-yl)-2H-indazole

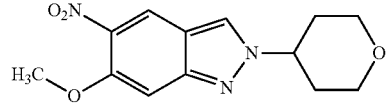 [SMILES: COc1cc2nn(C3CCOCC3)cc2cc1[N+](=O)[O-]]

To a solution of 2.4 g (10.8 mmol) of 2-azido-4-methoxy-5-nitrobenzaldehyde (Intermediate 2A) in 70 ml of dichloromethane were added 1.12 ml (10.8 mmol) of tetrahydro-2H-pyran-4-amine [38041-19-9] and 5 g of activated 4 angstrom molecular sieve. The reaction was stirred at room temperature for 3 h. The solution was filtered through Celite and the Celite was washed with dichloromethane, and the solvent was removed under reduced pressure. The crude product was dissolved in 50 ml of dry toluene and heated at 120° C. for 1 h. The mixture was allowed to come to room temperature and the solvent was removed under reduced pressure. The residue was purified by flash chromatography (Biotage Isolera, cyclohexane/ethyl acetate). This gave 2.22 g (8.0 mmol) of the title compound.

LC-MS (Method A): Rt=3.15 min; m/z=278 (M+H)+

$^1$H-NMR (300 MHz, CDCl$_3$): δ=2.19-2.29 (m, 4H), 3.55-3.66 (m, 2H), 3.97 (s, 3H), 4.11-4.22 (m, 2H), 4.56-4.68 (m, 1H), 7.12 (s, 1H), 8.08 (s, 1H), 8.21 (s, 1H)

Intermediate 3B tert-Butyl 4-(6-methoxy-5-nitro-2H-indazol-2-yl)piperidine-1-carboxylate

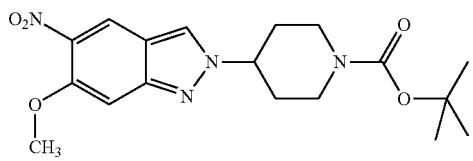 [SMILES: COc1cc2nn(C3CCN(C(=O)OC(C)(C)C)CC3)cc2cc1[N+](=O)[O-]]

To a solution of 2.65 g (11.9 mmol) of 2-azido-4-methoxy-5-nitrobenzaldehyde (Intermediate 2A) in 50 ml of dichloromethane were added a solution of 2.38 g (11.9 mmol) of tert-butyl 4-aminopiperidine-1-carboxylate [87120-72-7] in 20 ml of dichloromethane and 5 g of activated molecular sieve (4 angstroms). Thereafter, the mixture was stirred at room temperature for 3.5 h. A further solution of 0.79 g (4.0 mmol) of tert-butyl 4-aminopiperidine-1-carboxylate in 20 ml of dichloromethane and 5 g of activated 4 angstrom molecular sieve were added, and the mixture was stirred at room temperature for 19 h. The solution was filtered through Celite and washed through with dichloromethane, and the filtrate was concentrated under reduced pressure, dissolved in 50 ml of anhydrous toluene and then the mixture was heated at 120° C. for 1 h. The mixture was allowed to come to room temperature, the solvent was removed under reduced pressure and the residue was purified by flash chromatography (Biotage Isolera, 100 g silica gel column, cyclohexane/ethyl acetate), giving 4.25 g (11.3 mmol) of the title compound.

LC-MS (Method A): Rt=3.93 min; m/z=399 (M+Na)+

$^1$H-NMR (300 MHz, CDCl3): δ=1.49 (s, 9H), 2.08 (ddd, 2H), 2.24 (d, 2H), 2.95 (dd, 2H), 3.97 (s, 3H), 4.33 (d, 2H), 4.47-4.59 (m, 1H), 7.11 (s, 1H), 8.06 (s, 1H), 8.21 (s, 1H)

Intermediate 3C 2-(1,1-Dioxidotetrahydro-2H-thiopyran-4-yl)-6-methoxy-5-nitro-2H-indazole

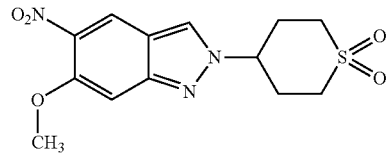 [SMILES: COc1cc2nn(C3CCS(=O)(=O)CC3)cc2cc1[N+](=O)[O-]]

2.5 g (13.5 mmol) of tetrahydro-2H-thiopyran-4-amine 1,1-dioxide [116529-31-8] were dissolved in 100 ml of dichloromethane. Then 3.0 g (13.5 mmol) of 2-azido-4-methoxy-5-nitrobenzaldehyde (Intermediate 2A) and 12 g of activated 4 angstrom molecular sieve were added. The mixture was stirred at room temperature under argon for 18 h, then filtered through Celite, and the Celite was washed with dichloromethane. The filtrate was concentrated under reduced pressure, 60 ml of anhydrous toluene were added, then the mixture was heated at 120° C. for 1.5 h. The reaction was cooled down to room temperature, and the solvents were concentrated under reduced pressure. This gave 4.39 g (13.5 mmol) of the title compound.

LC-MS (Method A): Rt=3.04 min; m/z=326 (M+H)+

$^1$H-NMR (300 MHz, DMSO-d6): δ=2.41-2.48 (m, 2H), 2.53-2.67 (m, 2H), 3.27 (s, 2H), 3.38-3.51 (m, 2H), 3.91 (s, 3H), 4.90-5.02 (m, 1H), 7.31 (s, 1H), 8.39 (s, 1H), 8.67 (s, 1H)

Intermediate 3D

6-Methoxy-5-nitro-2-(tetrahydro-2H-thiopyran-4-yl)-2H-indazole

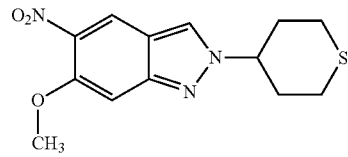 [SMILES: COc1cc2nn(C3CCSCC3)cc2cc1[N+](=O)[O-]]

To 0.949 g (4.3 mmol) of 2-azido-4-methoxy-5-nitrobenzaldehyde (Intermediate 2A) in 75 ml of dichloromethane were added 0.5 g (4.3 mmol) of tetrahydro-2H-thiopyran-4-amine [21926-00-1] and 2 g of activated 4 angstrom molecular sieve. Thereafter, the mixture was stirred at room temperature for 72 h. A further 75 mg (0.64 mmol) of tetrahydro-2H-thiopyran-4-amine [21926-00-1] and 2 g of activated 4 angstrom molecular sieve were added, and the mixture was stirred at room temperature for 4 h. The mixture was filtered through Celite, the filtrate was concentrated under reduced pressure, 20 ml of anhydrous toluene were added and the mixture was heated at 120° C. for 1.5 h. The reaction was cooled down to room temperature and the solvent was removed under reduced pressure. After the residue had been purified (Biotage Isolera (100 g silica gel column), cyclohexane/ethyl acetate gradient), 0.938 g (3.2 mmol) of the title compound was obtained.

LC-MS (Method A): Rt=3.64 min; m/z=294 (M+H)+

¹H-NMR (300 MHz, CDCl₃): δ=2.23-2.38 (m, 2H), 2.51-2.60 (m, 2H), 2.81-2.94 (m, 4H), 3.97 (s, 3H), 4.34-4.46 (m, 1H), 7.11 (s, 1H), 8.06 (s, 1H), 8.21 (s, 1H)

Intermediate 3E

6-Methoxy-5-nitro-2-(1-oxidotetrahydro-2H-thiopyran-4-yl)-2H-indazole (Isomer Mixture)

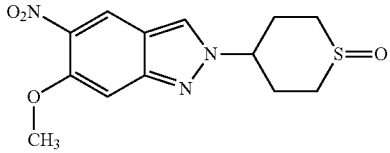 [SMILES: COc1cc2nn(C3CCS(=O)CC3)cc2cc1[N+](=O)[O-]]

To a solution of 850 mg (2.9 mmol) of 6-methoxy-5-nitro-2-(tetrahydro-2H-thiopyran-4-yl)-2H-indazole (Intermediate 3D) in 51 ml of 2:1 tetrahydrofuran/water at 0° C. were added 445 mg (0.724 mmol) of Oxone, and the reaction was stirred for 0.5 h. Two additions each of 445 mg (0.724 mmol) of Oxone were made within 1 h. Then 0.5 g of sodium metabisulphite was added and the reaction was partitioned between water and ethyl acetate, the organic phase was removed, the aqueous phase was extracted three times with ethyl acetate, and the organic phases were combined, washed with sodium chloride solution, dried over sodium sulphate, filtered and concentrated under reduced pressure. After purification (Biotage Isolera, 50 g silica gel column, dichloromethane/methanol), 710 mg (2.3 mmol) of the title compound were obtained.

LC-MS (Method A): Rt=2.76 & 2.83 min; m/z=310 (M+H)+

¹H-NMR (300 MHz, CDCl₃): δ=2.29-2.43 (m, 2H), 2.71-3.03 (m, 4H), 3.28 (d, 1H) 3.40-3.48 (m, 1H), 3.96-4.03 (m, 3H), 4.57-4.77 (m, 1H), 7.10 (s, 1H), 8.09-8.22 (m, 2H)

Intermediate 3F tert-Butyl rel-(1S,4S,5R)-5-(6-methoxy-5-nitro-2H-indazol-2-yl)-2-azabicyclo[2.2.1]heptane-2-carboxylate

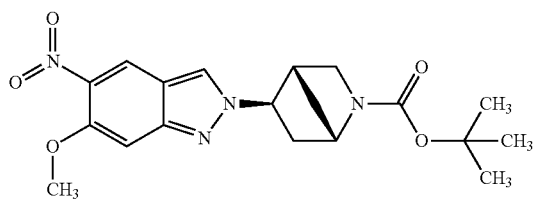 [SMILES: COc1cc2nn([C@@H]3C[C@@H]4C[C@H]3CN4C(=O)OC(C)(C)C)cc2cc1[N+](=O)[O-]]

Intermediate 3G tert-Butyl rel-(1S,4S,5S)-5-(6-methoxy-5-nitro-2H-indazol-2-yl)-2-azabicyclo[2.2.1]heptane-2-carboxylate

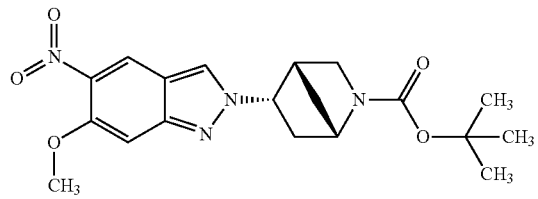 [SMILES: COc1cc2nn([C@H]3C[C@@H]4C[C@H]3CN4C(=O)OC(C)(C)C)cc2cc1[N+](=O)[O-]]

To a solution of 314 mg (1.4 mmol) of 2-azido-4-methoxy-5-nitrobenzaldehyde (Intermediate 2A) in 20 ml of dichloromethane were added a solution of 330 mg (1.55 mmol) of tert-butyl 5-amino-2-azabicyclo[2.2.1]heptane-2-carboxylate [207405-62-7] in 10 ml of dichloromethane and 0.773 ml (7.0 mmol) of trimethoxymethane [149-73-5], and the mixture was stirred at room temperature for 24 h. 30 ml of anhydrous toluene were added to the mixture, dichloromethane was partly evaporated off, and the solution was then heated at 120° C. for 1 h. The mixture was allowed to come to room temperature, the solvents were removed under reduced pressure and purification was effected by column chromatography on silica gel (Biotage Isolera (50 g silica gel column), cyclohexane/ethyl acetate), giving 193 mg (0.5 mmol) of Intermediate 3F and 336 mg (0.87 mmol) of Intermediate 3G.

LC-MS (Method A): Rt=4.03 min; m/z=389 (M+H)+

¹H-NMR (300 MHz, CDCl3): δ=1.48 (s, 9H), 1.78 (dd, 1H), 2.31-2.52 (m, 3H), 2.89-2.93 (m, 1H), 3.18 (dd, 1H), 3.38 (dd, 1H), 3.95 (s, 3H), 4.42 (d, 1H), 4.67 (dd, 1H), 7.10 (s, 1H), 8.08 (s, 1H), 8.18 (s, 1H). (Intermediate 3F)

LC-MS (Method A): Rt=3.88 min; m/z=333 (M-tBu+H)+

¹H-NMR (300 MHz, CDCl3): δ=1.47 (d, 9H), 1.80-1.94 (m, 2H), 2.34-2.57 (m, 2H), 2.78 (dd, 1H), 3.13-3.23 (m, 2H), 3.96 (s, 3H), 4.39 (d, 1H), 5.07-5.14 (m, 1H), 7.08 (s, 1H), 8.05 (d, 1H), 8.19 (s, 1H) (Intermediate 3G)

Intermediate 3H

6-Chloro-5-nitro-2-(tetrahydro-2H-pyran-4-yl)-2H-indazole

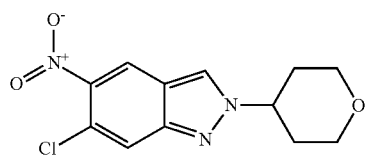 [SMILES: O=[N+]([O-])c1cc2cn(C3CCOCC3)nc2cc1Cl]

To a solution of 2.5 g (11.0 mmol) of 2-azido-4-chloro-5-nitrobenzaldehyde (Intermediate 2B) and 1.1 ml of 4-aminotetrahydro-2H-pyran in 50 ml of dichloromethane were added 6 ml (55 mmol) of trimethoxymethane (CAS 149-73-5), and the mixture was stirred at room temperature for 17 h. 50 ml of anhydrous toluene were added and the solvent was partly evaporated and the residue was heated at 120° C. for 1 h. The mixture was concentrated and the residue was purified by column chromatography on silica gel (Biotage Isolera, cyclohexane/ethyl acetate). This gave 2.06 g of the title compound as a yellow solid.

$^1$H-NMR (300 MHz, CDCl3): δ=2.20-2.30 (m, 4H), 3.56-3.66 (m, 2H), 4.14-4.23 (m, 2H), 4.62-4.75 (m, 1H), 7.85 (s, 1H), 8.19 (s, 1H), 8.34 (s, 1H).

Intermediate 3I

6-Chloro-2-(1,1-dioxidotetrahydro-2H-thiopyran-4-yl)-5-nitro-2H-indazole

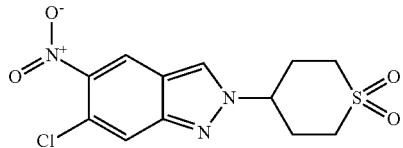 [SMILES: O=[N+]([O-])c1cc2cn(C3CCS(=O)(=O)CC3)nc2cc1Cl]

2.13 g of tetrahydro-2H-thiopyran-4-amine 1,1-dioxide hydrochloride (1:1) were dissolved in a mixture of water and methanol, and purified by means of an SCX cartridge (eluent: 2M ammonia in methanol). The resulting amine was dissolved in 50 ml of dichloromethane, and this solution was added to 2-azido-4-chloro-5-nitrobenzaldehyde (Intermediate 2B) in 50 ml of dichloromethane. The mixture was stirred at room temperature for 17 h, 50 ml of anhydrous toluene were added, and the solvent was partly evaporated. Then the mixture was heated at 120° C. for 1.5 h and allowed to come to room temperature, and the solids were filtered off and washed with diethyl ether. This gave 3 g of the title compound.

$^1$H-NMR (300 MHz, DMSO-d6): δ=2.42-2.45 (m, 2H), 2.53-2.69 (m, 2H), 3.20-3.28 (m, 2H), 3.40-3.53 (m, 2H), 4.99-5.11 (m, 1H), 8.08 (s, 1H), 8.67 (s, 1H), 8.87 (d, 1H)

Intermediate 3J 4-(6-Methoxy-5-nitro-2H-indazol-2-yl)pyrrolidin-2-one

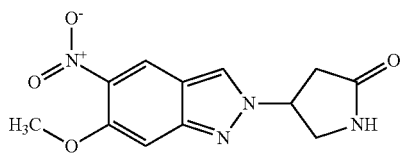 [SMILES: COc1cc2nn(C3CNC(=O)C3)cc2cc1[N+](=O)[O-]]

Analogously to the preparation of Intermediate 3I, 122 mg (0.9 mmol) of 4-aminopyrrolidin-2-one hydrochloride (1:1) were reacted with 0.2 g of 2-azido-4-methoxy-5-nitrobenzaldehyde (Intermediate 2A). This gave 200 mg of the title compound as a yellow solid.

$^1$H-NMR (300 MHz, DMSO): δ=2.65 (dd, 1H), 2.89 (dd, 1H), 3.48-3.53 (m, 1H), 3.86 (dd, 1H), 3.91 (s, 3H), 5.46-5.55 (m, 1H), 7.31-7.32 (m, 1H), 7.87 (s, 1H), 8.41 (s, 1H), 8.66 (d, 1H)

Intermediate 3K

Methyl 5-nitro-2-(tetrahydro-2H-pyran-4-yl)-2H-indazole-6-carboxylate

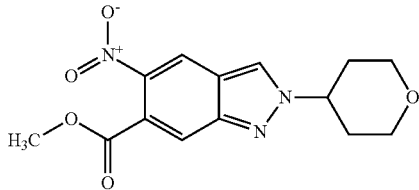 [SMILES: COC(=O)c1cc2nn(C3CCOCC3)cc2cc1[N+](=O)[O-]]

Preparation Method a), Nitration:
To an ice-cold solution of 985 mg of methyl 2-(tetrahydro-2H-pyran-4-yl)-2H-indazole-6-carboxylate (Intermediate 6A, crude product, contains fractions of triphenylphosphine oxide) in 8 ml of sulphuric acid were added 528 mg of potassium nitrate in portions. The mixture was left to stir in an ice-water cooling bath for 2 h and at room temperature for 17 h. The mixture was added to ice-water and extracted three times with ethyl acetate, and the combined organic phases were washed with sodium chloride solution, filtered through a hydrophobic filter and concentrated. This gave 1.14 g of the title compound.

UPLC-MS (Method C): Rt=0.96 min; mass found 305.00.
$^1$H-NMR (400 MHz, DMSO-d$_6$): δ [ppm]=2.00-2.21 (m, 4H), 3.31 (s, 1H), 3.43-3.62 (m, 2H), 4.03 (dt, 2H), 4.85-4.99 (m, 1H), 8.07-8.12 (m, 1H), 8.69 (s, 1H), 8.89-8.91 (m, 1H).

Preparation Method b), Mitsunobu Reaction:
2.00 g of methyl 5-nitro-1H-indazole-6-carboxylate (Intermediate 7A) were initially charged in 15 ml of THF. Thereafter, 3.56 g of triphenylphosphine, 1.20 g of tetrahydro-2H-pyran-4-ol, 1.9 ml of N-ethyl-N-isopropylpropan-2-amine and 1.9 ml of diisopropyl azodicarboxylate were added, and the mixture was stirred at room temperature for 20 h. Thereafter, another 0.3 equivalent of tetrahydro-2H-pyran-4-ol, 0.5 equivalent of triphenylphosphine and 0.5 equivalent of diisopropyl azodicarboxylate were added, and the mixture was stirred at room temperature for 4.5 h. Water was added, the mixture was extracted three times with ethyl acetate, and the extracts were washed with sodium chloride solution, filtered through a hydrophobic filter and concentrated. The residue was purified by column chromatography on silica gel (Isolera, hexane/ethyl acetate). This gave 1.92 g of the title compound (containing triphenylphosphine oxide as an accompanying component).

UPLC-MS (Method C): Rt=0.96 min; mass found 305.00.

Intermediate 3L

Methyl 5-nitro-2-[(3S)-tetrahydrofuran-3-yl]-2H-indazole-6-carboxylate

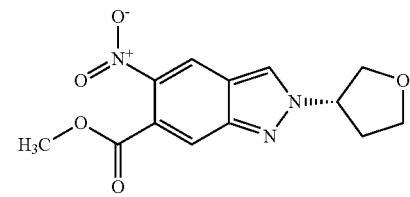

3.00 g of methyl 5-nitro-1H-indazole-6-carboxylate (Intermediate 7A) were initially charged in 25 ml of THF. Thereafter, 5.34 g of triphenylphosphine, 1.55 g of (3R)-tetrahydrofuran-3-ol, 3.5 ml of N-ethyl-N-isopropylpropan-2-amine and 4.0 ml of diisopropyl azodicarboxylate were added, and the mixture was stirred at room temperature for 17 h. Thereafter, another 0.3 equivalent of (3R)-tetrahydrofuran-3-ol, 0.5 equivalent of triphenylphosphine and 0.5 equivalent of diisopropyl azodicarboxylate were added, and the mixture was stirred at room temperature for 4 h. Water was added, the mixture was extracted three times with ethyl acetate, and the extracts were washed with sodium chloride solution, filtered through a hydrophobic filter and concentrated. The residue was purified by column chromatography on silica gel (Isolera, hexane/ethyl acetate). This gave 1.85 g of the title compound (containing triphenylphosphine oxide as an accompanying component).

UPLC-MS (Method C): Rt=0.90 min; mass found 291.00.

Intermediate 3M

Methyl 5-nitro-2-[(3R)-tetrahydrofuran-3-yl]-2H-indazole-6-carboxylate

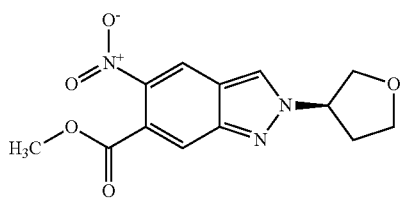

Analogously to the preparation of Intermediate 3L, 3.00 g of methyl 5-nitro-1H-indazole-6-carboxylate (Intermediate 7A) were reacted with 1.55 g of (3S)-tetrahydrofuran-3-ol. This gave 3.41 g of the title compound (containing triphenylphosphine oxide as an accompanying component).

UPLC-MS (Method C): Rt=0.90 min; mass found 291.00.

Intermediate 3N

Methyl 5-nitro-2-[(3S)-tetrahydrothiophen-3-yl]-2H-indazole-6-carboxylate

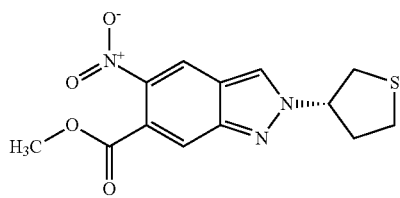 [SMILES: COC(=O)c1cc2nn([C@H]3CCOC3)cc2cc1[N+](=O)[O-]]

Step A: Preparation of (3R)-tetrahydrothiophen-3-yl 4-methylbenzenesulphonate

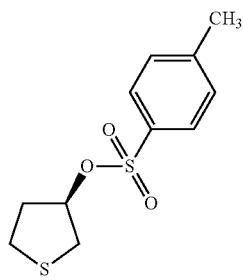 [SMILES: Cc1ccc(S(=O)(=O)O[C@@H]2CCSC2)cc1]

A solution of 1.00 g of (3R)-tetrahydrothiophen-3-ol in 20 ml of dichloromethane was cooled with an ice-water cooling bath, and 1.92 g of 4-methylbenzenesulphonyl chloride were added in portions. Thereafter, 2.7 ml of triethylamine and 56 mg of N,N-dimethylpyridin-4-amine (DMAP) were added, and the mixture was stirred at room temperature for 20 h. The mixture was added to saturated sodium hydrogencarbonate solution and stirred, and the organic phase was removed. The aqueous phase was extracted twice with dichloromethane, and the combined organic phases were washed with 1 M hydrochloric acid solution and saturated sodium carbonate solution, filtered through a hydrophobic filter and concentrated. The crude product was purified by column chromatography on silica gel (Isolera, hexane/ethyl acetate). This gave 443 mg of a colourless oil.

$^1$H-NMR (400 MHz, DMSO-$d_6$): δ [ppm]=1.81-1.92 (m, 1H), 2.08-2.16 (m, 1H), 2.44 (s, 3H), 2.73-2.90 (m, 3H), 3.02 (dd, 1H), 5.22 (tt, 1H), 7.50 (d, 2H), 7.79-7.86 (m, 2H).

Step B 304 mg of methyl 5-nitro-1H-indazole-6-carboxylate (Intermediate 7A) and 338 mg of (3R)-tetrahydrothiophen-3-yl 4-methylbenzenesulphonate were initially charged in 10 ml of 2-methyltetrahydrofuran. 0.54 g potassium carbonate was added and the mixture was stirred at 70° C. for 41.5 h. 2 ml of DMSO were added and the mixture was stirred at 70° C. for a further 21 h. The mixture was diluted with water and extracted three times with ethyl acetate. The combined organic phases were concentrated and purified by preparative HPLC. This gave 175 mg of methyl 5-nitro-2-[(3S)-tetrahydrothiophen-3-yl]-2H-indazole-6-carboxylate.

$^1$H-NMR (500 MHz, DMSO-$d_6$): δ [ppm]=2.52-2.56 (m, 1H, concealed signal), 2.60-2.68 (m, 1H), 2.92-3.05 (m, 2H), 3.33-3.45 (m, 2H, concealed signal), 3.85 (s, 3H), 5.48 (quin, 1H), 8.09 (s, 1H), 8.71 (s, 1H), 8.94-8.96 (m, 1H).

Intermediate 3O

Methyl 5-nitro-2-(tetrahydro-2H-thiopyran-4-yl)-2H-indazole-6-carboxylate

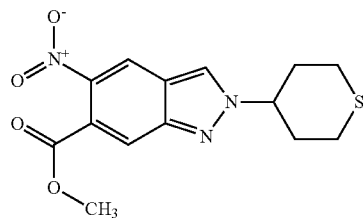 [SMILES: COC(=O)c1cc2nn(C3CCSCC3)cc2cc1[N+](=O)[O-]]

Preparation Method a):

Analogously to the preparation of Intermediate 3N, stage B, 2.71 g of methyl 5-nitro-1H-indazole-6-carboxylate (Intermediate 7A) were reacted with 5.00 g of tetrahydro-2H-thiopyran-4-yl 4-methylbenzenesulphonate in the presence of 5.07 g of potassium carbonate in 20 ml of DMF at 70° C. within 18 h.

Column chromatography purification on silica gel (Isolera, hexane/ethyl acetate) gave 1.09 g of the title compound.

UPLC-MS (Method C): Rt=1.12 min; mass found 321.00.

Preparation Method b):

Analogously to the preparation of Intermediate 3L, 2.50 g of methyl 5-nitro-1H-indazole-6-carboxylate (Intermediate 7A) were reacted with 1.74 g of tetrahydro-2H-thiopyran-4-ol. Column chromatography purification on silica gel (Isolera, hexane/ethyl acetate) gave 1.42 g of the title compound as a crude product.

UPLC-MS (Method C): Rt=1.12 min; mass found 321.00.

Intermediate 3P

Methyl 2-[1-(tert-butoxycarbonyl)piperidin-4-yl]-5-nitro-2H-indazole-6-carboxylate

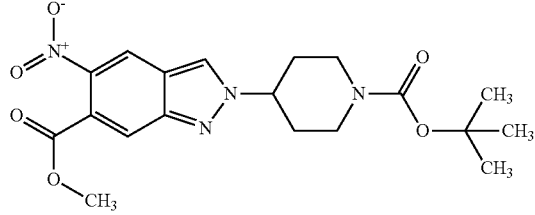 [SMILES: COC(=O)c1cc2nn(C3CCN(C(=O)OC(C)(C)C)CC3)cc2cc1[N+](=O)[O-]]

Analogously to the preparation of Intermediate 3L, 2.00 g of methyl 5-nitro-1H-indazole-6-carboxylate (Intermediate 7A) were reacted with 2.37 g of tert-butyl 4-hydroxypiperidine-1-carboxylate, 3.56 g of triphenylphosphine, 2.3 ml of N-ethyl-N-isopropylpropan-2-amine and 2.6 ml of diisopropyl azodicarboxylate in 20 ml of THF at room temperature within 20.5 h. After column chromatography purification on silica gel, 1.44 g of the title compound were obtained as a crude product (containing fractions of triphenylphosphine oxide as well as other constituents).

$^1$H-NMR (500 MHz, DMSO-$d_6$, selected signals): δ [ppm]=1.43 (s), 2.12-2.19 (m, 2H), 2.97 (broad singlet, 2H), 3.84 (s, 3H), 4.03 (d, 3H), 4.06-4.19 (broad signal, 2H), 4.82-4.91 (m, 1H), 7.52-7.67 (m, 13H), 8.07 (s, 1H), 8.68 (s, 1H), 8.89-8.91 (m, 1H).

Intermediate 4A

6-Methoxy-2-(tetrahydro-2H-pyran-4-yl)-2H-indazol-5-amine

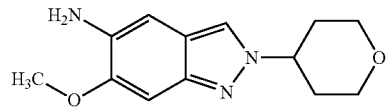

222 mg of 10% palladium on charcoal (50% w/w) were initially charged under nitrogen, then a solution of 2.22 g (8.0 mmol) of 6-methoxy-5-nitro-2-(tetrahydro-2H-pyran-4-yl)-2H-indazole (Intermediate 3A) in 120 ml of ethanol was added. The reaction was then stirred in a hydrogen atmosphere under standard pressure for 17 h. The solution was filtered through Celite, then the Celite was washed with ethanol and 20% ethanol/dichloromethane. The filtrate was concentrated under reduced pressure and admixed with ethanol, and the solids formed were filtered off and dried. This gave 1.5 g (6.0 mmol) of the title compound.

LC-MS (Method A): Rt=0.43 min; m/z=248 (M+H)+

$^1$H-NMR (300 MHz, CDCl$_3$): δ=2.14-2.24 (m, 4H), 3.53-3.63 (m, 2H), 3.82-3.90 (m, 2H), 3.92 (s, 3H), 4.10-4.17 (m, 2H), 4.45-4.57 (m, 1H), 6.75 (s, 1H), 6.95 (s, 1H), 7.63 (d, 1H)

Intermediate 4B tert-Butyl 4-(5-amino-6-methoxy-2H-indazol-2-yl)piperidine-1-carboxylate

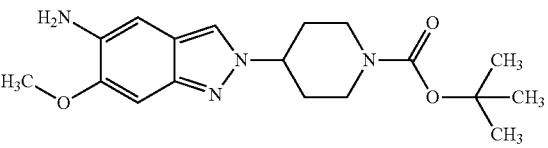

220 mg of 10% palladium on charcoal (50% w/w) were initially charged, followed by evaporation and purging with nitrogen. Then a solution of 2.1 g (5.6 mmol) of tert-butyl 4-(6-methoxy-5-nitro-2H-indazol-2-yl)piperidine-1-carboxylate (Intermediate 3B) in 80 ml of ethanol was added. The mixture was stirred in a hydrogen atmosphere under standard pressure for 24 h. The solution was filtered through Celite and washed through with ethanol, and the filtrate was concentrated under reduced pressure. Thereafter, dichloromethane and cyclohexane were added and the mixture was concentrated. This gave 1.81 g (5.2 mmol) of the title compound.

LC-MS (Method A): Rt=2.53 min; m/z=347 (M+H)+

$^1$H NMR (300 MHz, CDCl$_3$): δ=1.48 (9H, s), 2.04 (2H, ddd), 2.19 (2H, d), 2.92 (2H, t), 3.84 (2H, s), 3.91 (3H, s), 4.21-4.34 (2H, m), 4.36-4.48 (1H, m), 6.75 (1H, s), 6.94 (1H, s), 7.60 (1H, s)

Intermediate 4C

2-(1,1-Dioxidotetrahydro-2H-thiopyran-4-yl)-6-methoxy-2H-indazol-5-amine

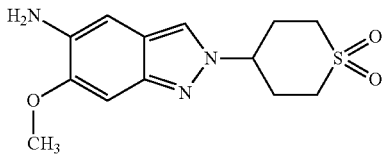

4.39 g (13.5 mmol) of 2-(1,1-dioxidotetrahydro-2H-thiopyran-4-yl)-6-methoxy-5-nitro-2H-indazole (Intermediate 3C) in 150 ml of ethanol and 439 mg of 10% palladium on charcoal were stirred under a hydrogen atmosphere at room temperature for 21 h. The hydrogen atmosphere was removed, another 439 mg of 10% palladium on charcoal were added, and the mixture was stirred in a hydrogen atmosphere for 71 h. The hydrogen atmosphere was removed, a further 50 ml of ethanol and 439 mg of 10% palladium on charcoal were added, and the mixture was stirred under a hydrogen atmosphere for 16 h. The mixture was filtered through Celite, and the Celite was washed with ethanol with 10% ethanol/dichloromethane and 25% ethanol/dichloromethane. After concentration, this gave 2.55 g (8.6 mmol) of the title compound.

LC-MS (Method A): Rt=0.43 min; m/z=296 (M+H)+

$^1$H-NMR (300 MHz, DMSO-d6): δ=2.32-2.39 (m, 2H), 2.44-2.58 (m, 2H), 3.22-3.29 (m, 2H), 3.37-3.45 (m, 2H), 3.82 (s, 3H), 4.62 (s, 2H), 4.68-4.79 (m, 1H), 6.62 (s, 1H), 6.86 (s, 1H), 7.91 (s, 1H)

Intermediate 4D

6-Methoxy-2-(1-oxidotetrahydro-2H-thiopyran-4-yl)-2H-indazol-5-amine (Isomer Mixture)

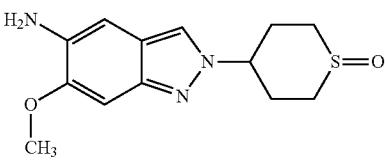

A mixture of 710 mg (2.3 mmol) of 6-methoxy-5-nitro-2-(1-oxidotetrahydro-2H-thiopyran-4-yl)-2H-indazole (Intermediate 3E) in 50 ml of ethanol and 71 mg of 10% palladium on carbon was put under a hydrogen atmosphere for 24 h. Then another 71 mg of 10% palladium on carbon were added and the mixture was stirred under a hydrogen atmosphere for 5 h. The reaction was filtered through Celite, the Celite was washed with ethanol and the filtrate was concentrated under reduced pressure. 426 mg (1.5 mmol) of the title compound were obtained.

LC-MS (Method A): Rt=0.44 min; m/z=280 (M+H)+

$^1$H-NMR (300 MHz, CDCl3): δ=2.26-2.44 (m, 2H), 2.63-2.96 (m, 4H), 3.20-3.28 (m, 1H), 3.35-3.46 (m, 1H), 3.91-3.93 (m, 3H), 4.50-4.62 (m, 1H), 6.74-6.77 (m, 1H), 6.92 (s, 1H), 7.61-7.71 (m, 1H)

Intermediate 4E tert-Butyl rel-(1S,4S,5R)-5-(5-amino-6-methoxy-2H-indazol-2-yl)-2-azabicyclo[2.2.1]heptane-2-carboxylate

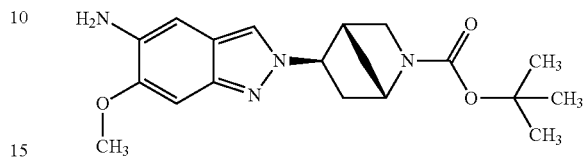

A mixture of 193 mg (0.497 mmol) of tert-butyl rel-(1S,4S,5R)-5-(6-methoxy-5-nitro-2H-indazol-2-yl)-2-azabicyclo[2.2.1]heptane-2-carboxylate (Intermediate 3F) and 40 mg of 10% palladium on carbon in 20 ml of ethanol was treated with a hydrogen atmosphere for 5 h. The mixture was filtered through Celite and washed through with ethanol, and the solvent was removed under reduced pressure. This gave 150 mg (0.418 mmol) of the target compound.

LC-MS (Method A): Rt=2.64 min; m/z=359 (M+H)+

$^1$H-NMR (300 MHz, CDCl3): δ=1.49 (s, 9H), 1.72 (t, 1H), 2.23-2.42 (m, 3H), 2.88 (s, 1H), 3.11-3.21 (m, 1H), 3.35 (dd, 1H), 3.85 (s, 2H), 3.91 (s, 3H), 4.40 (d, 1H), 4.58 (dd, 1H), 6.73 (s, 1H), 6.94 (s, 1H), 7.63 (s, 1H).

Intermediate 4F tert-Butyl rel-(1S,4S,5S)-5-(5-amino-6-methoxy-2H-indazol-2-yl)-2-azabicyclo[2.2.1]heptane-2-carboxylate

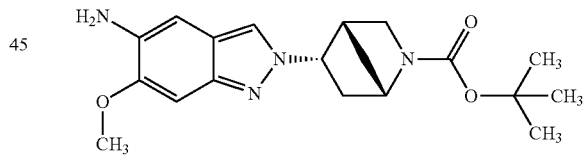

A mixture of 336 mg (0.865 mmol) of tert-butyl rel-(1S,4S,5S)-5-(6-methoxy-5-nitro-2H-indazol-2-yl)-2-azabicyclo[2.2.1]heptane-2-carboxylate (Intermediate 3G) and 72 mg of 10% palladium on charcoal in 20 ml of ethanol was treated with a hydrogen atmosphere for 19 h. The mixture was filtered through Celite and washed through with ethanol, and the solvent was removed under reduced pressure. This gave 297 mg (0.829 mmol) of the title compound.

LC-MS (Method A): Rt=2.50 & 2.53 min; m/z=359 (M+H)+

$^1$H-NMR (300 MHz, CDCl3): δ=1.45 (d, 9H), 1.74-1.91 (m, 2H), 2.27-2.51 (m, 2H), 2.72-3.01 (m, 1H), 3.08-3.18 (m, 2H), 3.84-3.85 (m, 2H), 3.91 (s, 3H), 4.29-4.40 (m, 1H), 5.00-5.07 (m, 1H), 6.74 (s, 1H), 6.89-6.94 (m, 1H), 7.60-7.65 (m, 1H).

Intermediate 4G

6-Chloro-2-(tetrahydro-2H-pyran-4-yl)-2H-indazol-5-amine

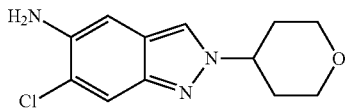

1.39 g of 6-chloro-5-nitro-2-(tetrahydro-2H-pyran-4-yl)-2H-indazole (Intermediate 3H) were initially charged in 20 ml of ethanol and 3 ml of water. Thereafter, 132 mg of ammonium chloride and 2.76 g of iron were added, and the mixture was stirred at 90° C. for 1.5 h. The mixture was filtered through Celite, washed through with ethanol and concentrated. In the course of this, a solid precipitated out, which was filtered off with suction and washed with water and diethyl ether. After the solid had been dried, 183 mg of the title compound were obtained. Another wash of the Celite with a dichloromethane/THF mixture, subsequent concentration and extraction of the residue by stirring with diethyl ether and drying led to a further 617 mg of the title compound.

$^1$H-NMR (400 MHz, DMSO-$d_6$): δ [ppm]=1.99-2.12 (m, 4H), 3.43-3.55 (m, 2H), 3.93-4.03 (m, 2H), 4.54-4.67 (m, 1H), 4.93 (s, 2H), 6.87 (s, 1H), 7.60 (s, 1H), 8.09 (s, 1H).

Intermediate 4H

6-Chloro-2-(1,1-dioxidotetrahydro-2H-thiopyran-4-yl)-2H-indazol-5-amine

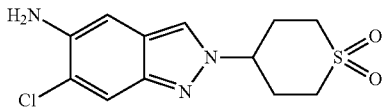

To a mixture of 2.78 g (8.4 mmol) of 6-chloro-2-(1,1-dioxidotetrahydro-2H-thiopyran-4-yl)-5-nitro-2H-indazole (Intermediate 3I) and 2.35 g (42 mmol) of iron powder in 44 ml of ethanol was added a solution of 1.35 g (25.3 mmol) of ammonium chloride in 22 ml of water, and the mixture was heated at 70° C. for 40 min. After cooling to room temperature, the mixture was filtered (Whatman filter cups, washing with ethanol) and the filtrate was concentrated. Thereafter, the mixture was partitioned between saturated aqueous sodium hydrogencarbonate solution and a mixture of 10% methanol in dichloromethane. The aqueous phase was re-extracted and the combined organic phases were filtered. After concentration under reduced pressure, 2.22 g of the title compound were obtained.

$^1$H-NMR (300 MHz, CDCl3): δ=2.60-2.76 (m, 4H), 3.06-3.18 (m, 2H), 3.51-3.63 (m, 2H), 4.00 (s, 2H), 4.62-4.71 (m, 1H), 6.87 (s, 1H), 7.70 (s, 2H).

Intermediate 4I rac-4-(5-Amino-6-methoxy-2H-indazol-2-yl)pyrrolidin-2-one

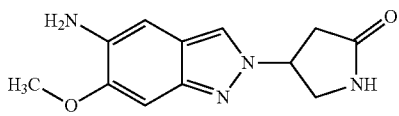 [SMILES: COc1cc2nn(C3CNC(=O)C3)cc2cc1N]

To 200 mg (0.724 mmol) of 4-(6-methoxy-5-nitro-2H-indazol-2-yl)pyrrolidin-2-one (Intermediate 3J) in 20 ml of ethanol were added 20 mg of 10% palladium on carbon (50% water-moist), and the mixture was stirred under a hydrogen atmosphere for 18 h. 20 mg of 10% palladium on charcoal (50% water-moist) were added and the mixture was stirred under a hydrogen atmosphere for 21 h. The mixture was filtered through Celite, the Celite was washed with ethanol and the filtrate was concentrated. This gave 119 mg of the title compound (as a crude product).

$^1$H-NMR (300 MHz, CDCl3): d=2.93-2.99 (m, 2H), 3.84-3.98 (m, 7H), 5.23-5.33 (m, 1H), 5.73-5.77 (m, 1H), 6.72 (s, 1H), 6.93 (s, 1H), 7.65 (s, 1H)

Intermediate 4J

Methyl 5-amino-2-(tetrahydro-2H-pyran-4-yl)-2H-indazole-6-carboxylate

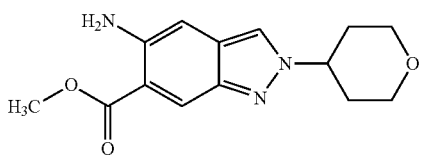 [SMILES: COC(=O)c1cc2nn(C3CCOCC3)cc2cc1N]

1.13 g of methyl 5-nitro-2-(tetrahydro-2H-pyran-4-yl)-2H-indazole-6-carboxylate (Intermediate 3K) were initially charged in 10 ml of ethanol and 2 ml of water. Thereafter, 84 mg of ammonium chloride and 1.76 g of iron were added, and the mixture was stirred at 90° C. for 2 h. The mixture was filtered through Celite and washed with ethanol, and some of the solvent was removed on a rotary evaporator. Thereafter, the mixture was extracted with ethyl acetate, and the extracts were washed with sodium chloride solution, filtered through a hydrophobic filter and concentrated. 892 mg of the title compound were obtained as a crude product.

$^1$H-NMR (400 MHz, DMSO-$d_6$): δ [ppm]=2.01-2.14 (m, 4H), 3.44-3.55 (m, 2H), 3.84 (s, 3H), 3.95-4.03 (m, 2H), 4.61-4.75 (m, 1H), 5.81 (s, 2H), 6.79-6.82 (m, 1H), 8.11 (d, 1H), 8.18-8.21 (m, 1H).

Intermediate 4K

Methyl 5-amino-2-[(3S)-tetrahydrothiophen-3-yl]-2H-indazole-6-carboxylate

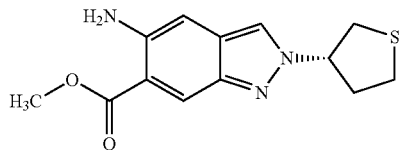 [SMILES: COC(=O)c1cc2nn([C@H]3CCOC3)cc2cc1N]

Analogously to the preparation of Intermediate 4J, 167 mg of methyl 5-nitro-2-[(3S)-tetrahydrothiophen-3-yl]-2H-indazole-6-carboxylate (Intermediate 3N) were reacted with 303 mg of iron, 15 mg of ammonium chloride in 7.5 ml of ethanol and 2.5 ml of water at 90° C. within 17.5 h. Purification of the crude product by preparative HPLC gave 91 mg of the title compound.

UPLC (Method C): Rt=0.83 min; mass found 277.00.

Intermediate 4L

Methyl 5-amino-2-[(3S)-tetrahydrofuran-3-yl]-2H-indazole-6-carboxylate

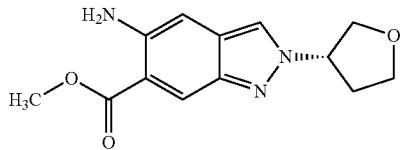

To 1.85 g of methyl 5-nitro-2-[(3S)-tetrahydrofuran-3-yl]-2H-indazole-6-carboxylate (Intermediate 3L, batch contained triphenylphosphine oxide) in 4.9 ml of water and 28 ml of ethanol were added 1.24 g of iron powder and 119 mg of ammonium chloride. The mixture was heated under reflux for 3 h, filtered through Celite and washed through with ethyl acetate. The filtrate was partly concentrated, ethyl acetate was added and the mixture was acidified to pH=3 with 1 N aqueous hydrochloric acid. The phases were separated and the aqueous phase was extracted with ethyl acetate. The aqueous phase was adjusted to pH=8 with 1 M sodium hydroxide solution and extracted with ethyl acetate. The combined organic phases were concentrated. This gave 759 mg of the title compound with small fractions of triphenylphosphine oxide.

$^1$H-NMR (500 MHz, DMSO-d$_6$): δ [ppm]=2.35-2.42 (m, 1H), 2.44-2.49 (m), 3.83-3.90 (m, 4H), 3.99-4.10 (m, 3H), 5.26-5.32 (m, 1H), 5.83 (s, 2H), 6.81 (d, 1H), 8.08 (d, 1H), 8.21 (s, 1H).

Intermediate 4M

Methyl 5-amino-2-[(3R)-tetrahydrofuran-3-yl]-2H-indazole-6-carboxylate

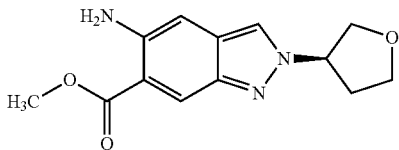 [SMILES: COC(=O)c1cc2nn([C@@H]3CCOC3)cc2cc1N]

Analogously to the preparation of Intermediate 4L, 200 mg of methyl 5-nitro-2-[(3R)-tetrahydrofuran-3-yl]-2H-indazole-6-carboxylate (Intermediate 3M, batch contained triphenylphosphine oxide) were reacted with 383 mg of iron and 37 mg of ammonium chloride in 4 ml of ethanol and 0.7 ml of water under reflux within 3 h. In a second reaction batch, 3.21 g of methyl 5-nitro-2-[(3R)-tetrahydrofuran-3-yl]-2H-indazole-6-carboxylate (Intermediate 3M, batch contained triphenylphosphine oxide) were reacted with 3.99 g of iron and 383 mg of ammonium chloride in 42 ml of ethanol and 7 ml of water. The two reaction batches were combined and worked up as in the preparation of Intermediate 4L. This gave 552 mg of the title compound (crude product) as a brown solid.

$^1$H-NMR (400 MHz, DMSO-d$_6$): δ [ppm]=2.31-2.49 (m), 3.83-3.90 (m, 5H), 3.98-4.12 (m, 3H), 5.26-5.33 (m, 1H), 5.84 (s, 2H), 6.80-6.83 (m, 1H), 8.11 (d, 1H), 8.21 (s, 1H).

Intermediate 4N

Methyl 5-amino-2-(tetrahydro-2H-thiopyran-4-yl)-2H-indazole-6-carboxylate

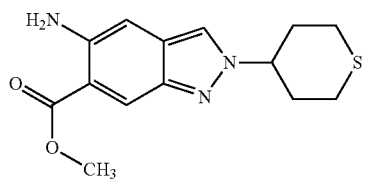 [SMILES: COC(=O)c1cc2nn(C3CCSCC3)cc2cc1N]

Analogously to the preparation of Intermediate 4J, 1.09 g of methyl 5-nitro-2-(tetrahydro-2H-thiopyran-4-yl)-2H-indazole-6-carboxylate (Intermediate 3O) were reacted with 1.27 g of iron, 61 mg of ammonium chloride in 10 ml of ethanol and 2 ml of water at 85° C. within 20.5 h. 992 mg of a crude product were obtained after analogous workup.

Intermediate 4O

Methyl 5-amino-2-[1-(tert-butoxycarbonyl)piperidin-4-yl]-2H-indazole-6-carboxylate

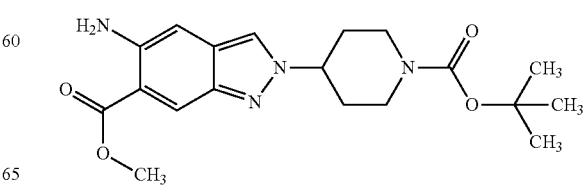

Analogously to the preparation of Intermediate 4J, 6.09 g of methyl 2-[1-(tert-butoxycarbonyl)piperidin-4-yl]-5-nitro-2H-indazole-6-carboxylate (Intermediate 3P) were reacted with 6.06 g of iron, 299 mg of ammonium chloride in 35 ml of ethanol and 7 ml of water at 85° C. within 19.5 h. 5.52 g of a crude product were obtained after analogous workup.

Intermediate 5A

N-(6-Methoxy-1H-indazol-5-yl)-6-(trifluoromethyl)pyridine-2-carboxamide

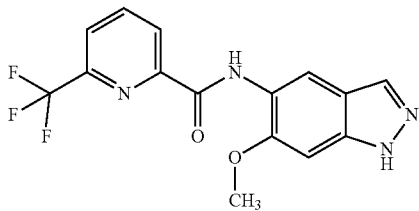 [SMILES: COc1cc2[nH]ncc2cc1NC(=O)c1cccc(C(F)(F)F)n1]

3.84 g (23.5 mmol) of 6-methoxy-1H-indazol-5-amine (CAS No.: 749223-61-8) and 4.95 g (25.9 mmol) of 6-(trifluoromethyl)pyridine-2-carboxylic acid were dissolved in 150 ml of tetrahydrofuran, and 3.60 g (23.5 mmol) of 1-hydroxy-1H-benzotriazole hydrate, 9.02 g (47.1 mmol) of 1-(3-dimethylaminopropyl)-3-ethylcarbodiimide hydrochloride and 9.84 ml (70.6 mmol) of triethylamine were added at 25° C. The solution was stirred at 25° C. for 24 h. After concentration of the solution, the residue was taken up in ethyl acetate, water was added and the aqueous phase was extracted three times with ethyl acetate. The combined organic phases were washed with saturated sodium chloride solution and dried over sodium sulphate and, after filtration, the solution was concentrated. The residue was purified by column chromatography purification on silica gel (Isolera flash purification system (Biotage), hexane/ethyl acetate). This gave 3.75 g of the title compound.

UPLC-MS (Method C): $R_t$=1.12 min

MS (ESIpos): m/z=337 (M+H)$^+$ $^1$H-NMR (400 MHz, DMSO-d6): δ=4.01 (s, 3H), 7.13 (s, 1H), 8.02 (s, 1H), 8.21 (dd, 1H), 8.40 (t, 1H), 8.47 (d, 1H), 8.74 (s, 1H), 10.42 (s, 1H), 12.91 (s, 1H).

Intermediate 6A

Methyl 2-(tetrahydro-2H-pyran-4-yl)-2H-indazole-6-carboxylate

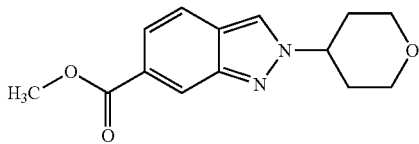 [SMILES: COC(=O)c1ccc2cn(C3CCOCC3)nc2c1]

Preparation Method A: Mitsunobu Reaction:

A suspension of 7.00 g of methyl 1H-indazole-6-carboxylate in 80 ml of THF was cooled by an ice-water cooling bath. 4.5 ml of tetrahydro-2H-pyran-4-ol, 3.1 g of triphenylphosphine and 2.3 ml of diisopropyl azodicarboxylate (DIAD, CAS 2446-83-5) were added and the mixture was left to stir at room temperature for 19 h. Another 3.1 g of triphenylphosphine and 2.3 ml of diisopropyl azodicarboxylate were added, and the mixture was stirred at room temperature for 71 h and at 70° C. for 5 h. Water was added, the mixture was extracted three times with ethyl acetate, and the combined organic phases were washed with sodium chloride solution and concentrated. The residue was purified by column chromatography on silica gel (Isolera, eluent: hexane/ethyl acetate). This gave 11.0 g of a solid which was extracted by stirring with diethyl ether. Drying gave 8.95 g of a crude product (according to UPLC analysis, contains the title compound together with triphenylphosphine oxide). The diethyl ether wash phase was concentrated. This gave 1.78 g of a solid (title compound as crude product, contains triphenylphosphine oxide).

UPLC-MS (Method C): Rt=0.94 min; mass found 260.00

Preparation Method B: Alkylation 5.00 g of methyl 1H-indazole-6-carboxylate were initially charged in 50 ml of DMF. 7.0 g of 4-bromotetrahydro-2H-pyran, 11.8 g of potassium carbonate and 7.07 g of potassium iodide were added, and the mixture was stirred at 100° C. for 16.5 h. Water was added, the mixture was extracted five times with ethyl acetate and the extracts were washed with sodium chloride solution and concentrated. This gave 8.99 g of an oil which was initially charged in 30 ml of DMF. 6.0 g of 4-bromotetrahydro-2H-pyran and 10.2 g of potassium carbonate were added, and the mixture was stirred at 120° C. for 20.5 h. Water was added, the mixture was extracted with ethyl acetate and the extract was washed with sodium chloride solution and concentrated. This gave 5.73 g of a residue (contained product according to UPLC, Rt=0.94 min). This was combined with 8.95 g of the crude product from Preparation method A, and purified by column chromatography on silica gel (Isolera, hexane/ethyl acetate). This gave 1.41 g of a solid which was extracted by stirring with diethyl ether. After drying, 991 mg of the title compound were obtained.

$^1$H-NMR (500 MHz, DMSO-d$_6$): δ [ppm]=2.08-2.19 (m, 4H), 3.54 (td, 2H), 3.88 (s, 3H), 3.99-4.06 (m, 2H), 4.83 (tt, 1H), 7.57 (dd, 1H), 7.81 (dd, 1H), 8.31 (q, 1H), 8.58 (d, 1H).

Intermediate 7A

Methyl 5-nitro-1H-indazole-6-carboxylate

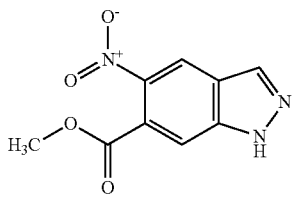 [SMILES: COC(=O)c1cc2[nH]ncc2cc1[N+](=O)[O-]]

4.60 g (26.1 mmol) of methyl 1H-indazole-6-carboxylate (CAS No: 170487-40-8) were dissolved in 120 ml of sulphuric acid (96%) and cooled to −15° C. in a three-neck flask having a CPG stirrer, dropping funnel and internal thermometer. Over a period of 15 min, the nitrating acid (10 ml of 96% sulphuric acid in 5 ml of 65% nitric acid), which had been prepared and cooled beforehand, was added dropwise to this solution. After the dropwise addition had ended, the mixture was stirred for a further 1 h (internal temperature at −13° C.). The reaction mixture was added to ice, and the precipitate was filtered off with suction, washed with water and dried in a drying cabinet at 50° C. under reduced pressure. 5.49 g of the title compound were obtained.

$^1$H NMR (400 MHz, DMSO-d6): δ [ppm]=3.87 (s, 3H), 7.96 (s, 1H), 8.44 (s, 1H), 8.70 (s, 1H), 13.98 (br. s., 1H).

WORKING EXAMPLES

Example 1

N-[6-Methoxy-2-(tetrahydro-2H-pyran-4-yl)-2H-indazol-5-yl]-6-(trifluoromethyl)pyridine-2-carboxamide

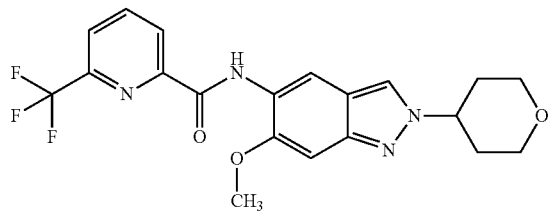 [SMILES: COc1cc2nn(C3CCOCC3)cc2cc1NC(=O)c1cccc(C(F)(F)F)n1]

To a mixture of 260 mg (1.05 mmol) of 6-methoxy-2-(tetrahydro-2H-pyran-4-yl)-2H-indazol-5-amine (Intermediate 4A), 201 mg (1.05 mmol) of 6-(trifluoromethyl)pyridine-2-carboxylic acid [CAS 131747-42-7] and 440 mg (1.2 mmol) of O-(7-azabenzotriazol-1-yl)-N,N,N',N'-tetramethyluronium hexafluorophosphate (HATU) [148893-10-1] in 5 ml of anhydrous dimethylformamide was added 0.366 ml (2.1 mmol) of N,N-diisopropylethylamine, and the mixture was stirred at room temperature for 64 h. Ethyl acetate and water were added to the reaction, the organic phase was removed and the aqueous phase was extracted twice with ethyl acetate. The combined organic phases were washed with sodium chloride solution, dried over sodium sulphate, filtered and concentrated under reduced pressure. After purification (Biotage Isolera, 50 g silica gel column, cyclohexane/ethyl acetate), 290 mg (0.69 mmol) of the title compound were obtained.

LC-MS (Method B): Rt=4.51 min; m/z=421 (M+H)+

$^1$H-NMR (400 MHz, DMSO-d6): δ=2.02-2.11 (m, 4H), 3.47-3.54 (m, 2H), 3.95-4.00 (m, 5H), 4.59-4.69 (m, 1H), 7.15 (s, 1H), 8.19 (dd, 1H), 8.35-8.45 (m, 3H), 8.67 (s, 1H), 10.48 (s, 1H)

Example 2

N-[6-Methoxy-2-(piperidin-4-yl)-2H-indazol-5-yl]-6-(trifluoromethyl)pyridine-2-carboxamide

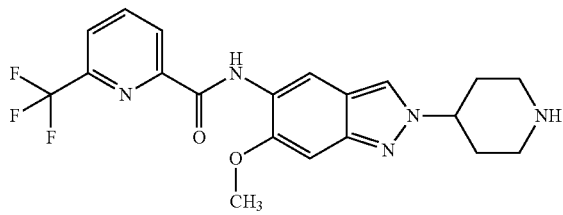 [SMILES: COc1cc2nn(C3CCNCC3)cc2cc1NC(=O)c1cccc(C(F)(F)F)n1]

Stage A tert-Butyl 4-[6-methoxy-5-({[6-(trifluoromethyl)pyridin-2-yl]carbonyl}amino)-2H-indazol-2-yl]piperidine-1-carboxylate

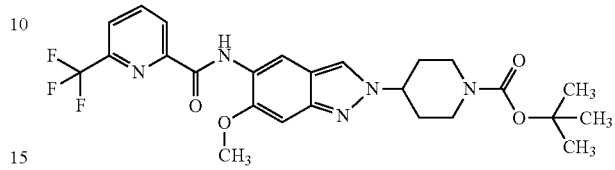

To a mixture of 913 mg (2.6 mmol) of tert-butyl 4-(5-amino-6-methoxy-2H-indazol-2-yl)piperidine-1-carboxylate (Intermediate 4B), 500 mg (2.6 mmol) of 6-(trifluoromethyl)pyridine-2-carboxylic acid [131747-42-7] and 1.1 g (2.9 mmol) of O-(7-azabenzotriazol-1-yl)-N,N,N',N'-tetramethyluronium hexafluorophosphate (HATU) [148893-10-1] in 10 ml of anhydrous dimethylformamide was added 0.918 ml (5.3 mmol) of N,N-diisopropylethylamine, and the mixture was stirred at room temperature for 16 h. Ethyl acetate and water were added, the organic phase was removed and extracted twice with ethyl acetate, and the organic phases were combined, washed with sodium chloride solution, dried over sodium sulphate, filtered and concentrated under reduced pressure. After purification by column chromatography (Biotage Isolera, 50 g silica gel column, cyclohexane/ethyl acetate), 1.13 g (2.2 mmol) of tert-butyl 4-[6-methoxy-5-({[6-(trifluoromethyl)pyridin-2-yl]carbonyl}amino)-2H-indazol-2-yl]piperidine-1-carboxylate were obtained.

LC-MS (Method A): Rt=4.49 min; m/z=464 (M-(tBu+H))+

$^1$H-NMR (300 MHz, CDCl$_3$): δ=1.49 (s, 9H), 2.05-2.26 (m, 4H), 2.88-2.99 (m, 2H), 4.03 (s, 3H), 4.26-4.35 (m, 2H), 4.46-4.56 (m, 1H), 7.07 (s, 1H), 7.83-7.88 (m, 2H), 8.12 (dd, 1H), 8.49 (d, 1H), 8.82 (s, 1H), 10.70 (s, 1H)

Stage B

To 1.13 g (2.18 mmol) of tert-butyl 4-[6-methoxy-5-({[6-(trifluoromethyl)pyridin-2-yl]carbonyl}amino)-2H-indazol-2-yl]piperidine-1-carboxylate were added 10 ml of 4 M hydrogen chloride in dioxane and 2 ml of methanol, and the mixture was stirred at room temperature for 45 minutes. The solvent was concentrated under reduced pressure. The residue was purified (SCX cartridge, eluent: 2 M ammonia in methanol), giving 820 mg (2.0 mmol) of N-[6-methoxy-2-(piperidin-4-yl)-2H-indazol-5-yl]-6-(trifluoromethyl)pyridine-2-carboxamide.

LC-MS (Method B): Rt=3.23 min; m/z=420 (M+H)+

$^1$H-NMR (300 MHz, CDCl3): δ=2.00-2.15 (m, 2H), 2.23-2.32 (m, 2H), 2.79-2.90 (m, 2H), 3.31 (td, 2H), 4.03 (s, 3H), 4.40-4.52 (m, 1H), 7.07 (s, 1H), 7.83-7.90 (m, 2H), 8.12 (dd, 1H), 8.49 (d, 1H), 8.83 (s, 1H), 10.68-10.72 (m, 1H)

Example 3

N-{6-Methoxy-2-[1-(2,2,2-trifluoroethyl)piperidin-4-yl]-2H-indazol-5-yl}-6-(trifluoromethyl)pyridine-2-carboxamide

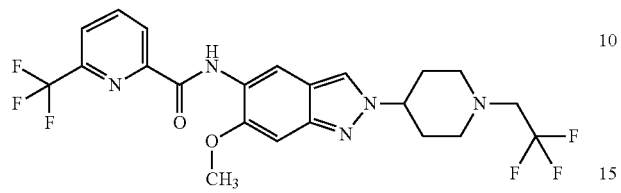

To a solution of 132 mg (0.315 mmol) of N-[6-methoxy-2-(piperidin-4-yl)-2H-indazol-5-yl]-6-(trifluoromethyl)pyridine-2-carboxamide (Example 2) in 5 ml of dichloromethane were added 0.088 ml (0.63 mmol) of triethylamine and 0.091 ml (0.63 mmol) of 2,2,2-trifluoroethyl trifluoromethanesulphonate [6226-25-1], the reaction was stirred at room temperature for 2 h. Then anhydrous tetrahydrofuran was added and the reaction was heated at 55° C. for 19.5 h. The reaction was cooled to room temperature and then dichloromethane and water were added, the organic phase was removed, the aqueous phase was extracted twice with dichloromethane, and the combined organic phases were concentrated under reduced pressure. After purification (Biotage Isolera, 25 g silica gel column, cyclohexane/ethyl acetate), 107 mg (0.213 mmol) of the title compound were obtained.

LC-MS (Method B): Rt=5.11 min; m/z=502 (M+H)+
$^1$H-NMR (400 MHz, DMSO-d6): δ=2.02-2.12 (m, 4H), 2.52-2.61 (m, 2H), 3.03 (d, 2H), 3.19-3.26 (m, 2H), 3.96 (s, 3H), 4.35-4.45 (m, 1H), 7.13 (s, 1H), 8.19 (dd, 1H), 8.35-8.45 (m, 3H), 8.66 (s, 1H), 10.47 (s, 1H)

Example 4

N-[6-Methoxy-2-(1-methylpiperidin-4-yl)-2H-indazol-5-yl]-6-(trifluoromethyl)pyridine-2-carboxamide

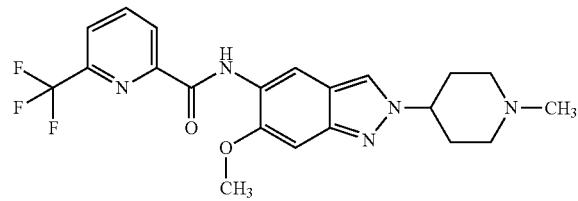 [SMILES: COc1cc2nn(C3CCN(C)CC3)cc2cc1NC(=O)c1cccc(C(F)(F)F)n1]

To a solution of 150 mg (0.358 mmol) of N-[6-methoxy-2-(piperidin-4-yl)-2H-indazol-5-yl]-6-(trifluoromethyl)pyridine-2-carboxamide (Example 2) in 0.5 ml of tetrahydrofuran and 0.5 ml of methanol was added 0.1 ml of 37% aqueous formaldehyde [50-00-0], and then the mixture was stirred at room temperature for 20 minutes. 108 mg (0.508 mmol) of sodium triacetoxyborohydride were added and the mixture was stirred at room temperature for 1 h. The mixture was acidified dropwise with 1 M aqueous hydrochloric acid solution and concentrated under reduced pressure. After prepurification (SCX cartridge, 2 M ammonia in methanol), purification was additionally effected by column chromatography (Biotage Isolera, 25 g silica gel column, dichloromethane/methanol). After freeze-drying, 113 mg (0.261 mmol) of the title compound were obtained.

LC-MS (Method B): Rt=3.24 min; m/z=434 (M+H)+
$^1$H-NMR (400 MHz, DMSO-d6): δ=2.05 (dd, 6H), 2.20 (s, 3H), 2.84-2.90 (m, 2H), 3.95 (s, 3H), 4.29-4.38 (m, 1H), 7.15 (s, 1H), 8.19 (dd, 1H), 8.33-8.45 (m, 3H), 8.66 (s, 1H), 10.47 (s, 1H)

Example 5

N-[2-(1-Glycoloylpiperidin-4-yl)-6-methoxy-2H-indazol-5-yl]-6-(trifluoromethyl)pyridine-2-carboxamide

To a mixture of 75 mg (0.179 mmol) of N-[6-methoxy-2-(piperidin-4-yl)-2H-indazol-5-yl]-6-(trifluoromethyl)pyridine-2-carboxamide (Example 2), 15 mg (0.197 mmol) of hydroxyacetic acid [79-14-1], 75 mg (0.197 mmol) of O-(7-azabenzotriazol-1-yl)-N,N,N',N'-tetramethyluronium hexafluorophosphate (HATU) [148893-10-1] in 2 ml of N,N-dimethylformamide was added 0.062 ml (0.358 mmol) of N,N-diisopropylethylamine, and the mixture was stirred at room temperature for 22 h. Ethyl acetate and water were added to the mixture, the organic phase was removed and extracted twice with ethyl acetate, and the organic phases were combined, washed with sodium chloride solution, dried over sodium sulphate, filtered and concentrated under reduced pressure. After purification (Biotage Isolera, 25 g silica gel column, ethyl acetate/methanol, then mass-based automated purification (Method E)), 19.2 mg (0.040 mmol) of the title compound were obtained.

LC-MS (Method B): Rt=4.03 min; m/z=478 (M+H)+
$^1$H-NMR (400 MHz, DMSO-d6): δ=1.85-2.05 (m, 2H), 2.12 (dd, 2H), 2.83 (dd, 1H), 3.16 (dd, 1H), 3.84 (d, 1H), 3.95 (s, 3H), 4.13 (d, 2H), 4.46 (d, 1H), 4.55 (s, 1H), 4.63-4.73 (m, 1H), 7.13 (s, 1H), 8.19 (dd, 1H), 8.34-8.45 (m, 3H), 8.66 (s, 1H), 10.47 (s, 1H)

Example 6

N-[6-Methoxy-2-(1'-methyl-1,4'-bipiperidin-4-yl)-2H-indazol-5-yl]-6-(trifluoromethyl)pyridine-2-carboxamide

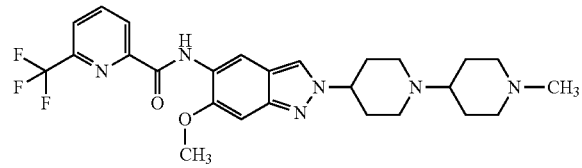 [SMILES: COc1cc2nn(C3CCN(C4CCN(C)CC4)CC3)cc2cc1NC(=O)c1cccc(C(F)(F)F)n1]

To 14 mg (0.119 mmol) of 1-methylpiperidin-4-one [1445-73-4] in 2 ml of dichloromethane were added 50 mg (0.119 mmol) of N-[6-methoxy-2-(piperidin-4-yl)-2H-indazol-5-yl]-6-(trifluoromethyl)pyridine-2-carboxamide (Example 2) and 7 microliters of acetic acid. The mixture was stirred at room temperature for 45 minutes, then 38 mg (0.179 mmol) of sodium triacetoxyborohydride were added and the mixture was stirred at room temperature for 19 h. A further 14 mg (0.119 mmol) of 1-methyl-4-piperidinone in 1 ml of dichloromethane and 7 microliters of acetic acid were added, and the mixture was stirred at room temperature for 45 minutes. Then 38 mg (0.179 mmol) of sodium triacetoxyborohydride were added, and the mixture was stirred at room temperature for 24 h. The solvent was removed under reduced pressure, the mixture was partitioned between a saturated sodium hydrogencarbonate solution and a dichloromethane/methanol mixture, and the organic phase was removed and concentrated under reduced pressure. After purification (Biotage Isolera, 25 g silica gel column, 2 M ammonia in methanol/dichloromethane), then Biotage Isolera (11 g of KP—SI NH2, cyclohexane/ethyl acetate and ethyl acetate/methanol gradient) and lyophilization, 21 mg (0.041 mmol) of the title compound were obtained.

LC-MS (Method B): Rt=2.78 min; m/z=517 (M+H)+

$^1$H-NMR (400 MHz, DMSO-d6): δ=1.38-1.50 (m, 2H), 1.67 (d, 2H), 1.81 (dd, 2H), 1.97-2.09 (m, 4H), 2.10 (s, 3H), 2.18-2.35 (m, 3H), 2.77 (dd, 2H), 2.97 (d, 2H), 3.95 (s, 3H), 4.27-4.37 (m, 1H), 7.13 (s, 1H), 8.19 (dd, 1H), 8.33-8.45 (m, 3H), 8.65 (s, 1H), 10.47 (s, 1H)

Example 7

N-[6-Methoxy-2-(1-sulphamoylpiperidin-4-yl)-2H-indazol-5-yl]-6-(trifluoromethyl)pyridine-2-carboxamide

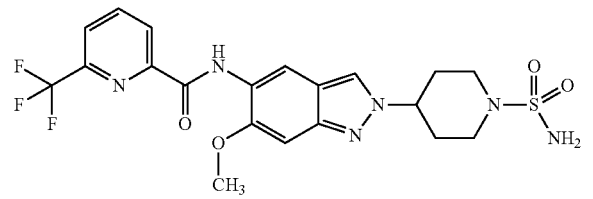 [SMILES: COc1cc2nn(C3CCN(S(N)(=O)=O)CC3)cc2cc1NC(=O)c1cccc(C(F)(F)F)n1]

To 50 mg (0.119 mmol) of N-[6-methoxy-2-(piperidin-4-yl)-2H-indazol-5-yl]-6-(trifluoromethyl)pyridine-2-carboxamide (Example 2) in 2 ml of dioxane were added 23 mg (0.239 mmol) of sulphamide [7803-58-9]. The mixture was heated to 110° C. for 10 h. The mixture was cooled, dichloromethane, methanol and water were added, and the organic phase was removed and filtered. The solvent was concentrated under reduced pressure and the residue was purified by flash chromatography (Biotage Isolera, 25 g silica gel column, dichloromethane/methanol). This gave 45 mg (0.090 mmol) of the title compound.

LC-MS (Method A): Rt=3.69 min; m/z=499 (M+H)+

$^1$H-NMR (300 MHz, DMSO-d6): 2.13-2.24 (m, 4H), 2.72-2.85 (m, 2H), 3.58-3.64 (m, 2H), 3.99 (s, 3H), 4.52-4.57 (m, 1H), 6.84 (s, 2H), 7.18 (s, 1H), 8.22 (dd, 1H), 8.37-8.49 (m, 3H), 8.70 (s, 1H), 10.51 (s, 1H)

Example 8

N-{2-[1-(Acetylsulphamoyl)piperidin-4-yl]-6-methoxy-2H-indazol-5-yl}-6-(trifluoromethyl)pyridine-2-carboxamide

To 44 mg (0.088 mmol) of N-[6-methoxy-2-(1-sulphamoylpiperidin-4-yl)-2H-indazol-5-yl]-6-(trifluoromethyl)pyridine-2-carboxamide (Example 7) in 2 ml of acetonitrile were added 0.031 ml (0.177 mmol) of N,N-diisopropylethylamine, 11 mg (0.088 mmol) of N,N-dimethylpyridin-4-amine and 0.1 ml of a solution of 0.1 ml of acetyl chloride in 1.0 ml of acetonitrile. The mixture was stirred at room temperature for 1 h. Ethyl acetate and water were added, the organic phase was removed and extracted twice with ethyl acetate, and the organic phases were combined, washed with sodium chloride solution, filtered and concentrated under reduced pressure. After purification (Biotage Isolera, 25 g silica gel column, cyclohexane/ethyl acetate) and lyophilization overnight, 21.8 mg (0.04 mmol) of the title compound were obtained.

LC-MS (Method B): Rt=4.36 min; m/z=541 (M+H)+

$^1$H-NMR (400 MHz, DMSO-d6): 1.97 (s, 3H), 2.05-2.21 (m, 4H), 3.06 (t, 2H), 3.74 (d, 2H), 3.96 (s, 3H), 4.51-4.61 (m, 1H), 7.15 (s, 1H), 8.19 (dd, 1H), 8.34-8.45 (m, 3H), 8.67 (s, 1H), 10.48 (s, 1H), 11.48 (s, 1H)

Example: 9

N-(2-{1-[2-(Dimethylamino)ethyl]piperidin-4-yl}-6-methoxy-2H-indazol-5-yl)-6-(trifluoromethyl)pyridine-2-carboxamide

To 50 mg (0.119 mmol) of N-[6-methoxy-2-(piperidin-4-yl)-2H-indazol-5-yl]-6-(trifluoromethyl)pyridine-2-carboxamide (Example 2) in 2 ml of anhydrous dimethylformamide were added 41 mg (0.298 mmol) of potassium carbonate and 24 mg (0.167 mmol) of 2-chloro-N,N-dimethylethanamine hydrochloride (1:1) [4584-46-7]. The mixture was stirred at room temperature for 18 h and at 60° C. for 8 h, and then cooled down to room temperature. Ethyl acetate and water were added to the mixture, the organic phase was removed, the aqueous phase was extracted three times with ethyl acetate, and the combined organic phases were washed with sodium chloride solution, dried (sodium sulphate), then filtered and concentrated. After purification of the residue (Biotage Isolera (11 g of KP—NH2), cyclohexane/ethyl acetate gradient, methanol/ethyl acetate gradient, then lyophilization overnight), 6.9 mg (0.014 mmol) of the title compound were obtained.

LC-MS (Method B): Rt=2.91 min; m/z=491 (M+H)+

¹H-NMR (400 MHz, DMSO-d6): δ=2.00-2.10 (m, 12H), 2.31-2.44 (m, 4H), 2.99 (d, 2H), 3.95 (s, 3H), 4.30-4.39 (m, 1H), 7.14 (s, 1H), 8.19 (dd, 1H), 8.34-8.45 (m, 3H), 8.66 (s, 1H), 10.47 (s, 1H)

Example: 10

N-{6-Methoxy-2-[1-(oxetan-3-yl)piperidin-4-yl]-2H-indazol-5-yl}-6-(trifluoromethyl)pyridine-2-carboxamide

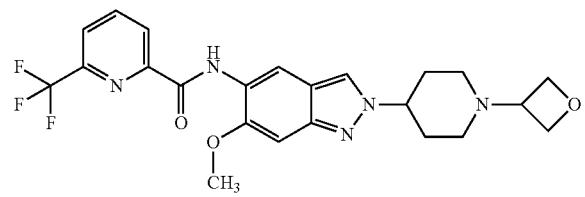 [SMILES: COc1cc2nn(C3CCN(C4COC4)CC3)cc2cc1NC(=O)c1cccc(C(F)(F)F)n1]

To 100 mg (0.24 mmol) of N-[6-methoxy-2-(piperidin-4-yl)-2H-indazol-5-yl]-6-(trifluoromethyl)pyridine-2-carboxamide (Example 2) in 3 ml of dichloromethane were added a solution of 26 mg (0.36 mmol) of 3-oxetanone [6704-31-0] in 1 ml of dichloromethane and 0.027 ml (0.48 mmol) of acetic acid. The mixture was stirred at room temperature for 0.5 h. 76 mg (0.36 mmol) of sodium triacetoxyborohydride were added, and the mixture was stirred at room temperature for 67 h. By addition of a dichloromethane/methanol mixture and saturated sodium hydrogencarbonate solution, two phases were produced, the organic phase was removed and the solvent was removed under reduced pressure. After purification (Biotage Isolera, 25 g silica gel column, dichloromethane/methanol), 36.5 mg (0.077 mmol) of the title compound were obtained.

LC-MS (Method B): Rt=3.27 min; m/z=476 (M+H)+

¹H-NMR (400 MHz, DMSO-d6): δ=1.95-2.12 (m, 6H), 2.81 (d, 2H), 3.40-3.48 (m, 1H), 3.96 (s, 3H), 4.41-4.46 (m, 3H), 4.54 (dd, 2H), 7.14 (s, 1H), 8.19 (dd, 1H), 8.35-8.45 (m, 3H), 8.66 (s, 1H), 10.48 (s, 1H)

Example: 11

N-[2-(1,1-Dioxidotetrahydro-2H-thiopyran-4-yl)-6-methoxy-2H-indazol-5-yl]-6-(trifluoromethyl)pyridine-2-carboxamide

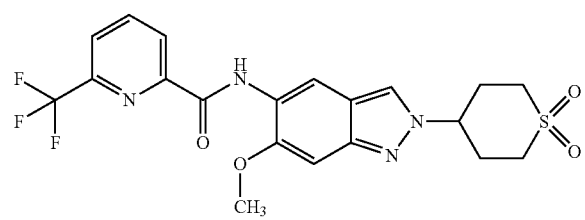 [SMILES: COc1cc2nn(C3CCS(=O)(=O)CC3)cc2cc1NC(=O)c1cccc(C(F)(F)F)n1]

To a mixture of 2.55 g (8.6 mmol) of 2-(1,1-dioxidotetrahydro-2H-thiopyran-4-yl)-6-methoxy-2H-indazol-5-amine (Intermediate 4C), 1.73 g (9.1 mmol) of 6-(trifluoromethyl)pyridine-2-carboxylic acid [131747-42-7] and 3.45 g (9.1 mmol) of O-(7-azabenzotriazol-1-yl)-N,N,N',N'-tetramethyluronium hexafluorophosphate (HATU) [148893-10-1] in 30 ml of DMF were added 3 ml (17.3 mmol) of N-ethyl-N-isopropylpropan-2-amine, and the mixture was stirred at room temperature for 15 h. Ethyl acetate and water were added, the organic phase was removed and extracted three times with ethyl acetate, and the organic phases were combined, washed with sodium chloride solution, dried over sodium sulphate, filtered and concentrated under reduced pressure. The residue was admixed with dichloromethane, and the resultant solid was extracted by stirring with 100 ml of ethyl acetate. The solvent was concentrated under reduced pressure, and the residue was dried at 60° C. for 24 h and at 90° C. for 24 h. This gave 2.57 g (5.5 mmol) of the title compound.

LC-MS (Method B): Rt=4.29 min; m/z=469 (M+H)+

¹H-NMR (400 MHz, DMSO-d6): δ=2.40 (dd, 2H), 2.49-2.61 (m, 2H), 3.21-3.25 (m, 2H), 3.44 (t, 2H), 3.96 (s, 3H), 4.80-4.89 (m, 1H), 7.17 (s, 1H), 8.19 (dd, 1H), 8.37-8.45 (m, 3H), 8.67 (s, 1H), 10.48 (s, 1H)

Example 12 rac-N-[6-Methoxy-2-(1-oxidotetrahydro-2H-thiopyran-4-yl)-2H-indazol-5-yl]-6-(trifluoromethyl)pyridine-2-carboxamide

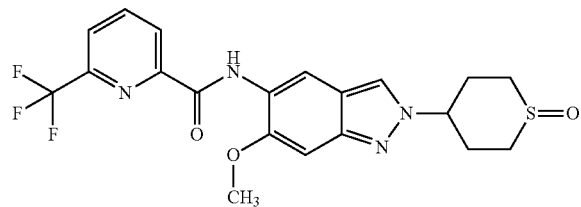 [SMILES: COc1cc2nn(C3CCS(=O)CC3)cc2cc1NC(=O)c1cccc(C(F)(F)F)n1]

To a mixture of 426 mg (1.52 mmol) of rac-6-methoxy-2-(1-oxidotetrahydro-2H-thiopyran-4-yl)-2H-indazol-5-amine (Intermediate 4D), 306 mg (1.6 mmol) of 6-(trifluoromethyl)pyridine-2-carboxylic acid [131747-42-7] and 609 mg (1.6 mmol) of O-(7-azabenzotriazol-1-yl)-N,N,N',N'-tetramethyluronium hexafluorophosphate (HATU) [148893-10-1] in 10 ml of dimethylformamide was added 0.531 ml (3.0 mmol) of N,N-diisopropylethylamine, and then the mixture was stirred at room temperature for 23 h. Ethyl acetate and water were added to the reaction, the organic phase was removed and extracted three times with ethyl acetate, and the organic phases were combined, washed with sodium chloride solution, dried over sodium sulphate and filtered, and the solvent was concentrated under reduced pressure. After purification (Biotage Isolera, 50 g silica gel column, dichloromethane/methanol), 560 mg (1.2 mmol) of the title compound were obtained.

LC-MS (Method A): Rt=3.42 & 3.47 min; m/z=453 (M+H)+

¹H-NMR (300 MHz, CDCl3): δ=2.31-2.47 (m, 2H), 2.66-3.02 (m, 4H), 3.24-3.29 (m, 1H), 3.39-3.49 (m, 1H), 4.04 (d, 3H), 4.62-4.70 (m, 1H), 7.05 (d, 1H), 7.85-7.89 (m, 2H), 8.12 (dd, 1H), 8.49 (d, 1H), 8.84 (d, 1H), 10.71 (s, 1H)

Example: 13

N-{2-[1-(2-Hydroxyethyl)piperidin-4-yl]-6-methoxy-2H-indazol-5-yl}-6-(trifluoromethyl)pyridine-2-carboxamide

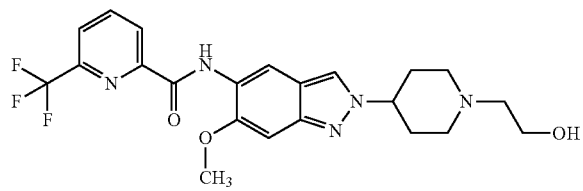 [SMILES: COc1cc2nn(C3CCN(CCO)CC3)cc2cc1NC(=O)c1cccc(C(F)(F)F)n1]

Stage A:

N-{2-[1-(2-{[tert-Butyl(dimethyl)silyl]oxy}ethyl)piperidin-4-yl]-6-methoxy-2H-indazol-5-yl}-6-(trifluoromethyl)pyridine-2-carboxamide

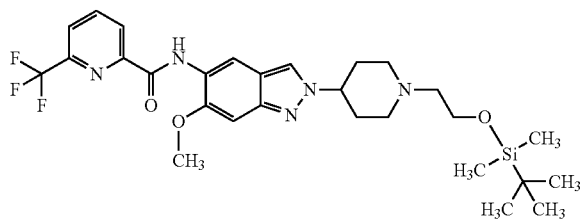 [SMILES: COc1cc2nn(C3CCN(CCO[Si](C)(C)C(C)(C)C)CC3)cc2cc1NC(=O)c1cccc(C(F)(F)F)n1]

To a solution of 85 mg (0.2 mmol) of N-[6-methoxy-2-(piperidin-4-yl)-2H-indazol-5-yl]-6-(trifluoromethyl)pyridine-2-carboxamide (Example 2) in 5 ml of dichloromethane were added 0.155 ml (0.81 mmol) of {[tert-butyl(dimethyl)silyl]oxy}acetaldehyde [102191-92-4] and 0.046 ml (0.81 mmol) of acetic acid. The mixture was stirred for 5 minutes, then 86 mg (0.41 mmol) of sodium triacetoxyborohydride were added and the mixture was stirred for 1 hour. Saturated sodium hydrogencarbonate solution was added, the mixture was stirred for 5 minutes and filtered, and the solvent was removed under reduced pressure. After purification on silica gel (Biotage Isolera, 25 g silica gel column, cyclohexane/ethyl acetate gradient, then an ethyl acetate/methanol gradient), 57 mg (0.099 mmol) of N-{2-[1-(2-{[tert-butyl(dimethyl)silyl]oxy}ethyl)piperidin-4-yl]-6-methoxy-2H-indazol-5-yl}-6-(trifluoromethyl)pyridine-2-carboxamide were obtained.

LC-MS (Method A): Rt=3.41 min; m/z=578 (M+H)+
$^1$H-NMR (300 MHz, CDCl$_3$): δ=0.08 (s, 6H), 0.91 (s, 9H), 2.24-2.26 (m, 6H), 2.57-2.66 (m, 2H), 3.06-3.18 (m, 2H), 3.75-3.83 (m, 2H), 4.03 (s, 3H), 4.30-4.40 (m, 1H), 7.06 (s, 1H), 7.83-7.90 (m, 2H), 8.11 (dd, 1H), 8.47-8.51 (m, 1H), 8.82 (s, 1H), 10.69-10.71 (m, 1H)

Stage B:

To 57 mg (0.099 mmol) of N-{2-[1-(2-{[tert-butyl(dimethyl)silyl]oxy}ethyl)piperidin-4-yl]-6-methoxy-2H-indazol-5-yl}-6-(trifluoromethyl)pyridine-2-carboxamide (Stage A) were added 3 ml of a 4 M hydrogen chloride solution in dioxane, and the mixture was stirred at room temperature for 1 h. The solvent was concentrated under reduced pressure and the residue was purified by means of an SCX cartridge (solvent: 2 M ammonia in methanol). After removal of the solvent under reduced pressure and lyophilization overnight, 41 mg (0.088 mmol) of N-{2-[1-(2-hydroxyethyl)piperidin-4-yl]-6-methoxy-2H-indazol-5-yl}-6-(trifluoromethyl)pyridine-2-carboxamide were obtained.

LC-MS (Method B): Rt=3.22 min; m/z=464 (M+H)+
$^1$H-NMR (400 MHz, DMSO-d6): δ=2.01-2.19 (m, 6H), 2.42 (t, 2H), 2.98 (d, 2H), 3.50 (ddd, 2H), 3.96 (s, 3H), 4.34-4.39 (m, 2H), 7.14 (s, 1H), 8.19 (dd, 1H), 8.33-8.45 (m, 3H), 8.66 (s, 1H), 10.47 (s, 1H)

Example 14 rel-N-{2-[(1S,4S,5R)-2-Azabicyclo[2.2.1]hept-5-yl]-6-methoxy-2H-indazol-5-yl}-6-(trifluoromethyl)pyridine-2-carboxamide

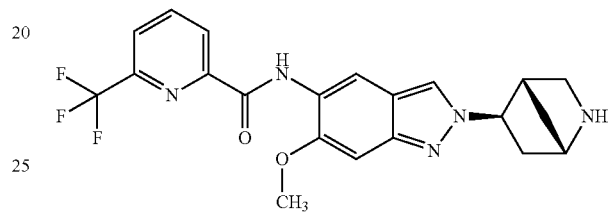

Stage A:

tert-Butyl rel-(1S,4S,5R)-5-[6-methoxy-5-({[6-(trifluoromethyl)pyridin-2-yl]carbonyl}amino)-2H-indazol-2-yl]-2-azabicyclo[2.2.1]heptane-2-carboxylate

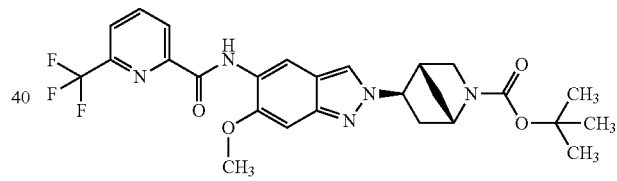

To a mixture of 150 mg (0.418 mmol) of tert-butyl rel-(1S,4S,5R)-5-(5-amino-6-methoxy-2H-indazol-2-yl)-2-azabicyclo[2.2.1]heptane-2-carboxylate (Intermediate 4E), 84 mg (0.439 mmol) of 6-(trifluoromethyl)pyridine-2-carboxylic acid [131747-42-7] and 167 mg (0.439 mmol) of O-(7-azabenzotriazol-1-yl)-N,N,N',N'-tetramethyluronium hexafluorophosphate (HATU) [148893-10-1] in 3 ml of DMF was added 0.146 ml (0.84 mmol) of N-ethyl-N-isopropylpropan-2-amine, and the mixture was stirred at room temperature for 16 h. Water and ethyl acetate were added, the organic phase was removed and extracted twice with ethyl acetate, and the combined organic phases were washed with sodium chloride solution, dried over sodium sulphate, filtered and concentrated. After purification (Biotage Isolera (25 g silica gel column), cyclohexane/ethyl acetate), 151 mg (0.284 mmol) of tert-butyl rel-(1S,4S,5R)-5-[6-methoxy-5-({[6-(trifluoromethyl)pyridin-2-yl]carbonyl}amino)-2H-indazol-2-yl]-2-azabicyclo[2.2.1]heptane-2-carboxylate were obtained.

LC-MS (Method A): Rt=4.62 min; m/z=532 (M+H)+
$^1$H-NMR (300 MHz, CDCl$_3$): δ=1.50 (s, 9H), 1.81-1.72 (m, 1H), 2.28-2.43 (m, 3H), 2.93 (d, 1H), 3.14-3.40 (m, 2H), 4.03 (s, 3H), 4.41 (d, 1H), 4.64-4.69 (m, 1H), 7.06 (s, 1H), 7.83-7.91 (m, 2H), 8.11 (dd, 1H), 8.49 (d, 1H), 8.81 (s, 1H), 10.70 (s, 1H).

Stage B:

To 151 mg (0.284 mmol) of tert-butyl rel-(1S,4S,5R)-5-[6-methoxy-5-({[6-(trifluoromethyl)pyridin-2-yl]carbonyl}amino)-2H-indazol-2-yl]-2-azabicyclo[2.2.1]heptane-2-carboxylate were added 3 ml of 4 M hydrogen chloride solution in dioxane and 1 ml of methanol and the mixture was stirred at room temperature for 1 h, the solvent was removed under reduced pressure, purification was effected with an SCX cartridge (eluent: 2 M ammonia in methanol), the solvent was removed under reduced pressure and 116 mg (0.269 mmol) of the title compound were obtained.

LC-MS (Method A): Rt=2.73 & 2.82 min; m/z=432 (M+H)+

$^1$H-NMR (300 MHz, CDCl$_3$): δ=1.59 (s, 1H), 2.14-2.31 (m, 2H), 2.39-2.48 (m, 1H), 2.78-2.89 (m, 2H), 3.05 (dd, 1H), 3.68-3.72 (m, 1H), 4.02 (s, 3H), 4.64 (dd, 1H), 7.07 (s, 1H), 7.83-7.92 (m, 2H), 8.11 (dd, 1H), 8.49 (d, 1H), 8.81 (s, 1H), 10.70 (s, 1H).

Example 15 rel-N-{2-[(1S,4S,5S)-2-Azabicyclo[2.2.1]hept-5-yl]-6-methoxy-2H-indazol-5-yl}-6-(trifluoromethyl)pyridine-2-carboxamide

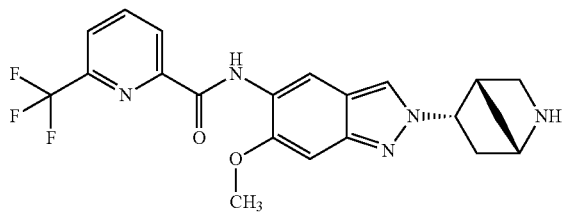 [SMILES: COc1cc2nn([C@H]3C[C@@H]4C[C@H]3CN4)cc2cc1NC(=O)c1cccc(C(F)(F)F)n1]

Stage A:

tert-Butyl rel-(1S,4S,5S)-5-[6-methoxy-5-({[6-(trifluoromethyl)pyridin-2-yl]carbonyl}amino)-2H-indazol-2-yl]-2-azabicyclo[2.2.1]heptane-2-carboxylate

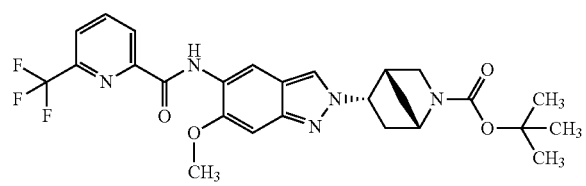 [SMILES: COc1cc2nn([C@H]3C[C@@H]4C[C@H]3CN4C(=O)OC(C)(C)C)cc2cc1NC(=O)c1cccc(C(F)(F)F)n1]

To a mixture of 297 mg (0.829 mmol) of tert-butyl rel-(1S,4S,5S)-5-(5-amino-6-methoxy-2H-indazol-2-yl)-2-azabicyclo[2.2.1]heptane-2-carboxylate (Intermediate 4F), 166 mg (0.87 mmol) of 6-(trifluoromethyl)pyridine-2-carboxylic acid [131747-42-7] and 331 mg (0.87 mmol) of O-(7-azabenzotriazol-1-yl)-N,N,N',N'-tetramethyluronium hexafluorophosphate (HATU) [148893-10-1] in 3 ml of DMF was added 0.289 ml (1.66 mmol) of N-ethyl-N-isopropylpropan-2-amine, and the mixture was stirred at room temperature for 17 h. Ethyl acetate and water were added, the organic phase was removed, the aqueous phase was extracted twice with ethyl acetate, the organic phases were combined, washed with sodium chloride solution, dried over sodium sulphate and filtered, and the solvents were removed under reduced pressure. After purification (Biotage Isolera (25 g silica gel column), cyclohexane/ethyl acetate), 383 mg (0.721 mmol) of tert-butyl rel-(1S,4S,5S)-5-[6-methoxy-5-({[6-(trifluoromethyl)pyridin-2-yl]carbonyl}amino)-2H-indazol-2-yl]-2-azabicyclo[2.2.1]heptane-2-carboxylate were obtained.

LC-MS (Method A): Rt=4.47 min; m/z=532 (M+H)+

$^1$H-NMR (300 MHz, CDCl3): δ=1.50 (d, 9H), 1.80 (d, 1H), 1.88-1.95 (m, 1H), 2.32-2.42 (m, 2H), 2.53 (d, 0.5H), 2.98 (d, 0.5H), 3.13-3.21 (m, 2H), 4.04 (s, 3H), 4.38 (d, 1H), 5.07-5.07 (m, 1H), 7.04 (s, 1H), 7.83-7.91 (m, 2H), 8.12 (dd, 1H), 8.50 (d, 1H), 8.81 (s, 1H), 10.68-10.73 (m, 1H)

Stage B:

To 383 mg (0.72 mmol) of tert-butyl rel-(1S,4S,5S)-5-[6-methoxy-5-({[6-(trifluoromethyl)pyridin-2-yl]carbonyl}amino)-2H-indazol-2-yl]-2-azabicyclo[2.2.1]heptane-2-carboxylate were added 3 ml of 4 M hydrogen chloride in dioxane and 1 ml of methanol, and the mixture was left to stir at room temperature for 1 h. The solvent was removed under reduced pressure and the residue was purified with an SCX cartridge with 2 M ammonia in methanol. The solvent was removed under reduced pressure, giving 245 mg (0.568 mmol) of the title compound.

LC-MS (Method A): Rt=2.74 & 2.84 min; m/z=432 (M+H)+

$^1$H-NMR (300 MHz, CDCl3): δ=1.79-1.89 (m, 2H), 2.27-2.39 (m, 2H), 2.65 (d, 1H), 2.78 (d, 1H), 2.97 (s, 1H), 3.69 (d, 1H), 4.03 (s, 3H), 4.96-5.02 (m, 1H), 7.07 (s, 1H), 7.85 (dd, 1H), 8.00 (s, 1H), 8.11 (dd, 1H), 8.49 (d, 1H), 8.82 (s, 1H), 10.70 (s, 1H).

Example 16

N-[2-(1,1-Dioxidotetrahydro-2H-thiopyran-4-yl)-6-hydroxy-2H-indazol-5-yl]-6-(trifluoromethyl)pyridine-2-carboxamide

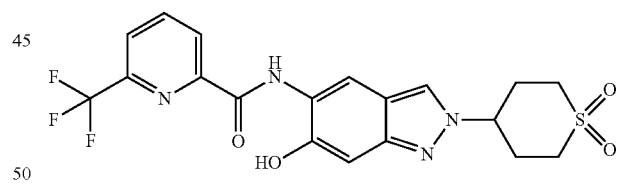

A mixture of 0.216 g (0.461 mmol) of N-[2-(1,1-dioxidotetrahydro-2H-thiopyran-4-yl)-6-methoxy-2H-indazol-5-yl]-6-(trifluoromethyl)pyridine-2-carboxamide (Example 11) and 0.187 g (0.507 mmol) of tetra-n-butylammonium iodide in 10 ml of dichloromethane under argon was cooled to −70° C. 3.7 ml (3.7 mmol) of 1 M boron trichloride in dichloromethane were added gradually, and the mixture was left to stir at −70° C. for 10 minutes, then at room temperature for 1 h. The mixture was cooled to −70° C. and a further 0.92 ml (0.92 mmol) of 1 M boron trichloride in dichloromethane was added, and the mixture was left to stir at room temperature for 7 h. The mixture was poured onto water and extracted with dichloromethane/methanol (5×25 ml 9:1, then 4×25 ml 4:1). The aqueous phase was basified with sodium hydrogencarbonate solution and extracted with dichloromethane/methanol (10×25 ml 4:1). The combined organic phases were dried, concentrated and purified by flash chromatography (Biotage Isolera (50 g of silica gel), methanol in dichloromethane). This gave 0.110 g of the title compound in solid form.

LC-MS (Method B); Rt=3.41 min; m/z=455 (M+H)+

1H-NMR (300 MHz, DMSO-d6): δ [ppm]=2.35-2.65 (m, 4H, under DMSO), 3.2-3.36 (m, 2H, under HOD), 3.38-3.52 (m, 2H), 4.76-4.89 (m, 1H), 6.95 (s, 1H), 8.21 (dd, 1H), 8.34 (s, 1H), 8.37-8.49 (m, 2H), 8.68 (s, 1H), 10.55 (S, 1H), 10.71 (s, 1H).

Example 17

N-[6-(Cyclopropylmethoxy)-2-(1,1-dioxidotetrahydro-2H-thiopyran-4-yl)-2H-indazol-5-yl]-6-(trifluoromethyl)pyridine-2-carboxamide

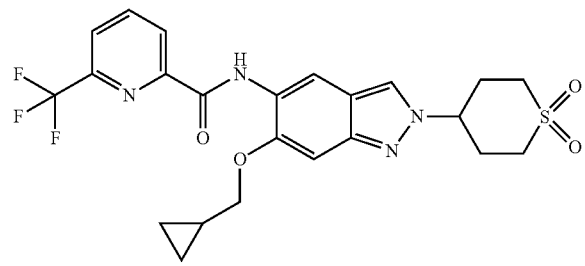 [SMILES: O=C(Nc1cc2cn(C3CCS(=O)(=O)CC3)nc2cc1OCC1CC1)c1cccc(C(F)(F)F)n1]

To a mixture of 0.107 g (0.235 mmol) of N-[2-(1,1-dioxidotetrahydro-2H-thiopyran-4-yl)-6-hydroxy-2H-indazol-5-yl]-6-(trifluoromethyl)pyridine-2-carboxamide (Example 16), 0.080 g (0.307 mmol) of triphenylphosphine and 0.022 g (0.307 mmol) of cyclopropylmethanol in 4 ml of tetrahydrofuran was added 0.060 ml (0.307 mmol) of diisopropyl azodicarboxylate. The mixture was stirred at room temperature under argon for 3 h. Triphenylphosphine (about 40 mg) and diisopropyl azodicarboxylate (about 0.03 ml) were dissolved in 0.5 ml of tetrahydrofuran, and this solution was added to the reaction mixture. The mixture was diluted with water and extracted three times with dichloromethane, and the combined organic phases were concentrated. The residue was purified by flash chromatography (Biotage Isolera (50 g of silica gel), ethyl acetate/cyclohexane) and additionally by preparative HPLC (Method F). This gave 0.015 g of the title compound in solid form.

LC-MS (Method B); Rt=4.87 min; m/z=509 (M+H)+

1H-NMR (400 MHz, DMSO-d6): δ [ppm]=0.40-0.47 (m, 2H), 0.62-0.69 (m, 2H), 1.29-1.40 (m, 1H), 2.37-2.46 (m, 2H, under DMSO), 2.51-2.63 (m, 2H), 3.23-3.33 (m, 2H, under HOD), 3.4-3.5 (m, 2H), 4.03 (d, 2H), 4.82-4.91 (m, 1H), 7.12 (s, 1H), 8.22 (dd, 1H), 8.38-8.49 (m, 3H), 8.75 (s, 1H), 10.71 (s, 1H).

Example 18 rel-N-{6-Methoxy-2-[(1S,4S,5R)-2-methyl-2-azabicyclo[2.2.1]hept-5-yl]-2H-indazol-5-yl}-6-(trifluoromethyl)pyridine-2-carboxamide

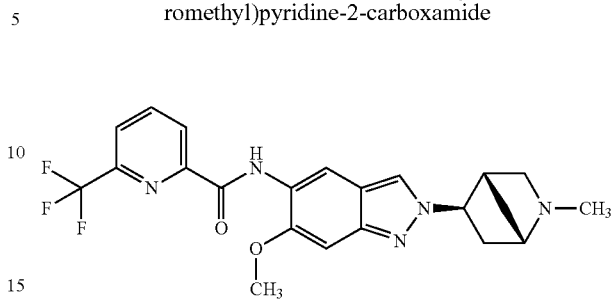

To 114 mg (0.265 mmol) of rel-N-{2-[(1S,4S,5R)-2-azabicyclo[2.2.1]hept-5-yl]-6-methoxy-2H-indazol-5-yl}-6-(trifluoromethyl)pyridine-2-carboxamide (Example 14) in 0.5 ml of tetrahydrofuran and 0.5 ml of methanol was added 0.065 ml of 37% (percent by weight) aqueous formaldehyde solution, and the mixture was stirred at room temperature for 0.5 h. 80 mg (0.376 mmol) of sodium triacetoxyborohydride were added, and the mixture was stirred at room temperature for 1 h. 1 M hydrochloric acid was added to the mixture, and purification was effected with an SCX cartridge with 2 M ammonia in methanol. Removal of the solvent and drying gave 104 mg (0.233 mmol) of the title compound.

LC-MS (Method B): Rt=3.38 min; m/z=446 (M+H)+

1H-NMR (400 MHz, DMSO-d6): δ=1.59 (d, 1H), 1.92 (d, 1H), 2.10-2.17 (m, 1H), 2.25-2.28 (m, 4H), 2.30-2.40 (m, 1H), 2.59-2.60 (m, 1H), 2.67 (dd, 1H), 3.18 (s, 1H), 3.95 (s, 3H), 4.59 (dd, 1H), 7.15 (s, 1H), 8.19 (dd, 1H), 8.35-8.45 (m, 3H), 8.65 (s, 1H), 10.47 (s, 1H).

Example 19 rel-N-{6-Methoxy-2-[(1S,4S,5S)-2-methyl-2-azabicyclo[2.2.1]hept-5-yl]-2H-indazol-5-yl}-6-(trifluoromethyl)pyridine-2-carboxamide

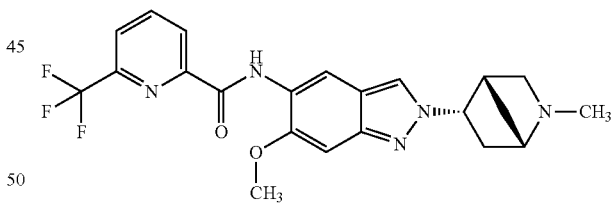

To 245 mg (0.568 mmol) of rel-N-{2-[(1S,4S,5S)-2-azabicyclo[2.2.1]hept-5-yl]-6-methoxy-2H-indazol-5-yl}-6-(trifluoromethyl)pyridine-2-carboxamide (Example 15) in 2.0 ml of tetrahydrofuran and 2.0 ml of methanol was added 0.139 ml of 37% (percent by weight) aqueous formaldehyde solution [50-00-0], and the mixture was stirred at room temperature for 0.5 h. 171 mg (0.807 mmol) of sodium triacetoxyborohydride were added, and the mixture was stirred for 1 h. 1 M hydrochloric acid was added to the mixture, and purification was effected with an SCX cartridge with 2 M ammonia in methanol. Removal of the solvent and drying gave 237 mg (0.532 mmol) of the title compound.

LC-MS (Method B): Rt=3.35 min; m/z=446 (M+H)+

1H-NMR (400 MHz, DMSO-d6): δ=1.60 (d, 1H), 1.78 (dd, 1H), 1.93-2.08 (m, 2H), 2.22 (s, 3H), 2.34-2.40 (m, 1H), 2.50-2.53 (m, 1H), 2.86 (dd, 1H), 3.13 (s, 1H), 3.96 (s, 3H), 4.86-4.93 (m, 1H), 7.15 (s, 1H), 8.19 (dd, 1H), 8.37-8.46 (m, 3H), 8.67 (s, 1H), 10.48 (s, 1H).

Example 20 and Example 21

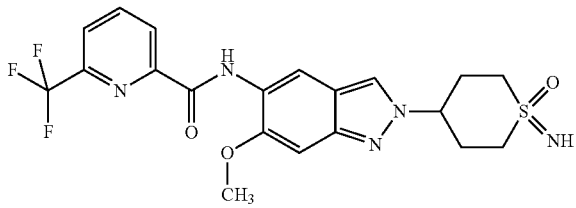 [SMILES: COc1cc2nn(C3CCS(=N)(=O)CC3)cc2cc1NC(=O)c1cccc(C(F)(F)F)n1]

N-[2-(1-Imino-1-oxidohexahydro-1λ⁴-thiopyran-4-yl)-6-methoxy-2H-indazol-5-yl]-6-(trifluoromethyl)pyridine-2-carboxamide (isomer 1, Example 20)
N-[2-(1-Imino-1-oxidohexahydro-1λ⁴-thiopyran-4-yl)-6-methoxy-2H-indazol-5-yl]-6-(trifluoromethyl)pyridine-2-carboxamide (isomer 2, Example 21)
Stage A:

N-(6-Methoxy-2-{1-oxido-1-[(trifluoroacetyl)imino]hexahydro-1λ⁴-thiopyran-4-yl}-2H-indazol-5-yl)-6-(trifluoromethyl)pyridine-2-carboxamide

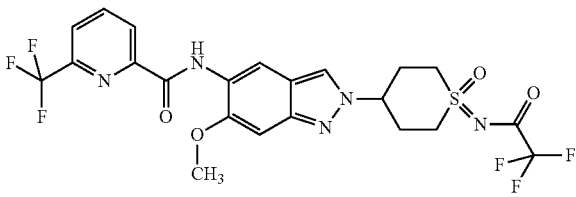 [SMILES: COc1cc2nn(C3CCS(=O)(=NC(=O)C(F)(F)F)CC3)cc2cc1NC(=O)c1cccc(C(F)(F)F)n1]

To 335 mg (0.74 mmol) of rac-N-[6-methoxy-2-(1-oxidotetrahydro-2H-thiopyran-4-yl)-2H-indazol-5-yl]-6-(trifluoromethyl)pyridine-2-carboxamide (Example 12) in 12 ml of dichloromethane were added 167 mg (1.48 mmol) of 2,2,2-trifluoroacetamide [354-38-1], 358 mg (1.1 mmol) of diacetoxy(phenyl)-lambda³-iodane [3240-34-4], 119 mg (3.0 mmol) of magnesium oxide [1309-48-4] and 32.7 mg (0.074 mmol) of rhodium(II) acetate dimer [15956-28-2], and the mixture was stirred at room temperature under argon for 18 h. 167 mg (1.48 mmol) of 2,2,2-trifluoroacetamide [354-38-1], 358 mg (1.1 mmol) of diacetoxy(phenyl)-λ³-iodane [3240-34-4], 119 mg (3.0 mmol) of magnesium oxide [1309-48-4] and 32.7 mg (0.074 mmol) of rhodium(II) acetate dimer [15956-28-2] were added and the mixture was stirred for a further 24 h. 50 ml of dichloromethane were added and the mixture was stirred for 1 h, then filtered (Whatman PTFE filter cup) and washed with 50 ml of dichloromethane. The solvent was removed under reduced pressure and the residue was purified (Biotage Isolera (50 g silica gel column), cyclohexane/ethyl acetate). This gave 265 mg (0.47 mmol) of (N-(6-methoxy-2-{1-oxido-1-[(trifluoroacetyl)imino]hexahydro-1λ⁴-thiopyran-4-yl}-2H-indazol-5-yl)-6-(trifluoromethyl)pyridine-2-carboxamide.

LC-MS (Method A): Rt=4.28 min; m/z=564 (M+H)+
¹H-NMR (300 MHz, CDCl3): δ=2.69-3.04 (m, 6H), 3.38 (t, 1H), 3.83 (s, 3H), 3.98 (d, 3H), 4.20-4.25 (m, 1H), 7.29 (s, 1H), 7.88 (d, 1H), 8.11-8.17 (m, 2H), 8.53 (d, 1H), 8.97 (s, 1H), 10.77 (d, 1H)

Stage B:
To 265 mg (0.471 mmol) of N-(6-methoxy-2-{1-oxido-1-[(trifluoroacetyl)imino]hexahydro-1λ⁴-thiopyran-4-yl}-2H-indazol-5-yl)-6-(trifluoromethyl)pyridine-2-carboxamide in 20 ml of methanol were added 325 mg (2.4 mmol) of potassium carbonate, and the mixture was stirred at room temperature for 2 h. A further 325 mg (2.4 mmol) of potassium carbonate were added and the mixture was stirred at room temperature for 67 h. Methanol was removed, water was added, and the resultant solids were filtered off and purified (Biotage Isolera (25 g silica gel column), methanol/dichloromethane). Two isomers of the title compound were obtained (isomer 1 (Example 20): 46.2 mg (0.099 mmol) and isomer 2 (Example 21): 10 mg (0.021 mmol)).

Example 20

LC-MS (Method B): Rt=3.79 min; m/z=468 (M+H)+
¹H-NMR (400 MHz, DMSO-d6): δ=2.26-2.34 (m, 2H), 2.50-2.60 (m, 2H), 3.10-3.18 (m, 2H), 3.33-3.38 (m, 2H), 3.65 (s, 1H), 3.96 (s, 3H), 4.77-4.86 (m, 1H), 7.16 (s, 1H), 8.19 (dd, 1H), 8.45-8.33-8.45 (m, 3H), 8.67 (s, 1H), 10.48 (s, 1H).

Example 21

LC-MS (Method B): Rt=3.86 min; m/z=468 (M+H)+
¹H-NMR (400 MHz, DMSO-d6): δ=2.34 (dd, 2H), 2.50-2.58 (m, 2H), 3.12-3.27 (m, 4H), 3.80 (s, 1H), 3.96 (s, 3H), 4.75-4.84 (m, 1H), 7.17 (s, 1H), 8.19 (dd, 1H), 8.36-8.45 (m, 3H), 8.67 (s, 1H), 10.48 (s, 1H).

Example 22

N-[6-Methoxy-2-(5-oxopyrrolidin-3-yl)-2H-indazol-5-yl]-6-(trifluoromethyl)pyridine-2-carboxamide

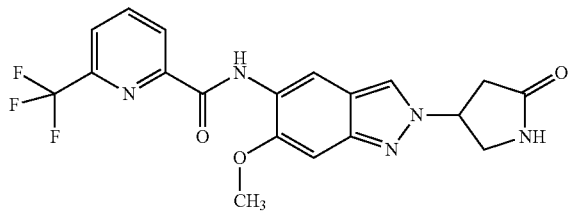

A mixture of 119 mg (0.483 mmol) of 4-(5-amino-6-methoxy-2H-indazol-2-yl)pyrrolidin-2-one (Intermediate 4I), 92 mg (0.483 mmol) of 6-(trifluoromethyl)pyridine-2-carboxylic acid and 193 mg (0.507 mmol) of HATU in 5 ml of DMF and 0.168 ml (0.966 mmol) of N,N-diisopropylethylamine was stirred at room temperature for 18 h. Water and ethyl acetate were added, then the solvent was partly removed under reduced pressure, water was added, and extraction was effected with a mixture of methanol/dichloromethane. The mixture was filtered and concentrated. Thereafter, the crude product was recrystallized from hot ethanol. This gave 64 mg of the title compound.

¹H-NMR (400 MHz, DMSO-d6): d=2.65 (dd, 1H), 2.83 (dd, 1H), 3.48 (dd, 1H), 3.82 (dd, 1H), 3.96 (s, 3H), 5.34-5.42 (m, 1H), 7.18 (s, 1H), 7.83 (s, 1H), 8.19 (dd, 1H), 8.37-8.46 (m, 3H), 8.67 (s, 1H), 10.48 (s, 1H).

Example 23

6-(Difluoromethyl)-N-[6-methoxy-2-(tetrahydro-2H-pyran-4-yl)-2H-indazol-5-yl]pyridine-2-carboxamide

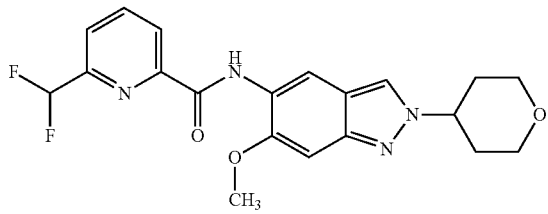 [SMILES: COc1cc2nn(C3CCOCC3)cc2cc1NC(=O)c1cccc(C(F)F)n1]

To a mixture of 80 mg of 6-methoxy-2-(tetrahydro-2H-pyran-4-yl)-2H-indazol-5-amine (Intermediate 4A), 73 mg of 6-(difluoromethyl)pyridine-2-carboxylic acid [1256824-41-5] and 124 mg of N-[3-(dimethylamino)propyl]-N'-ethylcarbodiimide (EDC, CAS 1892-57-5) and 50 mg of 1H-benzotriazol-1-ol hydrate (1:1) (HOBt, CAS123333-53-9] in 2.5 ml of dimethylformamide were added 135 microliters of triethylamine, and the mixture was stirred at room temperature for 17 h. Ethyl acetate and water were added to the reaction, the organic phase was removed and the aqueous phase was extracted three times with ethyl acetate. The combined organic phases were concentrated and the residue was purified by preparative HPLC. This gave 56 mg of the title compound.

UPLC-MS (Method C): Rt=1.11 min; mass found 402.15.

$^1$H-NMR (400 MHz, DMSO-$d_6$): δ [ppm]=2.02-2.16 (m, 4H), 3.46-3.57 (m, 2H), 3.95-4.04 (m, 5H), 4.60-4.70 (m, 1H), 7.14 (t, 1H), 7.16 (s, 1H), 7.97-8.00 (m, 1H), 8.27-8.37 (m, 3H), 8.69 (s, 1H), 10.55 (s, 1H).

Example 24

N-[6-Methoxy-2-(tetrahydro-2H-pyran-4-yl)-2H-indazol-5-yl]-6-(morpholin-4-yl)pyridine-2-carboxamide

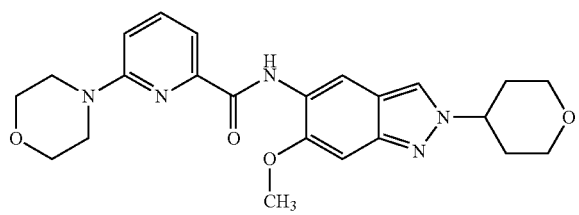 [SMILES: COc1cc2nn(C3CCOCC3)cc2cc1NC(=O)c1cccc(N2CCOCC2)n1]

Analogously to Example 23, 30 mg of 6-methoxy-2-(tetrahydro-2H-pyran-4-yl)-2H-indazol-5-amine (Intermediate 4A) were reacted with 33 mg of 6-(morpholin-4-yl)pyridine-2-carboxylic acid. Purification by preparative HPLC gave 9 mg of the title compound.

UPLC-MS (Method C): Rt=1.08 min; mass found 437.21.

$^1$H-NMR (400 MHz, DMSO-$d_6$): δ [ppm]=2.03-2.16 (m, 4H), 3.48-3.57 (m, 2H), 3.57-3.65 (m, 4H), 3.76-3.85 (m, 4H), 3.97 (s, 3H), 3.98-4.05 (m, 2H), 4.61-4.70 (m, 1H), 7.13-7.19 (m, 2H), 7.46 (d, 1H), 7.82 (dd, 1H), 8.35 (s, 1H), 8.65 (s, 1H), 10.80 (s, 1H).

Example 25

N-[6-Methoxy-2-(tetrahydro-2H-pyran-4-yl)-2H-indazol-5-yl]-2-methyl-1,3-thiazole-4-carboxamide

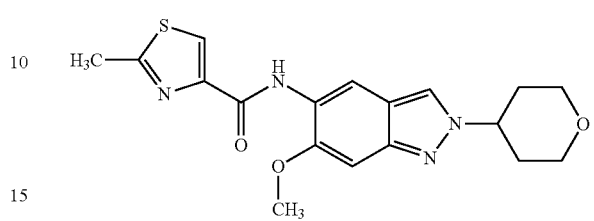

Analogously to Example 23, 30 mg of 6-methoxy-2-(tetrahydro-2H-pyran-4-yl)-2H-indazol-5-amine (Intermediate 4A) and 23 mg of 2-methyl-1,3-thiazole-4-carboxylic acid were reacted. Purification by preparative HPLC gave 19 mg of the title compound.

UPLC-MS (Method C): Rt=1.03 min; mass found 372.13.

$^1$H-NMR (400 MHz, DMSO-$d_6$): δ [ppm]=2.03-2.16 (m, 4H), 2.77 (s, 3H), 3.47-3.59 (m, 2H), 3.94-4.05 (m, 5H), 4.61-4.71 (m, 1H), 7.16 (s, 1H), 8.30 (s, 1H), 8.36 (s, 1H), 8.63 (s, 1H), 9.83 (s, 1H).

Example 26

6-Amino-N-[6-methoxy-2-(tetrahydro-2H-pyran-4-yl)-2H-indazol-5-yl]pyridine-2-carboxamide

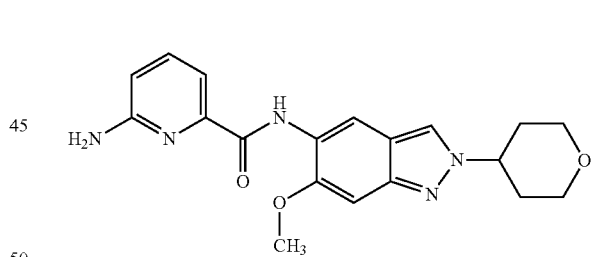

Analogously to Example 23, 30 mg of 6-methoxy-2-(tetrahydro-2H-pyran-4-yl)-2H-indazol-5-amine (Intermediate 4A) and 22 mg of 6-aminopyridine-2-carboxylic acid were reacted. Purification by preparative HPLC gave 23 mg of the title compound.

UPLC-MS (Method C): Rt=0.87 min; mass found 367.16.

$^1$H-NMR (400 MHz, DMSO-$d_6$): δ [ppm]=2.01-2.14 (m, 4H), 3.45-3.56 (m, 2H), 3.94-4.04 (m, 5H), 4.59-4.68 (m, 1H), 6.35 (broad singlet, 2H), 6.66-6.71 (m, 1H), 7.11 (s, 1H), 7.27-7.31 (m, 1H), 7.59 (dd, 1H), 8.32 (s, 1H), 8.66 (s, 1H), 10.57 (s, 1H).

Example 27

2-Isopropyl-N-[6-methoxy-2-(tetrahydro-2H-pyran-4-yl)-2H-indazol-5-yl]pyrimidine-4-carboxamide

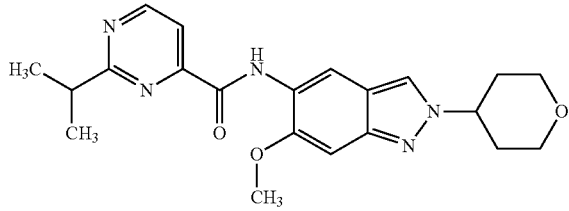 [SMILES: COc1cc2nn(C3CCOCC3)cc2cc1NC(=O)c1ccnc(C(C)C)n1]

Analogously to Example 23, 30 mg of 6-methoxy-2-(tetrahydro-2H-pyran-4-yl)-2H-indazol-5-amine (Intermediate 4A) and 26 mg of 2-isopropylpyrimidine-4-carboxylic acid were reacted. For workup, the mixture was added to water, and the precipitate was filtered off with suction, washed with water and diethyl ether, and dried. This gave 33 mg of the title compound.

UPLC-MS (Method C): Rt=1.19 min; mass found 395.00.

$^1$H-NMR (300 MHz, DMSO-$d_6$): δ [ppm]=1.38 (d, 6H), 2.00-2.17 (m, 4H), 3.21-3.31 (m, signal concealed by DMSO signal), 3.45-3.59 (m, 2H), 3.94-4.06 (m, 5H), 4.60-4.71 (m, 1H), 7.18 (s, 1H), 7.96 (d, 1H), 8.38 (s, 1H), 8.68 (s, 1H), 9.08 (d, 1H), 10.81 (s, 1H).

Example 28

6-(2-Hydroxypropan-2-yl)-N-[6-methoxy-2-(tetrahydro-2H-pyran-4-yl)-2H-indazol-5-yl]pyridine-2-carboxamide

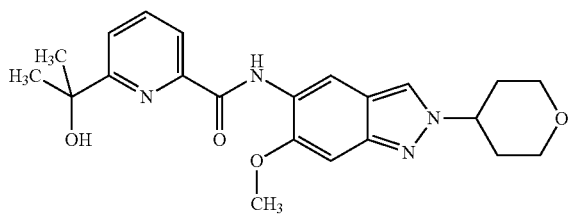 [SMILES: COc1cc2nn(C3CCOCC3)cc2cc1NC(=O)c1cccc(C(C)(C)O)n1]

Analogously to Example 23, 80 mg of 6-methoxy-2-(tetrahydro-2H-pyran-4-yl)-2H-indazol-5-amine (Intermediate 4A) and 85 mg of potassium 6-(2-hydroxypropan-2-yl)pyridine-2-carboxylate (Intermediate V3-1) in THF were reacted. Purification by preparative HPLC gave 62 mg of the title compound.

UPLC-MS (Method C): Rt=0.99 min; mass found 410.20.

$^1$H-NMR (400 MHz, DMSO-$d_6$): δ [ppm]=1.56 (s, 6H), 2.02-2.15 (m, 4H), 3.47-3.56 (m, 2H), 3.95-4.03 (m, 5H), 4.58-4.70 (m, 1H), 5.43 (s, 1H), 7.15 (s, 1H), 7.92 (dd, 1H), 7.98-8.08 (m, 2H), 8.35 (s, 1H), 8.66 (s, 1H), 10.91 (s, 1H).

Example 29

N-[6-Methoxy-2-(tetrahydrofuran-3-yl)-2H-indazol-5-yl]-6-(trifluoromethyl)pyridine-2-carboxamide

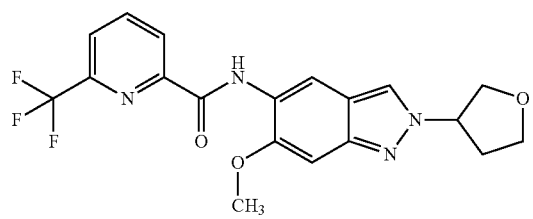 [SMILES: COc1cc2nn(C3CCOC3)cc2cc1NC(=O)c1cccc(C(F)(F)F)n1]

A mixture of 250 mg of N-(6-methoxy-1H-indazol-5-yl)-6-(trifluoromethyl)pyridine-2-carboxamide (Intermediate 5A), 174 mg of 3-iodotetrahydrofuran (1.5 equivalents) and 244 mg of potassium carbonate (3.0 equivalents) in 4 ml of DMF was stirred at 100° C. for 16 h. Another 0.7 equivalent of 3-iodotetrahydrofuran and 1.5 equivalents of potassium carbonate were added, and the mixture was left to stir at 100° C. for 24 h. Water was added, the mixture was extracted three times with ethyl acetate, and the combined organic phases were washed with sodium chloride solution, filtered through a hydrophobic filter and concentrated. The crude product was purified by HPLC. This gave 49.3 mg of the title compound.

$^1$H-NMR (400 MHz, DMSO-$d_6$): δ [ppm]=2.35-2.48 (m, 2H, concealed by solvent signal), 3.89 (td, 1H), 3.97-4.12 (m, 6H), 5.25-5.32 (m, 1H), 7.18 (s, 1H), 8.21 (dd, 1H), 8.35-8.43 (m, 2H), 8.45-8.48 (m, 1H), 8.69 (s, 1H), 10.51 (s, 1H).

Example 30

N-[6-Chloro-2-(tetrahydro-2H-pyran-4-yl)-2H-indazol-5-yl]-6-(trifluoromethyl)pyridine-2-carboxamide

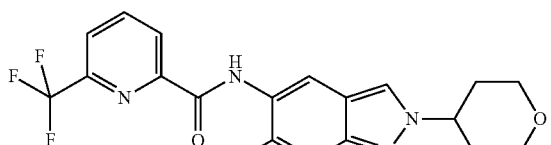

100 mg of 6-chloro-2-(tetrahydro-2H-pyran-4-yl)-2H-indazol-5-amine (Intermediate 4G) and 99 mg of 6-(trifluoromethyl)pyridine-2-carboxylic acid were converted analogously to Example 23 in THF. Purification by preparative HPLC gave 21 mg of the title compound.

UPLC-MS (Method C): Rt=1.29 min; mass found 424.09.

$^1$H-NMR (300 MHz, DMSO-$d_6$): δ [ppm]=2.03-2.19 (m, 4H), 3.43-3.59 (m, 2H), 3.96-4.06 (m, 2H), 4.76 (dt, 1H), 7.95 (s, 1H), 8.23 (dd, 1H), 8.37-8.48 (m, 2H), 8.57 (s, 1H), 8.63 (s, 1H), 10.52 (s, 1H).

Example 31

N-[6-Chloro-2-(tetrahydro-2H-pyran-4-yl)-2H-indazol-5-yl]-6-(difluoromethyl)pyridine-2-carboxamide

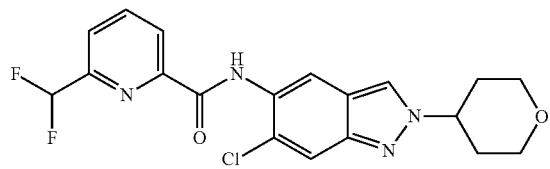 [SMILES: O=C(Nc1cc2cn(C3CCOCC3)nc2cc1Cl)c1cccc(C(F)F)n1]

100 mg of 6-chloro-2-(tetrahydro-2H-pyran-4-yl)-2H-indazol-5-amine (Intermediate 4G) and 89 mg of 6-(difluoromethyl)pyridine-2-carboxylic acid were converted analogously to Example 23 in THF. For workup, the mixture was admixed with water, and the precipitate was filtered off with suction, washed with water and diethyl ether, and dried. This gave 138 mg of the title compound.

UPLC-MS (Method C): Rt=1.22 min; mass found 406.00.

$^1$H-NMR (400 MHz, DMSO-$d_6$): δ [ppm]=2.04-2.17 (m, 4H), 3.46-3.61 (m, 2H), 3.96-4.05 (m, 2H), 4.70-4.81 (m, 1H), 7.13 (t, 1H), 7.94 (s, 1H), 7.97-8.04 (m, 1H), 8.28-8.37 (m, 2H), 8.52-8.58 (m, 1H), 8.64 (s, 1H), 10.58 (s, 1H).

Example 32

N-[6-Chloro-2-(1,1-dioxidotetrahydro-2H-thiopyran-4-yl)-2H-indazol-5-yl]-6-(2-hydroxypropan-2-yl)pyridine-2-carboxamide

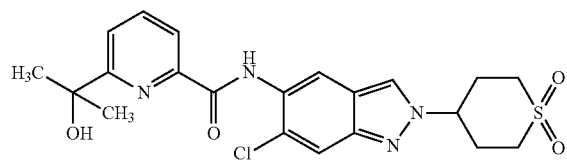 [SMILES: CC(C)(O)c1cccc(C(=O)Nc2cc3cn(C4CCS(=O)(=O)CC4)nc3cc2Cl)n1]

A mixture of 100 mg of 6-chloro-2-(1,1-dioxidotetrahydro-2H-thiopyran-4-yl)-2H-indazol-5-amine (Intermediate 4H), 110 mg of potassium 6-(2-hydroxypropan-2-yl)pyridine-2-carboxylate (Intermediate V3-1), 140 mg HATU and 63 microliters of N-ethyl-N-isopropylpropan-2-amine in 2 ml of DMF was stirred at room temperature for 20 h. The mixture was admixed with water and the precipitated solids were filtered off, washed three times with water and three times with diethyl ether and dried. This gave 144 mg of the title compound.

UPLC-MS (Method C): Rt=0.99 min; mass found 462.00.

$^1$H-NMR (400 MHz, DMSO-$d_6$): δ [ppm]=1.55 (s, 6H), 2.40-2.65 (m, partly concealed by a solvent signal), 2.51-2.67 (m, 3H), 3.22-3.28 (m, partly concealed by a solvent signal), 3.41-3.52 (m, 2H), 4.95 (tt, 1H), 5.46 (s, 1H), 7.92-8.10 (m, 4H), 8.57 (d, 1H), 8.74 (s, 1H), 10.88 (s, 1H).

Example 33

Methyl 2-(tetrahydro-2H-pyran-4-yl)-5-({[6-(trifluoromethyl)pyridin-2-yl]carbonyl}amino)-2H-indazole-6-carboxylate

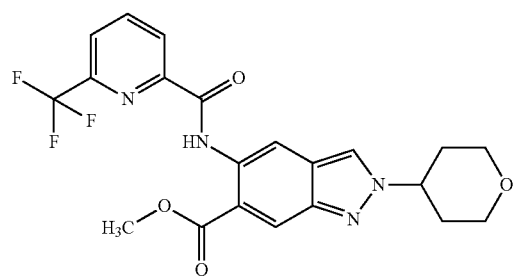 [SMILES: COC(=O)c1cc2nn(C3CCOCC3)cc2cc1NC(=O)c1cccc(C(F)(F)F)n1]

To a solution of 450 mg of methyl 5-amino-2-(tetrahydro-2H-pyran-4-yl)-2H-indazole-6-carboxylate (Intermediate 4J) in 10 ml of DMF were added 406 mg of 6-(trifluoromethyl)pyridine-2-carboxylic acid, 684 mg of HATU and 307 microliters of N-ethyl-N-isopropylpropan-2-amine, and the mixture was stirred at room temperature for 24 h. The mixture was admixed with water and the precipitate was filtered off with suction and washed three times with water and three times with diethyl ether. After drying, 677 mg of the title compound were obtained.

UPLC-MS (Method C): Rt=1.27 min; mass found 448.00.

$^1$H-NMR (400 MHz, DMSO-$d_6$): δ [ppm]=2.07-2.24 (m, 4H), 3.49-3.63 (m, 2H), 3.97 (s, 3H), 3.99-4.11 (m, 2H), 4.78-4.92 (m, 1H), 8.18-8.28 (m, 1H), 8.37-8.55 (m, 3H), 8.64 (s, 1H), 9.08 (s, 1H), 12.55 (s, 1H).

Example 34

N-[6-(2-Hydroxypropan-2-yl)-2-(tetrahydro-2H-pyran-4-yl)-2H-indazol-5-yl]-6-(trifluoromethyl)pyridine-2-carboxamide

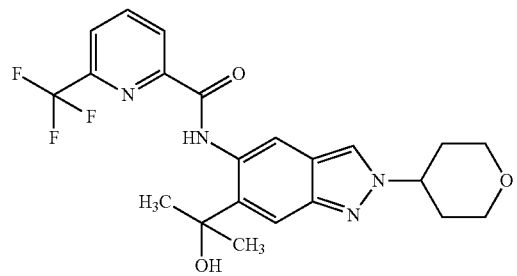 [SMILES: CC(C)(O)c1cc2nn(C3CCOCC3)cc2cc1NC(=O)c1cccc(C(F)(F)F)n1]

300 mg of methyl 2-(tetrahydro-2H-pyran-4-yl)-5-({[6-(trifluoromethyl)pyridin-2-yl]carbonyl}amino)-2H-indazole-6-carboxylate (Example 33) were initially charged in 5 ml of THF. The mixture was cooled with an ice-water cooling bath, and 1.1 ml of 3 M methylmagnesium bromide solution (in diethyl ether) were added cautiously. The mixture was left to stir while being cooled by the cooling bath for 1 h and then at room temperature for 4.5 h. Saturated aqueous ammonium chloride solution was added, the mixture was extracted three times with ethyl acetate, and the combined organic phases were washed with sodium chloride solution, filtered through a hydrophobic filter and concentrated. The residue was admixed with diethyl ether and left to stir for 10 min. The solids were filtered off with suction, washed three times with diethyl ether and dried. 241 mg of the title compound were obtained.

UPLC-MS (Method C): Rt=1.11 min; mass found 448.0.

$^1$H-NMR (400 MHz, DMSO-$d_6$): δ [ppm]=1.61 (s, 6H), 2.02-2.18 (m, 4H), 3.52 (td, 2H), 3.95-4.05 (m, 2H), 4.71 (tt, 1H), 5.93 (s, 1H), 7.58 (s, 1H), 8.15 (d, 1H), 8.33-8.47 (m, 3H), 8.72 (s, 1H), 12.36 (s, 1H).

Example 35

Methyl 2-[(3S)-tetrahydrofuran-3-yl]-5-({[6-(trifluoromethyl)pyridin-2-yl]carbonyl}amino)-2H-indazole-6-carboxylate

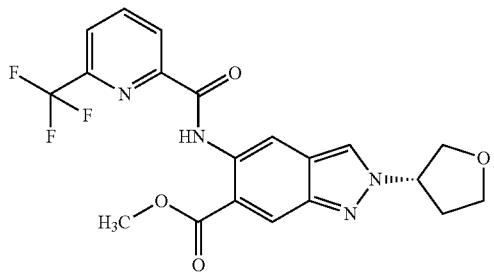 [SMILES: COC(=O)c1cc2nn([C@H]3CCOC3)cc2cc1NC(=O)c1cccc(C(F)(F)F)n1]

To a solution of 759 mg of methyl 5-amino-2-[(3S)-tetrahydrofuran-3-yl]-2H-indazole-6-carboxylate (Intermediate 4L) in 10 ml of THF were added 666 mg of 6-(trifluoromethyl)pyridine-2-carboxylic acid, 1.12 g of O-(benzotriazol-1-yl)-N,N,N',N'-tetramethyluronium tetrafluoroborate (TBTU, CAS 125700-67-6) and 0.61 ml of N-ethyl-N-isopropylpropan-2-amine, and the mixture was stirred at room temperature for 18 h. Water was added, the mixture was extracted three times with ethyl acetate, and the extracts were washed with sodium chloride solution, filtered through a hydrophobic filter and concentrated. Purification of the crude product by column chromatography on silica gel (Isolera, hexane/ethyl acetate) gave 824 mg of the title compound.

UPLC-MS (Method C): Rt=1.24 min; mass found 434.00.

$^1$H-NMR (400 MHz, DMSO-$d_6$, selected signals from the crude product): δ [ppm]=2.38-2.59 (m, masked by solvent signal), 3.85-3.98 (m, 4H), 4.03-4.14 (m, 3H), 5.38-5.46 (m, 1H), 8.17-8.22 (m, 1H), 8.35-8.41 (m, 1H), 8.44-8.48 (m, 2H), 8.58 (s, 1H), 9.05 (s, 1H), 12.51 (s, 1H).

Example 36

N-{6-(2-Hydroxypropan-2-yl)-2-[(3S)-tetrahydrofuran-3-yl]-2H-indazol-5-yl}-6-(trifluoromethyl)pyridine-2-carboxamide

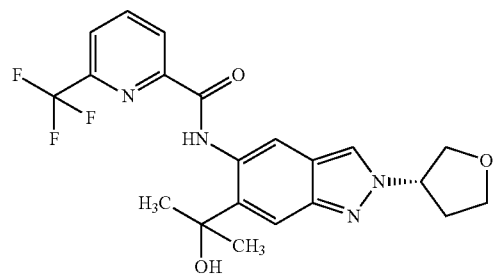 [SMILES: CC(C)(O)c1cc2nn([C@H]3CCOC3)cc2cc1NC(=O)c1cccc(C(F)(F)F)n1]

Analogously to Example 34, 819 mg of methyl 2-[(3S)-tetrahydrofuran-3-yl]-5-({[6-(trifluoromethyl)pyridin-2-yl]carbonyl}amino)-2H-indazole-6-carboxylate (Example 35) were reacted with 2.42 ml of 3 M methylmagnesium bromide solution (in diethyl ether) in 13 ml of THF. 774 mg of a crude product were obtained, which was purified by column chromatography on silica gel (Biotage Isolera, hexane/ethyl acetate). After further purification by preparative HPLC, 431 mg of the title compound (analysis by chiral HPLC: ee 98.5%) were obtained.

Chiral Analysis:

| | |
|---|---|
| System: | Agilent 1260/Agilent 1290 |
| Column: | Chiralpak IB 3 μm 100 × 4.6 mm |
| Solvent: | hexane/2-propanol 5-50% B (v/v), 10 min + 0.1% DEA |
| Flow rate: | 1.0 mL/min |
| Temperature: | 25° C. |
| Solution: | 1.0 mg/mL EtOH/MeOH 1:1 |
| Injection: | 5.0 μl |
| Detection: | DAD 254 nm |

| Peak | Rt in min | Purity in % | |
|---|---|---|---|
| 1 | 9.52 | 99.2 | ee: 98.5% (title compound) |
| 2 | 10.18 | 0.8 | corresponds to Example 38 (Rt: 10.16) |

$^1$H-NMR (400 MHz, DMSO-$d_6$): δ [ppm]=1.63 (s, 6H), 2.37-2.49 (m, concealed by solvent signal), 2.53-2.58 (m, 1H), 3.90 (td, 1H), 3.99-4.15 (m, 3H), 5.30-5.38 (m, 1H), 5.97 (s, 1H), 7.60 (s, 1H), 8.17 (dd, 1H), 8.34-8.48 (m, 3H), 8.73 (s, 1H), 12.38 (s, 1H).

Example 37

Methyl 2-[(3R)-tetrahydrofuran-3-yl]-5-({[6-(trifluoromethyl)pyridin-2-yl]carbonyl}amino)-2H-indazole-6-carboxylate

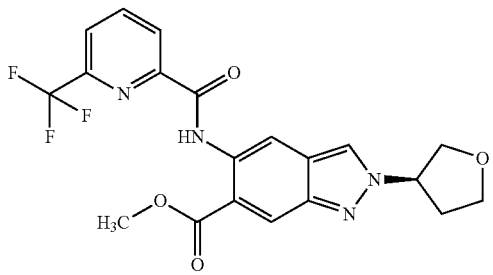 [SMILES: COC(=O)c1cc2nn([C@@H]3CCOC3)cc2cc1NC(=O)c1cccc(C(F)(F)F)n1]

Analogously to the preparation of Example 35, 552 mg of methyl 5-amino-2-[(3R)-tetrahydrofuran-3-yl]-2H-indazole-6-carboxylate (Intermediate 4M) in 10 ml of THF were reacted with 460 mg of 6-(trifluoromethyl)pyridine-2-carboxylic acid, 773 mg of O-(benzotriazol-1-yl)-N,N,N',N'-tetramethyluronium tetrafluoroborate (TBTU, CAS 125700-67-6) and 0.42 ml of N-ethyl-N-isopropylpropan-2-amine and purified. 794 mg of a solid as the title compound were obtained.

UPLC-MS (Method C): Rt=1.23 min; mass found 434.00.

Example 38

N-{6-(2-Hydroxypropan-2-yl)-2-[(3R)-tetrahydrofuran-3-yl]-2H-indazol-5-yl}-6-(trifluoromethyl)pyridine-2-carboxamide

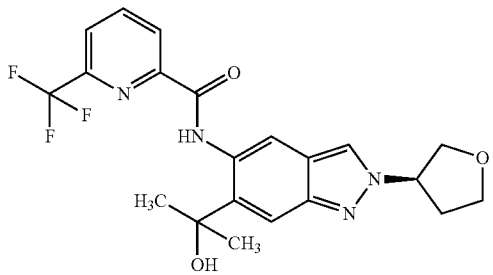 [SMILES: CC(C)(O)c1cc2nn([C@@H]3CCOC3)cc2cc1NC(=O)c1cccc(C(F)(F)F)n1]

Analogously to the preparation of Example 36, 794 mg of methyl 2-[(3R)-tetrahydrofuran-3-yl]-5-({[6-(trifluoromethyl)pyridin-2-yl]carbonyl}amino)-2H-indazole-6-carboxylate (Example 37) were reacted with 2.35 ml of 3 M methylmagnesium bromide solution (in diethyl ether) in 11 ml of THF. 777 mg of a crude product were obtained, which was purified by column chromatography on silica gel (Biotage Isolera, hexane/ethyl acetate). After further purification by preparative HPLC, 394 mg of the title compound (analysis by chiral HPLC: ee 99.1%) were obtained.

Chiral Analysis:

| System: | Agilent 1260/Agilent 1290 |
|---|---|
| Column: | Chiralpak IB 3 μm 100 × 4.6 mm |
| Solvent: | hexane/2-propanol 5-50% B (v/v), 10 min + 0.1% DEA |
| Flow rate: | 1.0 mL/min |
| Temperature: | 25° C. |
| Solution: | 1.0 mg/mL EtOH/MeOH 1:1 |
| Injection: | 5.0 μl |
| Detection: | DAD 254 nm |

| Peak | Rt in min | Purity in % | |
|---|---|---|---|
| 1 | 9.57 | 0.4 | corresponds to Example 36 (Rt: 9.52) |
| 2 | 10.16 | 99.6 | ee: 99.1% (title compound) |

$^1$H-NMR (400 MHz, DMSO-$d_6$): δ [ppm]=1.62 (s, 6H), 2.37-2.49 (m, concealed by solvent signal), 3.90 (td, 1H), 3.99-4.15 (m, 3H), 5.30-5.39 (m, 1H), 5.97 (s, 1H), 7.60 (s, 1H), 8.17 (dd, 1H), 8.34-8.49 (m, 3H), 8.73 (s, 1H), 12.38 (s, 1H).

Example 39

Methyl 2-[(3S)-tetrahydrothiophen-3-yl]-5-({[6-(trifluoromethyl)pyridin-2-yl]carbonyl}amino)-2H-indazole-6-carboxylate

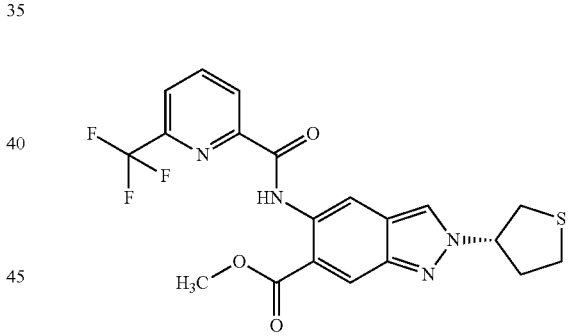

Analogously to the preparation of Example 35, 91 mg of methyl 5-amino-2-[(3S)-tetrahydrothiophen-3-yl]-2H-indazole-6-carboxylate (Intermediate 4K) in 3 ml of THF were reacted with 72 mg of 6-(trifluoromethyl)pyridine-2-carboxylic acid, 120 mg of O-(benzotriazol-1-yl)-N,N,N',N'-tetramethyluronium tetrafluoroborate (TBTU, CAS 125700-67-6) and 65 microliters of N-ethyl-N-isopropylpropan-2-amine at room temperature within 23 h. After aqueous workup, the crude product was admixed with dimethyl sulphoxide, and the remaining solids were filtered off and washed three times with diethyl ether and dried. This gave 50 mg of the title compound.

UPLC-MS (Method C): Rt=1.38 min; mass found 450.00.

$^1$H-NMR (400 MHz, DMSO-$d_6$): δ [ppm]=2.60-2.73 (m, 1H), 2.96-3.07 (m, 2H), 3.35-3.46 (m, 2H), 3.97 (s, 3H), 5.41 (quin, 1H), 8.19-8.24 (m, 1H), 8.37-8.44 (m, 1H), 8.45-8.51 (m, 2H), 8.68 (s, 1H), 9.08 (s, 1H), 12.54 (s, 1H).

Example 40

N-{6-(2-Hydroxypropan-2-yl)-2-[(3S)-tetrahydrothiophen-3-yl]-2H-indazol-5-yl}-6-(trifluoromethyl)pyridine-2-carboxamide

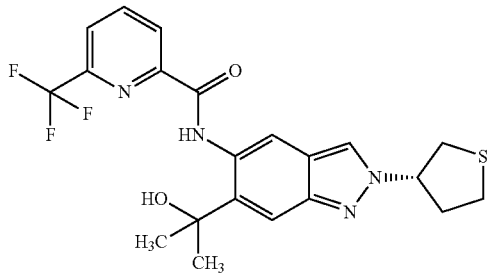 [SMILES: CC(C)(O)c1cc2nn([C@H]3CCSC3)cc2cc1NC(=O)c1cccc(C(F)(F)F)n1]

A solution of 50 mg of methyl 2-[(3S)-tetrahydrothiophen-3-yl]-5-({[6-(trifluoromethyl)pyridin-2-yl]carbonyl}amino)-2H-indazole-6-carboxylate (Example 39) in 2 ml of THF was cooled with an ice-water cooling bath, and a methylmagnesium bromide solution (3 M in diethyl ether) was added. The mixture was stirred while cooling with an ice bath for 30 min, then at room temperature for 69 h. The mixture was admixed with saturated aqueous ammonium chloride solution and extracted three times with ethyl acetate, and the extracts were filtered through a hydrophobic filter and concentrated. This gave 51 mg of the title compound as a crude product.

UPLC-MS (Method C): Rt=1.23 min; mass found 450.00.

Example 41

N-{2-[(3S)-1,1-Dioxidotetrahydrothiophen-3-yl]-6-(2-hydroxypropan-2-yl)-2H-indazol-5-yl}-6-(trifluoromethyl)pyridine-2-carboxamide

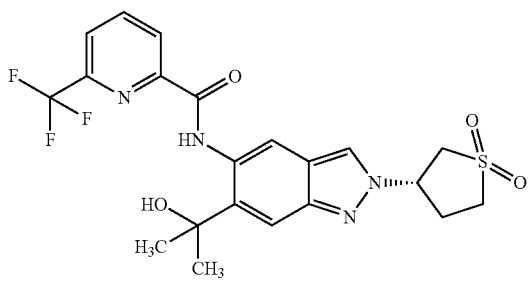 [SMILES: CC(C)(O)c1cc2nn([C@H]3CCS(=O)(=O)C3)cc2cc1NC(=O)c1cccc(C(F)(F)F)n1]

A mixture of 51 mg of N-{6-(2-hydroxypropan-2-yl)-2-[(3S)-tetrahydrothiophen-3-yl]-2H-indazol-5-yl}-6-(trifluoromethyl)pyridine-2-carboxamide (Example 40) in 3 ml of dichloromethane was cooled with an ice-water cooling bath. 56 mg of 3-chloroperbenzoic acid (CAS 937-14-4, about 77 percent) were added in portions and the mixture was stirred at room temperature for 19 h. Another 50 mg of the 3-chloroperbenzoic acid were added, and the mixture was stirred at room temperature for 26 h. The mixture was concentrated and the residue was purified by preparative HPLC. 7 mg of the title compound were obtained, which were blanketed with pentane and a little dichloromethane three times, decanting off the solvents each time. Drying gave 7 mg of the title compound.

UPLC-MS (Method C): Rt=1.08 min; mass found 482.00.
$^1$H-NMR (400 MHz, CHLOROFORM-d): δ [ppm]=1.33-2.34 (broad signal, contains singlet at 1.84 ppm), 2.88 (q, 2H), 3.23-3.34 (m, 1H), 3.62-3.76 (m, 2H), 3.81-3.89 (m, 1H), 5.39 (quin, 1H), 7.75 (s, 1H), 7.88 (d, 1H), 8.02 (s, 1H), 8.11-8.17 (m, 1H), 8.53 (d, 1H), 8.90 (s, 1H), 12.35 (s, 1H).

Example 42

Methyl 2-(tetrahydro-2H-thiopyran-4-yl)-5-({[6-(trifluoromethyl)pyridin-2-yl]carbonyl}amino)-2H-indazole-6-carboxylate

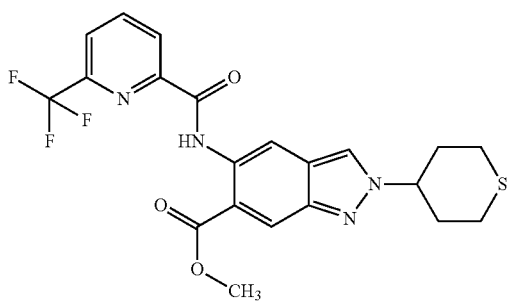 [SMILES: COC(=O)c1cc2nn(C3CCSCC3)cc2cc1NC(=O)c1cccc(C(F)(F)F)n1]

Analogously to the preparation of Example 35, a solution of 992 mg of methyl 5-amino-2-(tetrahydro-2H-thiopyran-4-yl)-2H-indazole-6-carboxylate (Intermediate 4N) in 10 ml of THF were reacted with 694 mg of 6-(trifluoromethyl)pyridine-2-carboxylic acid, 1.08 g of O-(benzotriazol-1-yl)-N,N,N',N'-tetramethyluronium tetrafluoroborate (TBTU, CAS 125700-67-6) and 0.59 ml of N-ethyl-N-isopropylpropan-2-amine. Extracting the crude product by stirring with diethyl ether gave 1.29 g of the title compound.

UPLC-MS (Method C): Rt=1.39 min; mass found 464.00.

Example 43

N-[6-(2-Hydroxypropan-2-yl)-2-(tetrahydro-2H-thiopyran-4-yl)-2H-indazol-5-yl]-6-(trifluoromethyl)pyridine-2-carboxamide

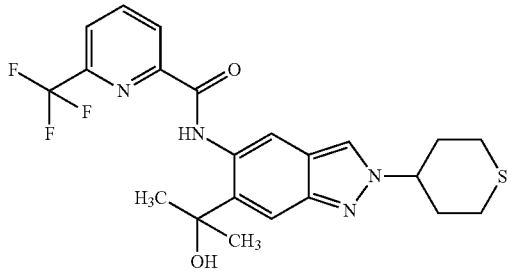

Analogously to the preparation of Example 34, 1.29 g of methyl 2-(tetrahydro-2H-thiopyran-4-yl)-5-({[6-(trifluoromethyl)pyridin-2-yl]carbonyl}amino)-2H-indazole-6-carboxylate (Example 42) in 10 ml of THF were reacted with 3.1 ml of 3 M methylmagnesium bromide solution (in diethyl ether). The crude product obtained after analogous aqueous workup was extracted by stirring with diethyl ether. 893 mg of the title compound were obtained.

UPLC-MS (Method C): Rt=1.25 min; mass found 464.00.

Example 44

N-[2-(1,1-Dioxidotetrahydro-2H-thiopyran-4-yl)-6-(2-hydroxypropan-2-yl)-2H-indazol-5-yl]-6-(trifluoromethyl)pyridine-2-carboxamide

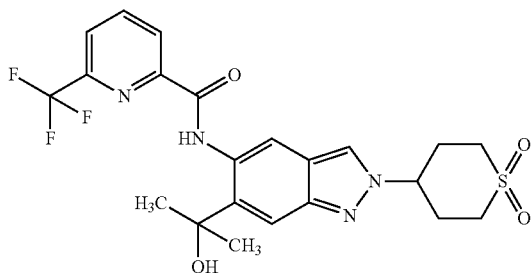 [SMILES: CC(C)(O)c1cc2nn(C3CCS(=O)(=O)CC3)cc2cc1NC(=O)c1cccc(C(F)(F)F)n1]

A solution of 893 mg of N-[6-(2-hydroxypropan-2-yl)-2-(tetrahydro-2H-thiopyran-4-yl)-2H-indazol-5-yl]-6-(trifluoromethyl)pyridine-2-carboxamide (Example 43) in 15 ml of dichloromethane was cooled with an ice-water cooling bath, and 1.16 g of 3-chloroperbenzoic acid (CAS 937-14-4, about 77 percent) were added in portions. Thereafter, the mixture was stirred in an ice-water cooling bath for 1 h and at room temperature for 19 h. Water was added, and the organic phase was removed and extracted three times with dichloromethane. The combined organic phases were washed with sodium chloride solution, filtered through a hydrophobic filter and concentrated. Purification of the crude product by preparative HPLC gave 342 mg of the title compound.

$^1$H-NMR (400 MHz, DMSO-d$_6$): δ [ppm]=1.63 (s, 6H), 2.38-2.66 (m, partly concealed by a solvent signal), 3.25-3.54 (m, partly concealed by a solvent signal), 4.93 (tt, 1H), 5.99 (s, 1H), 7.62 (s, 1H), 8.17 (dd, 1H), 8.37 (t, 1H), 8.42-8.50 (m, 2H), 8.74 (s, 1H), 12.40 (s, 1H).

Example 45

Methyl 2-(piperidin-4-yl)-5-({[6-(trifluoromethyl)pyridin-2-yl]carbonyl}amino)-2H-indazole-6-carboxylate

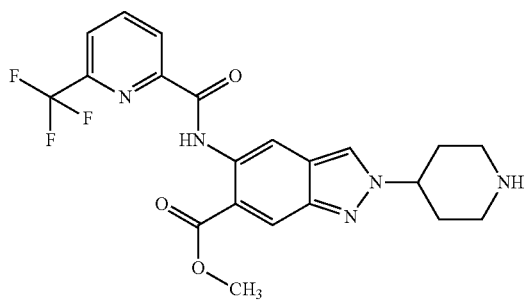 [SMILES: COC(=O)c1cc2nn(C3CCNCC3)cc2cc1NC(=O)c1cccc(C(F)(F)F)n1]

Stage A

Methyl 2-[1-(tert-butoxycarbonyl)piperidin-4-yl]-5-({[6-(trifluoromethyl)pyridin-2-yl]carbonyl}amino)-2H-indazole-6-carboxylate

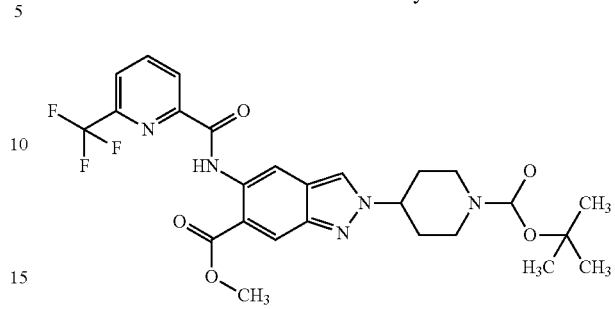

Analogously to the preparation of Example 35, a solution of 5.52 g of methyl 5-amino-2-[1-(tert-butoxycarbonyl)piperidin-4-yl]-2H-indazole-6-carboxylate (Intermediate 4O) in 30 ml of THF were reacted with 2.66 g of 6-(trifluoromethyl)pyridine-2-carboxylic acid, 3.58 g of O-(benzotriazol-1-yl)-N,N,N',N'-tetramethyluronium tetrafluoroborate (TBTU, CAS 125700-67-6) and 1.9 ml of N-ethyl-N-isopropylpropan-2-amine. After analogous workup, the crude product was purified by column chromatography purification on silica gel (Isolera, hexane/ethyl acetate). This gave 3.85 g of a yellow foam which was admixed with diethyl ether. The remaining solids were filtered off with suction, washed three times with diethyl ether and dried. 1.70 g of the title compound were obtained.

UPLC-MS (Method C): Rt=1.46 min; mass found 547.00.

Stage B 1.70 g of methyl 2-[1-(tert-butoxycarbonyl)piperidin-4-yl]-5-({[6-(trifluoromethyl)pyridin-2-yl]carbonyl}amino)-2H-indazole-6-carboxylate were initially charged in 20 ml of dichloromethane. 2.4 ml of trifluoroacetic acid were added, and the mixture was stirred at room temperature for 20 h. This was followed by concentration, dilution of the residue with ethyl acetate and cautious addition of saturated sodium hydrogencarbonate solution. In the course of this, a solid precipitated out. Dichloromethane and ethyl acetate were removed on a rotary evaporator, and the solids were filtered off, washed twice with water and three times with diethyl ether, and dried. This gave 1.39 g of methyl 2-(piperidin-4-yl)-5-({[6-(trifluoromethyl)pyridin-2-yl]carbonyl}amino)-2H-indazole-6-carboxylate in solid form.

UPLC-MS (Method C): Rt=0.93 min; mass found 447.00.

Example 46

N-[6-(2-Hydroxypropan-2-yl)-2-(piperidin-4-yl)-2H-indazol-5-yl]-6-(trifluoromethyl)pyridine-2-carboxamide

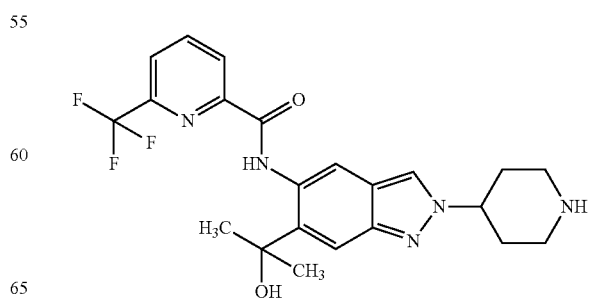

595 mg of methyl 2-(piperidin-4-yl)-5-({[6-(trifluoromethyl)pyridin-2-yl]carbonyl}amino)-2H-indazole-6-carboxylate (Example 45) were initially charged in 10 ml of THF. The mixture was cooled with an ice-water cooling bath, and 2.2 ml of 3 M methylmagnesium bromide solution (in diethyl ether) were added cautiously. The mixture was left to stir while being cooled by the cooling bath for 2 h and then stirred at room temperature for 24 h. Another 2.5 equivalents of the methylmagnesium bromide solution were added and the mixture was left to stir at room temperature for 93 h. Saturated aqueous ammonium chloride solution was added, the mixture was extracted three times with ethyl acetate, and the combined organic phases were washed with sodium chloride solution, filtered through a hydrophobic filter and concentrated. Purification of the residue by preparative HPLC gave 81 mg of the title compound.

UPLC-MS (Method C): Rt=1.02 min; mass found 447.19.

$^1$H-NMR (400 MHz, DMSO-d$_6$): δ [ppm]=1.62 (s, 6H), 1.88-2.11 (m, 4H), 2.39 (br. s., 1H), 2.65 (t, 2H), 3.09 (d, 2H), 4.45-4.56 (m, 1H), 5.97 (s, 1H), 7.59 (s, 1H), 8.17 (d, 1H), 8.34-8.49 (m, 3H), 8.72 (s, 1H), 12.38 (s, 1H).

Example 47

N-[6-Methoxy-2-(tetrahydro-2H-pyran-4-yl)-2H-indazol-5-yl]-4-(trifluoromethyl)-1,3-thiazole-2-carboxamide

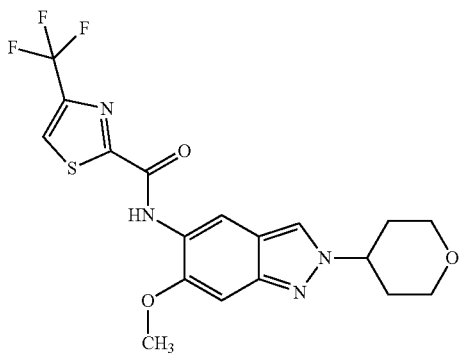 [SMILES: COc1cc2nn(C3CCOCC3)cc2cc1NC(=O)c1nc(C(F)(F)F)cs1]

To a solution of 80 mg of 6-methoxy-2-(tetrahydro-2H-pyran-4-yl)-2H-indazol-5-amine (Intermediate 4A) in 2 ml of THF were added 77 mg of 4-(trifluoromethyl)-1,3-thiazole-2-carboxylic acid, 148 mg of HATU and 68 microliters of N-ethyl-N-isopropylpropan-2-amine, and the mixture was stirred at room temperature for 21.5 h. The mixture was admixed with water and the precipitated solids were filtered off with suction, washed three times with water and three times with diethyl ether, and dried. This gave 121 mg of the title compound.

UPLC-MS (Method C): Rt=1.22 min; mass found 426.00.

$^1$H-NMR (400 MHz, DMSO-d$_6$): δ [ppm]=2.03-2.16 (m, 4H), 3.48-3.57 (m, 2H), 3.94-4.04 (m, 5H), 4.63-4.72 (m, 1H), 7.19 (s, 1H), 8.41 (s, 1H), 8.43 (s, 1H), 8.90 (d, 1H), 9.78 (s, 1H).

Example 48

N-[6-Methoxy-2-(tetrahydro-2H-pyran-4-yl)-2H-indazol-5-yl]-3-(pyridin-4-yl)-1,2,4-oxadiazole-5-carboxamide

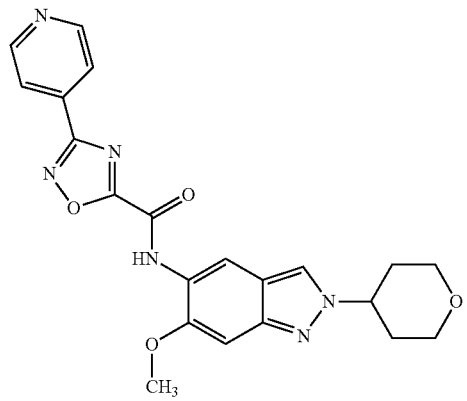 [SMILES: COc1cc2nn(C3CCOCC3)cc2cc1NC(=O)c1nc(-c2ccncc2)no1]

To a solution of 80 mg of 6-methoxy-2-(tetrahydro-2H-pyran-4-yl)-2H-indazol-5-amine (Intermediate 4A) in 2 ml of THF were added 77 mg of 3-(pyridin-4-yl)-1,2,4-oxadiazole-2-carboxylic acid, 148 mg of HATU and 68 microliters of N-ethyl-N-isopropylpropan-2-amine, and the mixture was stirred at room temperature for 21.5 h. The mixture was admixed with water and the precipitated solids were filtered off with suction, washed three times with water and three times with diethyl ether, and dried. This gave 99 mg of the title compound.

UPLC-MS (Method C): Rt=0.98 min; mass found 420.00.

$^1$H-NMR (400 MHz, DMSO-d$_6$): δ [ppm]=2.04-2.16 (m, 4H), 2.53 (br. s., 1H), 3.48-3.58 (m, 2H), 3.95-4.05 (m, 5H), 4.64-4.75 (m, 1H), 7.21 (s, 1H), 8.03-8.07 (m, 2H), 8.39 (s, 1H), 8.44 (s, 1H), 8.86-8.91 (m, 2H), 10.11 (s, 1H).

Example 49

N-[6-Methoxy-2-(tetrahydro-2H-pyran-4-yl)-2H-indazol-5-yl]-3-methyl-1,2,4-oxadiazole-5-carboxamide

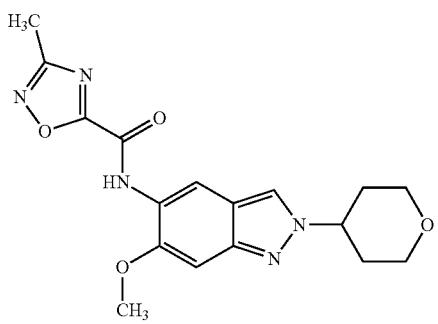 [SMILES: COc1cc2nn(C3CCOCC3)cc2cc1NC(=O)c1nc(C)no1]

To a solution of 80 mg of 6-methoxy-2-(tetrahydro-2H-pyran-4-yl)-2H-indazol-5-amine (Intermediate 4A) in 2 ml of THF were added 50 mg (1.2 equivalents) of 3-methyl-1,2,4-oxadiazole-5-carboxylic acid, 148 mg (1.2 equivalents) of HATU and 68 microliters of N-ethyl-N-isopropylpropan-2-amine, and the mixture was stirred at room temperature for 21.5 h. Then another 0.6 equiv. of HATU and 0.6 equiv. of 3-methyl-1,2,4-oxadiazole-5-carboxylic acid were added and the mixture was stirred at room temperature for 24 h. The mixture was admixed with water and the precipitated solids were filtered off with suction, washed three times with water and three times with diethyl ether, and dried. Purification of the solids by preparative HPLC gave 25 mg of the title compound in solid form.

UPLC-MS (Method C): Rt=0.96 min; mass found 357.14.

$^1$H-NMR (400 MHz, DMSO-d$_6$): δ [ppm]=2.03-2.16 (m, 4H), 2.49 (s, masked by solvent signal), 3.47-3.58 (m, 2H), 3.91-4.05 (m, 5H), 4.63-4.73 (m, 1H), 7.18 (s, 1H), 8.41 (s, 1H), 8.37 (s, 1H), 9.89 (br. s., 1H).

Example 50

N-[6-Chloro-2-(tetrahydro-2H-pyran-4-yl)-2H-indazol-5-yl]-4-(trifluoromethyl)-1,3-thiazole-2-carboxamide

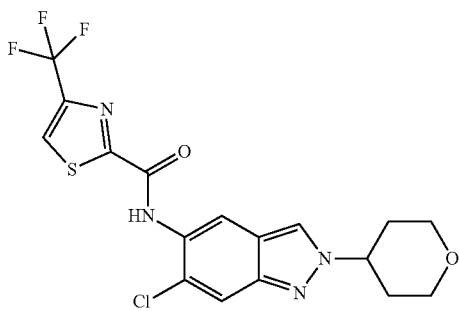 [SMILES: O=C(Nc1cc2cn(C3CCOCC3)nc2cc1Cl)c1nc(C(F)(F)F)cs1]

To a solution of 80 mg of 6-chloro-2-(tetrahydro-2H-pyran-4-yl)-2H-indazol-5-amine (Intermediate 4G) in 2 ml of THF were added 75 mg of 4-(trifluoromethyl)-1,3-thiazole-2-carboxylic acid, 145 mg of HATU and 66 microliters of N-ethyl-N-isopropylpropan-2-amine, and the mixture was stirred at room temperature for 20 h. The mixture was admixed with water and extracted three times with ethyl acetate, and the combined organic phases were concentrated and purified by preparative HPLC. This gave 84 mg of the title compound in solid form.

UPLC-MS (Method C): Rt=1.27 min; mass found 430.05

$^1$H-NMR (400 MHz, DMSO-d$_6$): δ [ppm]=2.05-2.18 (m, 5H), 3.46-3.59 (m, 2H), 3.98-4.06 (m, 2H), 4.74-4.83 (m, 1H), 7.92 (s, 1H), 8.06 (s, 1H), 8.58 (d, 1H), 8.90 (d, 1H), 10.54 (s, 1H).

Example 51

1-(Difluoromethyl)-N-[6-methoxy-2-(tetrahydro-2H-pyran-4-yl)-2H-indazol-5-yl]-1H-pyrazole-3-carboxamide

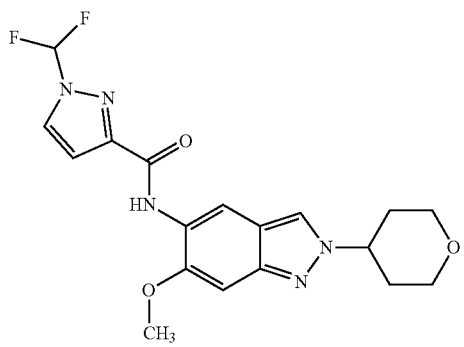 [SMILES: COc1cc2nn(C3CCOCC3)cc2cc1NC(=O)c1ccn(C(F)F)n1]

To a solution of 100 mg of 6-methoxy-2-(tetrahydro-2H-pyran-4-yl)-2H-indazol-5-amine (Intermediate 4A) in 2.5 ml of THF were added 50 mg of 1-(difluoromethyl)-1H-pyrazole-3-carboxylic acid, 185 mg of HATU and 85 microliters of N-ethyl-N-isopropylpropan-2-amine, and the mixture was stirred at room temperature for 21.5 h. Water was added, the mixture was extracted three times with ethyl acetate and the extract was concentrated. The residue was purified by preparative HPLC (method included the addition of ammonia). 109 mg of the title compound were obtained in solid form.

UPLC-MS (Method D): Rt=0.99 min; mass found 391.15.

$^1$H-NMR (500 MHz, DMSO-d$_6$): δ [ppm]=2.02-2.13 (m, 4H), 3.51 (td, 2H), 3.92-4.02 (m, 5H), 4.64 (tt, 1H), 7.02 (d, 1H), 7.15 (s, 1H), 7.96 (t, 1H), 8.34-8.36 (m, 1H), 8.44 (d, 1H), 8.50 (s, 1H), 9.39 (s, 1H).

Example 52

N-{2-[1-(3-Hydroxy-3-methylbutyl)piperidin-4-yl]-6-methoxy-2H-indazol-5-yl}-6-(trifluoromethyl)pyridine-2-carboxamide

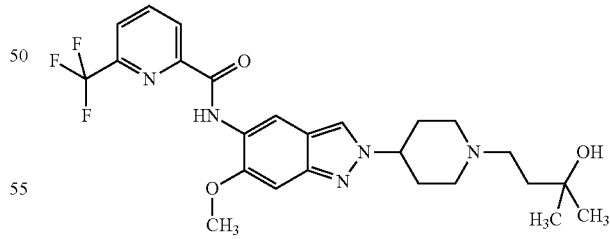

Analogously to the preparation of Example 9, 200 mg of N-[6-methoxy-2-(piperidin-4-yl)-2H-indazol-5-yl]-6-(trifluoromethyl)pyridine-2-carboxamide (Example 2) were reacted with 88 mg of 4-bromo-2-methylbutan-2-ol and potassium carbonate and potassium iodide. Purification by preparative HPLC gave 38 mg of the title compound.

UPLC-MS (Method D): Rt=0.92 min; mass found 505.23

$^1$H-NMR (400 MHz, DMSO-d$_6$): δ [ppm]=1.12 (s, 6H), 1.53-1.60 (m, 2H), 2.00-2.17 (m, 6H), 2.43-2.49 (m), 3.03

(d, 2H), 3.99 (s, 3H), 4.40 (dt, 1H), 7.18 (s, 1H), 8.19-8.25 (m, 1H), 8.36-8.49 (m, 3H), 8.69 (s, 1H), 10.51 (s, 1H).

Example 53

2-(Piperidin-4-yl)-5-({[6-(trifluoromethyl)pyridin-2-yl]carbonyl}amino)-2H-indazole-6-carboxamide

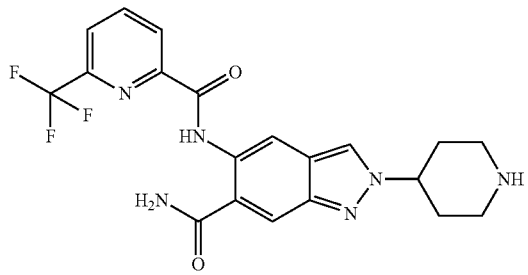 [SMILES: NC(=O)c1cc2nn(C3CCNCC3)cc2cc1NC(=O)c1cccc(C(F)(F)F)n1]

100 mg of methyl 2-(piperidin-4-yl)-5-({[6-(trifluoromethyl)pyridin-2-yl]carbonyl})amino)-2H-indazole-6-carboxylate (Example 45) were stirred with an ammonia solution (7 M in methanol) in a closed vessel at room temperature for 20.5 h and at 50° C. for 22 h. After dilution with water, a solid precipitated out. The reaction mixture was concentrated a little on a rotary evaporator, and the solids were filtered off and washed three times with water. Since the wash phases contained fractions of the product, the solids and the wash phases were concentrated together and purified by preparative HPLC (method included addition of ammonia). After extracting the product purified by HPLC from diethyl ether by stirring and drying, 14 mg of the title compound were obtained (slightly contaminated by a secondary component according to UPLC analysis (89% title compound, 11% secondary component: UV detector—TIC smooth trace)).

UPLC-MS (Method D): Rt=0.91 min; mass found 432.15.
1H-NMR (400 MHz, DMSO-d6): δ [ppm]=1.90-2.11 (m, 4H), 2.60-2.72 (m), 3.04-3.15 (m, 2H), 3.36-3.44 (m, 1H), 4.57 (tt, 1H), 7.89 (s, 1H), 8.17 (dd, 1H), 8.23 (s, 1H), 8.31-8.41 (m, 2H), 8.45 (d, 1H), 8.52 (s, 1H), 9.01 (s, 1H), 13.07 (s, 1H).

Example 54

2-(Piperidin-4-yl)-5-({[6-(trifluoromethyl)pyridin-2-yl]carbonyl}amino)-2H-indazole-6-carboxylic Acid

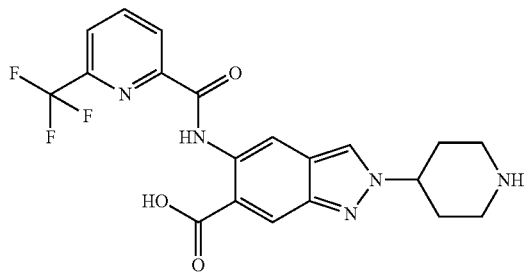 [SMILES: O=C(Nc1cc2cn(C3CCNCC3)nc2cc1C(=O)O)c1cccc(C(F)(F)F)n1]

100 mg of methyl 2-(piperidin-4-yl)-5-({[6-(trifluoromethyl)pyridin-2-yl]carbonyl}amino)-2H-indazole-6-carboxylate (Example 45) were initially charged in 1 ml of THF and 0.4 ml of methanol. A solution of 94 mg of lithium hydroxide monohydrate in 0.8 ml of water was added, and the mixture was stirred at room temperature for 19 h. The mixture was diluted with water and brought to pH=7 with 10% aqueous citric acid solution. The precipitated solids were filtered off, washed three times with water, dried under reduced pressure, extracted by stirring with diethyl ether, filtered off, washed with diethyl ether and dried again under reduced pressure. 65 mg of the title compound were obtained.

1H-NMR (analysis of the title compound prior to extraction by stirring with diethyl ether, 400 MHz, DMSO-d6): δ [ppm]=2.21 (d, 2H), 2.45-2.59 (signals masked by DMSO signal), 3.03-3.13 (m, 2H), 3.43-3.51 (signal masked by water signal), 4.74-4.90 (m, 1H), 8.12 (dd, 1H), 8.33 (t, 1H), 8.37-8.43 (m, 2H), 8.62 (s, 1H), 9.01 (s, 1H), 15.09 (br. s., 1H).

UPLC-MS (Method C): Rt=0.84 min; mass found 433.00.

Example 55

Methyl 2-(1-methylpiperidin-4-yl)-5-({[6-(trifluoromethyl)pyridin-2-yl]carbonyl}amino)-2H-indazole-6-carboxylate

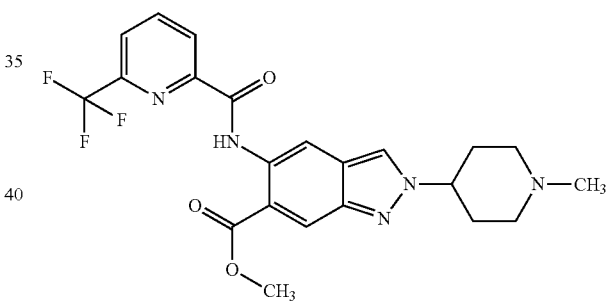

To 250 mg (0.56 mmol) of methyl 2-(piperidin-4-yl)-5-({[6-(trifluoromethyl)pyridin-2-yl]carbonyl}amino)-2H-indazole-6-carboxylate (Example 45) in 1.5 ml of tetrahydrofuran and 1.5 ml of methanol was added 0.20 ml of formaldehyde solution (37 percent in water), and the mixture was stirred at RT for 45 minutes. 200 mg of sodium triacetoxyborohydride were added and the mixture was stirred at RT for 18 h. The reaction mixture was acidified to pH 4 by adding 10 percent aqueous citric acid solution, the lower-boiling solvents were evaporated off and the mixture was diluted with water. The precipitated solids were filtered off and dissolved in an ethyl acetate/water mixture. The mixture was admixed with saturated aqueous sodium hydrogencarbonate solution, extracted three times with ethyl acetate, washed with saturated sodium chloride solution, filtered through a hydrophobic filter and concentrated. This gave 191 mg of the title compound.

1H-NMR (400 MHz, DMSO-d6): δ [ppm]=2.06-2.21 (m, 6H), 2.24 (s, 3H), 2.92 (d, 2H), 3.96 (s, 3H), 4.49-4.58 (m, 1H), 8.22 (dd, 1H), 8.40 (t, 1H), 8.45-8.50 (m, 2H), 8.61-8.64 (m, 1H), 9.07 (s, 1H), 12.56 (s, 1H).

Example 56

2-[1-(3-Hydroxy-3-methylbutyl)piperidin-4-yl]-5-({[6-(trifluoromethyl)pyridin-2-yl]carbonyl}amino)-2H-indazole-6-carboxamide

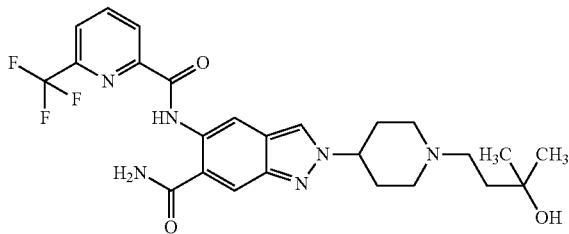 [SMILES: CC(C)(O)CCN1CCC(n2cc3cc(NC(=O)c4cccc(C(F)(F)F)n4)c(C(N)=O)cc3n2)CC1]

A mixture of 250 mg of methyl 2-(piperidin-4-yl)-5-({[6-(trifluoromethyl)pyridin-2-yl]carbonyl}amino)-2H-indazole-6-carboxylate (Example 45), 112 mg of 4-bromo-2-methylbutan-2-ol and 463 mg of potassium carbonate and 139 mg of potassium iodide in 3 ml of DMSO was stirred at 80° C. for 19.5 h. 2.8 ml of 2 M sodium hydroxide solution were added and the mixture was stirred at 50° C. for 3 h. The mixture was acidified to pH=4 with 10 percent aqueous citric acid solution, and the precipitated solids were filtered off, washed three times with water and dried under reduced pressure. Thereafter, the solids were extracted by stirring with diethyl ether. After drying, 135 mg of a solid were obtained. A mixture of 132 mg of this solid, 130 mg of HATU, 119 microliters of N-ethyl-N-isopropylpropan-2-amine in 3 ml of THF was stirred at room temperature for 45 min. 100 microliters of ammonia solution (33 percent) were added and the mixture was stirred at room temperature for 17 h, diluted with water and extracted four times with ethyl acetate, and the combined organic phases were concentrated and purified by HPLC (eluent contained formic acid). After freeze-drying, 42 mg of the title compound were obtained.

UPLC-MS (Method C): Rt=0.73 min; mass found 518.23.
$^1$H-NMR (400 MHz, DMSO-$d_6$, possible fractions of formic acid in substance sample of the title compound): δ [ppm]=1.11 (s, 6H), 1.54-1.60 (m, 2H), 2.06-2.20 (m, 6H), 3.05 (br d, 3H), 3.35 (br s, 2H), 4.49-4.58 (m, 1H), 7.88 (s, 1H), 8.14-8.23 (m, 2.6H), 8.32-8.39 (m, 2H), 8.42-8.46 (m, 1H), 8.54 (s, 1H), 9.00 (s, 1H), 13.07 (s, 1H).

Example 57

2-(1-Methylpiperidin-4-yl)-5-({[6-(trifluoromethyl)pyridin-2-yl]carbonyl}amino)-2H-indazole-6-carboxamide

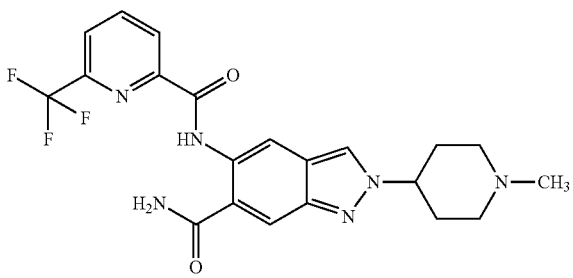 [SMILES: CN1CCC(n2cc3cc(NC(=O)c4cccc(C(F)(F)F)n4)c(C(N)=O)cc3n2)CC1]

A mixture of 184 mg of methyl 2-(1-methylpiperidin-4-yl)-5-({[6-(trifluoromethyl)pyridin-2-yl]carbonyl}amino)-2H-indazole-6-carboxylate (Example 55) in 5.0 ml of ammonia solution (7 M in methanol) at 50° C. was stirred in a pressure vessel for 47.5 h. The mixture was diluted with water and extracted three times with ethyl acetate, and the combined organic phases were concentrated. The residue was admixed with dimethyl sulphoxide, and the remaining solids were filtered off and washed with diethyl ether. In the wash phase, a solid precipitated out again and was filtered off. The wash phase was concentrated and purified by HPLC (eluent contained formic acid). After freeze-drying, 10 mg of the title compound were obtained.

UPLC-MS (Method C): Rt=0.71 min; mass found 446.17.
$^1$H-NMR (400 MHz, DMSO-$d_6$): δ [ppm]=2.08-2.21 (m, 6H), 2.24 (s, 3H), 2.87-2.97 (m, 2H), 4.45-4.55 (m, 1H), 7.88 (s, 1H), 8.15-8.19 (m, 1H), 8.23 (s, 1H), 8.31-8.40 (m, 2H), 8.42-8.46 (m, 1H), 8.54 (s, 1H), 9.00 (s, 1H), 13.07 (s, 1H).

Example 58

N-{6-Methoxy-2-[1-(2-methoxyethyl)piperidin-4-yl]-2H-indazol-5-yl}-6-(trifluoromethyl)pyridine-2-carboxamide

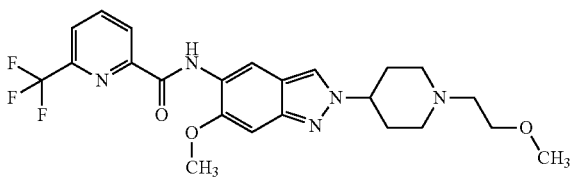 [SMILES: COCCN1CCC(n2cc3cc(NC(=O)c4cccc(C(F)(F)F)n4)c(OC)cc3n2)CC1]

120 mg of N-{2-[1-(2-hydroxyethyl)piperidin-4-yl]-6-methoxy-2H-indazol-5-yl}-6-(trifluoromethyl)pyridine-2-carboxamide (Example 13) in 5 ml of THF were admixed at 0° C. with 23 mg of sodium hydride (60 percent in mineral oil), and the mixture was stirred for 0.5 h. 0.1 ml of a solution of 0.17 ml of methyl iodide in 1.0 ml of THF was added, and the mixture was heated to room temperature within 3 h. 2 ml of DMF were added and the mixture was stirred for 3 h. Water and ethyl acetate were added, the organic phase was removed, and the aqueous phase was extracted with ethyl acetate, washed with saturated sodium chloride solution, dried with sodium sulphate and concentrated. Purification (Biotage Isolera, silica gel, then preparative HPLC) gave 13 mg of the title compound.

$^1$H-NMR (400 MHz, DMSO-$d_6$): δ [ppm]=2.03-2.09 (m, 4H), 2.11-2.21 (m, 2H), 2.51 (dd, 2H), 2.98 (d, 2H), 3.22 (s, 3H), 3.44 (t, 2H), 3.95 (s, 3H), 4.29-4.39 (m, 1H), 7.14 (s, 1H), 8.18-8.20 (m, 1H), 8.34-8.45 (m, 3H), 8.66 (s, 1H), 10.47 (s, 1H).

Assessment of Physiological Efficacy
IRAK4 Kinase Assay

The IRAK4-inhibitory activity of the substances according to the invention was measured in the IRAK4 TR-FRET assay (TR-FRET=Time Resolved Fluorescence Resonance Energy Transfer) described hereinafter.

Recombinant fusion protein from N-terminal GST (glutathione S-transferase) and human IRAK4, expressed in baculovirus-infected insect cells (Hi5, BTI-TN-5B1-4, cell line purchased from Invitrogen, catalogue No. B855-02) and purified via affinity chromatography, was used as enzyme. The substrate used for the kinase reaction was the biotinylated peptide biotin-Ahx-KKARFSRFAGSSPSQAS-FAEPG (C-terminus in amide form) which can be purchased, for example, from Biosyntan GmbH (Berlin-Buch).

For the assay, 11 different concentrations in the range from 20 µM to 0.073 nM were prepared from a 2 mM solution of the test substance in DMSO. 50 nl of the respective solution were pipetted into a black low-volume 384-well microtitre plate (Greiner Bio-One, Frickenhausen, Germany), 2 µl of a solution of IRAK4 in assay buffer [50 mM HEPES pH 7.5, 5 mM MgCl2, 1.0 mM dithiothreitol, 30 µM activated sodium orthovanadate, 0.1% (w/v) of bovine gamma-globulin (BGG) 0.04% (v/v) nonidet-P40 (Sigma)] were added and the mixture was incubated for 15 min to allow prebinding of the substances to the enzyme prior to the kinase reaction. The kinase reaction was then started by addition of 3 µl of a solution of adenosine triphosphate (ATP, 1.67 mM=final concentration in 5 µl of assay volume: 1 mM) and peptide substrate (0.83 µM=final concentration in 5 µl assay volume: 0.5 µM) in assay buffer, and the resulting mixture was incubated at 22° C. for the reaction time of 45 min. The concentration of the IRAK4 was adjusted to the respective activity of the enzyme and set such that the assay was carried out in the linear range. Typical concentrations were in the order of about 0.2 nM. The reaction was stopped by addition of 5 µl of a solution of TR-FRET detection reagents [0.1 µM streptavidin-XL665 (Cisbio Bioassays; France, catalogue No. 610SAXLG)] and 1.5 nM anti-phosphoserine antibody [Merck Millipore, "STK Antibody", catalogue No. 35-002] and 0.6 nM LANCE EU-W1024-labelled anti-mouse-IgG antibody (Perkin-Elmer, product No. AD0077; alternatively, it is possible to use a terbium cryptate-labelled anti-mouse-IgG antibody from Cisbio Bioassays) in aqueous EDTA solution (100 mM EDTA, 0.4% [w/v] bovine serum albumin [BSA] in 25 mM HEPES pH 7.5).

The resulting mixture was incubated at 22° C. for 1 h to allow formation of a complex of the biotinylated phosphorylated substrate and the detection reagents. The amount of the phosphorylated substrate was then evaluated by measuring the resonance energy transfer from europium chelate-labelled anti-mouse-IgG antibody to streptavidin-XL665. To this end, the fluorescence emissions at 620 nm and 665 nm were measured after excitation at 350 nm in a TR-FRET measuring instrument, for example a Rubystar (BMG Labtechnologies, Offenburg, Germany) or a Viewlux (Perkin-Elmer). The ratio of the emissions at 665 nm and 622 nm was taken as a measure of the amount of phosphorylated substrate. The data were normalized (enzyme reaction without test substance=0% inhibition; all other assay components but no enzyme=100% inhibition). Typically, the test substances were tested on the same microtitre plates at 11 different concentrations in the range from 20 µM to 0.073 nM (20 µM, 5.7 µM, 1.6 µM, 0.47 µM, 0.13 µM, 38 nM, 11 nM, 3.1 nM, 0.89 nM, 0.25 nM and 0.073 nM). The dilution series were prepared prior to the assay (2 mM to 7.3 nM in 100% DMSO) by serial dilutions. The IC50 values were calculated using a 4-parameter fit.

TABLE 1

IC$_{50}$ values of the example compounds in the IRAK4 kinase assay

| Example | IC$_{50}$ [nM] |
|---|---|
| 1 | 3 |
| 2 | 1 |
| 3 | 7 |
| 4 | 1 |
| 5 | 2 |
| 6 | 2 |
| 8 | 8 |
| 9 | 1 |
| 10 | 3 |
| 11 | 3 |
| 12 | 2 |
| 13 | 1 |
| 17 | 20 |
| 18 | 2 |
| 19 | 9 |
| 20 | 4 |
| 21 | 3 |
| 22 | 13 |
| 23 | 1 |
| 24 | 2 |
| 25 | 10 |
| 26 | 6 |
| 27 | 111 |
| 28 | 3 |
| 29 | 10 |
| 30 | 47 |
| 31 | 22 |
| 32 | 34 |
| 33 | 11 |
| 34 | 6 |
| 36 | 28 |
| 38 | 31 |
| 41 | 16 |
| 44 | 5 |
| 46 | 3 |
| 47 | 65 |
| 48 | 691 |
| 49 | 3782 |
| 50 | 496 |
| 51 | 6 |
| 52 | 1 |
| 53 | 1 |
| 54 | 75 |
| 55 | 1 |
| 56 | 4 |
| 57 | 2 |
| 58 | 2 |

TNF-α Secretion in THP-1 Cells

With the aid of this test, it is possible to test substances for their ability to inhibit secretion of TNF-α (tumour necrosis factor alpha) in THP-1 cells (human monocytic acute leukaemia cell line). TNF-α is a cytokine involved in inflammatory processes. In this test, TNF-α secretion is triggered by incubation with bacterial lipopolysaccharide (LPS).

THP-1 cells are kept in continuous suspension cell culture [RPMI 1460 medium with L-Glutamax (Gibco, Cat No. 61870-044) supplemented with foetal calf serum (FCS) 10% (Invitrogen, Cat No. 10082-147), 1% penicillin/streptomycin (Gibco BRL, Cat No. 15140-114)] and should not exceed a cell concentration of 1×10$^6$ cells/ml. The assay is carried out in cell culture medium (RPMI 1460 medium with L-Glutamax supplemented with FCS 10%).

In each case 2-2.5 µl of the cell suspension (corresponds to 4000 cells) per well were dispensed into a 384-well test plate (Greiner, Cat No. 784076), in each of which 40-50 nl substance had been dissolved in 100% DMSO. This was done using 10 different concentrations in the range from 20 µM to 0.073 nM for each substance. The cells were incubated at room temperature for 15 min. 2-2.5 µl of 0.1 µg/ml LPS (Sigma, *Escherichia coli* 055:B5, Cat. No. L5418)

dissolved in cell culture medium (final concentration 0.05 µg/ml) were then dispensed into each well. As neutral control, cells were treated with 0.05 µg/ml LPS and 1% DMSO and, as inhibitor control, with 1% DMSO only.

The plates were centrifuged at 80 g for 30 s and incubated at 37° C., 5% $CO_2$ and 95% atmospheric humidity for 17 h. The amount of TNF-α was determined using the TNF-alpha HTRF Detection Kit (Cisbio, Cat No. 62TNFPEB/C). To this end, 2 µl of the detection solution in each case, consisting of anti-TNF-α-XL665 conjugate and anti-TNF-α-cryptate conjugate dissolved in the reconstitution buffer in accordance with the manufacturer's instructions, were added for the HTRF (Homogeneous Time-Resolved Fluorescence) test. After the addition, the mixture was incubated either at room temperature for 3 h or at 4° C. overnight. The signals were then read at 620/665 nm using an HTRF-enabled measuring instrument such as the BMG PheraStar.

The activity of the substances is expressed as the ratio between neutral and inhibitor control in percent. The $IC_{50}$ values were calculated using a 4-parameter fit.

TABLE 2

$IC_{50}$ values of the example compounds with respect to the secretion of TNF-α in THP-1 cells

| Example | $IC_{50}$ [µM] |
|---------|----------------|
| 1 | 0.21 |
| 2 | 0.13 |
| 3 | 0.75 |
| 4 | 0.14 |
| 5 | 0.21 |
| 8 | 0.52 |
| 10 | 0.17 |
| 12 | 0.10 |
| 13 | 0.14 |
| 17 | 0.11 |
| 18 | 0.06 |
| 19 | 0.19 |
| 20 | 0.06 |
| 21 | 0.17 |
| 22 | 0.15 |
| 23 | 0.23 |
| 24 | 0.17 |
| 25 | 0.84 |
| 26 | 0.22 |
| 27 | 1.79 |
| 28 | 0.41 |
| 29 | 0.63 |
| 30 | 0.28 |
| 31 | 0.09 |
| 32 | 0.28 |
| 33 | 1.80 |
| 34 | 0.23 |
| 36 | 0.54 |
| 38 | 0.63 |
| 44 | 0.17 |
| 46 | 0.09 |

In Vitro LPS (Lipopolysaccharide)-Induced Cytokine Production in Human PBMCs (Peripheral Blood Mononuclear Cells)

The effect of the inventive compounds of the general formula (I) on induced cytokine production in human PBMCs was examined. Cytokine production was induced here by LPS, a TLR4 ligand, which leads to activation of the IRAK4-mediated signal path.

The human PBMCs were obtained from anti-coagulated human whole blood. To this end, 15 ml of Ficoll-Paque (Biochrom, Cat. No. L6115) were initially charged in Leucosep tubes and 20 ml of human blood were added. After centrifugation of the blood at 800 g for 15 min at room temperature, the plasma including the platelets was removed and discarded. The PBMCs were transferred into centrifugation tubes and made up with PBS (phosphate-buffered saline) (Gibco, Cat. No. 14190). The cell suspension was centrifuged at room temperature at 250 g for 10 min and the supernatant was discarded. The PBMCs were resuspended in complete medium (RPMI 1640, without L-glutamine (PAA, Cat. No. E15-039), 10% FCS; 50 U/ml penicillin, 50 µg/ml streptomycin (PAA, Cat. No. P11-010) and 1% L-glutamine (Sigma, Cat. No. G7513)).

The assay was also carried out in complete medium. The PBMCs were sown in 96-well plates at a cell density of $2.5 \times 10^5$ cells/well. The compounds according to the invention were subjected to serial dilution in a constant volume of 100% DMSO and used in the assay at 8 different concentrations in the range from 10 µM to 3 nM such that the final DMSO concentration was 0.4% DMSO. Prior to the actual stimulation, the cells were then pre-incubated therewith for 30 min. To induce cytokine secretion, the cells were stimulated with 0.1 µg/ml LPS (Sigma, *Escherichia coli* 0128: B12, Cat. No. L2887) for 24 hours. Cell viability was determined using the CellTiter-Glo luminescent assay (Promega, Cat. No. G7571 (G755/G756A)) in accordance with the manufacturer's instructions. The amount of secreted TNF-α in the cell culture supernatant was determined using the Human ProInflammatory 9-Plex Tissue Culture Kit (MSD, Cat. No. K15007B) in accordance with the instructions of the manufacturer. By way of example, Example Compounds 44 and 46 and Example Compound 52 have activity ≤1 µM.

Cell Proliferation Measurement

The antiproliferative activity of the inventive compounds of the general formula (I) was examined in vitro in human ABC-DLBCL cells (see Table 3). For this purpose 4000 TMD-8 cells (both from ATCC) at 30 µl/cavity in growth medium (RPMI (Biochrom: FG 1215), 20% FCS (Biochrom: S 0615)) were transferred into a 384-cavity plate (Perkin Elmer, white) and incubated at 37° C. overnight. After 24 h, cells on one plate (0 h plate) were treated with 30 µl/cavity of CTG solution (Promega Cell Titer Glo (catalogue # G755B and G756B)) and incubated at room temperature for 10 min, and luminescence was measured by means of a VICTOR V (Perkin Elmer), in order to determine cell viability on commencement of treatment. The cells on the test plate were treated with the inventive compounds of the general formula (I) and incubated at 37° C. for 72 h. The compounds were added to the cells in a 7-stage, 3-fold dilution series using an HP D300 digital dispenser. As control, the cells were treated with vehicle (DMSO). After 72 h, the cells were treated with 30 µl/cavity of CTG solution (Promega Cell Titer Glo (catalogue # G755B and G756B)) and incubated at room temperature for 10 min, and luminescence was measured by means of a VICTOR V (Perkin Elmer), in order to determine cell viability at the end of treatment. The percentage effect on cell growth and the IC50 derived therefrom were determined for each test substance using the values from the 0 h plate (=maximum inhibition) and the DMSO control (=minimum inhibition). The $IC_{50}$ values were calculated using a 4-parameter fit.

TABLE 3

$IC_{50}$ values of the example compounds with respect to proliferation inhibitors in TMD-8 cells

| Example | $IC_{50}$ [mol/l] |
|---------|-------------------|
| 2 | 8.61E−06 |
| 1 | 2.82E−05 |

TABLE 3-continued

IC$_{50}$ values of the example compounds with respect to proliferation inhibitors in TMD-8 cells

| Example | IC$_{50}$ [mol/l] |
|---|---|
| 4 | 4.08E−06 |
| 5 | 1.55E−05 |
| 23 | 8.52E−06 |
| 13 | 5.85E−06 |
| 24 | 2.81E−05 |
| 28 | 3.51E−06 |
| 10 | 2.33E−05 |
| 12 | 1.15E−05 |
| 21 | 1.48E−05 |
| 20 | 1.61E−05 |
| 18 | 3.45E−06 |
| 44 | 1.88E−05 |
| 46 | 1.41E−05 |

NF-kB Reporter Assay

The effect of the inventive compounds of the general formula (I) on the NF-kB signalling pathway was examined in vitro in human DLBCL cells (see Table 4). 10 000 TMD-8-NF-kB-luc reporter cells at 30 μl/cavity in growth medium (RPMI (Biochrom: FG 1215), 20% FCS (Biochrom: S 0615)) were transferred into a 384-cavity plate (Perkin Elmer, white) and incubated at 37° C. overnight. After 24 h, the cells were treated with the test substances and incubated at 37° C. for 6 h. The test substances were added to the cells in a 7-stage, 3-fold dilution series using an HP D300 digital dispenser. As control, the cells were treated with the vehicle (DMSO). After 6 h, the cells were treated with 30 μl/well One-Glo solution (Promega, E6110) and incubated at room temperature for 10 min, and the luminescence was measured using a VICTOR V (Perkin Elmer) in order to determine the NF-kB reporter activity at the end of the treatment. The percentage effect of the NF-kB reporter activity and the IC$_{50}$ derived therefrom were determined for each test substance with the aid of the values for an NF-kB pathway inhibitor (I-kappa B kinase inhibitor) (−)-7-[2-(cyclopropylmethoxy)-6-hydroxyphenyl]-5-[(3S)-3-piperidinyl]-1,4-dihydro-2H-pyrido[2,3-d][1,3]oxazin-2-one (CAS Number 600734-02-9; see WO 2003076447) (=maximum inhibition) and the DMSO control (=minimum inhibition). The IC$_{50}$ values were calculated using a 4-parameter fit.

TABLE 4

IC$_{50}$ values for the example compounds with respect to the inhibition of NF-kB activity in TMD-8-NF-kB-luc cells

| Example | IC$_{50}$ [mol/l] |
|---|---|
| 2 | 9.45E−06 |
| 1 | 1.56E−05 |
| 4 | 7.41E−06 |
| 5 | 5.10E−06 |
| 23 | 3.84E−06 |
| 13 | 5.10E−06 |
| 24 | 2.26E−05 |
| 28 | 2.68E−06 |
| 10 | 2.89E−05 |
| 12 | 6.81E−06 |
| 21 | 5.19E−06 |
| 20 | 2.18E−05 |
| 18 | 5.52E−06 |
| 44 | 1.46E−05 |
| 46 | 1.34E−05 |

In Vivo Model of IL-1β-Mediated Inflammation

To evaluate the potential efficacy of the inventive compounds of the general formula (I) in IL-1β-mediated disorders, IL-1β is administered i.p. to female Balb/c mice (about 8 weeks old, Charles River Laboratories, Germany) and the effect of the inventive compounds on IL-1β-mediated cytokine secretion is examined. There are 5 animals in each group. The control group is treated with the vehicles used for dissolving the substance and the IL-1β. 90 μg of IL-1β/kg body weight (R&D, Cat. No. 401-ML/CF) are administered i.p to each of the groups treated with substance and the positive control group. The substance or its vehicle in the positive control group is administered before the administration of IL-1β. 2 hours after administration of the IL-1β, TNF-α is determined in the plasma after the final removal of blood using the Mouse ProInflammatory 7-Plex Tissue Culture Kit (MSD, Cat. No. K15012B) in accordance with the manufacturer's instructions.

In Vivo Adjuvant-Induced Arthritis Model

To determine the anti-inflammatory activity of the inventive compounds of the general formula (I), they are examined for their in vivo efficacy in an arthritis model. For this purpose, male Lewis rats (about 100-125 g, Charles River Laboratories, Germany) are each administered subcutaneously with 100 μl of a complete Freund's adjuvant (CFA) solution (M. tuberculosis H37Ra [Difo Lab, Cat. No.— 231141] dissolved in Incomplete Freund's adjuvant [Difco Lab, Cat. No.—263910]) into the tailhead on day 0. There are n=8 rats in each group. Both a healthy control group and a disease control group are included in the study. Each control group is given p.o. treatment only with the vehicle of the test substance. The treatment with different dosages of the test substance is conducted in a preventative manner, i.e. starting from day 0, by oral administration. On day 0, the starting condition of the animals is additionally determined in terms of the disease activity scores (rating of the severity of arthritis based on a points system). In this scoring system, according to the extent of joint inflammation, points were awarded from 0 to 4 for the presence of an erythema including joint swelling (0=none; 1=slight; 2=moderate; 3=distinct; 4=severe) for both hind paws and added up. To determine the anti-inflammatory efficacy of the compounds, the disease status of the animals is scored by means of disease activity scoring starting from day 8, when the animals first exhibit signs of arthritis, and subsequently 3 times per week, until the end (day 20). Statistical analysis is effected using single-factor variance analysis (ANOVA) and comparison with the control group by means of multiple comparative analysis (Dunnett's test).

The s.c. administration of CFA in rats leads to acute arthritis with distinct joint inflammation in rats.

The invention claimed is:

1. A compound of formula (I)

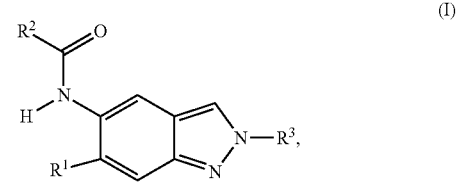

wherein:
R$^1$ is halogen, cyano, C(=O)OH, C(=O)OR$^a$, C(=O)NH$_2$, C(=O)N(H)R$^a$, C(=O)N(R$^a$)R$^b$, C(=O)R$^d$, hydroxyl or $C_1$-$C_6$-alkyl, wherein the $C_1$-$C_6$-alkyl radical can optionally be mono- or polysubstituted identically or differently by hydroxyl, halogen, cyano, C(=O)OH, C(=O)$R^a$, S(=O)$_2$—$C_1$-$C_6$-alkyl, $NH_2$, $NHR^a$, $N(R^a)R^b$, an optionally mono- to hexa-fluorine-substituted $C_1$-$C_6$-alkoxy or $C_3$-$C_7$-cycloalkoxy, a 4- to 7-membered heterocycloalkyl optionally mono- to trisubstituted identically or differently by $R^c$, or is $C_1$-$C_6$-alkoxy, where the $C_1$-$C_6$-alkoxy radical may optionally be mono- or polysubstituted identically or differently by hydroxyl, halogen, cyano, C(=O)OH, C(=O)$R^a$, S(=O)$_2$—$C_1$-$C_6$-alkyl, $NH_2$, $NHR^a$, $N(R^a)R^b$, an optionally mono- to tetra-fluorine-substituted $C_3$-$C_7$-cycloalkyl, an optionally mono- to penta-fluorine-$_{substituted}$ $C_1$-$C_6$-alkoxy, an optionally mono- to tetra-fluorine-substituted $C_3$-$C_7$-cycloalkoxy, a 4- to 7-membered heterocycloalkyl optionally mono- or polysubstituted identically or differently by $R^c$, or is $C_3$-$C_7$-cycloalkyloxy or 4- to 7-membered heterocycloalkyloxy wherein $C_3$-$C_7$-cycloalkyloxy and 4- to 7-membered heterocycloalkyloxy may optionally be mono- or polysubstituted identically or differently by hydroxyl, fluorine, cyano, $C_1$-$C_6$-alkyl or $C_1$-$C_6$-alkoxy;

$R^a$ is $C_1$-$C_6$-alkyl, $C_3$-$C_7$-cycloalkyl, or 4- to 7-membered heterocycloalkyl, wherein $C_1$-$C_6$-alkyl, $C_3$-$C_7$-cycloalkyl and 4- to 7-membered heterocycloalkyl are optionally mono- or polysubstituted identically or differently by fluorine, hydroxyl, cyano, $C_1$-$C_4$-alkyl, $C_1$-$C_4$-alkoxy or $C_3$-$C_7$-cycloalkyl;

$R^b$ is $C_1$-$C_6$-alkyl or $C_3$-$C_7$-cycloalkyl;

or $R^a$ and $R^b$ together with the nitrogen atom to which they are bonded form a 5- or 6-membered heterocycle which may optionally be mono- or disubstituted identically or differently by hydroxyl, halogen, cyano, or $C_1$-$C_6$-alkyl;

$R^c$ is hydroxyl, fluorine, chlorine, cyano, $C_1$-$C_4$-alkyl or $C_1$-$C_4$-alkoxy;

$R^d$ is hydrogen, $C_3$-$C_7$-cycloalkyl, or $C_1$-$C_6$-alkyl which may optionally be substituted by a hydroxyl group;

$R^2$ is 5-membered heteroaryl which may be monosubstituted by $R^4$ and monosubstituted by $R^5$; or $R^2$ is 6-membered heteroaryl which may be monosubstituted by $R^4$ and mono- or disubstituted identically or differently by $R^5$;

$R^3$ is a group selected from:

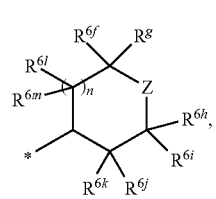

$R^{3a}$

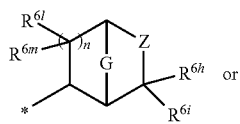

$R^{3b}$ or

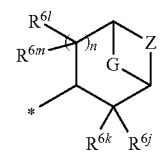

$R^{3c}$ where * represents the bonding site of the group to the rest of the molecule;

$R^4$ is hydrogen, halogen, hydroxyl, C(=O)OH, cyano, $NH_2$, $NHR^a$, $N(R^a)R^b$, C(=O)$R^a$, N(H)C(=O)$R^a$, C(=O)$NH_2$, C(=O)N(H)$R^a$, C(=O)$N(R^a)R^b$, S(=O)$R^a$, S(=O)$_2R^a$, S(=O)$_2NH_2$, S(=O)$_2NHR^a$ or S(=O)$_2$ $N(R^a)R^b$, or is $C_1$-$C_6$-alkyl, where $C_1$-$C_6$-alkyl may optionally be substituted by one to five fluorine atoms and may optionally be mono- or disubstituted identically or differently by hydroxyl, bromine, chlorine, cyano, C(=O)OH, S(=O)$_2$—$C_1$-$C_6$-alkyl, $NH_2$, $NHR^a$, $N(R^a)R^b$, $C_3$-$C_7$-cycloalkyl, $C_1$-$C_4$-alkoxy, $C_3$-$C_7$-cycloalkoxy, trifluoromethoxy, or is $C_1$-$C_6$-alkoxy, where $C_1$-$C_6$-alkoxy may optionally be substituted by one to five fluorine atoms and may optionally be mono- or disubstituted identically or differently by hydroxyl, chlorine, bromine, cyano, C(=O)OH, S(=O)$_2$—$C_1$-$C_6$-alkyl, $NH_2$, $NHR^a$, $N(R^a)R^b$, $C_3$-$C_7$-cycloalkyl, $C_1$-$C_4$-alkoxy, $C_3$-$C_7$-cycloalkoxy, trifluoromethoxy, or is $C_3$-$C_7$-cycloalkyl or is $C_3$-$C_7$-cycloalkyloxy, where $C_3$-$C_7$-cycloalkyl and $C_3$-$C_7$-cycloalkyloxy may optionally be substituted by one to four fluorine atoms and may optionally be mono- or disubstituted identically or differently by hydroxyl, chlorine, bromine, cyano, C(=O)$R^d$, C(=O)OH, $C_1$-$C_6$-alkyl or $C_1$-$C_4$-alkoxy, or is 4-7-membered heterocycloalkyl which may optionally be substituted by one to four fluorine atoms and may optionally be mono- or disubstituted identically or differently by hydroxyl, chlorine, bromine, cyano, $NH_2$, $NHR^a$, $N(R^a)R^b$, C(=O)$R^d$, C(=O)OH, $C_1$-$C_6$-alkyl, trifluoromethyl, 2,2,2-trifluoroethyl, cyclopropyl, cyclopropylmethyl or $C_1$-$C_4$-alkoxy, or is phenyl or 5- or 6-membered heteroaryl, wherein said phenyl and 5- or 6-membered heteroaryl may optionally be mono- to disubstituted identically or differently by fluorine, chlorine, bromine, hydroxyl, cyano, C(=O)OH, S(=O)$_2$—$C_1$-$C_4$-alkyl, $NH_2$, $NHR^a$, $N(R^a)R^b$, N(H)C(=O)$R^a$, $C_1$-$C_4$-alkoxy, trifluoromethoxy or $C_1$-$C_4$-alkyl, where $C_1$-$C_4$-alkyl may optionally be mono- to trisubstituted by fluorine;

$R^5$ is hydrogen, halogen, hydroxyl, cyano, $C_1$-$C_4$-alkoxy, trifluoromethoxy or $C_1$-$C_6$-alkyl, wherein $C_1$-$C_6$-alkyl may optionally be substituted by one to five fluorine atoms, $R^{6f}$ is hydrogen, fluorine, C(=O)OH, C(=O)$NH_2$, trifluoromethyl, hydroxymethyl, methoxymethyl, cyano or $C_1$-$C_6$-alkyl, $R^{6g}$ is hydrogen, fluorine or $C_1$-$C_6$-alkyl; or $R^{6f}$ and $R^{6g}$ together with the carbon atom to which they are bonded form a $C_3$-$C_7$-cycloalkyl; or $R^{6f}$ and $R^{6g}$ together are an oxo group;

$R^{6h}$ is hydrogen, trifluoromethyl or $C_1$-$C_6$-alkyl; and $R^{6i}$ is hydrogen or $C_1$-$C_6$-alkyl; or $R^{6h}$ and $R^{6i}$ together are an oxo group, $R^{6j}$ is hydrogen, fluorine, $NH_2$, $N(H)R^a$, $N(R^a)R^b$, $C_1$-$C_6$-alkyl, hydroxyl, cyano, $C_1$-$C_4$-alkoxy, $C(=O)OH$, $C(=O)NH_2$, $C(=O)N(H)R^a$, $C(=O)N(R^a)R^b$, hydroxymethyl, dimethylaminomethyl, or trifluoromethyl, $R^{6k}$ is hydrogen, fluorine or $C_1$-$C_6$-alkyl; or $R^{6j}$ and $R^{6k}$ together with the carbon atom to which they are bonded form a $C_3$-$C_7$-cycloalkyl, $R^{6l}$ is hydrogen or methyl, $R^{6m}$ is hydrogen or methyl, G is —$CH_2$— or —$CH_2CH_2$—, n in the formula $R^{3a}$ is 0, 1 or 2, n in the formula $R^{3b}$ is 1 or 2, n in the formula $R^{3c}$ is 0 or 1, z is a group selected from the group consisting of $NR^7$, O, S, $S(=O)$, $S(=O)_2$, and $S(=O)(=NH)$;

$R^7$ is hydrogen, $C(=O)R^e$, $C(=O)OR^a$, $C(=O)NH_2$, $C(=O)N(H)R^a$, $C(=O)N(R^a)R^b$, $S(=O)_2R^a$, $S(=O)_2NH_2$, $S(=O)_2N(R^a)H$, $S(=O)_2N(R^a)R^b$, $S(=O)_2NHC(=O)CH_3$, $S(=O)_2NHC(=O)CH_2CH_3$ or $C_1$-$C_6$-alkyl, wherein $C_1$-$C_6$-alkyl may optionally be mono- to pentasubstituted by fluorine atoms and mono- to disubstituted identically or differently by hydroxyl, chlorine, bromine, cyano, $C(=O)R^a$, $C(=O)OH$, $C(=O)NH_2$, $C(=O)N(H)R^a$, $C(=O)N(R^a)R^b$, $S(=O)_2$—$C_1$-$C_6$-alkyl, $NH_2$, $NHR^a$, $N(R^a)R^b$, morpholin-4-yl, 4-methylpiperazin-1-yl, $C_3$-$C_7$-cycloalkyl, $C_1$-$C_4$-alkoxy or $C_3$-$C_7$-cycloalkoxy, or is $C_3$-$C_7$-cycloalkyl which may optionally be mono- to tetrasubstituted by fluorine atoms and may optionally be mono- to disubstituted identically or differently by hydroxyl, methyl, ethyl, trifluoromethyl or cyano, or is a 4-7-membered heterocycloalkyl bonded to the rest of the molecule by a carbon atom or is 4-7-membered heterocycloalkyl-$C_1$-$C_4$-alkyl which may optionally be mono-to hexasubstituted by fluorine atoms and mono- to trisubstituted identically or differently by hydroxyl, chlorine, bromine, cyano, $C_1$-$C_6$-alkyl, $C_1$-$C_6$-alkoxy, trifluoromethyl, 2,2,2-trifluoroethyl, trifluoromethoxy, cyclopropyl, or cyclopropylmethyl, $R^e$ is $C_1$-$C_6$-alkyl, where $C_1$-$C_6$-alkyl may optionally be mono- to trisubstituted identically or differently by hydroxyl, fluorine, chlorine, cyano, $C(=O)R^a$, $C(=O)OH$, $NH_2$, $NHR^a$, $N(R^a)R^b$, $C_3$-$C_7$-cycloalkyl, $C_1$-$C_4$-alkoxy, trifluoromethoxy or $C_3$-$C_7$-cycloalkoxy; or $R^e$ is $C_3$-$C_7$-cycloalkyl, where $C_3$-$C_7$-cycloalkyl may optionally be mono- to tetrasubstituted by fluorine and may optionally be monosubstituted by hydroxyl, or a diastereomer, an enantiomer, a metabolite, a salt, a solvate, or a solvate of a salt thereof.

2. The compound according to claim 1, or a diastereomer, an enantiomer, a metabolite, a salt, a solvate, or a solvate of a salt thereof, wherein $R^1$ is hydroxymethyl, 1-hydroxyethyl or 2-hydroxypropan-2-yl.

3. The compound according to claim 1, or a diastereomer, an enantiomer, a metabolite, a salt, a solvate, or a solvate of a salt thereof, wherein $R^2$ is a pyridin-2-yl radical substituted at the 6 position by $C_1$-$C_6$-alkyl, where $C_1$-$C_6$-alkyl is optionally substituted by up to 5 fluorine atoms; or $R^2$ is a pyridin-2-yl radical substituted at the 6 position by cyano, chlorine, cyclopropyl, cyclopropylmethyl, $NH_2$, $NH(C_1$-$C_4$-alkyl), $N(C_1$-$C_4$-alkyl)$_2$, $C_1$-$C_4$-alkoxy, 2,2,2-trifluoroethoxy, 2-hydroxypropan-2-yl, morpholin-4-yl, 4-methylpiperazin-1-yl or piperazin-1-yl.

4. The compound according to claim 3, or a diastereomer, an enantiomer, a metabolite, a salt, a solvate, or a solvate of a salt thereof, wherein $R^2$ is a pyridin-2-yl radical substituted at the 6 position by trifluoromethyl, difluoromethyl, methyl, 2,2,2-trifluoroethyl, 1,1-difluoroethyl, ethyl, isopropyl, tert-butyl, cyano, chlorine, cyclopropyl, cyclopropylmethyl, $NH_2$, $NH(C_1$-$C_4$-alkyl), $N(C_1$-$C_4$-alkyl)$_2$, $C_1$-$C_4$-alkoxy, 2,2,2-trifluoroethoxy, 2-hydroxypropan-2-yl, morpholin-4-yl, 4-methylpiperazin-1-yl or piperazin-1-yl.

5. The compound according to claim 4, or a diastereomer, an enantiomer, a metabolite, a salt, a solvate, or a solvate of a salt thereof, wherein $R^2$ is 6-(trifluoromethyl)pyridin-2-yl, 6-(difluoromethyl)pyridin-2-yl, 6-(1,1-difluoroethyl)pyridin-2-yl, 6-aminopyridin-2-yl or 6-(2-hydroxypropan-2-yl)pyridin 2-yl.

6. The compound according to claim 1, or a diastereomer, an enantiomer, a metabolite, a salt, a solvate, or a solvate of a salt thereof, wherein $R^1$ is $C(=O)NH_2$, 2-hydroxypropan-2-yl or methoxy;

$R^2$ is 6-(trifluoromethyl)pyridin-2-yl, 6-(difluoromethyl)pyridin-2-yl, 6-aminopyridin-2-yl, 4-(trifluoromethyl)-1,3-thiazol-2-yl, or 1-(difluoromethyl)-1H-pyrazol-3-yl; and $R^3$ is tetrahydro-2H-pyran-4-yl, 1,1-dioxidotetrahydro-2H-thiopyran-4-yl, tetrahydrofuran-3-yl, (3S)-tetrahydrofuran-3-yl, (3R)-tetrahydrofuran-3-yl or (3S)-1,1-dioxidotetrahydrothiophen-3-yl; or $R^3$ is piperidin-4-yl, 1-(2,2,2-trifluoroethyl)piperidin-4-yl, 1-methylpiperidin-4-yl, 1-glycoloylpiperidin-4-yl, 1'-methyl-1,4'-bipiperidin-4-yl, 1-(acetylsulphamoyl)piperidin-4-yl, [2-(dimethylamino)ethyl]piperidin-4-yl, 1-(oxetan-3-yl)piperidin-4-yl, 1-(2-hydroxyethyl)piperidin-4-yl or 1-(3-hydroxy-3-methylbutyl)piperidin-4-yl.

7. The compound according to claim 1, wherein the compound is selected from the group consisting of:

(1) N-[6-methoxy-2-(tetrahydro-2H-pyran-4-yl)-2H-indazol-5-yl]-6-(trifluoromethyl)pyridine-2-carboxamide;

(2) N-[6-methoxy-2-(piperidin-4-yl)-2H-indazol-5-yl]-6-(trifluoromethyl)pyridine-2-carboxamide;

(3) N-{6-methoxy-2-[1-(2,2,2-trifluoroethyl)piperidin-4-yl]-2H-indazol-5-yl}-6-(trifluoromethyl)pyridine-2-carboxamide;

(4) N-[6-methoxy-2-(1-methylpiperidin-4-yl)-2H-indazol-5-yl]-6-(trifluoromethyl)pyridine-2-carboxamide;

(5) N-[2-(1-glycoloylpiperidin-4-yl)-6-methoxy-2H-indazol-5-yl]-6-(trifluoromethyl)pyridine-2-carboxamide;

(6) N-[6-methoxy-2-(1'-methyl-1,4'-bipiperidin-4-yl)-2H-indazol-5-yl]-6-(trifluoromethyl)pyridine-2-carboxamide;

(7) N-[6-methoxy-2-(1-sulphamoylpiperidin-4-yl)-2H-indazol-5-yl]-6-(trifluoromethyl)pyridine-2-carboxamide;

(8) N-{2-[1-(acetylsulphamoyl)piperidin-4-yl]-6-methoxy-2H-indazol-5-yl}-6-(trifluoromethyl)pyridine-2-carboxamide;

(9) N-(2-{1-[2-(dimethylamino)ethyl]piperidin-4-yl}-6-methoxy-2H-indazol-5-yl)-6-(trifluoromethyl)pyridine-2-carboxamide;

(10) N-{6-methoxy-2-[1-(oxetan-3-yl)piperidin-4-yl]-2H-indazol-5-yl}-6-(trifluoromethyl)pyridine-2-carboxamide;

(11) N-[2-(1,1-dioxidotetrahydro-2H-thiopyran-4-yl)-6-methoxy-2H-indazol-5-yl]-6-(trifluoromethyl)pyridine-2-carboxamide;
(12) N-[6-methoxy-2-(1-oxidotetrahydro-2H-thiopyran-4-yl)-2H-indazol-5-yl]-6-(trifluoromethyl)pyridine-2-carboxamide;
(13) N-{2-[1-(2-hydroxyethyl)piperidin-4-yl]-6-methoxy-2H-indazol-5-yl}-6-(trifluoromethyl)pyridine-2-carboxamide;
(14) rel-N-{2-[(1R,4R,5S)-2-azabicyclo[2.2.1]hept-5-yl]-6-methoxy-2H-indazol-5-yl}-6-(trifluoromethyl)pyridine-2-carboxamide;
(15) rel-N-{2-[(1R,4R,5R)-2-azabicyclo[2.2.1]hept-5-yl]-6-methoxy-2H-indazol-5-yl}-6-(trifluoromethyl)pyridine-2-carboxamide;
(16) N-[2-(1,1-dioxidotetrahydro-2H-thiopyran-4-yl)-6-hydroxy-2H-indazol-5-yl]-6-(trifluoromethyl)pyridine-2-carboxamide;
(17) N-[6-(cyclopropylmethoxy)-2-(1,1-dioxidotetrahydro-2H-thiopyran-4-yl)-2H-indazol-5-yl]-6-(trifluoromethyl)pyridine-2-carboxamide;
(18) rel-N-{6-methoxy-2-[(1R,4R,5S)-2-methyl-2-azabicyclo[2.2.1]hept-5-yl]-2H-indazol-5-yl}-6-(trifluoromethyl)pyridine-2-carboxamide;
(19) rel-N-{6-methoxy-2-[(1R,4R,5R)-2-methyl-2-azabicyclo[2.2.1]hept-5-yl]-2H-indazol-5-yl}-6-(trifluoromethyl)pyridine-2-carboxamide;
(20) N-[2-(1-imino-1-oxidohexahydro-1$\lambda^4$-thiopyran-4-yl)-6-methoxy-2H-indazol-5-yl]-6-(trifluoromethyl)pyridine-2-carboxamide (isomer 1);
(21) N-[2-(1-imino-1-oxidohexahydro-1$\lambda^4$-thiopyran-4-yl)-6-methoxy-2H-indazol-5-yl]-6-(trifluoromethyl)pyridine-2-carboxamide (isomer 2);
(22) N-[6-methoxy-2-(5-oxopyrrolidin-3-yl)-2H-indazol-5-yl]-6-(trifluoromethyl)pyridine-2-carboxamide;
(23) 6-(difluoromethyl)-N-[6-methoxy-2-(tetrahydro-2H-pyran-4-yl)-2H-indazol-5-yl]pyridine-2-carboxamide;
(24) N-[6-methoxy-2-(tetrahydro-2H-pyran-4-yl)-2H-indazol-5-yl]-6-(morpholin-4-yl)pyridine-2-carboxamide;
(25) N-[6-methoxy-2-(tetrahydro-2H-pyran-4-yl)-2H-indazol-5-yl]-2-methyl-1,3-thiazole-4-carboxamide;
(26) 6-amino-N-[6-methoxy-2-(tetrahydro-2H-pyran-4-yl)-2H-indazol-5-yl]pyridine-2-carboxamide;
(27) 2-isopropyl-N-[6-methoxy-2-(tetrahydro-2H-pyran-4-yl)-2H-indazol-5-yl]pyrimidine-4-carboxamide;
(28) 6-(2-hydroxypropan-2-yl)-N-[6-methoxy-2-(tetrahydro-2H-pyran-4-yl)-2H-indazol-5-yl]pyridine-2-carboxamide;
(29) N-[6-methoxy-2-(tetrahydrofuran-3-yl)-2H-indazol-5-yl]-6-(trifluoromethyl)pyridine-2-carboxamide;
(30) N-[6-chloro-2-(tetrahydro-2H-pyran-4-yl)-2H-indazol-5-yl]-6-(trifluoromethyl)pyridine-2-carboxamide;
(31) N-[6-chloro-2-(tetrahydro-2H-pyran-4-yl)-2H-indazol-5-yl]-6-(difluoromethyl)pyridine-2-carboxamide;
(32) N-[6-chloro-2-(1,1-dioxidotetrahydro-2H-thiopyran-4-yl)-2H-indazol-5-yl]-6-(2-hydroxypropan-2-yl)pyridine-2-carboxamide;
(33) methyl 2-(tetrahydro-2H-pyran-4-yl)-5-({[6-(trifluoromethyl)pyridin-2-yl]carbonyl}amino)-2H-indazole-6-carboxylate;
(34) N-[6-(2-hydroxypropan-2-yl)-2-(tetrahydro-2H-pyran-4-yl)-2H-indazol-5-yl]-6-(trifluoromethyl)pyridine-2-carboxamide;
(35) methyl 2-[(3S)-tetrahydrofuran-3-yl]-5-({[6-(trifluoromethyl)pyridin-2-yl]carbonyl}amino)-2H-indazole-6-carboxylate;
(36) N-{6-(2-hydroxypropan-2-yl)-2-[(3S)-tetrahydrofuran-3-yl]-2H-indazol-5-yl}-6-(trifluoromethyl)pyridine-2-carboxamide;
(37) methyl 2-[(3R)-tetrahydrofuran-3-yl]-5-({[6-(trifluoromethyl)pyridin-2-yl]carbonyl}amino)-2H-indazole-6-carboxylate;
(38) N-{6-(2-hydroxypropan-2-yl)-2-[(3R)-tetrahydrofuran-3-yl]-2H-indazol-5-yl}-6-(trifluoromethyl)pyridine-2-carboxamide;
(39) methyl 2-[(3S)-tetrahydrothiophen-3-yl]-5-({[6-(trifluoromethyl)pyridin-2-yl]carbonyl}amino)-2H-indazole-6-carboxylate;
(40) N-{6-(2-hydroxypropan-2-yl)-2-[(3S)-tetrahydrothiophen-3-yl]-2H-indazol-5-yl}-6-(trifluoromethyl)pyridine-2-carboxamide;
(41) N-{2-[(3S)-1,1-dioxidotetrahydrothiophen-3-yl]-6-(2-hydroxypropan-2-yl)-2H-indazol-5-yl}-6-(trifluoromethyl)pyridine-2-carboxamide;
(42) methyl 2-(tetrahydro-2H-thiopyran-4-yl)-5-({[6-(trifluoromethyl)pyridin-2-yl]carbonyl}amino)-2H-indazole-6-carboxylate;
(43) N-[6-(2-hydroxypropan-2-yl)-2-(tetrahydro-2H-thiopyran-4-yl)-2H-indazol-5-yl]-6-(trifluoromethyl)pyridine-2-carboxamide;
(44) N-[2-(1,1-dioxidotetrahydro-2H-thiopyran-4-yl)-6-(2-hydroxypropan-2-yl)-2H-indazol-5-yl]-6-(trifluoromethyl)pyridine-2-carboxamide;
(45) methyl 2-(piperidin-4-yl)-5-({[6-(trifluoromethyl)pyridin-2-yl]carbonyl}amino)-2H-indazole-6-carboxylate;
(46) N-[6-(2-hydroxypropan-2-yl)-2-(piperidin-4-yl)-2H-indazol-5-yl]-6-(trifluoromethyl)pyridine-2-carboxamide;
(47) N-[6-methoxy-2-(tetrahydro-2H-pyran-4-yl)-2H-indazol-5-yl]-4-(trifluoromethyl)-1,3-thiazole-2-carboxamide;
(48) N-[6-methoxy-2-(tetrahydro-2H-pyran-4-yl)-2H-indazol-5-yl]-3-(pyridin-4-yl)-1,2,4-oxadiazole-5-carboxamide;
(49) N-[6-methoxy-2-(tetrahydro-2H-pyran-4-yl)-2H-indazol-5-yl]-3-methyl-1,2,4-oxadiazole-5-carboxamide;
(50) N-[6-chloro-2-(tetrahydro-2H-pyran-4-yl)-2H-indazol-5-yl]-4-(trifluoromethyl)-1,3-thiazole-2-carboxamide;
(51) 1-(difluoromethyl)-N-[6-methoxy-2-(tetrahydro-2H-pyran-4-yl)-2H-indazol-5-yl]-1H-pyrazole-3-carboxamide;
(52) N-{2-[1-(3-hydroxy-3-methylbutyl)piperidin-4-yl]-6-methoxy-2H-indazol-5-yl}-6-(trifluoromethyl)pyridine-2-carboxamide;
(53) 2-(piperidin-4-yl)-5-({[6-(trifluoromethyl)pyridin-2-yl]carbonyl}amino)-2H-indazole-6-carboxamide;
(54) 2-(piperidin-4-yl)-5-({[6-(trifluoromethyl)pyridin-2-yl]carbonyl}amino)-2H-indazole-6-carboxylic acid;
(55) methyl 2-(1-methylpiperidin-4-yl)-5-({[6-(trifluoromethyl)pyridin-2-yl]carbonyl}amino)-2H-indazole-6-carboxylate;
(56) 2-[1-(3-hydroxy-3-methylbutyl)piperidin-4-yl]-5-({[6-(trifluoromethyl)pyridin-2-yl]carbonyl}amino)-2H-indazole-6-carboxamide;
(57) 2-(1-methylpiperidin-4-yl)-5-({[6-(trifluoromethyl)pyridin-2-yl]carbonyl}amino)-2H-indazole-6-carboxamide; and
(58) N-{6-methoxy-2-[1-(2-methoxyethyl)piperidin-4-yl]-2H-indazol-5-yl}-6-(trifluoromethyl)pyridine-2-carboxamide, or a diastereomer, an enantiomer, a metabolite, a salt, a solvate, or a solvate of a salt thereof.

8. A pharmaceutical composition comprising a compound of formula (I) according to claim 1 in combination with an inert, non-toxic, pharmaceutically suitable excipient.

\* \* \* \* \*